(12) United States Patent
Lee et al.

(10) Patent No.: US 10,913,942 B2
(45) Date of Patent: Feb. 9, 2021

(54) YEAST STRAIN WITH XYLOSE UTILIZING CAPACITY

(71) Applicant: KOREA INSTITUTE OF SCIENCE AND TECHNOLOGY, Seoul (KR)

(72) Inventors: Sun Mi Lee, Seoul (KR); Sangdo Yook, Seoul (KR); Youngsoon Um, Seoul (KR); Gyeongtaek Gong, Seoul (KR); Jiwon Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 43 days.

(21) Appl. No.: 16/204,020

(22) Filed: Nov. 29, 2018

(65) Prior Publication Data

US 2020/0102549 A1    Apr. 2, 2020

(30) Foreign Application Priority Data

Oct. 2, 2018 (KR) .................. 10-2018-0117860

(51) Int. Cl.
| | |
|---|---|
| *C12N 9/92* | (2006.01) |
| *C12N 1/16* | (2006.01) |
| *C12P 7/64* | (2006.01) |
| *C12N 9/12* | (2006.01) |
| *C12N 15/01* | (2006.01) |
| *C12N 15/52* | (2006.01) |
| *C07K 14/39* | (2006.01) |

(52) U.S. Cl.
CPC ............... *C12N 9/92* (2013.01); *C12N 1/16* (2013.01); *C12N 9/1205* (2013.01); *C12P 7/64* (2013.01); *C12Y 207/01017* (2013.01); *C12Y 503/01005* (2013.01)

(58) Field of Classification Search
None
See application file for complete search history.

(56) References Cited

U.S. PATENT DOCUMENTS 9,096,876 B2    8/2015 Stephanopoulos et al.
2012/0329109 A1   12/2012 Chua et al.

FOREIGN PATENT DOCUMENTS

KR    10-2016-0043498 A    4/2016
WO    WO 2013/192520 A1    12/2013

OTHER PUBLICATIONS

Ledesma-Amaro et al., "Metabolic engineering of Yarrowia lipolytica to produce chemicals and fuels from xylose", Metabolic Engineering, 2016, vol. 38, pp. 115-124.
Li et al., "Enabling xylose utilization in Yarrowia lipolytica for lipid production", Biotechnology Journal, 2016, vol. 11, pp. 1230-1240.
Rodriguez et al., "Engineering xylose utilization in Yarrowia lipolytica by understanding its cryptic xylose pathway", Biotechnology Biofuels, 2016, vol. 9, pp. 149-164.
Yook et al., "Engineering xylose isomerase-based pathway in Yarrowia lipolytica for efficient conversion of xylose to lipid", 2018 Synthetic Biology: Engineering, Evolution & Design (SEED), Jun. 3-7, 2008, Total 5 pages.

*Primary Examiner* — Suzanne M Noakes
*Assistant Examiner* — Jae W Lee
(74) *Attorney, Agent, or Firm* — Birch, Stewart, Kolasch & Birch, LLP

(57) ABSTRACT

Disclosed herein are a yeast strain capable of utilizing xylose as a carbon source and a method for producing lipids using the same. The yeast strain is obtained by adaptively evolving a wild-type yeast strain which cannot utilize xylose as a carbon source so that it can produce high density lipids and then transforming the adaptively evolved strain to obtain the ability to metabolize xylose. Since the strain does not have the xylose metabolic pathway based on oxidoreductase, it can produce biodiesel and biomaterials based on lipid and lignocellulosic biomass at a high yield without a problem of cofactor imbalance and can greatly improve the economic feasibility and sustainability of the production processes of biodiesel and biomaterials.

18 Claims, 5 Drawing Sheets

Specification includes a Sequence Listing.

SEQUENCE LISTING

<160> NUMBER OF SEQ ID NOS: 101

<210> SEQ ID NO 1
<211> LENGTH: 1314
<212> TYPE: DNA
<213> ORGANISM: Artificial Sequence
<220> FEATURE:
<223> OTHER INFORMATION: xylA

<400> SEQUENCE: 1

| | | | | | |
|---|---|---|---|---|---|
| atggctaagg | agtatttccc | tcagattcag | aagatcaagt | tcgacggcaa | ggacagcaaa | 60 |
| aaccccctgg | ctttccatta | ttacgacgcc | gagaaggaag | tgatgggcaa | gaagatgaag | 120 |
| gactggctgc | ggttcgcaat | ggcatggtgg | cacaccctgt | gcgcagaggg | agcagatcag | 180 |
| ttcggaggag | gcaccaagtc | ttttccatgg | aacgagggca | cagacgccat | cgagatcgcc | 240 |
| aagcagaagg | tggatgccgg | cttcgagatc | atgcagaagc | tgggcatccc | ctactattgt | 300 |
| tttcacgacg | tggatctggt | gtccgagggc | aactctatcg | gcgagtacga | gtccaatctg | 360 |
| aaggccgtgg | tggcctatct | gaaggacaag | cagaaggaga | ccggcatcaa | gctgctgtgg | 420 |
| agctccgcca | acgtgttcgg | ccacaagagg | tacatgaacg | gcgcctctac | caatcccgac | 480 |
| tttgatgtgg | tggcccgcgc | catcgtgcag | atcaagaacg | ccatcgatac | aggcatcgag | 540 |
| ctgggcgccg | agaattacgt | gttttggggc | ggccggagg | gctatatgtc | tctgctgaat | 600 |
| acagaccaga | agagagagaa | ggagcacatg | gccaccatgc | tgacaatggc | cagggattac | 660 |
| gcccgcagca | agggcttcaa | gggcacctt | ctgatcgagc | ccaagcctat | ggagcctaca | 720 |
| aagcaccagt | atgacgtgga | taccgagaca | gccatcggct | tcctgaaggc | ccacaatctg | 780 |
| gacaaggact | tcaaggtgaa | catcgaagtg | aatcacgcca | ccctggccgg | ccacacattc | 840 |
| gagcacgagc | tggcatgcgc | agtggacgca | ggaatgctgg | gaagcatcga | cgccaacagg | 900 |
| ggcgattacc | agaatggctg | ggacaccgat | cagtttccta | tcgatcagta | tgagctggtg | 960 |
| caggcatgga | tggagatcat | caggggagga | ggattcgtga | ccggaggaac | aaactttgac | 1020 |
| gccaagaccc | ggagaaatag | cacagacctg | gaggatatca | tcatcgccca | cgtgtccgga | 1080 |
| atggatgcaa | tggcacgggc | cctggagaac | gcagcaaagc | tgctgcagga | gtccccatac | 1140 |
| accaagatga | agaaggagag | atatgcctct | ttcgacagcg | gcatcggcaa | ggactttgag | 1200 |
| gatggcaagc | tgacactgga | gcaggtgtac | gagtatggca | agaagaatgg | cgagcctaag | 1260 |
| cagacctcag | ggaagcagga | gctgtacgaa | gccatcatcg | caatgtatca | gtga | 1314 |

<210> SEQ ID NO 2
<211> LENGTH: 1643
<212> TYPE: DNA
<213> ORGANISM: Yarrowia lipolytica

<400> SEQUENCE: 2

| | | | | | |
|---|---|---|---|---|---|
| atgtatctcg | gactggatct | ttcgactcaa | cagctcaagg | gcatcattct | ggacacaaaa | 60 |
| acgctggaca | cggtcacaca | agtccatgtg | gactttgagg | acgacttgcc | gcagttcaac | 120 |
| accgaaaagg | gcgtctttca | cagctctaca | gtggccggag | aaatcaatgc | tcctgtggca | 180 |
| atgtgggggg | cagctgtgga | cttgctgata | gagcgtctgt | caaggaaat | agacctttcc | 240 |
| acgatcaagt | ttgtgtcggg | ctcgtgccag | caacacggct | ctgtttatct | caacagcagc | 300 |
| tacaaggagg | gcctgggttc | tctggacaaa | cacaaagact | tgtctacagg | agtgtcatcc | 360 |
| ttactggcgc | tcgaagtcag | ccccaattgg | caggatgcaa | gcacggagaa | ggagtgtgcg | 420 |
| cagtttgagg | ctgcagtcgg | cggtcccgag | cagctggctg | agatcactgg | ctctcgagca | 480 |

```
catactcgtt tcaccgggcc ccagattctc aaggtcaagg aacgcaaccc caaggtattc      540
aaggccacgt cacgggtcca gctcatatcc aactttctag catctctgtt tgccggcaag      600
gcgtgcccct ttgatcttgc tgacgcctgt ggaatgaatc tgtgggacat ccagaatggc      660
cagtggtgca agaaactcac agatctcatc accgatgaca cccactcggt cgagtccctc      720
cttggagacg tggaaacaga ccccaaggct ctactgggca aaatctcgcc ctatttcgtc      780
tccaagggct tctctcccct tgtcaggtg gcacagttca caggcgacaa cccaggcact       840
atgctggctc tccccttaca ggccaatgac gtgattgtgt ctttgggaac atctacgacc      900
gccctcgtcg taacaaacaa gtacatgccc gaccccggat accatgtgtt caaccacccc      960
atggagggat acatgggcat gctgtgctac tgcaacgag gtctagcacg agagaagatc      1020
cgagacgagc ttggaggctg ggacgagttt aatgaggcgg ccgagaccac caacacagtg     1080
tctgctgacg atgtccatgt tggcatctac tttccactac gagaaatcct tcctcgagca     1140 ggtcccttg aacgacgttt catctacaac agacaaagtg aacagcttac agagatggct      1200
tctccagagg actcactggc aaccgaacac aaaccgcagg ctcaaaatct caaggacacg     1260
tggccgccac aaatggacgc cactgccatc attcaaagcc aggccctcag tatcaaaatg     1320
agactccaac gcatgatgca tggcgatatt ggaaaggtgt attttgtggg aggcgcctcg     1380
gtcaacactg ctatctgcag cgtaatgtct gccatcttaa aaccaacaaa gggcgcttgg     1440
agatgtggtc tggaaatggc aaacgcttgt gccattggaa gtgcccatca cgcctggctt     1500
tgcgacccca acaagacagg ccaggtacag gttcacgaag aagaggtcaa atacaagaat     1560
gtggacacag acgtgctact caaggcgttc aagctggccg aaaacgcctg cctggagaaa     1620
taactaacta ccacaccaac aca                                             1643
```

<210> SEQ ID NO 3
<211> LENGTH: 9688
<212> TYPE: DNA
<213> ORGANISM: Artificial Sequence
<220> FEATURE:
<223> OTHER INFORMATION: pMCS-UAS1B16-TEF-XylA-CYCt

<400> SEQUENCE: 3

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgagctcggt acccgctttt      420
cgtagataat ggaatacaaa tgatatccca gagtatacac atggatagta tacactgaca      480
cgacaattct gtatctcttt atgttaacta ctgtgaggcg ttaaatagag cttgatatat      540
aaaatgttac atttcacagt ctgaacttttt gcagattacc taatttggta agatattaat      600
tatgaactga aagttgatgg catccctaaa tttgatgaaa gggcgcggga tccggccgg       660 gaattcgaag gtaccaagga agcatgcggt acccgaattc ctgaggtgtc tcacaagtgc      720
cgtgcagtcc cgcccccact tgcttctctt tgtgtgtagt gtacgtacat tatcgagacc      780
gttgttcccg cccacctcga tccggtctag actgaggtgt ctcacaagtg ccgtgcagtc      840
```

-continued

```
ccgcccccac ttgcttctct ttgtgtgtag tgtacgtaca ttatcgagac cgttgttccc      900
gcccacctcg atccggggat ccctgaggtg tctcacaagt gccgtgcagt cccgccccca      960
cttgcttctc tttgtgtgta gtgtacgtac attatcgaga ccgttgttcc cgcccacctc     1020
gatccgggtc gacctgaggt gtctcacaag tgccgtgcag tccgccccc acttgcttct      1080
ctttgtgtgt agtgtacgta cattatcgag accgttgttc cgcccacct cgatccggga     1140
gctcctgagg tgtctcacaa gtgccgtgca gtcccgcccc cacttgcttc tctttgtgtg     1200
tagtgtacgt acattatcga gaccgttgtt cccgcccacc tcgatccggt ctagactgag     1260
gtgtctcaca agtgccgtgc agtcccgccc ccacttgctt ctctttgtgt gtagtgtacg     1320
tacattatcg agaccgttgt cccgcccac ctcgatccgg ggatccctga ggtgtctcac     1380
aagtgccgtg cagtcccgcc cccacttgct tctctttgtg tgtagtgtac gtacattatc     1440
gagaccgttg ttcccgccca cctcgatccg gtcgacctg aggtgtctca caagtgccgt     1500
gcagtcccgc ccccacttgc ttctctttgt gtgtagtgta cgtacattat cgagaccgtt     1560
gttcccgccc acctcgatcc gggcatgcgg tacccgaatt cctgaggtgt ctcacaagtg     1620
ccgtgcagtc ccgcccccac ttgcttctct ttgtgtgtag tgtacgtaca ttatcgagac     1680
cgttgttccc gcccacctcg atccggtcta gactgaggtg tctcacaagt gccgtgcagt     1740
cccgccccca cttgcttctc tttgtgtgta gtgtacgtac attatcgaga ccgttgttcc     1800
cgcccacctc gatccgggga tccctgaggt gtctcacaag tgccgtgcag tccgccccc     1860
acttgcttct ctttgtgtgt agtgtacgta cattatcgag accgttgttc cgcccacct     1920
cgatccgggt cgacctgagg tgtctcacaa gtgccgtgca gtcccgcccc cacttgcttc     1980
tctttgtgtg tagtgtacgt acattatcga gaccgttgtt cccgcccacc tcgatccggg     2040
agctcctgag gtgtctcaca agtgccgtgc agtcccgccc ccacttgctt ctctttgtgt     2100
gtagtgtacg tacattatcg agaccgttgt tcccgcccac ctcgatccgg tctagactga     2160
ggtgtctcac aagtgccgtg cagtcccgcc cccacttgct tctctttgtg tgtagtgtac     2220
gtacattatc gagaccgttg ttcccgccca cctcgatccg ggatccctg aggtgtctca     2280
caagtgccgt gcagtcccgc ccccacttgc ttctctttgt gtgtagtgta cgtacattat     2340
cgagaccgtt gttcccgccc acctcgatcc gggtcgacct gaggtgtctc acaagtgccg     2400
tgcagtcccg cccccacttg cttctctttg tgtgtagtgt acgtacatta tcgagaccgt     2460
tgttcccgcc cacctcgatc cgggcatgcc tgcagaagct tagagaccgg gttggcggcg     2520
tatttgtgtc ccaaaaaaca gccccaattg ccccaattga ccccaaattg acccagtagc     2580
gggcccaacc ccggcgagag cccccttcac cccacatatc aaacctcccc cggttcccac     2640
acttgccgtt aagggcgtag ggtactgcag tctggaatct acgcttgttc agactttgta     2700
ctagtttctt tgtctggcca tccgggtaac ccatgccgga cgcaaaatag actactgaaa     2760
attttttgc tttgtggttg ggactttagc caagggtata aaagaccacc gtccccgaat     2820
tacctttcct cttcttttct ctctctcctt gtcaactcac acccgaaatc gttaagcatt     2880
tccttctgag tataagaatc attcaaaggc gcgccatggc taaggagtat ttccctcaga     2940
ttcagaagat caagttcgac ggcaaggaca gcaaaaaccc cctggctttc cattattacg     3000
acgccgagaa ggaagtgatg ggcaagaaga tgaaggactg gctgcggttc gcaatggcat     3060
ggtggcacac cctgtgcgca gagggagcag atcagttcgg aggaggcacc aagtcttttc     3120
catggaacga gggcacagac gccatcgaga tcgccaagca gaaggtggat gccggcttcg     3180
agatcatgca gaagctgggc atcccctact attgttttca cgacgtggat ctggtgtccg     3240
```

```
agggcaactc tatcggcgag tacgagtcca atctgaaggc cgtggtggcc tatctgaagg    3300
acaagcagaa ggagaccggc atcaagctgc tgtggagctc cgccaacgtg ttcggccaca    3360
agaggtacat gaacggcgcc tctaccaatc ccgactttga tgtggtggcc cgcgccatcg    3420
tgcagatcaa gaacgccatc gatacaggca tcgagctggg cgccgagaat tacgtgtttt    3480
ggggcggccg ggagggctat atgtctctgc tgaatacaga ccagaagaga gagaaggagc    3540
acatggccac catgctgaca atggccaggg attacgcccg cagcaagggc ttcaagggca    3600
cctttctgat cgagcccaag cctatggagc ctacaaagca ccagtatgac gtggataccg    3660
agacagccat cggcttcctg aaggcccaca atctggacaa ggacttcaag gtgaacatcg    3720
aagtgaatca cgccaccctg gccggccaca cattcgagca cgagctggca tgcgcagtgg    3780
acgcaggaat gctgggaagc atcgacgcca acaggggcga ttaccagaat ggctgggaca    3840
ccgatcagtt tcctatcgat cagtatgagc tggtgcaggc atggatggag atcatcaggg    3900
gaggaggatt cgtgaccgga ggaacaaact ttgacgccaa gacccggaga aatagcacag    3960
acctggagga tatcatcatc gcccacgtgt ccggaatgga tgcaatggca cgggccctgg    4020
agaacgcaga aaagctgctg caggagtccc catacaccaa gatgaagaag agagatatg    4080 cctctttcga cagcggcatc ggcaaggact ttgaggatgg caagctgaca ctggagcagg    4140
tgtacgagta tggcaagaag aatggcgagc taagcagac ctcagggaag caggagctgt    4200
acgaagccat catcgcaatg tatcagtgaa tgcatacca gttaattaag gcacgtgcct    4260
aaaaaggatc gataccgtcg acctcgagtc atgtaattag ttatgtcacg cttacattca    4320
cgccctcccc ccacatccgc tctaaccgaa aaggaaggag ttagacaacc tgaagtctag    4380
gtccctattt atttttttat agttatgtta gtattaagaa cgttatttat atttcaaatt    4440 tttcttttt ttctgtacag acgcgtgtac gcatgtaaca ttatactgaa accttgcttt    4500
gagaaggttt tgggacgctc ggctaacttg tttaaacaac tgcaggcatg caagcttggc    4560
gtaatcatgg tcatagctgt ttcctgtgtg aaattgttat ccgctcacaa ttccacacaa    4620
catacgagcc ggaagcataa agtgtaaagc ctggggtgcc taatgagtga gctaactcac    4680
attaattgcg ttgcgctcac tgcccgcttt ccagtcggga aacctgtcgt gccagctgca    4740
ttaatgaatc ggccaacgcg cggggagagg cggtttgcgt attgggcgct cttccgcttc    4800
ctcgctcact gactcgctgc gctcggtcgt tcggctgcgg cgagcggtat cagctcactc    4860
aaaggcggta atacggttat ccacagaatc aggggataac gcaggaaaga acatgtgagc    4920
aaaaggccag caaaaggcca ggaaccgtaa aaaggccgcg ttgctggcgt ttttccatag    4980
gctccgcccc cctgacgagc atcacaaaaa tcgacgctca agtcagaggt ggcgaaaccc    5040
gacaggacta taaagatacc aggcgtttcc ccctggaagc tccctcgtgc gctctcctgt    5100
tccgaccctg ccgcttaccg gatacctgtc cgcctttctc ccttcgggaa gcgtggcgct    5160
ttctcaatgc tcacgctgta ggtatctcag ttcggtgtag tcgttcgct ccaagctggg    5220 ctgtgtgcac gaaccccccg ttcagcccga ccgctgcgcc ttatccggta actatcgtct    5280
tgagtccaac ccggtaagac acgacttatc gccactggca gcagccactg gtaacaggat    5340
tagcagagcg aggtatgtag gcggtgctac agagttcttg aagtggtggc ctaactacgg    5400
ctacactaga aggacagtat ttggtatctg cgctctgctg aagccagtta ccttcggaaa    5460
aagagttggt agctcttgat ccggcaaaca aaccaccgct ggtagcggtg ttttttttgt    5520
ttgcaagcag cagattacgc gcagaaaaaa aggatctcaa gaagatcctt tgatcttttc    5580
```

```
tacggggtct gacgctcagt ggaacgaaaa ctcacgttaa gggattttgg tcatgagatt      5640
atcaaaaagg atcttcacct agatccttt aaattaaaaa tgaagtttta aatcaatcta      5700
aagtatatat gagtaaactt ggtctgacag ttaccaatgc ttaatcagtg aggcacctat      5760
ctcagcgatc tgtctatttc gttcatccat agttgcctga ctccccgtcg tgtagataac      5820
tacgatacgg gagggcttac catctggccc cagtgctgca atgataccgc gagacccacg      5880
ctcaccggct ccagatttat cagcaataaa ccagccagcc ggaagggccg agcgcagaag      5940
tggtcctgca actttatccg cctccatcca gtctattaat tgttgccggg aagctagagt      6000
aagtagttcg ccagttaata gtttgcgcaa cgttgttgcc attgctacag gcatcgtggt      6060
gtcacgctcg tcgtttggta tggcttcatt cagctccggt tcccaacgat caaggcgagt      6120
tacatgatcc cccatgttgt gcaaaaaagc ggttagctcc ttcggtcctc cgatcgttgt      6180
cagaagtaag ttggccgcag tgttatcact catggttatg gcagcactgc ataattctct      6240
tactgtcatg ccatccgtaa gatgcttttc tgtgactggt gagtactcaa ccaagtcatt      6300
ctgagaatag tgtatgcggc gaccgagttg ctcttgcccg cgtcaatac gggataatac       6360 cgcgccacat agcagaactt taaaagtgct catcattgga aaacgttctt cggggcgaaa      6420
actctcaagg atcttaccgc tgttgagatc cagttcgatg taacccactc gtgcacccaa      6480
ctgatcttca gcatctttta ctttcaccag cgtttctggg tgagcaaaaa caggaaggca      6540
aaatgccgca aaaagggaa taagggcgac acgaaatgt tgaatactca tactcttcct        6600
ttttcaatat tattgaagca tttatcaggg ttattgtctc atgagcggat acatatttga      6660
atgtatttag aaaaataaac aaatagggg tccgcgcaca tttccccgaa aagtgccacc       6720
tgacgtctaa gaaaccatta ttatcatgac attaacctat aaaaataggc gtatcacgag      6780
gcccagatcc tctagagtcg aagcggccgc tatgtctgat aaaaggatgt aacataggca     6840
agctgctcgt gagtgttgag tacgaacctt agatccaaat caccgcacc cacggatata      6900 cttgcttgaa tatacagtag tatgcggccg cttcgacacc atatcatata aaactaacaa      6960
tgcattgctt attacgaaga ctacccgttg ctatctccac accgttatct ccacggtcca      7020
aaggctgctc aatgtgctgc atacgtaacg tggggtgcaa ccttgagcac atagtacttt      7080
tccgaaaacc ggcgataatt aagtgtgcac tccaactttt cacactgagc gtaaatgtg       7140 gagaagaaat cggcactaaa aagtcaggta gactggaaaa tgcgccatga atgaatatc       7200 tcttgctaca gtaatgccca gcatcgaggg gtattgtgtc accaacacta tagtggcagc      7260
tgaagcgctc gtgattgtag tatgagtctt tattggtgat gggaagagtt cactcaatat      7320
tctcgttact gccaaaacac cacggtaatc ggccagacac catggatgta gatcaccaag      7380
cctgtgaatg ttattcgagc taaaatgcac atggttggtg aaaggagtag ttgctgtcga      7440
attccgtcgt cgcctgagtc atcatttatt taccagttgg ccacaaaccc ttgacgatct      7500
cgtatgtccc ctccgacata ctccggccg gctggggtac gttcgatagc gctatcggca      7560
tcgacaaggt ttgggtccct agccgatacc gcactacctg agtcacaatc ttcggaggtt      7620
tagtcttcca catagcacgg gcaaaagtgc gtatatatac aagagcgttt gccagccaca      7680
gattttcact ccacacacca catcacacat acaaccacac atatccacaa tggaacccga     7740
aactaagaag accaagactg actccaagaa gattgttctt ctcggcggcg acttctgtgg      7800
ccccgaggtg attgccgagg ccgtcaaggt gctcaagtct gttgctgagg cctccggcac      7860
cgagtttgtg tttgaggacc gactcattgg aggagctgcc attgagaagg agggcgagcc      7920
catcaccgac gctactctcg acatctgccg aaaggctgac tctattatgc tcggtgctgt      7980
```

-continued

```
cggaggcgct gccaacaccg tatggaccac tcccgacgga cgaaccgacg tgcgacccga    8040
gcagggtctc ctcaagctgc gaaaggacct gaacctgtac gccaacctgc gaccctgcca    8100
gctgctgtcg cccaagctcg ccgatctctc ccccatccga aacgttgagg gcaccgactt    8160
catcattgtc cgagagctcg tcggaggtat ctactttgga gagcgaaagg aggatgacgg    8220
atctggcgtc gcttccgaca ccgagaccta ctccgttcct gaggttgagc gaattgcccg    8280
aatggccgcc ttcctggccc ttcagcacaa ccccctctt cccgtgtggt ctcttgacaa    8340
ggccaacgtg ctggcctcct ctcgactttg gcgaaagact gtcactcgag tcctcaagga    8400
cgaattcccc cagctcgagc tcaaccacca gctgatcgac tcggccgcca tgatcctcat    8460
caagcagccc tccaagatga atggtatcat catcaccacc aacatgtttg gcgatatcat    8520
ctccgacgag gcctccgtca tccccggttc tctgggtctg ctgccctccg cctctctggc    8580
ttctctgccc gacaccaacg aggcgttcgg tctgtacgag ccctgtcacg atctgccccc    8640
cgatctcggc aagcagaagg tcaacccat tgccaccatt ctgtctgccg ccatgatgct    8700
caagttctct cttaacatga agcccgccgg tgacgctgtt gaggctgccg tcaaggagtc    8760
cgtcgaggct ggtatcacta ccgccgatat cggaggctct cctccacct ccgaggtcgg    8820 agacttgttg ccaacaaggt caaggagctg ctcaagaagg agtaagtcgt ttctacgacg    8880
cattgatgga aggagcaaac tgacgcgcct gcggttggt ctaccggcag ggtccgctag    8940
tgtataagac tctataaaaa gggccctgcc ctgctaatga aatgatgatt tataatttac    9000
cggtgtagca accttgacta aagaagcag attgggtgtg tttgtagtgg aggacagtgg    9060
tacgttttgg aaacagtctt cttgaaagtg tcttgtctac agtatattca ctcataacct    9120
caatagccaa gggtgtagtc ggtttattaa aggaagggag ttgtggctga tgtggataga    9180
tatctttaag ctggcgactg cacccaacga gtgtggtggt agcttgttac tgtatattcg    9240
gtaagatata ttttgtgggg ttttagtggt gtttggtagg ttagtgcttg gtatatgagt    9300
tgtaggcatg acaatttgga aagggtgga ctttgggaat attgtgggat ttcaatacct    9360
tagtttgtac agggtaattg ttacaaatga tacaaagaac tgtatttctt ttcatttgtt    9420
ttaattggtt gtatatcaag tccgttagac gagctcagtg ccatggcttt tggcactgta    9480
tttcattttt agaggtacac tacattcagt gaggtatggt aaggttgagg cataatgaa    9540 ggcaccttgt actgacagtc acagacctct caccgagaat tttatgagat atactcgggt    9600 tcatttagg ctccgattcg attcaaatta ttactgtcga aatcggttga gcatccgttg    9660
atttccgaac agatctggcc ctttcgtc                                       9688
```

<210> SEQ ID NO 4
<211> LENGTH: 9394
<212> TYPE: DNA
<213> ORGANISM: Artificial Sequence
<220> FEATURE:
<223> OTHER INFORMATION: pMCS-UAS1B12-TEF-XK-CYCt

<400> SEQUENCE: 4

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
```

-continued

```
tacgccagct ggcgaaaggg ggatgtgctg caaggcgatt aagttgggta acgccagggt    360
tttcccagtc acgacgttgt aaaacgacgg ccagtgaatt cgagctcggt acccgctttt    420
cgtagataat ggaatacaaa tggatatcca gagtatacac atggatagta tacactgaca    480
cgacaattct gtatctcttt atgttaacta ctgtgaggcg ttaaatagag cttgatatat    540
aaaatgttac atttcacagt ctgaacttt gcagattacc taatttggta agatattaat     600
tatgaactga agttgatgg catccctaaa tttgatgaaa gggcgcggga tccgcccgg     660 gaattcgaag gtaccaagga agcatgcggt acccgaattc ctgaggtgtc tcacaagtgc    720
cgtgcagtcc cgccccact tgcttctctt tgtgtgtagt gtacgtacat tatcgagacc     780
gttgttcccg cccacctcga tccggtctag actgaggtgt ctcacaagtg ccgtgcagtc    840
ccgcccccac ttgcttctct ttgtgtgtag tgtacgtaca ttatcgagac cgttgttccc    900
gcccacctcg atccggggat ccctgaggtg tctcacaagt gccgtgcagt cccgccccca    960
cttgcttctc tttgtgtgta gtgtacgtac attatcgaga ccgttgttcc cgcccacctc   1020
gatccgggtc gacctgaggt gtctcacaag tgccgtgcag tcccgccccc acttgcttct   1080
ctttgtgtgt agtgtacgta cattatcgag accgttgttc cgcccacct cgatccggga   1140 gctcctgagg tgtctcacaa gtgccgtgca gtcccgcccc cacttgcttc tctttgtgtg   1200
tagtgtacgt acattatcga ccgttgttt cccgcccacc tcgatccggt ctagactgag    1260
gtgtctcaca agtgccgtgc agtcccgccc ccacttgctt ctctttgtgt gtagtgtacg   1320
tacattatcg agaccgttgt tcccgcccac ctcgatccgg ggatccctga ggtgtctcac   1380
aagtgccgtg cagtcccgcc ccacttgct tctctttgtg tgtagtgtac gtacattatc    1440
gagaccgttg ttcccgccca cctcgatccg ggtcgacctg aggtgtctca caagtgccgt   1500
gcagtcccgc ccccacttgc ttctctttgt gtgtagtgta cgtacattat cgagaccgtt   1560
gttcccgccc acctcgatcc gggcatgcgg tacccgaatt cctgaggtgt ctcacaagtg   1620
ccgtgcagtc ccgccccac ttgcttctct tgtgtgtag tgtacgtaca ttatcgagac    1680
cgttgttccc gcccacctcg atccggtcta gactgaggtg tctcacaagt gccgtgcagt   1740 cccgcccca cttgcttctc tttgtgtgta gtgtacgtac attatcgaga ccgttgttcc    1800
cgcccacctc gatccgggga tccctgaggt gtctcacaag tgccgtgcag tcccgccccc   1860
acttgcttct ctttgtgtgt agtgtacgta cattatcgag accgttgttc ccgcccacct   1920
cgatccgggt cgacctgagg tgtctcacaa gtgccgtgca gtcccgcccc cacttgcttc   1980
tctttgtgtg tagtgtacgt acattatcga ccgttgttt cccgcccacc tcgatccggg   2040
agctcctgag gtgtctcaca agtgccgtgc agtcccgccc ccacttgctt ctctttgtgt   2100
gtagtgtacg tacattatcg agaccgttgt cccgcccac ctcgatccgg tctagactga    2160
ggtgtctcac aagtgccgtg cagtcccgcc ccacttgct tctctttgtg tgtagtgtac    2220
gtacattatc gagaccgttg ttcccgccca cctcgatccg gggatccctg aggtgtctca   2280
caagtgccgt gcagtcccgc ccccacttgc ttctctttgt gtgtagtgta cgtacattat   2340
cgagaccgtt gttcccgccc acctcgatcc gggtcgacct gaggtgtctc acaagtgccg   2400
tgcagtcccg ccccacttg cttctctttg tgtgtagtgt acgtacatta tcgagaccgt    2460
tgttcccgcc cacctcgatc cgggcatgcc tgcagaagct tagagaccgg gttggcggcg   2520
tatttgtgtc caaaaaaca gccccaattg ccccaattga ccccaaattg acccagtagc    2580
gggcccaacc ccgcgagag ccccccttcac cccacatatc aaacctcccc cggttcccac    2640
acttgccgtt aagggcgtag ggtactgcag tctggaatct acgcttgttc agactttgta    2700
```

```
ctagtttctt tgtctggcca tccgggtaac ccatgccgga cgcaaaatag actactgaaa    2760
atttttttgc tttgtggttg ggactttagc caagggtata aaagaccacc gtccccgaat    2820 taccttttcct cttcttttct ctctctcctt gtcaactcac acccgaaatc gttaagcatt    2880
tccttctgag tataagaatc attcaaaggc gcgccatgtc caatttactg accgtacacc    2940
aaaatttgcc tgcattaccg gtcgatgcaa cgagtgatga ggttcgcaag aacctgatgg    3000
acatgttcag ggatcgccag gcgttttctg agcatacctg aaaatgctt ctgtccgttt    3060 gccggtcgtg ggcggcatgg tgcaagttga ataaccggaa atggtttccc gcagaacctg    3120
aagatgttcg cgattatctt ctatatcttc aggcgcgcgg tctggcagta aaaactatcc    3180
agcaacattt gggccagcta acatgcttc atcgtcggtc cgggctgcca cgaccaagtg    3240
acagcaatgc tgtttcactg gttatgcggc ggatccgaaa agaaaacgtt gatgccggtg    3300
aacgtgcaaa acaggctcta gcgttcgaac gcactgattt cgaccaggtt cgttcactca    3360
tggaaaatag cgatcgctgc caggatatac gtaatctggc atttctgggg attgcttata    3420
acaccctgtt acgtatagcc gaaattgcca ggatcagggt taaagatatc tcacgtactg    3480
acggtgggag aatgttaatc catattggca gaacgaaaac gctggttagc accgcaggtg    3540
tagagaaggc acttagcctg ggggtaacta aactggtcga gcgatggatt tccgtctctg    3600
gtgtagctga tgatccgaat aactaccgt tttgccgggt cagaaaaaat ggtgttgccg    3660
cgccatctgc caccagccag ctatcaactc gcgccctgga agggattttt gaagcaactc    3720
atcgattgat ttacgcgct aaggatgact ctggtcagag atacctggcc tggtctggac    3780
acagtgcccg tgtcggagcc gcgcgagata tggcccgcgc tggagtttca ataccggaga    3840
tcatgcaagc tggtggctgg accaatgtaa atattgtcat gaactatatc cgtaccctgg    3900
atagtgaaac aggggcaatg gtgcgcctgc tggaagatgg cgattagtta attaaggcac    3960
gtgcctaaaa aggatcgata ccgtcgacct cgagtcatgt aattagttat gtcacgctta    4020
cattcacgcc ctccccccac atccgctcta accgaaaagg aaggagttag acaacctgaa    4080
gtctaggtcc ctatttattt ttttatagtt atgttagtat taagaacgtt atttatattt    4140 caaattttc ttttttttct gtacagacgc gtgtacgcat gtaacattat actgaaaacc    4200
ttgcttgaga aggttttggg acgctcggct aacttgttta acaactgca ggcatgcaag    4260 cttggcgtaa tcatggtcat agctgttcc tgtgtgaaat tgttatccgc tcacaattcc    4320
acacaacata cgagccggaa gcataaagtg taaagcctgg ggtgcctaat gagtgagcta    4380
actcacatta attgcgttgc gctcactgcc cgctttccag tcgggaaacc tgtcgtgcca    4440
gctgcattaa tgaatcggcc aacgcgcggg gagaggcggt ttgcgtattg ggcgctcttc    4500
cgcttcctcg ctcactgact cgctgcgctc ggtcgttcgg ctgcggcgag cggtatcagc    4560
tcactcaaag gcggtaatac ggttatccac agaatcaggg gataacgcag aaagaacat    4620 gtgagcaaaa ggccagcaaa aggccaggaa ccgtaaaaag gccgcgttgc tggcgttttt    4680
ccataggctc cgcccccctg acgagcatca aaaaatcga cgctcaagtc agaggtggcg    4740
aaacccgaca ggactataaa gataccaggc gtttccccct ggaagctccc tcgtgcgctc    4800
tcctgttccg accctgccgc ttaccggata cctgtccgcc tttctccctt cgggaagcgt    4860
ggcgctttct caatgctcac gctgtaggta tctcagttcg gtgtaggtcg ttcgctccaa    4920
gctgggctgt gtgcacgaac cccccgttca gcccgaccgc tgcgccttat ccggtaacta    4980
tcgtcttgag tccaacccgg taagacacga cttatcgcca ctggcagcag ccactggtaa    5040
```

```
caggattagc agagcgaggt atgtaggcgg tgctacagag ttcttgaagt ggtggcctaa      5100
ctacggctac actagaagga cagtatttgg tatctgcgct ctgctgaagc cagttacctt      5160
cggaaaaaga gttggtagct cttgatccgg caaacaaacc accgctggta gcggtggttt      5220
ttttgtttgc aagcagcaga ttacgcgcag aaaaaaagga tctcaagaag atcctttgat      5280
cttttctacg gggtctgacg ctcagtggaa cgaaaactca cgttaaggga ttttggtcat      5340
gagattatca aaaggatctt caccctagat ccttttaaat taaaaatgaa gttttaaatc      5400
aatctaaagt atatatgagt aaacttggtc tgacagttac caatgcttaa tcagtgaggc      5460
acctatctca gcgatctgtc tatttcgttc atccatagtt gcctgactcc ccgtcgtgta      5520
gataactacg atacgggagg gcttaccatc tggccccagt gctgcaatga taccgcgaga      5580
cccacgctca ccggctccag atttatcagc aataaaccag ccagccggaa gggccgagcg      5640
cagaagtggt cctgcaactt tatccgcctc catccagtct attaattgtt gccgggaagc      5700
tagagtaagt agttcgccag ttaatagttt gcgcaacgtt gttgccattg ctacaggcat      5760
cgtggtgtca cgctcgtcgt ttggtatggc ttcattcagc tccggttccc aacgatcaag      5820
gcgagttaca tgatccccca tgttgtgcaa aaaagcggtt agctccttcg gtcctccgat      5880
cgttgtcaga agtaagttgg ccgcagtgtt atcactcatg gttatggcag cactgcataa      5940
ttctcttact gtcatgccat ccgtaagatg cttttctgtg actggtgagt actcaaccaa      6000
gtcattctga gaatagtgta tgcggcgacc gagttgctct tgcccggcgt caatacggga      6060
taataccgcg ccacatagca gaactttaaa agtgctcatc attggaaaac gttcttcggg      6120
gcgaaaactc tcaaggatct taccgctgtt gagatccagt tcgatgtaac ccactcgtgc      6180
acccaactga tcttcagcat cttttacttt caccagcgtt tctgggtgag caaaaacagg      6240
aaggcaaaat gccgcaaaaa agggaataag ggcgacacgg aaatgttgaa tactcatact      6300 cttcctttt caatattatt gaagcattta tcagggttat tgtctcatga gcggatacat      6360
atttgaatgt atttagaaaa ataaacaaat aggggttccg cgcacatttc cccgaaaagt      6420
gccacctgac gtctaagaaa ccattattat catgacatta acctataaaa ataggcgtat      6480
cacgaggccc agatcctcta gagtcgaagc ggccgctatg tctgataaaa ggatgtaaca      6540
taggcaagct gctcgtgagt gttgagtacg aaccttagat ccaaatcacc cgcacccacg      6600
gatatacttg cttgaatata cagtagtatg cggccgcttc gacaccatat catataaaac      6660
taacaatgca ttgcttatta cgaagactac ccgttgctat ctccacaccg ttatctccac      6720
ggtccaaagg ctgctcaatg tgctgcatac gtaacgtggg gtgcaacctt gagcacatag      6780
tacttttccg aaaaccggcg ataattaagt gtgcactcca acttttcaca ctgagcgtaa      6840
aatgtggaga agaaatcggc actaaaaagt caggtagact ggaaaatgcg ccatgaaatg      6900
aatatctctt gctacagtaa tgcccagcat cgaggggtat tgtgtcacca acactatagt      6960
ggcagctgaa gcgctcgtga ttgtagtatg agtctttatt ggtgatggga agagttcact      7020
caatattctc gttactgcca aaacaccacg gtaatcggcc agacaccatg gatgtagatc      7080
accaagcctg tgaatgttat tcgagctaaa atgcacatgg ttggtgaaag gagtagttgc      7140
tgtcgaattc cgtcgtcgcc tgagtcatca tttatttacc agttggccac aaacccttga      7200
cgatctcgta tgtcccctcc gacatactcc cggccggctg gggtacgttc gatagcgcta      7260
tcggcatcga caaggtttgg gtccctagcc gataccgcac tacctgagtc acaatcttcg      7320
gaggtttagt cttccacata gcacgggcaa aagtgcgtat atatacaaga gcgtttgcca      7380
gccacagatt ttcactccac acaccacatc acacatacaa ccacacacat ccacaatgga      7440
```

-continued

```
acccgaaact aagaagacca agactgactc caagaagatt gttcttctcg gcggcgactt       7500
ctgtggcccc gaggtgattg ccgaggccgt caaggtgctc aagtctgttg ctgaggcctc       7560
cggcaccgag tttgtgtttg aggaccgact cattggagga gctgccattg agaaggaggg       7620
cgagcccatc accgacgcta ctctcgacat ctgccgaaag gctgactcta ttatgctcgg       7680
tgctgtcgga ggcgctgcca acaccgtatg gaccactccc gacggacgaa ccgacgtgcg       7740
acccgagcag ggtctcctca agctgcgaaa ggacctgaac ctgtacgcca acctgcgacc       7800
ctgccagctg ctgtcgccca agctcgccga tctctccccc atccgaaacg ttgagggcac       7860
cgacttcatc attgtccgag agctcgtcgg aggtatctac tttggagagc gaaaggagga       7920
tgacggatct ggcgtcgctt ccgacaccga gacctactcc gttcctgagg ttgagcgaat       7980
tgcccgaatg gccgccttcc tggcccttca gcacaacccc cctcttcccg tgtggtctct       8040
tgacaaggcc aacgtgctgg cctcctctcg actttggcga aagactgtca ctcgagtcct       8100
caaggacgaa ttcccccagc tcgagctcaa ccaccagctg atcgactcgg ccgccatgat       8160
cctcatcaag cagccctcca agatgaatgg tatcatcatc accaccaaca tgtttggcga       8220
tatcatctcc gacgaggcct ccgtcatccc cggttctctg ggtctgctgc cctccgcctc       8280
tctggcttct ctgcccgaca ccaacgaggc gttcggtctg tacgagccct gtcacggatc       8340
tgcccccgat ctcggcaagc agaaggtcaa ccccattgcc accattctgt ctgccgccat       8400
gatgctcaag ttctctctta acatgaagcc cgccggtgac gctgttgagg ctgccgtcaa       8460
ggagtccgtc gaggctggta tcactaccgc cgatatcgga ggctcttcct ccacctccga       8520
ggtcggagac ttgttgccaa caaggtcaag gagctgctca agaaggagta agtcgtttct       8580
acgacgcatt gatggaagga gcaaactgac gcgcctgcgg gttggtctac cggcagggtc       8640
cgctagtgta taagactcta taaaagggc cctgccctgc taatgaaatg atgatttata       8700
atttaccggt gtagcaacct tgactagaag aagcagattg ggtgtgtttg tagtggagga       8760
cagtggtacg ttttggaaac agtcttcttg aaagtgtctt gtctacagta tattcactca       8820
taacctcaat agccaagggt gtagtcggtt tattaaagga agggagttgt ggctgatgtg       8880
gatagatatc tttaagctgg cgactgcacc caacgagtgt ggtggtagct tgttactgta       8940
tattcggtaa gatatatttt gtggggtttt agtggtgttt ggtaggttag tgcttggtat       9000
atgagttgta ggcatgacaa tttggaaagg ggtggacttt gggaatattg tgggatttca       9060
ataccttagt ttgtacaggg taattgttac aaatgataca agaactgta tttctttca       9120 tttgttttaa ttggttgtat atcaagtccg ttagacgagc tcagtgccat ggcttttggc       9180
actgtatttc atttttagag gtacactaca ttcagtgagg tatggtaagg ttagggcat       9240 aatgaaggca ccttgtactg acagtcacag acctctcacc gagaattta tgagatatac       9300 tcgggttcat tttaggctcc gattcgattc aaattattac tgtcgaaatc ggttgagcat       9360
ccgttgattt ccgaacagat ctggcccttt cgtc                                  9394
```

<210> SEQ ID NO 5
<211> LENGTH: 1386
<212> TYPE: DNA
<213> ORGANISM: Artificial Sequence
<220> FEATURE:
<223> OTHER INFORMATION: YALI0_A00891g

<400> SEQUENCE: 5

```
atggggggga aaacggggga aatcaaggta tcgggcggg gaaagggcg aatttggtta         60
```

```
tttgggtca aggaaaaacg ctggcgggct cgtattcccg ataaaaccgc tccgggactc      120
gcttttcagg tagcccgcac cggcgaaaaa gccagggatt gggtgaaaac attaaggttc      180
ggccctcaaa gttcacagtg gtcagcgcag tgtaaacacg tcgacccaca cacaccactc      240
cgccataacc acatctctcg agctcgctgt agacacaaga gcttccgtca cccgcatcca      300
tctcacagac acagacacac acccacacat tcacgcatca ccagacccac aagaaccgcc      360
acaatggaag attcagacgt gctgatgaga gatatcaacg acgacggact caagcccatg      420
gacgccatgg gagccggggg cgaagggacg ttcacagaac tgacacccac aacccgcggc      480
cagctggacg cctggatcgc acgactgacc gaatgccagc ctctcagcga agacgacgtc      540
aacgagctgt gcaacatggc caagggggtg ttgcagaagg aggaaaacgt gcagcccgtg      600
cacgcgccgg tgaccatctg tggagacgtg cacggccagt tccacgacct gatggagctg      660
ttcaaaatcg gcgggccgtg tccagacaca aactacctgt ttatgggaga ctacgtggac      720
cgaggctact actcggtcga aacggtgtcc tatctggtgg ccatgaaggt gcgatacccc      780
aaccgactga ccattctgcg aggaaaccac gagtcgcgac aaatcaccca ggtctacggc      840
ttctacgacg agtgtctgcg aaagtacgga aacgccaacg tgtggcgagc cttcacgtcg      900
ctgttcgact acttccccgt caccgccctg gtggagaacc aaatcttctg tctgcacgga      960
ggcctgtctc ccatgatcga gtccatcgac aacatccgag aactcaaccg attccaggag     1020
gtgccccacg acggccccat gtgcgacctg ctgtggtccg accccgatga ccgaggagga     1080
tggggaatga gccccgagg agccggcttc accttcggtg ccgacatttc gaacagttt      1140 aaccacacaa acaacctgag tctcatttca agagcacacc agctggtcat ggaaggcttc     1200
agctgggcac acgagcagca ggtggtcacc atcttctccg cccccaacta ctgctaccga     1260
tgcggaaacc aggccgccat catggaggtg gacgaaaacc tctcaaactc ctttttgcag     1320
tacgatcctt gtccccgtcc cggagagccc tccgtgtctc gacgaacccc cgactacttc     1380
ttgtag                                                                1386

<210> SEQ ID NO 6
<211> LENGTH: 325
<212> TYPE: DNA
<213> ORGANISM: Artificial Sequence
<220> FEATURE:
<223> OTHER INFORMATION: YALI0_A00935g

<400> SEQUENCE: 6
atgaaaataa tcaacatgtt gtctttgggg ggcaacactc tgaccggcaa cactctgacc       60
ggcaacactc tgaccggcaa caccctgact ggcaatactt cgaccgcctc tcacttttca      120
tcattaatcc tcgcccattt cctcaacaac attccttctt cgaactctgc tcatcttcga      180
actctgctca tcttcgggct ctgctcatct tcctgctact ctcttccagt tcccctggca      240
tacctccaac atccatcacc aagaccaata catacatgtt tcgtctcgat gcgatcaata      300
ttctcttttg gaatgcagag ggtga                                            325

<210> SEQ ID NO 7
<211> LENGTH: 1344
<212> TYPE: DNA
<213> ORGANISM: Artificial Sequence
<220> FEATURE:
<223> OTHER INFORMATION: YALI0_A02002g

<400> SEQUENCE: 7
atgaaaccag tcgcacttct cacatcctgt gtggctacat tgccgtgct taatggagcc       60
```

| | | | |
|---|---|---|---|
| attgcggccc | cttcagcccc | caaagtgctc | cagatccccg tcacaaagca ccacgagtct | 120 |
| gctgctgagg | tcaaccggac | cctcgctcta | gctcgtcgag acggagcgta caccgaaacg | 180 |
| gtccacaaca | aggagttctg | gtactccatc | tccatctcgc taggaacacc ggcccaacag | 240 |
| ttcaacgtgt | tgctggacac | gggctcgtca | gacctgtggg tgttcagcac ggaagactcg | 300 |
| accgactgcg | ctaacggagc | ctgcgaattc | acaggccagt tcaacgcaaa gtcgtcttct | 360 |
| acctaccact | acctcaacag | cgactacagc | atcacgtacg tgacggggtc ggctcatgga | 420 |
| gactgggtca | cggactcgct | ttcggtcggc | cccgtgactc tcagcaactt tcagtttgcc | 480 |
| gtggccgaca | aggcggtggg | caatactgcc | atcttcggta tctctctgga gggatccgag | 540 |
| tctctgaacc | atggacaaca | gcccgagtat | cccaactttc ccgtccagct caagaaccag | 600 |
| ggcttcatcg | acagaatagt | ctactctctt | tacctggaag atgtcaattc gccccagggc | 660 |
| actcttctac | tcggaggaat | cgactacgcc | aagttccagg tcctctcaa tgtgcttcag | 720 |
| cttcagaacg | ccaacgcttt | ccaggtcgag | taccaggga tcggaatcaa cggagctggg | 780 |
| ccctacggac | agcctcacgt | ggcggttttg | gactcgggaa cttcatacac gtttctgccc | 840 |
| gatgacatct | actacaccat | cttcgaccag | gtcggactat caagtcaagt gaaccagaac | 900 |
| accggtctca | actacgtcgc | atgtaacaca | cgcgttactc tggcgtttga tttcggaaat | 960 |
| ggagccatca | tcaatgtcga | ctctagcgag | ctggttctca agctgagcga cattcttggt | 1020 |
| gatccccaca | acaaccagtg | cgtctttgga | gtctcatcca atgacaacac ccacggtatc | 1080 |
| acccttttgg | gagacacctt | tctgcgatct | gcatatgtgg tttacgacat tgaaaacaag | 1140 |
| gaggttggta | ttgctcaggc | agtgtatacc | agcaactcca acgttcagcc cgtcacaggt | 1200 |
| gctcttggag | acagggtca | gcagcagagt | caaggtcaag gtcaaggtca aggtcgaggt | 1260 |
| caaggtcagg | gacagcagag | tcaaggccag | ggtcagggac aatatccctg ggatggacaa | 1320 |
| ccttttggat | caggtttctt | ctaa | | 1344 |

<210> SEQ ID NO 8
<211> LENGTH: 925
<212> TYPE: DNA
<213> ORGANISM: Artificial Sequence
<220> FEATURE:
<223> OTHER INFORMATION: YALI0_A02497g

<400> SEQUENCE: 8

| | | | |
|---|---|---|---|
| atgaaccgaa | acgactacga | cgacaaccga | ggcaacagcc gaaacgactc ctacggcaac | 60 |
| cagggccgaa | acgagggccg | aaacgagtcc | tacggaaaca caactccaa ctacggcaac | 120 |
| aactccaact | ccaactccaa | ctctggtttt | ggtggtaaca actccaactc tggattcggc | 180 |
| ggtaactcca | actccaactc | caactacgga | aacaactcca actccaacta cggaaacaac | 240 |
| tccaactcca | actccaacag | ctcctacgga | tccaactcca actccaacca tggtggcaac | 300 |
| gattcctacg | gtaacaactc | caactccaac | tccaactccc actacggaaa caactccaac | 360 |
| tccaactcca | actccaactc | caactacgga | aacaactcca actccaactc caactacgga | 420 |
| aacaactcca | acaactccaa | ctccaactcc | aactccaact ccaactccaa tgtcaacccc | 480 |
| tacgttgcca | agggtatcaa | catggtggag | gaaagttct tggaatgga ccagaagaac | 540 |
| gagactgcca | acgagcgaaa | gtacgaccag | aagattggcg agttcatcac ctccaagatt | 600 |
| ggcggcggca | acagggctc | ctccaactct | gcaaacaact ccaacaactc ttacggaaac | 660 |
| aacaacaact | ccaacaactc | caacaactcg | tcttccggcg gaattggcgt gagtattaca | 720 |

| | |
|---|---|
| acgatagatt gatctgttgc agcactacac aggactgctc caatcatggt taattgacca | 780 |
| caactaacat cagggcttca tttctagcca gctgtctgga aactccaact ccaacaacaa | 840 |
| ctccaacaac tacaacaaca acaacaacaa caacaacaac agtggaggtg acagccttca | 900 |
| ggacaagctt ggcgtgagta tttaa | 925 |

<210> SEQ ID NO 9
<211> LENGTH: 4266
<212> TYPE: DNA
<213> ORGANISM: Artificial Sequence
<220> FEATURE:
<223> OTHER INFORMATION: YALI0_A07997g

<400> SEQUENCE: 9

| | |
|---|---|
| atgcagtact gtactaacgc aggaactaga gcccggtcct cgtccacctc ttcagtgcaa | 60 |
| aaccagccgt caaagctctc tctcggtctc cagcatgtca aggaagaagc tgattcgctt | 120 |
| tcatcctcac gggccacgtc gccaggtacc actcccacaa cgttgcatc ttccagcccc | 180 |
| tctgcatcaa agacggcact ggagccctcc acctcctcac acgacttgtc taacacccgt | 240 |
| tccctggacc cctacgtcaa gacctctgtc ggaagcccca acctgtctcg ttcacgcacc | 300 |
| atttctgcgc ccgagttcaa gtccgagcgt gaaaagctca caaggagca gtcgccaggc | 360 |
| ttcaaaaagt cgtggctcaa ctccttcagc aagtggagat ctggcaaaga cgaaaagact | 420 |
| aaagatggca aggatgcatc ctcgtcgtcg ttaggaaaga gccctacagc cacgccttc | 480 |
| tcgaaaccca gcaaatcaca acccattgca tccaaggagc agcaaacgtc ggcatcgcta | 540 |
| tcaggcaagg ctgccccccac gacacaaacc accacaacga cgattccaga aatcgctcct | 600 |
| cctgtcgctg ctgccacagg agccactacc gtccctcctg catctactcc cacctctgcc | 660 |
| aacctcccga cttcaccccc tcggacagcc tctcctcgta tcaatgttga ggccgttgcc | 720 |
| atcccagaga agcccttccc gcctgtccac gcagcaggcg cctcaccggc ggtggcctcg | 780 |
| tccatcgcct cttctgcatc cacagatgtg ggatcgccca aggggttcct tctcaacact | 840 |
| ctgcggcggt tctccaagtc gcagccctcc acaggaggcg tagcgtcgtg tcccacgtcg | 900 |
| cgtgttttga caagaacag taaccgacgg aattgtgagc tcacgggtct tgagggcgtc | 960 |
| tcttctcgtc gagtgtcgtt tgatatcaac acgtatcatt cggaccctcc tcagcagatc | 1020 |
| cccgccggga gcccaagaa gggtaatgta gaggttggtg ccgatggttt gctccgtaag | 1080 |
| aatggcatgg tgatccaatc acccccctcag caccatgacc agcatcactt caacccattc | 1140 |
| aattcgggtg ttggacagcc cagacggcag gcggcaaaga cggctcctcc tgccacttca | 1200 |
| tccaagaccc cacagacggc agctcctgct caggcggctc aaacgcagac aacaaccct | 1260 |
| caaaagcctg ccactgcctc tccggcagcc aagcagctc cagttgcagt tcccaaacct | 1320 |
| gcagcacccg ctcccgcagc agcagcagca gcagtcccca aagagcccgt tgctcccaaa | 1380 |
| ataagccctc ctactgctgc gacggctgga gctgcttctg ccgcagcagc agcaatcccc | 1440 |
| tccaatggtg gctcctcagt cgcgacttcc acagtctctg ctgtaccttc cactggagct | 1500 |
| gtctccaacg gagtctcgtc ttctgcttcc tccacttcgt ccacgtcatc gacctcttcc | 1560 |
| aacaactcct ccctcacagt ccctaccggc gctcctgttc gagcatcctc tcccaatggc | 1620 |
| aagtctcctc ttggaaaacc gtcccaaccc catctcacag tagacatgca gaaggtcggg | 1680 |
| ggtcgctcac ccgtagggtc gcctcgagaa tcgccttctc cctcgcctac gacctctggt | 1740 |
| ctctcacgat ccaattctgg acgttccaag tttgttatca tgcgaaatgg taaggaggtg | 1800 |
| gagttcacca aggcgtcggt ctacaataag gagaacactc tggctcgttc gggctcactg | 1860 |

```
accaagaaac gatcgccccg aaactcgccc aaaaactctc ctattgctgg ctctcctcgg   1920
tctgcatctc ccctggcagc caaggcgtca cccagcaagc ccccctcacc tactaaggaa   1980
actgccaagg acagtaccaa agacactaaa acgtctcctc ctccgggcga cgacgaggtg   2040
ccctctatct ccaacctcat tatcgacacg cctctcaaga catcccatga aatgtacaac   2100
gagaaggacg agtcggacga ggacaacccg ctggatgtgg acgtagagaa actgtatact   2160
cggtgctgtc atctgcgaga gattctgccg atcccagcta ctctaaaaca gatcaaggcc   2220
caaaaggcgc ctctttccct gcgtctgatg aatcccagac ccacgttgat tgagatccag   2280
tcatttgccg actttgtggc tgtggctccg gtcagtacac ttgttctgga taatgtgacc   2340
ctcactccgg atatgttttc actgttgttt gcggcaatga gtgcttcgca atggctcgaa   2400
aagctgtctc ttcgaaacac tagcattgac gagatgtcat ggaagcgcct gtgctacttg   2460
ttggccatga actccaagct tgttcggctg gacttgtcgc atcagatgaa gcgggacaag   2520
gacaaggagc tcaagcagcg aaccccctccc actgtggatt ggaagctgtt gtgcgatgct   2580
ctacagtacg gcaaaggtat ggaggaactt gtgctcaacg gctgtttagt gccttctgag   2640
gtgtttgagc atctcatgtt gggcgcatgc aaaaatacaa aacgtctcgg actagcattc   2700
aacgatttgg gccccgagga gatgcatttc gttggccaat ggatgactgg cgagtgtgag   2760
ggtctcgata ttggaggtaa ccatctgact tacgtggagg aggaggagga ggtgagacaa   2820
gaaggagccg aaggtacaga aaggggggag caggaggaga aggaggagaa ggaggagaag   2880
gaggaggagg aggagaagga ggagaaggag gagaagaagg ataaggtgcc cgtttccgaa   2940
tcaaccgaac ctaccgctct tgatgttctt ctggattcac tctccgacaa ggagctgaac   3000
ctgcggttcc tttccctgaa ctccacgcac ctcgaggcct ctcccacgac cgaaaagctc   3060
atcactgccc tttccaagct gcagaatctc cggttttttag atctctcttc taactctgga   3120 ctcttttccct cccttacgac tcatctgtgt aaagctctac cgcttttccc agatttgcgc   3180
cgaattcatc tcgattactg cgacttgagc cctcgtgatg tggtgcagat ttcagacgct   3240
ttggcgcaat gtaagtcgct tctgcatgtt tcccttgttg gaaacacgcg catggaccga   3300
acttgtgtgg cagctctgac tgtagccgtt cgggtttcaa agtccatcta ccttcttgac   3360
cttgaacaga gtctcgtacc caagatggag cagcgacgaa tcgtgcatta ctgcatgcgc   3420
aacatggagc ggttggtata cggcaaggca acctctgaaa acgagattga ccatgagatt   3480
gaggtcggag aagacaaccg ggatatcttt gacgtgggta aggacattgc ttctactgtc   3540
gatgatattc tcgagtttaa ccaggagacg tgccaggtta gtgacatgct acttcagcgt   3600
gcctaccacg ttaagactcg ggttcagaag gttatggacg agctgtttgc caagcgaaac   3660
aacggcgagc tgacctacga ggacaaggag ctgcttgttc gttactgttt cctcgatgct   3720
actttgaacg agactcttca gaactttgag aagcagcgaa agcagcccca gacccagggt   3780
cccaccgtcc atcctctgac tcacatgatg ggcctggcag gcaacgaacc tcagatcaag   3840
gctcctgatc tccaggttga gggagtggat gaaggtcgtc ccgctctttc ccgaaactcg   3900
tcgtcggcgt ctatccaggc tcgacgacag gagctcgagg agggagagtt cacaagtgg   3960 ggaacttttg tgatgcaggt tcgagagaac gagcccctt  ttcactctgg ccgaccttct   4020
ggagatgatc tgcgtaaggc gattctcaat gccaccggtg tgggcactgt tccgagttg   4080 attggcgaca ttattcattc tggagtggat gtcgaggagt tactcaacat ttctggtctg   4140
gatcagtacc gaaagacttt ggctgaggag actgaggatg gatctgctgt tcctatggag   4200
```

```
gttaaggccg agcgagatgc cattgacagt ttcttggagg atctggcccg ggtcagaagc    4260
agatga                                                                4266

<210> SEQ ID NO 10
<211> LENGTH: 277
<212> TYPE: DNA
<213> ORGANISM: Artificial Sequence
<220> FEATURE:
<223> OTHER INFORMATION: YALI0_A13849g

<400> SEQUENCE: 10
atgaaactgg aagcacacga cacaccgtca gcaagacatt ttggatactg caggtcgttt     60
gttagattgt cccataatct gctattggtc aagaatgatc aaggagatga gagtgtatac    120
gaggttgtgc gacaagtgcc aatggttcat gaaagggacc acagccaaaa aaaaaaatgt    180
tctcaagcag ctgcctggac ctacgaagat ctggtcggaa atttcgaagg attttgggtc    240
agtcgaggct ccgaaagtca aggaaccgat tccataa                             277

<210> SEQ ID NO 11
<211> LENGTH: 232
<212> TYPE: DNA
<213> ORGANISM: Artificial Sequence
<220> FEATURE:
<223> OTHER INFORMATION: YALI0_A15642g

<400> SEQUENCE: 11
atgtctaggt gtcgcaacga cgtggacgcg attgccacat gggatattgc caaagattcc     60
agtgtgcggc gtgggatgaa ggcgctgttt gaagaaaagc tggacacggg ggtccttgaa    120
gactaccagc tgaagcgaac cagctgagag cgaaccagct ggagcgaacc agttggagcg    180
aaccagttgg agcgaacaca tctggtgggt atgcatacga atgtggatct ga            232

<210> SEQ ID NO 12
<211> LENGTH: 2952
<212> TYPE: DNA
<213> ORGANISM: Artificial Sequence
<220> FEATURE:
<223> OTHER INFORMATION: YALI0_A15796g

<400> SEQUENCE: 12
atgaaactct catctgccgc cttggtggcc ttcgcagctc ctgtgattgc ccagcagacc     60
accaacacgt atgcaactac aactatcact agcatgcaca cggtcacggc tacactgacc    120
tgtgagccct ccgactacgt caccagtacc cgaacccctta ttgagtatga agatgataga    180
tgcatcgtca caactttgt ctactcacac tgcaagttcc tccccccttc taccacctgt    240 cccccccgagt tccagacttg ggtcacaaag accacggaaa cggagtcggg gttttctatt    300
tggaccactg aagtcgtggt gatggagtgc ttatctacac ctgtcagtgt ccccatcaca    360
accaccgatc ctgccaccat tcctgagtcc accgagcctg caacttccac cgagtccacc    420
actagtccag agacttctcc accaatctca gaggagccca gcttcggaga ggagcccact    480
acttcggaga agcccattac ttcggaggag cccactacat cccctgagac ctctaagcag    540
cccacgacct ctgagcagcc caccactaca tcggaggagc ccactacttc ggaggagccc    600
actacatcgg aggagcccac gactacatcg gaggggccca ctacatcgga agagcctact    660
acatcccctg agacctctga gcagcccacg acctctgagc agcccacgac ctctgagcag    720
cccacggcta tcggaggagg cccactacta tcggaagagc ctactacatc ccatgagacg    780
tctgagcagc ccacgacgtc tgagcaacca actacatccc ctgaaacttc tgctcctacc    840
```

```
actaatgagg agccgacatc ttcaagtcct gttacagacc cttgcaccac tgtcaccacc    900
atcgtgacca cacccccagg ggaagaacct acaacctaca caacaactgt tgacacctgt    960
tccagtgatc ctactcctca gccacaaact tccggatcta ccaccacaga tccttgcttg   1020
gagaccacca ctattgtttc tactcccatc accggcgagc ccagcacttt caccatcact   1080
acagacgtgt gctcgtcgtc cgttcccatc acagagtgtg tgacgaccat tgtctcaaat   1140
cctccaggtg aagtgcctac taccctgacg gttacgaccg acgtttgcac tcccgagcca   1200
actacagaga taaccagtgc tccagttacc gagtgcacca ctacagtggt ttctacacct   1260
ccaggtggtg atcctaccac catgaccgtt accactgacg tttgcactcc cgaaccagtg   1320
acctccgagc cagtgacctc cgagccagtg acctccgagc cagtgacctc cgagccagtg   1380
acctccgagc cagtgacctc cgagccagtg acctccgagc cagtgacctc cgaaccagtg   1440
acctccgaac cagtgacctc cgaaccagtg acctccgaac cagtgactcc tacagagtgc   1500
attacaaccg tggtctcgac tcctccaggt gaagagccta ctaccctgac gattacgact   1560
gacatttgca ctaccgagcc ccctactcag acaaccagtg ccccgttac ggagtgcaca    1620 actacagtgg tttctactcc cccaggaggc gaccctacta ccctgacgat taccactgac   1680
gtttgtactc ctgagccagt gacttcggag ccagtgtccc cacagagtg tatcacgacc    1740 gtggtttcaa cccctcccaa tggtgagccc accacactga cggtcacaac agattactgc   1800
cctcctgtga gcactcctgt ggtccctacc gactgtgtca aaccacaac tgtcaccacc    1860 actgatcctg ctggcgagcc ttccactgtg accaccacaa tcgataactg ccctacacct   1920
gaacccgtta ccaccaccga ctgcatcacc actacagttg tgaccaccgt aactgtttgt   1980
gaagacgagt gcactaccat ccccgtgact attactacag aagttccttc cctgcactct   2040
tccaccacca ttgtcaccac tatcgaaaac aagaccgtga ctctgactgt tccttgtgat   2100
cccgaagaga ccccctccat caccgagccc gtcgaggtgc cttctgtccc caccactgtc   2160
accgagatcc ttactgagac cacttcaata tgtgataacg aggagtgtta tgagaccact   2220
acagtggtaa ccaagacagt tgtccattct gtgcctgtcg aggagatcaa gcccactcct   2280
gaggttgaga agcctactcc tgaggttgag aagcctactc ctgaggttga aagcctacg    2340 cccgagaagc ctactcccga ggttcctgag aagcctactc ccgaggttcc tgagaagcct   2400
actcctgagg ttgagaagcc tacgcccgag aagcctactc ctgaggttcc tgagaagcct   2460
acgcccgaga agcctactcc cgaggttcct gagaagccta ctcctgaggt tgagaagcct   2520
acgcccgaga agcctactcc tgaggttcct gagaagccta ctcctgaggt tgagaagcct   2580
acgcccgaga agcctactcc tgaggttcct gagaagccta ctcctgaggt tgagaagcct   2640
acgcccgaga agcctactcc tgaggttccc cagagtgaga agcctacgcc cgagaagcct   2700
acgcccgaga acccacacc tgaggttccc gagcccgaac agccctctcc ttctcccgag    2760
aattcctctc ctcatcccca gcatccctct tctcctgaga cttccactcc tagtcagcca   2820
ggcgagcaac ccgtccccga gcagtctgtc cctgaaactc ctggatctgg cccagaacag   2880
gccaacctgg ctgttactct caaggccacg actctagctt cactgtttcc gctgatggct   2940
cttctcatct ag                                                       2952
```

<210> SEQ ID NO 13
<211> LENGTH: 913
<212> TYPE: DNA
<213> ORGANISM: Artificial Sequence
<220> FEATURE:

<223> OTHER INFORMATION: YALI0_A16863g

<400> SEQUENCE: 13

| | | | | | |
|---|---|---|---|---|---|
| atggatccct | ggctgcgaga | tctggtagcg | ggaacggtgg | cgggctccgt | gtccaccgtg | 60 |
| ttcatgcatc | cgctggacct | gctgaaaatc | cgactgcaac | tggacggaaa | cctggggacg | 120 |
| gtgctgagat | cgctgcgaca | gtcggacgga | ccctacgcgg | ggaaatttcg | gggcctgtac | 180 |
| aagggcctgt | atcgcggtct | gggcatcaat | ttactcggaa | acgccgcggg | atacggcgtc | 240 |
| tactttctc | tctacggcat | cgtcaagaaa | atgcacctgt | tgatggacc | ccacggctac | 300 |
| tttttcaacg | ctctcatcac | aggaacagcc | acaagcatag | cgaccaaccc | gctgtgggtg | 360 |
| ctcaagacgc | gaatctgctc | gacaaacgcc | ggccatgtgg | acgcatactc | ctccatgctc | 420 |
| gacggagtca | acggatcta | cagccaggaa | ggaatcaagg | gcttctggag | aggccagatc | 480 |
| ccgtctctgc | ttggagtggt | gcaggccgca | gttcagtttg | gattctatga | ctgggccaag | 540 |
| gaacaagtca | gctagcgcg | gtcgcgcgac | ccctccaaca | gctacgacat | ttcactcaca | 600 |
| aaagaagggg | ctcccagtta | tttgtcaacc | aaggagtact | tattgctgtc | gtccacgagt | 660 |
| aaggctgtgt | ccactgtttt | gctgtatcct | taccaggtgg | tgcgttccaa | gctccaacga | 720 |
| tacgatgccg | gaaagatgta | ctcttccatt | ggtgactgta | tcagcaagat | atacagcaat | 780 |
| ggcggcttct | ttgccttcta | tcgaggtcta | gtgccgaatt | tgcttcgcgt | tctgccagcc | 840 |
| acctgcatca | cttttgtcgt | ctatgaaaag | gtcaacgagc | agttggagga | gctgagatga | 900 |
| cgaggtgaga | tga | | | | | 913 |

<210> SEQ ID NO 14
<211> LENGTH: 3711
<212> TYPE: DNA
<213> ORGANISM: Artificial Sequence
<220> FEATURE:
<223> OTHER INFORMATION: YALI0_A17578g

<400> SEQUENCE: 14

| | | | | | |
|---|---|---|---|---|---|
| atggcgaaaa | aacgaaagaa | caagaccggc | aaggtccagg | atcgggccgc | cgacgaccag | 60 |
| ccggaggacg | cggttgcaga | tcagcacgtg | gacaagacgg | aagactcgga | accagacaat | 120 |
| caggagcacc | cagccacggg | cccaaatgac | gagatccagg | acccggcggg | cgacaaggtg | 180 |
| gaagacacgg | tggacaacgt | ggaaaacgcg | gacgacacgg | acaaaccgga | cctggatgaa | 240 |
| tcagacaaat | cagtccagac | gggatcacaa | gactcacgca | actcggaaaa | gacagatcaa | 300 |
| aagaccgaat | caaccgccga | atcaaccgaa | tcaaccgaat | cgactgaatc | gaccgttccg | 360 |
| aacaaaccca | atctctttc | tctttctgac | gaagacgatt | ccgaagacga | gccgtcggag | 420 |
| tcgtcggagc | cggcggagcc | gtcagagccg | gtcaaccctg | tacctgtcga | gactgtcgag | 480 |
| tctcccgtca | agacccaacc | tgagaacaag | ggctcgtctc | tcaatgactc | ttctatcaag | 540 |
| agctcttcta | ccaaaagctc | ttcgtctctc | aaggactcgt | ctatcaagga | cagatcggag | 600 |
| gtgacagttc | cctccggcga | gtcggactct | tcagattcgg | aaatggagtt | ccccaaggtg | 660 |
| gtttccgaac | tcctagacc | gtccactccc | aataccacat | ctcacgctga | agatccagat | 720 |
| cagacacccg | tggctcgggg | cggccagaga | agccccatg | tgaccatgga | ctcgactgca | 780 |
| tccctgacaa | ccccacgga | ctacgagcgt | gtgtaccgac | gtcgaaatac | cgccaacagc | 840 |
| acgcggtctc | ggatgaccgt | gcgagtggac | actgccgatc | tgcaatcgca | gtcgcccaca | 900 |
| cccagcaacg | gcatttccat | cgactcgttt | ctggagcaga | aggagctgtc | tttccggctg | 960 |
| gtcacctgga | atgtgcacaa | ccgggcccct | cctgttattg | aggacgagca | tctcgattcg | 1020 |

```
ctatttttgc cccagagcga cattactgtt cttgcgttgc aggaggctga tccggtcagt    1080
ggtcttgtaa gtactgctca gactctcaat ggatggaagg cggcggtgct ggagaccctc    1140
gaaaaggcca atgaggaaaa tcttcagaag gacgagactg tagtcaccgc cgaggaggtt    1200
gaagaggaga cggataatga taagacggag aatgataaga cggagaacga taagactgag    1260
aagagcgaca agtcggagtc aagtgacaag tctgacaaga agacaagaa agacaagtcc    1320 gagaagactg acaaagctcc aaagactgag actcataaaa agtccgcacc ctccgacaca    1380
gaagaatctg gatacgaatc gtcggcctct ggatacgagt cgtcggcctc caacaatcac    1440
gcctactacg acccctactc caactatgtt gtttcgtcca accagctgat tggtctgctg    1500
atcattgtga ttgcccgcaa gtcgctcatg agccagattt ccgacgttcg agtcaagtca    1560
gctggaacag gtcttctggg agtgtgggga aacaagggag ctgttcttgt ggaaatgcat    1620
attggccgag aagccaccag cacgcagtct tccaagggcg acttctttgt gcccggaaca    1680
cgagtctgtt tcctcaactg tcatctttca gccggagaca caacgttgt tcggcgacga    1740 tgggagattg accagatgta ccgacgcctg gagcttcctg ggcgtcccga atggtatgcc    1800
aaggtcaagg aaaacaagga cagcaacagc agcactgcct ctctggctac tgatgatgcc    1860
aggtacgccg attacaatgc atcaagcgag tttctgggca atgccacaga gtcttccgag    1920
agcgatgctg acgagaatga aagtcttcgt ggacctttca gtgcagctac cactatcacc    1980
gaaatgtctc ccaatctgaa cggacgagga ttcaacgata ccgaaagtgt ggtttcagct    2040
gattctcgtg cggaggcgt cttгactgg tctagtgatg ccgctgccgc cggtgcccag    2100
cgacctgctc gaccacatga aaactccaac ctcagtgtgg tcagtgaagc tgtttctgcc    2160
agctcacctc gaggcgaccc tcgaaccatc atcttcttcc tcggagatct caactaccga    2220
gtggacaaga ctcacgagga ggccctggag atgatcgaga agaacgattt cgccggcttg    2280
ctggctcacg accagcttct caaagatacc agagacggcc gtgttctcgc tggtctcaat    2340
gagtacccca tcaacttccc tcccacatac aagtacgttg aggataccgt ttccgagctg    2400
gacactctac gaactccttc ctacactgac cgaattctct cgcgagcctg ggaggctgt    2460 gagcttgttc agaagggata ccacagtcat atggagtaca ctgtcagtga tcacaagcct    2520
gtttcggccg agttttcgct atctctgcct ctgattgact ttgacaagcg cgctcagatt    2580
gtcaacaact atctcaagtc tgttggtgtt caggagaacc tcgaccggcc tgccgtcact    2640
gtttccccca tgagcctccg tgtccagctt gccgtgttga ccacccaaac tgttcctctg    2700
gtgatccaca atactggtca cactacagct cactgggaga tttcccagac tctggattc    2760 gacgatgata gcaaggacaa gaaggactcg tcgcccagta tcacccttc cagcaccacg    2820 ggccagcttc ttccgggtga ccaggaagtt gttgaggtca ccttctcggc tgccattgga    2880 gcgcccctctt gcgactcgtt tgcaattgtg catgtcaagg actccaagga cattttгtc    2940 gacactggct acgatgtgat gccttcatgt ttcggctcag acctcgatta cctgtccaga    3000
ttgcctaacg gagctcgaaa cggtctgtca gacggcggaa aagtggtcag caacatgcct    3060
caggagattt ggaagtgtgt ggattacctg tggtctgttg tcgatcggga cggagaagga    3120
ggaggcgacg gagacagatc tgctcgtccc agtatcgaga agcctggaac agctgctgtg    3180
tctcgagagt ctcccaaatc acctttggtt ggcctcttca cgtcccctgg tgacccgcat    3240
ctggagatgg atattcgaga ttggcttgat accgggtctc cctttaacgt ggagactctt    3300
aacgacaacc ctctgggtcc acagtctgtg gcttctcagc tacatttgct gttggcttct    3360
```

| | |
|---|---|
| ttgtcacaga gaatcattcc agagtatgcc tatctctctg tgcctgaaaa aaccatcgca | 3420 |
| gcaggcacgg gaagccgaat tccgtttatg ggaggaggag tggacaatac tgcggacgtg | 3480 |
| gctgcccata ttctggaggc tgtgcccaac gtgaatgcca acgtgatgat ttacatctgc | 3540 |
| tccttcatcc gtctgttggt agacagaaag gccatgactc tcaagacggc actggacgtg | 3600 |
| tttgcacctt tgctgatgga cagtcccaaa caaggaggcg tgtccaaggt gtggaagaag | 3660 |
| agtccaatca gttctgcaaa gctcctgcag cacatgatcg atacttatta g | 3711 |

<210> SEQ ID NO 15
<211> LENGTH: 4245
<212> TYPE: DNA
<213> ORGANISM: Artificial Sequence
<220> FEATURE:
<223> OTHER INFORMATION: YALI0_A17776g

<400> SEQUENCE: 15

| | |
|---|---|
| atggcgatgc gcaaaaacat tgtgtttcac gagccgaaac gcgtatccga aacagaatgg | 60 |
| cagtaccccg agactggcag catatgggta catgtcccca ccggatggcg aagtcccgat | 120 |
| gaattttttgg actggtgcaa gcagctcaac gccaagttag acactactaa gcgatatcgc | 180 |
| gtgtcgcaat cagggctaac gcgcacattt tccgtgctat caatctgcgg tctaacaagt | 240 |
| cagagccagg cgttcatgcg gtctgaaagc ctgcgagtca ttgagattcc cgacgagatg | 300 |
| attgtggatg tgcggggcaa tcttctggag cccctgggaa tccgcaatcg cgatggcatc | 360 |
| acctatttga acgccgatac cagcacggaa agcatcacaa atacaactac cacagagcca | 420 |
| accacagccg ataccacaga tacaaccgcg gcctcaaaac cagaaaccac tgcagatggc | 480 |
| agttcaacga caagaagcac agctcgcgac aatgctgtgt cgaccgctgg aagcactaca | 540 |
| gagccgccca cacgacgac tgcggaaccg gccaccagct tctccaacaa tccaagcccg | 600 |
| ccagtgtccc tgctcagtcc gattcctcca gctgtagaga cgatcgcatc gtctacgccc | 660 |
| caacagagtg aaagtcccat tgtgcggtcg cctgttgtgc ggcccagtga cagtgcacca | 720 |
| gctgcttcta cagccgccac tatggccgaa atagttgctc ctcagcctgt aacaacggaa | 780 |
| tcctcatatt ctaaaccaac agaagccatc caggcgggat tccaggccat caatggcatt | 840 |
| ggaaactcgc tgttgacgtt tcaggccaac ccccaagtca gccagcctca gcagacacag | 900 |
| cagacacagc agcctcagca gacacagcag acacagcaga tacagcagcc acagcagcca | 960 |
| cagcagatac agcagccaca gcagccacag cagccacagc agccacagca gacacagccg | 1020 |
| ccaaagcaga cgccaccgac acaacagact cagtcgatac agccggcaca gccgacacag | 1080 |
| ccggcacagc cgacacaaca gttccaaacg acgtcaaatg cgagcaacaa ttgcggctac | 1140 |
| aagacgcttt ttctctgcat tccgtatcta agggccgatc gaaagctggg cctatcgaaa | 1200 |
| attacccaat cgcagcaggt ggttccctat ttccaatcgg tttcgcaatt tcgagaatgg | 1260 |
| gtccagaggc tcttcccccac tcactacatg cctgctgaca tgtatggcat cactctcgat | 1320 |
| ccctcgcagt tgtcgggctc ggttgattcc atctccacca atcttatccc tatcacgcct | 1380 |
| gcgttccagg gttctccccca ctggtttatt tacagctatt cacctaattc gattgcgtca | 1440 |
| ccccaaaaca ttgccaatag cacacattct cgaactaatc ctgcgagaca cctcgcacct | 1500 |
| cagcaacaac aactgtttgg aatcactcag caaaactgga accggatggt ggacgtgtcg | 1560 |
| cgaaagcaca caaatattta tggcttgatg gataaacgac tgcaggcggt agagaaggag | 1620 |
| ctcgctagtc tcaaattcaa gctaggcgct ttggtttcac ttgagccccg tcaggaagcc | 1680 |
| gctgatcagc actgcatcaa actcggcaac cggatagatc agctccacag catgttgaac | 1740 |

```
cagatgggtg cagaggtcac ccatactgtc aactctcttc agaatcgagt tgaatccgcc    1800
ctatctcttt ctggcaacaa caacaacaac aacaacaacc acgccactaa cgctaacaac    1860
gctgtggtta ctccagaaaa gcgcgcctat cctttttgaag aagaacactt gacgaaaaga   1920
cgccgaagcg agcattctaa taatattatg tttaactccg agaacgggtt tgttcctccg    1980
cccatctcgc gtatgttgag cgagttgaga aagtttccca cattgacgtg tgtaaatccc    2040
aactccaaga tcactgctcg gtttgcagtc atggatggca agtgtgtctt gttggcaggc    2100
tccgaggaca agtgggagtt tgggtttgac gacgacgatg tgggaggcag tgagccagtc    2160
cacacgtgtg acaacgcaaa cagttctgcc aaggcttctc ccgaaattac cactcaaacg    2220
agtatctcaa atccgagcgc aataatcgac gctggtaact ctgctcaggc ttcacccgtg    2280
gttcagacct tctcagtcgc acagtcctcg cctgttaatc ctgttaccca gttgcatcct    2340
tcggtacatg ccccacaact acgaggccct gtgagccctg cagcacgggg ttcatcgcct    2400
ctgcttgtct acactcatac tcatcagtct ccgaccgtgt cttctccttt agttcagtgt    2460
gtgcaccccc agtctccctc ggctcctgcc cctaccttga cgtccgctgc tgctgaaaac    2520
gtgacagtcc ctgcttccac tccggcaatt ccttcagtcc ctgtgggtgc cctttctcaa    2580
gcaaatgcca ctggtgggta cgtggaagta ccctctcccg ttgagaaggc cgcgcccact    2640
cttcctgcag ctgcgaacca ggagttgaac aacctgtcac ctgaacccgc cctggctccc    2700
gtcactgtgg agacccccac agctgaccgt gctagaagcg gctctgagcc tgtctctggg    2760
gccaagcaag tgcacagcatc cgatcaagcc tctacagctg ctgcacatgg tcgtgtttct    2820
gagccggctg cttccgatcc tgcctctcaa gcagctgctt ctgaccgtac ttctaaggta    2880
tctgcctcac cagtggtgac ttccgcctca gacatgcata tgcgacgaaa cgaggcccgt    2940
aaacagcgcc agcagctttt ggagcaggag aagcgtatct ctgactctat cacggcgtcg    3000
ttcgctacca cagagaactc tcccgctatc gctcctactg caccacctcc tcgtcctcac    3060
ttctctcagt tggatgagcg cactctcgaa aggaacaggg aaagagccga agaggaacat    3120
ttggagcgag aagaacgtga gcgacgggag atggtacagc gagacgtgca aggacgtcgt    3180
aaggctgctc agaaagctca ggcccgtgcc aagtcccaac ttgcggatga acatgctgcc    3240
cgggaagctg cacacgaact tattcacgcc cgagttgctg ctgaaaggaa gcgtgctacc    3300
gttgaggagg ctgctaggaa agcgcgtctg caggccgaag ccgagagaca gagagaggaa    3360
gaggctgagg ctgaagcggc acggcagctg gagcagcggg tggtagaacg gcggaggaaa    3420
gaggttgaac aacaaaggaa ggagcaggag gccgaggctg agcttcgggg agttgctgag    3480
actgcaaagt ctgtgcaaga ggctagcagc aagctttcta ataggatcaa gaagacaaat    3540
caggctcgcg atgttgccgc agccataatc catcgtctga acggcaacaa ggacgatgaa    3600
gagagtggat cgcagtctgg tcgcgaacaa gaaacaactc cagtggcatc tgacgccttt    3660
tcccagtcag cttatccgca ggctactact gctgaatatg cttccagtgc taccgacact    3720
gcttcggctt ctacagggtc gtctatgaag gagcgagctg agaagatgcg ccagttgcga    3780
gacaagcaga aaaccatgca gcctatcaag acagaaatga actctgcgac tgacaatgag    3840
gccaatgata agtctgtcag atccagcaag ctgtccgaga agtctaccga aggacaaagg    3900
aagaagagga agagtgtgga cgagagcagc ggaaagcgag cggagactct gggaaggcat    3960
atcgaagacg ctcagaagcg tcctgacggc gtcaaaaagc gacccgacgt cactaagaag    4020
attgtatcca agaagggcat ctccaaacgc gctccttcca ctgccaaaat gagtatgttt    4080
```

-continued

```
gagcgtctga agaaaggcat tcctggcgag atcccgccac ctcctccacc gcctcctagg    4140
tcttctaaaa agggcaacaa gcgtaattcc aaggagaaga gtaaactcgc agtgtcttct    4200
gattcttcgt tgtcagatgc catctggatc gatatcagtg attaa                    4245
```

<210> SEQ ID NO 16
<211> LENGTH: 3828
<212> TYPE: DNA
<213> ORGANISM: Artificial Sequence
<220> FEATURE:
<223> OTHER INFORMATION: YALI0_A17853g

<400> SEQUENCE: 16

```
atgttgcgac tccaagtgta cgcaatttcg ccctgtctgg agtccgagac cgttactaca     60
tgggctccgg accggtccat gcagacgcga tctatcgacg aagcaggcat gcgggtggag    120
aaaaagttct tgcatttcac ggacccgcga tcttccttgc tggagctgtg ccacgagatt    180
gccgagcggt tcaagtccat ctaccctgac aactttgagc cccggatcga cttcctgcag    240
agcgacactg gcctcgacct gtcgcccagc tttgtgtctg agacgtgtt  caagtccgga    300 gatgtggtga gcgattct gcggctgccc acagacattg aggagttccg caagtttcag    360
ggcgaggctc ctggcatccg atttctagag gaggatgtgg gagaggcagg agaggtgtct    420
aagatcgaag cacaggtcga tgatagcacc atgagcagag atggccgcaa gcgaagacga    480
tacacactgc ccaaagagat caccaagcga ctcaagcggg actcgtccgt ctactccgac    540
gggtttggcg tgcgtgatcc cgagtcgttc gaccacacca tggaagagga ggctatctac    600
gcccacacag tgactgttcg acgtcctcgt tcccgataca gccagggagg caccggaacc    660
ggccacaact ccattctgga gagttctact acctcgctga tccccccctcc ccggccagat    720 ttcgcctcgt cctcgacgac tggaccttct cctcctgctt ccaacaacca ttatcctcag    780
ttggagagca gccaggttgc tgccggatca tctacaccca tccgtctttc ttccaagctc    840
ggatccactg ttgttgataa gggaaatgtg tcaaacccca cccctgttcg aggcagcact    900
tctctcgata ccattcagac acccgttctg tcgccgcagc ccaaggcagc tatccagggt    960 tccccccatga agagccctcc ccacgcacag aaggcaattt ccttgcctcc tgtgaagaag   1020
gagcccacct caaaggagtc taaagacaag gagcctgttg ccaagcgtgc caagattgag   1080
ccaagggtcg agcgcaagcc cgagcctgag agcgacactg cttttcttggc tgagtttagt   1140 gacgatggca agtttcccac agctctcatg caggcccgtg ctcaacaaaa ggctgccatc   1200
gaggagagcc ggctcactca gcaggctctt cggcttcaca ttaagagccc ccagtaccat   1260
attccttctg agttgggcga ccacatttct cctgccaaag caaaggcttc tctgaacgcg   1320
tggttggggt ggaagcatgc ccaggagagt aactctcccg atattgagtt agctcgacac   1380
cgactggttc attgcacttt ttccgcactg gctgaggccg ccaacaagca gctcgacatt   1440
gccaacaaca aggtgcagaa ggggcagttg atggcctacc gtgagacttt cagcgtgcgg   1500
gctgataaca gctacaagtg tctgacggcg gagcaagttg ctgctgagaa gctggctgct   1560
gatgaggagg tcgccaagga ggttgctcga attaaggcta gacaggtgag caaggatgcc   1620
cgggatacca gcgtcgtgt ccgtcgggag tccacagctg ctgctaatgc ccatgaggcg   1680
gccgtgatgg ctgccaagga agagcatgac cgtgcagagg cgatgcgtgc aagagaggca   1740
aaggttcgag agcaggaggg tgccgaggcg cgcaaggaga tgatcgagga cgagaaggca   1800
cgtcagctga gttgaagaa ggaggaggag gccaagaaga ggaaggagga ggaggccaag   1860
aagaggaagg aggaggaggc caagaagaag aaggaggagg aggccaagaa gaaggaggag   1920
```

-continued

```
gaggaggcta agaagaagaa ggaggaggag gctaagaaga aggaggagga ggccaagaag   1980
aagaaggagg aggaggctaa gaagaaggag gaggctaaga agaaggagga ggctaagaag   2040
aaggaggagg ctaagaagaa ggaggaagag gctaaactgc tcgagctgaa gaagaaggag   2100
gaggctaaga agaaggagga ggctaagaag aaggaggaag aggctaaact gctcgagctg   2160
aagaagaagg aggaggctgt ccgggcagct gaggaagcca agcgcaagga ggaggctaaa   2220
ctcaaggacg ctgaggccaa ggaaaaggct gccaaagagg ctgccaaaaa gctggaggtg   2280
gagatcaagg aaaaagctgc tcaagcggct aaggggtccg ccaaagctga ggcggacaag   2340
aagaagattg aggaggcaga gaaggccaag caacttgagg ctgaagaagc gcgagaggct   2400
cgagcccgac tagctcagga gcaacgagaa gccaaagcca aggccgctca ggaggcaaag   2460
gaggccaggg aagcgaagaa ggccgagcag caagccgctc gggaggctaa gctccgagca   2520
gccgcagagg ctaagagggc gagagcgcga gcagccgcag aagctaaaga agccaagctc   2580
cgggctgcag cagaggccaa agaagccaag gcccgagcag cagcagaagc acgtgaggca   2640
aagaagatgg ctgaagaagc aaaggccaag aaaaacgccg aagctgaggc gaagcagaaa   2700
gctgctgagt caaagactga ggtcaagaaa cgaacccttg gtgctgctaa agccgcgcct   2760
atttcttccc aggacacgca tgtttccgac tctcaggctg aggacaagat ggatgtcgac   2820
tctgattccg actctgagtc tgattctgat tctgattctg actccgactc tgattctgat   2880
tccgattctg actctgactc tgactctgac tctgactctg actctgactc tgactctgac   2940
tctgactctg actctgacaa cgggcccaaa cccgagatca aggcgaagcc ggcagccaag   3000
aagagttcac agatgcctcc ttccacccaa cctcctccca aagtgaagca gactgctccc   3060
aagtcttccc agcctactcc tgccaagaag gcaatgaagg aggagtctga gtctgagtct   3120
gattccgatt cggatgatga tgactctgat gacagtgact ctgacagcga ggacacctcc   3180
aagaagagaa ccattgtcaa gactcctgcc aagaacgcga aggctactac caagcctgag   3240
ccgaagactg ctgcgaagcc tgcttctaag actgaggcta agcctgcttc taagactgag   3300
gctaagcctg cttctaagac tggggccaag cccgcttcta aggctgagac caagcccact   3360
gtcaagactg aaccaaagac ggctgtcatg tctgagccag caaagactgc tcccaaggct   3420
actgcttcca gtcttccac tacagtgaag cccgaggcca acggctctgc tatcaaaaag   3480
gaaggcgagg ctcccaagaa gtctcctttc tccaatctca gtctctcca gtctttggcc   3540 aagatgggtg ttcctgaggt gaaggactcc attccttcca gccagccccg attctctcaa   3600
gcctcccaga agaagaccga aaaggaggag gagtccgact ccgatgatga ctccgacgac   3660
tccgacgact ccgacgactc ttctgacgat tctgatgatt cggacgattc tgatgactct   3720
gatgactctg acgagcagcc tgccgccaag actaagcgtg ctggagctgg gctcaagaaa   3780
aagaagaaga acagtgggtt tgccagcctc atgaacaagt ttatgtaa                3828
```

<210> SEQ ID NO 17
<211> LENGTH: 1908
<212> TYPE: DNA
<213> ORGANISM: Artificial Sequence
<220> FEATURE:
<223> OTHER INFORMATION: YALI0_A19646g

<400> SEQUENCE: 17

```
atggtcgcct acacggagcg actggcgtcc tttgaagaag cccgacttcc tcggcggaga    60
aagaaggtcc aatggcctca tgaacacccg gatccagagc agttggccaa ggcaggattc   120
```

| | |
|---|---|
| tatttcaacc ccagagtcga gagtccagac aatgtcacat gtttcttgtg tgaatgttcg | 180 |
| ctggacggct gggagctcga cgactgtcct ctcaaagagc atctggagca ctctcggggg | 240 |
| tgttcttggg ccaccattct gtccaaggac tggcagaatg aaaagaatca cgaccctcac | 300 |
| tgcaaagaga acataggcat gcgactcacc acctttgaca caaatggcc tctggagaag | 360 |
| aagcggggct ggccaacgtc gctcaaactg gccgaggcag gcttctactt tgcgcctacg | 420 |
| gtagccgaag aggatctggt tgtgtgcgcc tactgcgaca tttcccttga cggatgggaa | 480 |
| agaacagatg accctcttca tgagcatgag cgacgacgtc ccgagtgcta cttttcacc | 540 |
| agcatgaaga aggaggaggc tactaccaag aagaaacgaa gatcttctaa gcgagcttcc | 600 |
| aagaagattg aagaagtcgc cgatgagagt gttgtcattt tacagcagcc tgacaatggg | 660 |
| agtgttcaga ttctgtcgga tcccgaagag gagccagccc cccagcccat tagatccaag | 720 |
| aaggagggcc gacgaccaag cgcaaagact gctccgaaga tcagacaggt gtctgtagaa | 780 |
| gaagagcttg ccaagctgca gaaggaaatg gaggaggatg gagacatcaa tgttgccttg | 840 |
| gagcaaaagg aggatgtttc tgactttgag gttgaccttg agctcagcga gatggcaaaa | 900 |
| caggccgatt ctctggtcca taactttgat gaaggtatca gcgactttga ggaacctcac | 960 |
| cacaaccacc agcatgagcc tactcctgtc agatccaaca agcgaccttc taatgtcttc | 1020 |
| caggatgatc ctgcacctcc tgccaagcga cgaaagtctt ctgtggttcc ttctgcacca | 1080 |
| gttgctcgaa tttctctgcc tatttccgag ggtaccaata attgggaggt tttctctgga | 1140 |
| tcgtcttctc cagctcctca agagcacgaa gtggacaaag gagaagacgg cggtgatgac | 1200 |
| aatgatgatg aggaagacga cgacgacgac catgaggacg atgaggacga tggggacgat | 1260 |
| gaggacgatg aggatgagga ccagttcgtg gaggctaagg aaaacctcac cgaggaggac | 1320 |
| tgtgtggttg tttctcctgc caagcctctt gagaagattc ttgccaacga cgtgcaagct | 1380 |
| catgtggaac atgaagttga ggagcccgct cgtgaggaac aagaaaagga gcaagttccg | 1440 |
| gttcaggagg aggaggagga gggggaggaa ggaaaacggg aagaacctgt tcaggaggaa | 1500 |
| gcccagtcaa acaaaactac agatacccat agcactcctg ctgactctga gaggcgagac | 1560 |
| tctgagcgtc ggtcgagggc aatcacccga tctcctcttg ctgttcgcaa cctcaaccaa | 1620 |
| atcgttacca ccaaatccgc caccagcact ccagcacggt ccaaagcgag ccagtctcta | 1680 |
| caatgggagc ctgtggactg cgaccaggtc tttgacgtgt gtgagtcgag tcctcataag | 1740 |
| gagcctgatc acatcctcga catgacaatc acggagtggt acaagtacca gtcagtagag | 1800 |
| gccgagaagc ggctcatgga aaagtgcaac cgaatggtcg aggttgtgca gcgagaaggc | 1860 |
| cagagggcgc tgaaccatat caaggctctt cccacagttg atgggtag | 1908 |

<210> SEQ ID NO 18
<211> LENGTH: 996
<212> TYPE: DNA
<213> ORGANISM: Artificial Sequence
<220> FEATURE:
<223> OTHER INFORMATION: YALI0_B00748g

<400> SEQUENCE: 18

| | |
|---|---|
| atgatacccc caattacttt tccctactac catgaaatct ccgatcgata tggacttgtc | 60 |
| ttcccagaca gcacgccctc aaacggtctc catgacaatt tcatcaatcc actactcaag | 120 |
| gactggcaca cagacaatgt cactgttctc tggttgattt tgaggggaat ggacacccca | 180 |
| tccctcaagt cccacgacga tattgaagcc ttccagatgg atagcgaacg gatctgcctt | 240 |
| cgcatctttta acaactacta tgagctgttt ccaacctcag agagccttgt aaaggcgcag | 300 |

| | | | | |
|---|---|---|---|---|
| accccacatt | ccaatggatc | ccgattccaa | tccctcaagc | tgttatctca aatgaaactg | 360 |
| gaccgacaga | atccctgcag | cgtggtcaaa | tacacagccc | agctcgagtc gtccgcaatg | 420 |
| tactccaggg | tactcaagtt | gttgctcaaa | gacaaaactt | gcgattttac catcacatcc | 480 |
| accacgccca | cgtgctccga | ctccggctcc | gactccgact | ccgacccccga ctccgactcc | 540 |
| ttccccgtgc | actcgttctt | actcaccaac | ctctggccct | ttttcaaagc agtctcgtct | 600 |
| gcggagatgt | tgaaaaggga | gacccaaaca | ctccatctac | cgtttccgaa ggactgtgtg | 660 |
| gaaattctcg | tcgccttctt | ttacggaaat | aacgtccaaa | atacctcctg gagcttatcg | 720 |
| ctgtctctgt | ctctgctgga | aatgtctgcg | ctctacgaca | ttccggagct gaaaaatatt | 780 |
| gccatagagt | caattgtcag | cagtgctgaa | ccgttgtctc | tctctgtcgc tctcaaagcg | 840 |
| tggaaagtgg | ccaacgaaag | tgacgctcct | gaagtggagg | cgtttctagg gccgtatctg | 900 |
| aaaagacacg | tctccgaaat | tgaagcctcg | gaggaatcag | aggagttttc cgaatcacaa | 960 |
| ctgctgcaat | tactcctgca | gattgtcagg | ttgtag | | 996 |

```
<210> SEQ ID NO 19
<211> LENGTH: 1669
<212> TYPE: DNA
<213> ORGANISM: Artificial Sequence
<220> FEATURE:
<223> OTHER INFORMATION: YALI0_B08800g

<400> SEQUENCE: 19
```

| | | | | |
|---|---|---|---|---|
| atggagggcg | tgggagtgtg | gagagagggc | cccgggttgt | gctacacaaa gacgacgttt | 60 |
| ggaagcagtg | tccggagaat | atataagggt | gacgtttcgc | acattaggtg tggtggcggt | 120 |
| acagtagtgg | tgtgtgtgtg | tgtgtgtgtg | tcgttgcctc | agtcactcgc ccacttgctc | 180 |
| acctgtactt | gtcagtagct | tgttggttgg | tttcgcgctt | gcgccctttg atcgcgtacc | 240 |
| caataaggct | cacctgcatt | tgcgccaatt | ctaaactgtg | gaggcaaaaa ggctaacctt | 300 |
| cggcatgaca | ctacaggaat | ctgcaacagg | ctagatatcg | ggacaagacc agatacgtct | 360 |
| ttgacctcgt | ttccccgtca | aaaattgcat | gtccgacaac | gagaagctgg ccgcggcgat | 420 |
| gcgcacgcgc | ctcaacttcg | ccatggtcaa | ggtccagaag | ggctgggagg accggtccat | 480 |
| tgaccagata | gaggaggcga | ctaaccacca | ggaccaggcc | aaggacaaga tacacacaca | 540 |
| cacagacaag | aagggcgcac | agatacagac | acagtcacag | acagtcac agacgcagtc | 600 |
| acagacacag | acagacaaga | agggcgcaca | cacacaaccc | cccgcaaga cccacgcacg | 660 |
| cagcgacatc | tccgccgcag | caataggtcg | cacggtgggg | ggcacaagtc cggtcaagga | 720 |
| gcaggcggct | tcatcttctg | ctggagtgcg | ttcggcagac | tcgtctccaa gggtctcaca | 780 |
| ggcctcattt | gcagtgccgc | agacggccag | taccggcctg | ggactgtcaa taccgacctc | 840 |
| tccgacgcca | cgaaggcggc | cctccaagcg | gggacaccga | cgctcgacct cggacattct | 900 |
| acacaactcc | actggtggag | tgtccggcgt | cttcaaggtc | gacaagcccc aggagagggc | 960 |
| gtggggcact | ccggcgcagc | caaagcagtc | accccagaag | taccacgccc agattcagca | 1020 |
| cagctacccg | cccaactctt | acccgccaaa | cacctaccct | cagaacactt actacccccc | 1080 |
| tcctccccca | ccaacaacagc | atagtggtat | ccactaccct | ccacagcact accctcctcc | 1140 |
| tcctccgccg | cctccccccgc | cacaagatca | cggatctcct | acagtcacac cttcaggcat | 1200 |
| ggtgcaccac | tccccaccgc | acgccttggg | ccaggccttc | caaccccagc tccacagcc | 1260 |
| gtcccccccaa | catcaaagac | agtacaatta | cacccacgcc | ccgccctacg gatcgccacc | 1320 |

```
tcaatacagt caccagtcgc actcgccaac acgcccgtca ccgctgcatg gaccgccaca    1380
gacgcctccg acgtccaatc ccacgtcagc atcgggaacc agacccacgc tggcgcctct    1440
acacgtgtcg ctgccgccga tatccacgtc catcaactcg ccaacgtctg cgcctgacag    1500
agtcaccctg ccgcccatgc gtgctatcta cgagccggtg atgccgtatg ggacgttac     1560 gagtccccga gcgcatcttc cctctcccgc gcctcattca ccgggccaga gagaggtcga    1620
tgacgatgct gcagagtcgt tgatgtattt cagctctccg agaaggtaa                1669

<210> SEQ ID NO 20
<211> LENGTH: 1544
<212> TYPE: DNA
<213> ORGANISM: Artificial Sequence
<220> FEATURE:
<223> OTHER INFORMATION: YALI0_C06424g

<400> SEQUENCE: 20
atgggactcg ctaacatcat caaccgtgga gaaaagcccg agggctcggc cttcatggcg      60
gcctttgtgg ccgtgtttgt cgcgtttgga ggtattctgt ttggatacga cactggaacc    120
atttccggcg tcatggccat gccattcgtc aagaagacct ttacagatga cggcctggag    180
ttcacttctg agcagacctc gctcatcact tccattcttt ctgcaggcac cttcactgga    240
gccatttctg ctccctgggc ctctgatact ctgggaagac gactgggtct gatcctcttc    300
tgtgtcgtct tctctgttgg cgctattctt cagactgctg ccaccggccg aacgcttttg    360
attgtcggac gagttgttgc tggtcttggt gttggtggag tctcttccat cgttcctctt    420
taccagtctg aggttgcccc caagtggatc cgaggtgccg ttgtctccat ctaccagttt    480
gccatcacca ttggtcttct gctggctgcc attgtcaaca acgcaaccaa aaacaaagac    540
aacagtgctt cctaccgaat tcctctcggc cttcagcttc tgtgggccgt catcctgagt    600
ggaggtctca tcctgctacc ggagactcct cgattctgga tcaagaaggg cgagtacgac    660
aaggccgccg attccctgcg acgactacga cgacttcctg ttgagcacga ggctgtacag    720
aaggagctcc tggagatcca atcttctcac gaccacgaga tgcagatcgg tagcgccacc    780
tgggccgcct gcttctcccc caaggggtcc cagctgaagc gaatgctgac cggtattgcc    840
attcaggccc tgcagcagct caccggtatc aacttcatct tctactacgg aaccgagttc    900
ttcaagaagt ccaacatctc caaccccttc ctcatccaga tgatcaccaa cattgtcaac    960
gtggttatga ccatccccgg tatcatgttt gttgatcgag tcggacgacg aaagctgctg   1020
ttgatcggag ctatcgtcat gtgctcttcc gagtttatcg tggcggctgt tggtactgcc   1080
attgataacg agacctcctc aaaggttctg attgccttca cttgtacctt cattgccggt   1140
ttcgccgcca cctggggtcc tattgcctgg gttgtcattg gagagatttt ccctctacga   1200
atccgagcca agggtgttgc tctatgcgcc gcctccaact ggcttttcaa ctttgccatt   1260
gcctttgcaa ccccctacct cgtcgacgag gcccctggat cggccggtct caagaccaag   1320
gtcttcttca tctggggagg ctgcaacttc ctgtgcatcg ccttcacttc ttcatctacg   1380
agaccaaggg tcttactctg gaggaggtgg accagatgta cgccgagatc aagattgctt   1440
ctcgatccca ccagtttgtg cctaccactc gagtcgctgc ttacgacgag cacgcttctg   1500
acgacaagaa ggacggacag cacgtctaca ttgagtctgt ctag                    1544

<210> SEQ ID NO 21
<211> LENGTH: 2481
<212> TYPE: DNA
<213> ORGANISM: Artificial Sequence
```

<220> FEATURE:
<223> OTHER INFORMATION: YALI0_C07172g

<400> SEQUENCE: 21

```
atggcccgaa aatccacccc agagcctgag atgagacgca agactcgggt caaggccaac    60
attttgcatg tgagcaagga agggatattc gacagcgccg aaagtctgc tcagatcttt    120
gacaatgcgg gaaccaagcc tgggtcccag gcacagttac gtcaagagca acaacaagag   180
caacagacac aaacacaatc gcccatggca aagctgaagc aaatggtacg ccgaaacagt   240
gctcctcagc agccccagtt gcagcaaccc caccagtcac agcagcagca acagcagcag   300
cagcagcagc agcgacaaca gggtcaaccc caacaacaaa cactaaccac ccgtctgtat   360
ctccaaaaca gtctctggc acgacagaat ccaatctca acaccaaaat gtcggctttg     420
gaacaccata tgagcgaact tatcagtgaa aacatttgtt tgcggcaaaa gaatctcgag   480
ttgcagagaa gccacgacaa ttggttgcga tcgcatgtca gccagaatct caaaaagcaa   540
ctgcaacagc atatcaatgg aatcaacgat ttgatgcaag gactgttggg agaagtcgat   600
ggagactcgg agcaacgctc tcatgaatcg gcttctcagg agcactttga gctttccctt   660
tccagatcac tttcaaagac tcccgattct cgagctctat ctagaggttc tcctgtatct   720
ggcagacact cgctctctag aggttcggca agtcgacaga ccatgggtcc tgctgacttt   780
gcacgacgac ggtcttctcg acgtcgatca tcgttctttg gcgagctgcc cctgctgcag   840
gacgccgagg acgtgctcga tccttcggca gaacaattgc atttggaggc tcgagatgtc   900
gtcactccga tggctgacga cgttgaggga tgggtgagg ttccagttga cgaggtgaat   960
gctcacatgg aggagatgga gaagcagcat caggcagagg aggcagagag cgagatggat  1020
gttgatagag gagagaaggt gcatttcaat gagcacgtgg aggaacatta cgacgagcca  1080
atggaaatgg atactcagga gacacaggat acatcattct cctctgctgt ccgggagact  1140
tctttccctt cacctatcca agagactgtt caggagactt ctttcgcctc tcccgagcac  1200
gaatcgttcc cttccctgat ccaggagact tctttcccct cgcctgtgaa ggagaagtcg  1260
tcgtttgctt cacctataaa agagaacgcc tcttttgcat cgcctgccaa acagaagccc  1320
ttcccttcac caatcgacga gtcttctttc ccgtctccct tctccagctc cttccgacgg  1380
gtaacttctg cccccagagg agagcctatg gaggaagtgt ccacagatgg agagtccttt  1440
gcattccttc agcagcgatc tcgtcccaac tcgagccatt cacggcctaa ctctcgatcc  1500
gcttctcgca acatttcctc ccgccctgga tctcgggaga agcagatcca cgtgtttgcc  1560
gaccctgtat ccctgttaa ggaagctggc cttgaggcct ctgcccctgt gaacccagcc  1620
ccttcaaata aaccagctgc tgtctctaca accctcctc gatctcgtcc ttcattgttt   1680
gatacccccg agagtgccaa ggagcgacag gagaaggagc ggaagcgacg agagagcatg  1740
gagcaggtag tggaggatcc cgtgtcaccc tgttcccgtc ccagcagtcg acgatcttcc  1800
cgaagagcca gtactgagaa ggagaaggcg gctgaggagg ctgcaaagca tgaggagatg  1860
gaagttgagg aagagcatgt tcaggaggag aaggttgaaa ggagggttaa tcgttctcga  1920
cggacttcta ctaagacagc tgagtcactt cctgtatcta caggactcac gactgtggag  1980
tcttttggaga agcccgtttc gggaatgttt gaaaagggtc tcgagaagct tcagagtctg  2040
gacaacaacg tgactgcccg gaagagtcgc gctccaactg ccaccggtgg tgtcaaggtg  2100
actacatcaa gaaagagcac caaggccact gccaaacctt ccaagacctc tcctctgatg  2160
cagaaggatg ccaatggcag caaaaataat ggagccgatg gagtcaaggg caaggtcgag  2220
```

```
actgttaaaa catccaagct tgccgaaaag cccgtcaagc ccgtcaaggt ggcagctgat   2280
acggttgcca agaagcccat caagctggaa acccctgagc ctcgttctcg gcgatctcga   2340
ggggctcctg tcaactacaa gcttccctct gtgggttcca agctgcgtcg ggagaccgat   2400
ggctttgttg atgcagttgg agggctcaag cggtctctgg gtgcctgtga tgagaacggc   2460
atgaagcgac ggcgcatcta g                                             2481

<210> SEQ ID NO 22
<211> LENGTH: 1797
<212> TYPE: DNA
<213> ORGANISM: Artificial Sequence
<220> FEATURE:
<223> OTHER INFORMATION: YALI0_C08437g

<400> SEQUENCE: 22
atgactcgat ttactgccag gcagggcatc aaggcgccgc ggaagctggg aaacgctcag     60
agcggcgccg tattggccgc gcggaaacgg caacggcaag aaatggactt tctgaaggag    120
atgcggcagg ttatggaccg agatcatcag ggtccctcgg cggcggactg cgttcgagtt    180
agagaaggaa agaagcagcg ggaggcagat cggttcaaag cggacaatca gacggtgcgg    240
taccgtctgc ctaccaagtc ttgtgactac cagcgcagta tcgatgaggt tgtgagcggg    300
ttggctgctc gagtcgattt ttcgcgggag ggacgacgtt tgtcctttct gcgtcgaccc    360
gcggccccag aggttggaag ttcagattac gaggcgtttg aagcgacacg aaacaacttt    420
tatgctcaga tgcttgcgac tcccccagaa agggcgtttt gggtgacat tctacttcct    480 cgagggatgc tggatcagtt tgcctccatt aagagtgatt ctggggtgga cagagacggc    540
gaaccgactg tggcacacgt ggttccgatc attgaaggca agcctgtgat ccccaaggag    600
atggagggcg tttcagacct agcaatttct tccaaatggt accagagagc atgtcttctt    660
cgattccagg ctgcttttgg cacagatgat cgtcgcttgc atggcacatc tgtgcgtgtg    720
atgcagcaac agggccgaaa ccggatcttc gaactagaga cttttgttgga gatagctcta    780 gctgaaagac aaagactagt cgagaaggtg gaggaggttt tgaaagctgg gtataaggat    840
ctggacagca agagtgtgac agagaaaggc gctattgtct tcgactttga ttccaactcg    900
ttcgaaccat tccagtatga aaatggagct gtgagaagga tctacttctc tgtctgtggc    960
atgggtgctt ctgaatttgg actggcagga aacgtgtcgg ttcctatgag tgagtctatc   1020
aacaagctca tgtgggaact gttccgacac tctcttcgag ttagaggggt tggggagatg   1080
agttctgatg ctctgcagcg gatccaggct cgaaaacagg ccattatcga ctacaacaac   1140
ggcaaatcca agagaaacgt catcaatgag cgcatgtttg acgcaggaga aagaggtca    1200 cttgaggagg aactcatcag ggatattgct ctgcttgatc ctcaacccaa gggcaaggtc   1260
aagaaagacg ctgtgaaggt tgtcaatgga ggtgccaaga gggataccc tagtagggcg   1320 cctaaagaga cagaaaaagg tgataccagg ggttctagag atggaagtgc gtcgaatgga   1380
aagggttcca acactaggga aatgaaggct tccaacgact cgaacactag aggttctaga   1440
ggtgtccagg agatcaagac tcagactagc gacaccaaga gagaggttga tgagtttctt   1500
accattgaag acctcgtcga accttccggc aagaaatcca acaagaaatc caacaagaca   1560
gccagcaaga cagccagcaa gacagcgaaa aagacagtca gcacgacagt cagcaagaca   1620
gtcagcaaga cagtcagcaa gacagacaag cctcttagca agccttctaa taagtctgca   1680
tcggccactg tggaagacac gttccttgac atggacttt tgctagaaga gaaacccaag   1740
aagcgaaagg agtcaaagtc cacgaaaaag aggccgcgca agggtaagaa gttctag     1797
```

<210> SEQ ID NO 23
<211> LENGTH: 4143
<212> TYPE: DNA
<213> ORGANISM: Artificial Sequence
<220> FEATURE:
<223> OTHER INFORMATION: YALI0_C09031g

<400> SEQUENCE: 23

```
atgcgattct tcagtctat tgccctgcta gccactctgg cgttcgccaa ggaggtcgct      60
tcgcccatca catccttcga ggttggacag gctaacgaca tatccaacaa ggagggatac    120
accggtagcg cttgggagct ggactacaag tttgccctgt ctcctgaggc cgacaacgtg    180
cagcctggtg atcacttcac gtttgatatc gatgacaaca tgtctcttga cgctggaaac    240
tacgacttca tggtcaagga tcccaatggc aacgatatca tgcgaatcac taatgaaggc    300
catcacttta ccgctaccta caccgatttt gttgcttcca gaactaccca gattactggt    360
aagttcttca tgcagtccac tctcaacagc cagtatgtca agggccccgg tcccgtcacc    420
atcacttctt cttccggagg caagcagttc tctgatcaga tcgaggtcaa ggctgctgtc    480
gacgccggtg gagcttacaa gtacgcccag cgagtcggta accgaatcga atggaccatc    540
caggttcctg cttctcccta cgaccgaatg aagattgttg atcagcttgc tgatgccggc    600
tctacctaca ccacccccga tgctcttctc gaggatatga ctcttcactt ctaccacggt    660
ctgacccca cttgggacta cacctcctac gagaagatca ccgatgtgtc ccagtacgtt    720
cagctccagg acttccagac cgacgggttc accatgttcc ttagcaacat ccccgaggat    780
gatgtcaccg tccagatcac cttctactcc gagatcacct ccaagcagga gcagtactcc    840
aacaacatgg actggctcat gtgggagcga ggctacggct atcttcccga gccctctgga    900
gagcacaacg atggttcttc cggcgagggt aacgccaacg tcaacaacgg cattttccga    960
gctggccatg cttacggtgg tgctccttac gatgctccta ccggcggcaa cgatctgaac   1020
gctggtggtg agggtgacgg tgagggacga accaagacct cttctgttga gcccaccact   1080
tctgctgagc ctacttctgc tgagcccacc tccgagaccc gaaccccgt gtccgagtac   1140
atctccaagt ccaaggcacc tggtgagtat cacaacaact actactaaca aacccaccaa   1200
cacatactaa caataggcaa ccctggcgac ggatttgttg atcccgacc cacccttct   1260
acctatggtc ctgaggcc tcctcctgct tctgctggtc ctgagctttc cactgacaag   1320
acttcttcgg ttgagcctac ttcttctgct gatcctacta cctccgagga gcccacttcc   1380
tcagttgagc ctactacctc tgaggagccc tcttccgttg agacctcttc tgctgagcct   1440
aattcttctg ctgatcctac tacctccgag gagccctctt cttcagttga gcctactacc   1500
tccgaggagc cctcttccgt tgagacctct tctgctgagc tactacctc tgctgatcct   1560
acttcttctg ctgatcctac ttcttctgct gatcctacta cctccgagga gcccacttct   1620
tcagttgagc ctactacctc cgaggagccc acttcttcag ttgagcctac tacctctgag   1680
gagcccctctt ccgttgagac ctcttctact gagcctatta cctctgctga acctgctacc   1740
tctgaggagc ccacctcttc agtcgagccc acttcttctg ttcctgagtc tcccgagtcc   1800
tctgctgagc taccagcga agagacttct tccgctacct ccgaggagtc ttcttccgtt   1860
gagcccactc ccgagcctac ttcttccgtc gagcccactt ctgaggtttc ttctgctccc   1920
gagtctaccg agatcttcc cactgctccc aaatctacta ttgaggcccc tgttgttgcc   1980
aacaccaccg tctcttccac tctcgagccc acctcctcca tggctgagtc tactgttgag   2040
```

```
tccactgtcg agtccactgt tgaatctact actgaggtct cccccactcc cgagcccact    2100
tcttccgctc ccgagtccac ctccgagtct ccctcttccg ttgagtcttc ttccgtgttc    2160
tccaacacta ctaccgtttc ttccgccgct gtctcctccg ccgctgtttc ctccactcct    2220
tccgtgtctc tcgtctcttc taccctgtt tccattgaca cctgcatcga gaccgagact    2280
gtcaccgtga atggcactgt ctcgactgag accaaggatg tgtgcgctac ctcttctacc    2340
cctgctcccg tgtctaccaa cacctgcatt gaggttgaga ccaccaccgt ttctggaacc    2400
gcctctaccg ttaccaagga cgtttgtgct tctaccactc catctgccga cccctgcact    2460
gaggttgtta ctgttttgtc caacggtacc accactgtgg ttaccaagga cgtctgtgcc    2520
tccaccaccg tttcggctga tccctgcact tcaaccgagg ttgtgtctgt ctccggtgtt    2580
gtctccacca tcaccaagga tatctgcgct tctactactt cttcggatgc ctgcattgag    2640
gtcgagactg ccactgtcga cggctctgtc accacggttt ccaagaacgt gtgtgaccct    2700
gtcgtgactt ctgacgcctg tgttgtcacc gagactatct cttccaacgg ctccatctcc    2760
accgttacca aggacatctg cgcttctgcc acccctgtac ccactgtcac tgactcttgc    2820
acccaggtcg ataccgtgac tgtgtctgga accgagtctg ttgtcaccaa ggacttgtgc    2880
tcttctgctc ctgtttccac cgactcgtgt tttgtcacca aggttgtatc taaggacgga    2940
gctgtttcca ctgtgaccaa ggatacctgc gccccgctt ccactgactt ttgcactgtg    3000
gttgagactg ccactgtttc cggaactgaa actgttgtga ccaaggacgt gtgtgcttct    3060
gcaactatca ccgccactcc ttcttctgac gcttgcattg aggtttccac caccaccatc    3120
tccggtgttg cctctacagt caccaaggat gtgtgtgctc ctctctccac cgactcctgc    3180
attgttcgag atactgtcac cgcctccgga ctcgagactg tggttgccaa gaacacctgt    3240
gtcggaacca tcaccaagac cgtcacccac tgcgatggtg gttgcactga gctcccgtc    3300
actttgactg aggcccccgt ctcctccacc gccgttgtca ccacggtcgt tgagggcaag    3360
accgtcactg tcactgtttg cgacgaggat ttcaagacca atgagtctgt caccgtctct    3420
ggctctgctg ctgagattac ctccaccgtg gttgtaccca tgaccatcac caagactatc    3480
accaactgcg acaacggctg ctccgagatc ccgtcacta ttgtcgagac cccgttgcc    3540
tccaccgagg tgatcaccac cgtgattgaa acaagactc tcactgtgac tgtctgcaac    3600
gaggacttca ccactgaggc cgttgagact cctactcaga ctccagccca gtctacccct    3660
gttgtcactg tcgtctcttc ttctcccgcc gagtctcccg ctgtctccaa gattgtcaag    3720
accgtcactg tctgcaacgg cgctggctgc tccgaggccc agtctactga gaccgttact    3780
ctgcagaccg tccagactca atccacagag attgtctctg cccagcccac tcagtctgtg    3840
gccatcgagt ccaaggttga gtctcgagcc tcgactacta gcatcaccgt tgtcgagact    3900
tcccccgaga cttccacacc tgctcagccc aaggagtcta ctcctgctca gcccaaggag    3960
tctacccccg ctcaggagtc tacccccgct cagtcctcta ctgaggttcc cacacaggct    4020
cctcagcagt cttctcctgc tcctcagtgg cccgatgccc ctaaccccga gcaggccaac    4080
tctgcttcca ccaaggtgat tggagctctt gctctcctcc ccctctttgc attcctcatt    4140
taa                                                                  4143

<210> SEQ ID NO 24
<211> LENGTH: 2637
<212> TYPE: DNA
<213> ORGANISM: Artificial Sequence
<220> FEATURE:
<223> OTHER INFORMATION: YALI0_C09614g
```

<400> SEQUENCE: 24

```
atggacctga gactggtacc gaccagccgc gcgcgggtca acggctgat  ctcacgtgag   60
ccgtcgccgc tgcaactgca gcaaaaacga aggacgaat  cgagcttcgc gctcgaggag  120
atgcttagtc agcgccctcc gaccgacgtg cgctcgattc tcaactcggc ggtcgacgcg  180
ctgaggaaaa agccggaggc ggcggcggca gccgggaagt cacgtgagct ccagacgggc  240
tcgaccctgt tgtgaaaat  tcagccggcg ctgattaaca agctgcaagt ttcgacgcag  300
tttttgctgg tgaagattga tgatggcgaa ttctggatgg agcggtttgg cggcgacatt  360
tgggggtttt tcgagcgaag cgcggcacgt gataagcaga ccggatcccg tggccagctg  420
gactctcgac cccgtgacat ttcacatgac gacacggagg acacccagga ggacactctg  480
ccagatggtc aacaagacac ccaagaagat acaccaagac aggatattag tccacacaaa  540
ttgttggccc acaaaacatc tacaagtcac gtgttagaac cgaaccgttc tcgcatgcat  600
tcttcctcac gtgatgatat tctttcccgt gctcctgttg cctctagcaa gtcctcttcc  660
actactaata ccactaccca ggatggttca ttcacatctc taattgcatc tctaccacct  720
cctcaaccga cgttaacccc ctacattcct ctaaacctga cgaaaccagt ttcggcgcta  780
ccattgccat cagtttcggt ctctgagctc cttctgtcgt cctaccggac ccagctttac  840
tgctgtcgga cgtcgctcat ctactttgcc aaggccatgt ccaagtcacg tgctctgtgc  900
aagtccacgc tcgagaaaca tacgcagggc aagtctcgtg tttttccgc  ctcccagatg  960
cgcaaaatgt cgtataagct gtactctcgc gagttggcca agctcgtcca gccactcaat 1020
gaatggtctc aggtttacga gtaccacgag ttctgcaaga tgatgacaaa cacaaaagac 1080
gagtacgtga tccagtggaa agacagactg tcttattcgg ttttgtccga ttcgaaaaaa 1140
ctcgcagtgg aaatatctct tctcaagttc agagaaatgc aattacagag tattgttctg 1200
ttggaactgc tggcagtggc tccggtgacc aaaagtgctg acgctgctga cagtcaaaa  1260
cagatggagt tggaaaagca aagaagaag  gaagcaagga aatgggcct  ctacaagtcc 1320
agacgaaaca aggcagcggt ggaacaggag gaggctgcag aggagactct ggactacaag 1380
actctgttga tccagttgtt ttccagcatg tgcatctggc aacaattgtc ggattcaaaa 1440
tctgatcacg tgcacgagtt ttgcaagtcc gtggtcattc cgtatttctc gtcacgtgtt 1500
ccggaggtgg tcgaggactt gctgaagaga gcaggcctcg agagagaaac tagacacatt 1560
tctggtaagc aacaacaaca acaacaacaa caacaacaac aacaacaaca acaacaacag 1620
ccgctgaagc agaacaacaa gccgcgagag atcccatatg catcgcgcga ctcgcctacc 1680
ttgtcacgtg actcaaccgt gacaccgcgg gccaactctc cgtctttttc acgtgattcc 1740
gacacgttga attcggacat cagcacgagt tcaggtgtgt ctcgggtaac caattctagc 1800
cgcgcagctc gaacaggctc ggcccaggga gtcacgggat tacttaataa gccgcaggtt 1860
cggggcggac tcctcacctc ttcacggtca tttgattctc gtactcaggt gggcatgcgg 1920
ttcaagggca gtaaagagaa ggacaaggag gaggtgaagt gtacaaattc ggttgccggg 1980
accacaacgt cggctacagc ggagatgacg acgggcatgt tcagaaagtc acgtgacatc 2040
tccgtggcca cagcctcttc tcgtcattcg atggcggccc agtctcaggt ggctgccact 2100
cccgtgaagc ggactagacc ggttttgacc tcatttacag ccgagccgga caatccattc 2160
atcaacgaca gtcacgtggt tgacgagtct ccgtttgcca agcggatgag aggggagagc 2220
actggtccca ggagaaggct gggcctgggg gatggcactt ctgttgtttt cgatagtgcc 2280
```

```
agaagaaaaa gggaaggtag tgagaatcag attgatgact ctcctgttcg gtgcaatcgc    2340
tactcggttg ttatggagtc tcctacgaag tctaggactt taggtgtggg tcatggcaac    2400
tatggcggcg gtggtggtgg attattttca aacaaaccat ccaggatgtt ttccactacc    2460
ataaggccaa gcatggctgc tccagtggcg gcccctgctc ctgtaaatgt gtctgctact    2520
cccaagagac ggactcagcc cacgttgacg aaggagcagt acccaaggga ggataatccg    2580
ttttacaatg gaaccgatga tgctgtgatg gatacaagtc ctactaaacg ggtttag      2637

<210> SEQ ID NO 25
<211> LENGTH: 3345
<212> TYPE: DNA
<213> ORGANISM: Artificial Sequence
<220> FEATURE:
<223> OTHER INFORMATION: YALI0_C11165g

<400> SEQUENCE: 25
atgcttggat gggcccttgg cctcgtcgtc accgaggacc cctcccagct ggaatacctc      60
aagactcctg agaccaacca tatcttttgg gcctacgcca aaatcattcc gggcctggcc     120
gccgccaaca ttgtcactaa tgctggcgcc cttgccctga agatgggtct tgatgtcccc     180
tttgtcaaca gccgggatct ctcaatcccc cccactcacg atgagctcgt ggcaggcctt     240
cagttggtgc tgcaatactc cgccgagagt ggaagagatt ggtattctgc cgtcaaccct     300
acacttccaa tttacgccat caagtgggtg gttggcaagg ccgcccagcc ttacactgcc     360
gaggacttga aggtctcccg acgaactgtc ttcaacatgt acatggccca gaccattgct     420
cgtcatgctg agaacgctct taacgcaaag attgttatca acgatcctaa tgtcactgtt     480
acagtcgtca tcagtcccgc tcctgcttcc accgctcctg ccatttcgga ggctacctct     540
atgattcctg tgacttcatc cactcaggac tatcagaccg actcttctcc tgttcctgct     600
tcatctacag ccgatgcctc ttccactggc gactctggcg cctcttccac tggcggagtc     660
gatgcctctt ccactggcgg agccgatgcc tcttccactg atggtctctg gcctccacc     720 actggcggag ccgatgcctc caccactgat ggttctggag cctccactac tggcggagcc     780
cctgcctctt ccactggcga ctctggcgcc tcttccactg gcggagccga tgcctcttcc     840
actggcggag ccgatgcctc ttccactgat ggctctggtg cctccaccac tggcggagcc     900
gatgcctctt ccactgacgg ccctggcgcc tccaccactg gcggagccga tgcctcttcc     960
actgatggct ctggtgcctc caccactggc ggagccgatg cctcttccac tggcggagcc    1020
gatgcctctt ccactgatgg ctctggcgcc tccaccactg gcggagcccc tgcctcttcc    1080
actggcggag cccctgcctc ttccactggc ggagccgatg cctcttccac tggcggagcc    1140
cctgcctctt ccactggcgg agccgatgcc tcttccactg gcggagcccc tgcctcttcc    1200
actggcggag ccgatgcctc ttccactggc ggagcccctg cctcttccac tggcggagcc    1260
gatgcctctt ccactggcga ctctggcgcc tcttccactg gcggagccga tgcctcttcc    1320
actggcggag ccgatgcctc ttccactggc ggagccgatg cctcttccac tggcggagcc    1380
gatgcctctt ccactggcgg agccgatgcc tcttccactg atggttctgg agcctccact    1440
actggcggag cccctgcctc ttccactggc gactctggcg cctcttccac tggcggagcc    1500
gatgcctctt ccactggcgg agccgatgcc tcttccactg gcggagccga tgcctcttcc    1560
actggcgact ctggcgcctc ttccactggc ggagccgatg cctcttccac tggcgactct    1620
ggcgcctctt ccactggcgg agccgatgcc tcttccactg gcggagccga tgcctcttcc    1680
actggcggag ccgatgcctc ttccactggc ggagccgatg cctcttccac tggcggagcc    1740
```

```
gatgcctctt ccactgatgg ttctggagcc tccactactg gcggagccga tgcctcttcc    1800
actgatggtt ctggagcctc cactactggc ggcgttcctg ccatttcaac cggtggctcc    1860
ggctcttcca cagatgttga ccctgttact ccacgaaaa aggacacaga gacaaacaca     1920
gacgtctcta ctgccaccac taccggcgat aacaagggat ctcagtccgt acctgtcact    1980 gcccctctg ccacttctac tggcggttat gatggatctg atagcggaaa cggttctgac     2040
gacaatgatg atggaaatgg tgacggttct aacggtaacg gttctgacaa tgatggatct    2100
gacaacggca acgattctga cggtaacggc aatggttccg atggaaacgg caacggatct    2160
gacgacaacg gcaacggatc tgacgacaac ggcaacggat ctgacgacaa cggcaacgga    2220
tctgacggtt ccaacggtaa cggctctgat ggaaacggca acggctctga tggttccaac    2280
ggcaacggct ctgatggttc caacggcaac ggatctgacg acaacggcaa cggatctgac    2340
gacaacggca acggcaacgg atctgacgac aacggtaacg gatctgacga caacagcaac    2400
ggctctgatg aaacggcaa cggctctgac ggtgccaacg gcaacggatc tgacggttcc    2460
aacggcaacg gatctgacgg ttccaacggc aacggatctg acggttccaa cggtaacgga    2520
tctgacggtt ccaacggtaa cggatctgac ggttccaacg gtaacggctc tgacggttcc    2580
aacggtaacg gatctgacga caacggcaac ggatctgacg gttccaacgg taacggctct    2640 gatgaaacg gcaacggctc tgatggttcc aacggcaacg gctctgatgg ttccaacggc     2700
aacggatctg atggttccaa cggcaacgga tctgacgaca cgggtaacgg atctgacgac    2760
aacggcaacg gctctgatgg aaacggcaac ggctctgacg gttccaacgg caacggctct    2820
gatggaaacg gcaacggctc tgacggttcc aacggcaacg gctctgatgg ttccaacggc    2880
aacggatctg acggttccaa cggcaacggc tctgacggtt ccaacggcaa cggctctgac    2940
ggttccaacg gcaacggctc tgacggttcc aacggcaacg gctctgacgg ttccaacggc    3000
aacggctctg acggttccaa cggcaacggc tctgacggtt ccaacagcaa cggctctgac    3060
ggttccaacg gcaacggctc tgatggttcc aacggtaacg gctctgacgg aaacggtaac    3120
ggatctgatg gaaacaattc caatggatca gactctggag caagcaacgg cgttgattcc    3180
aagccccagt ccaccctcag agttgacagc actgccggac cttctgatat ccctcagtct    3240
ccccaggcca ctggatctgc tgaccaccct gcccaggcca atggagcctc taagctggtt    3300
gtcggtggct tcgctgctct tcccctgttc gctgctcttc tgtaa                    3345
```

<210> SEQ ID NO 26
<211> LENGTH: 873
<212> TYPE: DNA
<213> ORGANISM: Artificial Sequence
<220> FEATURE:
<223> OTHER INFORMATION: YALI0_C13728g

<400> SEQUENCE: 26

```
atgtatgctg aagagccagg gccagagaaa agagaggcaa aaaagaggcg gaaaaaaaaa      60
ggcaaaaaaa ggcaaaaaaa gtgtccgaaa agtggccga aaagtggtc gaaaaagtgg      120 ccaaaaaagt ggccgaaaaa gtggcaaaaa agtggccga aaagtggcc aaaaaagaaa      180 aaaaaaaga agaaaaaaac acacctggaa tcacctcccc ctaaaagatc gcgacgcctt      240
tctggtccgg gtcacgtgat cacagctttt gtctcacgcg cttgtcatgg ctggctgttt      300
cgacgtcagt ttctaccatc ttctgaaaga caagttggtg caaagttcaa cgttgccacc      360
aaggtcacca aactaacgtc aaaagagaga ccagacggac gagcgcaaga gtggagttgg      420
```

```
agttggagtg gagagttggg cttttttgtgg tcggtttgtg gtcgttttat ggtcgtcccg    480
acatcgtcgg tcgtagtttg tgtccgtttc gccgtttgtg tccgtttcgc cgtttgtgtc    540
cgtttcgccg tttgtgtccg tttcgccgtt tgtgtcgttt cgccgctcgt gtccgtttca    600
ccgcttgtgt cgtttggcct tgtgtccaaa acacagactc caaccaccaa caccaaccac    660
caacattgcc ctcttctagc cattgacact gctctcgatt actcactgcg acagcgtctc    720
ctcgtcaccc cgtcacccc tcaccccgtc acccgtcac ctgatcacca gcttgacccc    780
atcatcccat cacaaacacc atcaaccgct tcatctgact cccaccgact cacatttgac    840
tctgtgtttg actctgatct gactctgatc tga                                  873

<210> SEQ ID NO 27
<211> LENGTH: 2067
<212> TYPE: DNA
<213> ORGANISM: Artificial Sequence
<220> FEATURE:
<223> OTHER INFORMATION: YALI0_C14476g
<400> SEQUENCE: 27
atgtccgagc tggatgagat tcgagaggac tacctgtacg ctctggagga gctgacgggg    60
gtccagaagc ccatcatcac caacctcacg gtgattgccg aggaaaacag acacgctgcc   120
aaggccatta cccgagccat tgaggagcga ataagtaagg tgagtagcgg aggaaccaca   180
atgaggagat gccgacgaca aggacgagat caaaggacac agagcgacct gaaaacaccg   240
gtgccggcca cacggtacgc cgactcatgc tctatcaaag agtgacggtg tttaataagg   300
cgtagggtgt catgttggtg atcatgtgct gcgactgtgg ttatgggtgg cgttaacatg   360
aagcttggga caggttgacg attgattttg caacgtggca catgtataca acctctgatc   420
catcgattgg cttggtccaa ctcgtgtgat ggagtttgta tctccaggct gtcgttatgt   480
cttcgagaca acgatgtgat tagtgactga cgagagatca tactgcgaat gacgacacat   540
caataatctt ttccatatgc caccgccgcc tatatctatc tctacatact aacccagtgc   600
gctccagagt acaagctgcc agcaatgtac ctgctcgact ccatctgcaa gaacgtagga   660
gcaccataca caacctgctt cggtatcaac ttgtaccgca cttttgccga cacatacacc   720
caagttcccg aatcgatccg acgaaaactg atcgagctgt acggcacctg gaaaacgttg   780
ccggccacag gcggcatgct gttcccagca gaacccatgc gaaagattgc ctctttttctg   840
gaacgaatca acgaagtcac atcacgggcc acgccaaacc ccgcaacccc caacctgggc   900
acccccaacc ccgctactcc acctctaggc actccagttc ccggccaagg aggtttcgga   960
gtgcccaatg cgggcctgac acaaccccag ctgctggaga agtgcagcca cgtgatcgac  1020
atgacttctg accgtctaca acatattcca ggcgacgtcg atgccaagga acggattcct  1080
gtcctcaaac agctacaggc cgttcttcag tcccaggcca ttcctgtgtc gtacctgtcc  1140
aatattgagg ctcaattggc ctcttctcta gcccatgagg agaagaagct tgctgaatac  1200
gaagaaaacg agcgactaaa gcagcagcag cagcagcagc agcagcaaca gcagcagacg  1260
acaccaagca acttgctagc ttccctacaa gccgctggct tgttagcagg aggtatacct  1320
ggtggaatgc ctggaatgcc tggtatgcct ggaatgcctg gaatgccggc tatgcctggt  1380
atgcctgttc cacccatgcc tatgcctggt atgccttttc ccatgtttcc taaccttggt  1440
actgttcctg caccggacat taactctctg ttggcctctg gtgcctcttc tttgctgtct  1500
tccttggagt ctaacgacgt ggaactttct acgtcttctc tgctgaagcc tcgcccaat  1560
ctggtattca acctttacgg caagatgccc aaggtgtgca acatttgtgg gcggcggttc  1620
```

-continued

```
cgagataatc aggaccatgc ccgtatgcag cacatggact ggcatttccg aatcaataag    1680
aagatgcgcc aggacgaggg acgagctcag aacagaaggt ggtacctggc cgagcatttg    1740
tgggtggcag gagagcaaaa ggaggaaaaa gaagaaaagg tgcaaaaggt ggacatggaa    1800
agtgtcaaga acaatgggt tctggctccc agcagtgctt ctaagaagaa gcaggtttgt    1860
cccatttgca caggaggctt caacacggaa ctcagtgatg aagctgagga ctgggtgtgg    1920
acagacgcgt tcaggttgg agataagatc ttccatgcca cctgttatgc tgagagtgga    1980
aagctggcag agagcctggt gagaaagagg agaggagaag atagagaagg aaggacaaag    2040
agggagaagg tggagctcga ctactaa                                       2067
```

<210> SEQ ID NO 28
<211> LENGTH: 3203
<212> TYPE: DNA
<213> ORGANISM: Artificial Sequence
<220> FEATURE:
<223> OTHER INFORMATION: YALI0_C15532g

<400> SEQUENCE: 28

```
atgaagttca gcaaatttgt cctgtttggc ttggtgtttt tcaccacagc caattctcac     60
ccctcagagg cttacaaatc catcaagtcg attgtccatg agcacagctt gaagttggag    120
cacgtcatta gcaaacgaca ggtctctccc gataccaagt cattcattat ttccttccct    180
ggtgcttcaa ttgacgacat ctcccagcac atttcttcca tcgacaacct ggtcgcagga    240
aagtccgaac aaggcatcac tgctgacttc gatttgtctg aaagtcctga aaaccctacc    300
attattggag ttgcggctgt actcgatgag agtgtggctg aagcagtgga gcatcttccc    360
tttgctctcg ttgagcctga cggaaaaatt tacttgtggg actcactaga gcgaaattca    420
gatggtgttg tctactgtga tcagctccct ggttatgggc agcctggatt tgagcccttc    480
tatgatgatg atctgttggc ggaattgtcc gctcctactg gtgacagcaa agtccaagtg    540
gctactatta ctactgagat cattggtgta acatccgttg atggacaagc tacgaccatt    600
acatcaacca tcacctttac cagtactttg agtgagtgtg tgaggtaata atgcgttgtt    660
acgaacacct ggagcatggt cgctggttat tcatcctgtc tgttgggttc taaagtcatt    720
cactgctggt ggctagaaca agcggtgcat atttaaggtt gcgataccat aaataagctt    780
atcgagacag gatggtgca gcacgaaaat tacccttctc accatactaa cacagaacac    840
gccggataca cccgtgagta aagcagagag cagagagctt ttaagcaaaa aaaaaaaaaa    900
atcacatttt ctgctttcgc acacacaatg gaatcccatc taacacagta ttggccgaac    960
ccaccacagc tggtgctagt gagtacctca gcacaaaccc ccgggcccac catcctacta   1020
acacagaagc cgacgcaaat gacaacaaca acgtcaatgt caacagcaac aacaacattg   1080
atgacaatga tgtcattacc ggtgaccgtg ctgaggccgt gatcgtctac actgacgacc   1140
aaggagagcc gtgtgtggcc attcgtgagt atccgttatg atgacagaga ataagtttgg   1200
cttggcgatg aagattttga gctataagtg gcgcattgct cagtcgacag agcgctctaa   1260
tattttggca acccttcata gtaattcata ctgacacagc tacacccaca tacgagccta   1320
cttgcggctg taccaagaca tactatgtga ttcgaaagct caccgaagat cacacaatga   1380
tcagcacaaa cagtaataaa ggtgagtaag aacatcatgg tttattgagt tgaaaaaaac   1440
ctaacacagt ctctcctaca ggctccaacc atggcagctc tggatcgaac ggaaacacag   1500
ctgtcgacaa cggcaacaat ggtaacagca acagcaacga caatggcaac aacatcaacg   1560
```

| | |
|---|---|
| gaaacgacaa aagtggcaac gatgtcacct ctttcatcga tgacattcgt aactcaactc | 1620 |
| ctaccgcagt cgagtccact caattgtctc aatcatctgc tagctcgtca cccattctta | 1680 |
| ccaactcgag tcagtctttg gattcaattg cattttcgga ttctcaattc atcagtccaa | 1740 |
| ttgtgttatc tacaacgccc aactctggca gtacaacgcc ttctaactct ggtaccatta | 1800 |
| ccggctcgga ggtgacctct tccacctctc ccacctcttc tagtggctcc agcagttcca | 1860 |
| gtacgattct cccttcaagc tcttccgcta gcccttcaag taggccttca agtagctccg | 1920 |
| ccccagtttc tctagctct ccagtttcct ctagctctcc cagctcttcc aaccccggtt | 1980 |
| cttccagctc tagttctccc agctctagtt ctcccagctc cagctccagt tctcccagct | 2040 |
| ccagctccag ctctagttct cccagctcca gctccagctc cagctctagt tctcccagct | 2100 |
| ccagctccag ctctagttct cccagctcca gctccagctt cagctctagt tctcccagct | 2160 |
| ccagctccag ctctagttct tccagctcca gctctagttc tcccagtgcc agctcaagct | 2220 |
| cttccagttc cacttctctc agttccagtt ctagctcaag ctcttcctct agctctagcg | 2280 |
| ctccccctccc acttgttacg caacaaggca tgccttgggg tctctctcgt atttctcacc | 2340 |
| agtcgcctga gatggctccc taccaagatc ccatggtagg agaatatatt caccaacagt | 2400 |
| ttgtggaccc caatcccaag gtggtcgtgt acgtcgttga ttcaggcgtg aatatcaatc | 2460 |
| acgataactt tgcgaccaaa cccatttggc ttgcgaatta tgctgacagt gacgactctg | 2520 |
| atgccaatgg ccatggaaca tttgtggcag gtgttgtagc tggcaccaga tcaggtgtgg | 2580 |
| accccaacct gcaagtcaag agtatcaagg tattttctgg cgagactacc gacgcgtcta | 2640 |
| ttcttatgtc aggtattact cgtgccatta atgatttcaa ggctgacacc actccaggta | 2700 |
| agaaagctgt gttgaatctg tcgcttggtg gagacgtatc tactgcgtta gattctttga | 2760 |
| ttaagcaggc tgttgctgaa ggtatgtttg ttgctattgc tgccggaaac aacatggaaa | 2820 |
| atgcttgcaa caattctccg ggacgagttt ccacctctac ccctggttct gttacggttg | 2880 |
| gttcaattga cagaagcgac aaaattatctg tttacgctgg aaacaacaag ggaactgctt | 2940 |
| ggggaacgtg tattactggc tttgcccctg gttctgatat tatgtcctct atgaatactc | 3000 |
| ctaatgatgg atatggaatc ggatccggaa cctcatttgc tactcctatg gtggccggaa | 3060 |
| ttgccggcta cttgatgagt caggaaggta ccaaagatct aactcctgcg gagctcgagt | 3120 |
| caagaatcat gaacagcaat gatggtagaa ttcagggtga tctgaagaac tcacctaaca | 3180 |
| agatagccta caacggcgta tag | 3203 |

<210> SEQ ID NO 29
<211> LENGTH: 1311
<212> TYPE: DNA
<213> ORGANISM: Artificial Sequence
<220> FEATURE:
<223> OTHER INFORMATION: YALI0_C16148g

<400> SEQUENCE: 29

| | |
|---|---|
| atgagactca tccctctact tctcacaggc gcctacggcc tctccattcc cattgcagag | 60 |
| gtccagaact cccccgagga tctcagctct ctcgacaagc gacagacccc tccggaggtg | 120 |
| tcccagattg tcgacgcaac taaagacctc acccaggacc ctgcctggca ggccattggc | 180 |
| caaatgctga acggaggcaa cgctgccacc atggatacgg aacaaaagtc cagcgaggct | 240 |
| gctgctgctc agaccgagat tcagagcttg ctcacaaagt actactcgtc catcccaac | 300 |
| tggcagagca ttgtgagcac tgccaccgcc ggtcttaacc agggcagtgc aaacgggccg | 360 |
| gccggaggta acggcggaaa ccctgtaaac gggggtcctc aacagtccgg caacaacctc | 420 |

```
atggaccagc tcatgtccgc acaagcagcg gcatctcgac agctcgcttc tgcatcggca    480
gcctctgctg ctcgctcttc agcgcagtcc cagcctcctg cccccgccac agccgtggtt    540
gttcctgcca acaccatccc cactagagag cccgacggaa tcgcaggcac catgcccggc    600
attgtggtcc agagccagtc tcaaaactca cagtcttcga gctccccaa cactgcccct     660 gctggtaaca ttgcaggtac acgaaccggt ctcgtggtgt tgcagggccc cacctcgaca    720 ttgacccta gcagcacacc ccccgcaggc aacattgccg gtactcgatc tggactcatt     780
gtgttgcaga acacaaacac agcatcttct tctgcgtctt ccagaccacc ggcaccctcc    840
acggtcactg tgagccccag cagccccgaa acattgctg gaaccagatc tggttttgtt     900
gttgttggaa acactgcctc aagcagcagc agcagcagca gcagcagcag cagcagcagc    960
cccagcggtc cctccaccgt gacgcaaacc gcagctaccc ctacagatgc cactggagct   1020
cttcttcagg gcattgctgg tcttttgggt ggaggagcgc tcggaaacct cggcaacctg   1080
gtcggaggaa gttccatcgc tactcctacc ggtggcactc ttcctactgc tcctgcttct   1140
ggttcccaga gcgaccatcc acaacccgga cctgatggag tcgtgaccat caccattacc   1200
cccggcgcca tgttccccaa ggccaccacc tttgtcagcg gcgcagttcc caagggcgcc   1260
gctcctctac tcgctgtatc tctcgctgcc ctcatccctc ttttgttgta a             1311
```

<210> SEQ ID NO 30
<211> LENGTH: 3411
<212> TYPE: DNA
<213> ORGANISM: Artificial Sequence
<220> FEATURE:
<223> OTHER INFORMATION: YALI0_C16247g

<400> SEQUENCE: 30

```
atgcttctcc gatcacttct atttgcgtcg ttgcaaatct cagcagctct cgcccagact     60
gctctgacaa gtcccatcac ctctctggaa gtacatatcg ctcgaaagcc gaccgtcaaa    120
aaagcgttcc agtggaacac ctgggaggct gagatgggct tcgcatttga taatgtcact    180
gcttcagcca tccaaagtgg agactacttt gacttcacca tcaaaggccc tctcgcccct    240
tactccgagt cttctgaggt tcctctgacc tacgattttt acattgagac cgacaacaag    300
gagcagttgt tccacgtgac tgctactgac gacaaccact cctttcgagc caccgcaacc    360
gacttttttg actccccccc aggtgagact ttcaaccttg ctggaacttt cagtgtggac    420 ttttaattc ccgcgtctgc gccccttgtg gacagcgtct ttaccgtcgg ccctttcaaa     480
agcaccattt ctttttattct gcctactcct ttgaccacgc aagccaaggg tgagaaggtg    540
aaagtccaaa tgacacgcaa gggcacttac ctcattgccg agatcttctc tttggtgtac    600
cagtctgctg gtcaacctgc ccttcccaaa gatggtaggt tcaacagact acaggccacc    660 tctgggcta catttgagcg ggaaccgagc catccctggg gctttgttga tgcgtactat     720
atcgatgtca acttgaagag atacgatggt gcagggtccc cgattgatgc agactttgct    780
cctccgggaa acagttttgt caatgcgtcg gagatgtatt ctcatctaga ctggtacaaa    840
atgcctgcta ccctccaa ggcggttgga ctgtatgtgt cagcccgtag taaaatgagc      900
gggtccgatg atagctcttg tttttactac actggtaact accgatacgt tttttcattg    960
agtcccatct gtgttgccca gggtcgagga gccgagggct tgcccaacgg agagggtttg   1020
atagcagttg acgttgttgt tccgttggct acaagttctg aggtcaccac aagtagtgcc   1080
gaggctactt ctgaggtgac caccagtgct gatatctttt ctgaggtgac ttccagtact   1140
```

```
gaagctactc ctgaggcgac ttccagtgct gaggctacta ctgaggcgac ttccagtgcc    1200
gaggctactc ctgaggtgac ttccagtgcc gatgcctttt ctaatgtgac ttccagtgcc    1260
gaggctactc ctgaggtgac cactagtgct gatccctttt ccaatatgac ttccagtgct    1320
gttccctttt ctaatgtgac ttccagtgct gatagctctt ctgtggtgac cactagtgct    1380
gatccctttt ccaatgtgac ttccagtgct gatccctttt ctaatgtgac ttccagtgct    1440
aatagctctt ctgtggtgac cactagtgct gatccctttt ccaatgtgac ttccagtgct    1500
gttccctttt ctgatgtgac ttccagtgct gatgtctctt ctgaggtgac cactagtgct    1560
ggtccctttt ccaatatgac ttccagtgct gttcccattt ctaatgtgac ttccagtgct    1620
cacagctctt ccgagatgac gaccagtgcc gaggctactc ctgaggcgac caccagtgct    1680
gatagctctt ctgtggtgac tactagtgct ggtccctttt ccaatgtgac ttccagtgct    1740
gatccctttt ctaatgtgac ttccagtgct aacagctctt ctgatgtgac ttccagtgat    1800
gatgtctctt ctgaggtgac caccagtgct gatatctctt ctgaggtgac ttccagtgcc    1860
gaggctactt ctgaggtgac cacaagtgct gatagctctt ctgtggtgac cactagtgct    1920
ggtccctttt ccaatgtgac ttccagtgct gatccctttt ctaatgtgac ttccagtgct    1980
aacagctctt ctgatgtgac ttccagcgct gatgtctctt ctgaggtgac caccagtgct    2040 gatatcccctt ctgaggcgac ttccagtgcc gagactactc ctgaggtgac ttccagtgcc    2100
gaggctactt ctgaggtgac caccagtgct gatatctctt ccgaggtgac cgccagtgcc    2160
gaggctactc ctgaggcgac ttccagtgct gaggctactc ctgaagtgac ttccagtgct    2220
gaggctactc ctgatcctcc cagtagtgtc gagacttcca gtacatctga gagtgcatct    2280
gatgatgaga ctactagtgc ttcgactacc tctgaggaag ctttaaccgt gtttgtgacc    2340
gagcaagcaa taccgtgtc tgtgatcgag caaacaacta ccgtctcttc gtctgaacca    2400
accgcatctg cgtctgaacg agaaccaacc gtgtctgcta ccaactcgtc tactgccgct    2460
cccagaccct catctagcac caaggtcttc ataaacatca atagcactga tcctgtcact    2520
gggaaggtca ccagagcgcc cgtgactagt gctttgacca cctctgagga agctgcaacc    2580
atgtctgcga ccgagcaaac aacagccgtc ccttttatcta aaccaaccgc atttgcgtct    2640
gaacaagaat caactgtgtc tgccaccaac tcgtctacag cttccggacc ctcatccagc    2700
gccaaggtct tcataaacat caatagcact ggtcctgtct ctgataaggc caccagagcg    2760
cctacgttgc ttttaggata caacactact gccgcagaca gcggtaatca tgtgactgct    2820
accatcactg ttactagcac ttgtgccacc gccactgcca ccgtaacaac cggctgcatc    2880
actgttgtcg acggcgtcac ctcttccttc actgtcgtag ttgtccctag caaagctggt    2940
tctgggtctg atggttcttc caaggctgat tctactgcct caggaataca ttctggagtg    3000
attgactccg agtctgggga gaggcccaat gccgagccct ggtcagcaga gagcaaatcc    3060
gagtctcatt ttggatctac cagcacagaa aagagcgatt ctcagctcgg agacatttct    3120
gactcctctg atgttgctcc agacgttcct gatgttgctc cagactcctc tgtgttgct    3180 tccgacttct ctgaagctgc ttacgactca gcagatgttg gatattcctc tcgtgagtct    3240
attggcctgt atttgcctgg atcttcctct cgaccttcct ctggacccttt ctcgggcccc    3300 aacaactcct cctccatcag acccactccc tctactgatc aggccaacac tgcgtcttcc    3360
cttactgtcg gtgctgctgc agtccttttta ttagctgcca tggtggtcta g             3411

<210> SEQ ID NO 31
<211> LENGTH: 1428
```

<212> TYPE: DNA
<213> ORGANISM: Artificial Sequence
<220> FEATURE:
<223> OTHER INFORMATION: YALI0_D15752g

<400> SEQUENCE: 31

| | | | | | |
|---|---|---|---|---|---|
| atgtcaaact | tctttgaaca | ctctccggcc | caatctccag | ccactacaaa | ttcttccgtc | 60 |
| accaacccca | tccatcgaca | atcctcgtct | tcttcgttgc | acatgatggg | atatcggaat | 120 |
| cagggtactg | ctggtccaac | ctcggctacc | ggagccacta | cccccaccca | tggcccacc | 180 |
| acccatgctc | ccgtgcctat | ggttcccgtg | ggtctggatt | tgggcggaac | tacgtcagca | 240 |
| ccagcagcaa | gcgccacggg | tggactgcag | agcaaccggc | agtctccatc | gcctctcaag | 300 |
| cgagcacaaa | gccgacattt | tgatatcgac | acaaacaacc | cggccaactc | ggcgtccaaa | 360 |
| cggtcgtcct | tctcttcgac | cacgtcagcc | tcctctgtgt | ggcccggaac | aagtgccact | 420 |
| gccacagatg | catcgcggac | tacaactccc | tactacaacc | tgacccaggg | aatggccggc | 480 |
| ttaggcttgg | gaggccctat | cggcgtggct | atggggtcgg | gggttcctag | cccccatcct | 540 |
| ggaatgggaa | gtagtccttc | agttgtacct | ggaatggcac | ccatagcccc | caccctgtt | 600 |
| gcacctaccg | cggtacatcc | cggtctcgct | gacgacgacc | ttatcccac | agccatcgtc | 660 |
| atcaagaaca | taccgtttgc | catcaaaaag | gagcaactgc | tggacgtcat | gacccagttg | 720 |
| cggttgccac | tgcccctacgc | tttcaactac | cactttgata | acggcgtgtt | ccggggcctg | 780 |
| gcattcgcca | atttcaccac | tgctgacgaa | acggcagctg | tgattggctc | gcttaatgga | 840 |
| cgggagatcg | gtggtcgaaa | acttcgggtc | gagtataaaa | agatgctccc | tctcgccgaa | 900 |
| cgagaacgta | ttgagcggga | taagcgagag | cgacgcggcc | agctggagga | gcagcatcgt | 960 |
| ggccagggtg | gccagggagg | aggaaggcgg | aacgtcagtg | gtggtcatac | tcagcagcat | 1020 |
| ggaggtgccc | agcctccaca | gcagcagcag | cagcagcagc | agcagcagca | gcagcagtcc | 1080 |
| aaccttaccc | aatctggttc | tgtgggccaa | cccgcccaca | ctcttccctc | acatgtcact | 1140 |
| cctcacatgt | catatcccca | atactctcca | tcacccacac | ccacaccccc | tcctgccccc | 1200 |
| aagctggatc | tcaacgaccc | tgagactcta | gagtttact | cccagctcct | gctgttccgg | 1260 |
| gatgacgcca | aacgaacgga | aattgtctac | tcgcaccccac | tcctattgcc | ccagcaacgg | 1320 |
| cagatagtca | tgtcgttgtg | tgaccagctg | ggcctcattt | tcaactccga | ggcaaccggc | 1380 |
| cttgtggtgg | tgacccgaca | gagacagtat | acgaatacc | agtattag | | 1428 |

<210> SEQ ID NO 32
<211> LENGTH: 3351
<212> TYPE: DNA
<213> ORGANISM: Artificial Sequence
<220> FEATURE:
<223> OTHER INFORMATION: YALI0_D17820g

<400> SEQUENCE: 32

| | | | | | |
|---|---|---|---|---|---|
| atgagcccaa | agatataaa | gccagtgggt | ctgggatcg | ctctacccat | acaagacggt | 60 |
| aagatggact | ggactgatcc | cagctccggc | tacaacttca | tccaaggtga | cttttttggag | 120 |
| gtgtcaaaca | ccatcgcccc | cgatgccatc | ggtcgcggtg | cacttgacat | cacagctatt | 180 |
| ccgactgaga | acgatcttac | tgttaagctg | tttgacgagt | tttgccatga | cgacatgtac | 240 |
| gaatcggcga | ttgattccgc | ttcgcacaac | tccgtcaact | caacctcgaa | tccaacattt | 300 |
| gggtccccct | cgttggcgcc | gattgattca | gcccccatt | cagccaacgt | tacgcctcag | 360 |
| agcgtattgg | ctcagcatgg | actgatgggt | gctccggctg | ttcctgagca | gcagcagtca | 420 |

```
aacgtgcaca tccagcaaca ataccagacc caggtccata ctgaggatca ccagccccag    480
caagagcagg cccagactcc gtccttggct caccctcagc ggcaacccca tttccagaac    540
ctgcaaagtc agctagatca tgaacagcag acccagcatc aatctgacgc cgagcaccaa    600
acccaccacc agcaaacccc ccaccccgcaa acccaccacc agcaaaccca ccaccaacag   660
cagcttcaag tcgagttgga gaatcagact acgaatgagc ctccggttgg tcactatgct    720
cagcaactgt actctgcgga ccatcaactg cagcttcagg ctcacccgtc tgggcatgct    780
gctgtccagt ctcagctgca agttcgcccc cagacttctc tgtttcccaa ccatgatcat    840
gctgagtttg ttcaatcccg gtctcgggct cagcttcaag attctcagct ggttcatctt    900
cagcgaccag gccagactca gtttcatcat catcccactg ctcagtctca tattcaaact    960
cagaatcact tgaaccacgg cgatcctcct cagacaatgt ctggtcagat tcattttgat   1020
cgccagactc agttgaaact ggagttcgag ccacatccac atcctcctgt tcagtctcat   1080
tctggagttg gcatgcaatc tcatgctgag acttttcaaa atggtgctgc tcaacctcaa   1140
ccgagtgctc tgcagactgg ctctgcgcag ccttctcagg ctcagaacca acatccttct   1200
gccgtatcgg cgcagtcgac acccgaaact gtcccctcgc cctgtctgaa ctctccgccc   1260
gtgcatgcaa atgataccte tcctggaacc gtttctgccg gaaagcagtc taccactcct   1320
cagttccctg ctcagtatag ccagagtctt gatcagagta gtagtgagtc tcagctgcaa   1380
cggcagcaac tggttgtcca gaattcgtct ctcatttaca accagcagct tctgaactca   1440
ccattccaag ttccccaaca agcacaattc caaccccagc tcggagaacc gtcgcaggag   1500
ctgaccatgg ctcagtttcc tgctcaacaa gtgatgtctc cggtaactcg cacgcttcag   1560
tttcacgtgg gtgctgctcc ttctaacgcg actctgtcta accaaccatc acctaaccag   1620
ttccagatga ttgtcgctcc ggcagctccc atcggctttt cctctcgtcc ttggagaaca   1680
gacccgtttc aacgatggta ttctgcacgg atccagatgc cgttggaacc tgagacggca   1740
gaggatgtga acatctgcaa ccggcttgag cgagcgcttg ccaaggtcaa gatctgcgag   1800
gacctgcagt actcgaccgt cagggcgtgg gatatcaacc aacctctgac gctcggacag   1860
tacgacgcca tgaacaagtg tgaaggtgaa atcgtcgagt tgtcacacca tcgacttgac   1920
gagcgagagc agcgagagaa ggatgatgag aagctggctc tggagtgttc caggaacgag   1980
ttactggctc tgcatcttcg aaaccaactg atgcagttca aactcatgtt tcatggccac   2040
cctcatttcc acgcgctccg agtgtgtaac gaaacctgtc ttacgcgata ccctgcatat   2100
cccccctcctg ccaatgctgt ggttggagta gctggaagta atgcttcgac cgacaatatg   2160
aagctgtcac cgccaacact cctagaaccg ctctcaccac aggagctgcg gcggctagaa   2220
cagctcgagg aagaaaacga aaacgactac tccaactttc cttgggccca tagattggtg   2280
agcttgacac agcttgagcg atggaagcaa cgaacgcaca ttgtcggtga gctcttctac   2340
tcgtcccgac caatacacgc gaggcagata cgcaacattg tcaggtttct ggaagatgac   2400
tttatgcaca tcaaggtgac ctctcttcgc gcccgcgagg tactccggga gcacttcaag   2460
aaccccctacg tcactctgtt tgaccacctc cagcgtcaga gggtacctga acagaggaat   2520
ccccacatct accagtacgt tgagtcgatc atggacaatg tctacctgtc ggcctactac   2580
cgagtggagg ctaagaaggg cacacggaag ctggatggcc caggaggcga atacattcca   2640
gacgagaagg atattggaga gcggtactgt gggatatgtg acaagtggtt caagacgcga   2700
aaccacaatt gggcgtccca tatgacatct actcacggtg tctgctctgc aaccaagtcc   2760
atctacccctt tccctctagc tgtcattctc ggcataacctt ctacgaccca gaaggaggat   2820
```

```
gggcttgtgg tccaccagaa catcatcttc gagactaact ccgacggcga tcttcagatc   2880
cagaacgaat cccagccacg tcaccatctg ctgcccgaca aggacatcaa gctcagtggt   2940
ctgtgtccca tttgctgcca ctatgttccg ctctattgca agcgaggtgc cactgtctgg   3000
accacctggt tccgacacca ggacaagcat atccggagt tcaaccagga acgaaacgga    3060
ggtgtggctg tcaaccacaa caatccacga acaacaaga cacgaaaaga gcagatttgc    3120
aaggagcgga tgcaggcctg gagacagcaa caggaggaac ggatgagcaa gcgactcaaa   3180
aacgacgata tggcgttcct ggaggagggt gtggttgtcg ataatgttca aaatggcagc   3240
tggctcaatg aggagtttgc catgacccag gccgaggtca cgttgacgta ccagatgggg   3300
tatcaggagt ctgagcccgg tattgggagt ggcattcagg actttttta a             3351

<210> SEQ ID NO 33
<211> LENGTH: 2907
<212> TYPE: DNA
<213> ORGANISM: Artificial Sequence
<220> FEATURE:
<223> OTHER INFORMATION: YALI0_D18381g

<400> SEQUENCE: 33
atgattgcaa aaatacccct acttccgttc gtggtaggag ctctggctgt gtccaactcc     60
accgactcca ctctcaccga ctccactctc accaactcaa ctctcaccaa ctcacctctc    120
accaactcaa ctctcaccaa ctcaactctc accaacttca ccaactctac ccatgttccc    180
ttcacttctc ccgatttcta tcctactccc gaaattggca ctctggacgc ggacaagcgg    240
tggagagctg ctctgaacga gtccctggag attctgtctc agctgactct tgtcgaaaag    300
gtcaacatca ccacaggtct tggttgggga ggaggcacct gtgtcggcaa cactggcgga    360
gttcccagac tcggtcttaa gggtctctgt ctccaggacg gacctctggg aattgctcag    420
accgactacg tgactgtttt ccctgcgga attgccatgg cggccacctt tgacagaaac    480
ctggtccacc agagaggcac cgccattgga caggaggcca aggccaaggg agtcgatgtc    540
catctgggac ccgtcgtggg acctctggga cgacacgcaa cgggcggccg aaactgggag    600
ggcttttctc cggaccccta cctggccgga aagctcgtgt ccgaagctat ccgaggtatc    660
cagtccgaga cgtcatggc caccgtcaaa cacttcattg caatgagca ggagcactac     720 cggctctact ccgagtgggc tcgtttcgga ttcgacaacc tcaccacttc ggtatcctcc    780
aacattgacg atcgaaccat gcacgaggcc tacctgtggc cctttgccga cgccgtcaag    840
gccggagtgg cttcagtcat gtgttcgtac cagcagatca acggctcgtc gggctgccaa    900
aacagcgcca cgctcaacgg caagctcaag tccgagctcg ggttccaggg ctttgtggtg    960
tcggactggc aggcccagct cagcggagtg tccaatgctc tagccggact ggacatgagc   1020
atgcctggta acgacgtgga cggaaacatc ttctggggac cggacttgac caaaatggtg   1080
gctaacggca ctcttcccga gtccagactc gacgatatgt gctgcgaat ctctcacagcc   1140 accatctaca caggcatcga cgaaagagag cccaccttct ccgccttcac tactgaaacc   1200
tttggcaacc ccaaccccgt gcttatgttc aacatcaact acacctccac cttggtcaac   1260
ctccatctgg acacccgaac cgccttttct tccgtgtgg cgctggaggg agccgaggct   1320
gcagcagtcc ttctcaagaa cgacggaatt ctgcctctgc agggccccga gaatgtcgga   1380
gtgtttggag tcggctcgca aatcgggcca aagggagcct actgcgggtt ctccatgcaa   1440
tgctcggatg gagctctcat cgagggatgg ggaagtggaa ctgccaaccc aacagagtac   1500
```

| | |
|---|---:|
| acttctccgt acgaagcact ccgacaacga gccaaccaag ctggaggcca cgtgattgga | 1560 |
| accaccgagt cctggaacat gacgctgcct ctgatcatgg ctgacaactc ggacgttaac | 1620 |
| atcatctatg tgctgtccaa ctccggagag ggaggttcga ccgttctgga caacatggga | 1680 |
| gacagaaaca acgtgtctct gtggcacaat ggcgacgaac tgatcaccac tcttgccaac | 1740 |
| agctccagaa acaacattgt cgtcgttacc accgttggtc aggttgattt ggagccttgg | 1800 |
| atctcgcatc ccaacgtatc ggccgtggtt ctcactggtc ctgctggagc ctatggaggt | 1860 |
| aaagccatgg ccgaggttct ctatggagac gtcaacccat cgggaaagct gccttatacc | 1920 |
| attgccaagg accccaaga ctacattccg gtggttgtgg acattcccga agatggagct | 1980 |
| cctcaggcct actttgatga gggtgtctac atggactaca agatgtttga caagctcaac | 2040 |
| aagacagttc ggttcgagtt tggttacggg ctgtcttatt cggatttcga gtttggagac | 2100 |
| ctggatgtgg ttgtagacga gttcattttcc gagcttcttc cttctcctcc tcggcctatc | 2160 |
| attgttgaca gcccagcag caccagctcc aactcgtccc acggcgatct caaggctccc | 2220 |
| aagggtttca gcccattcg aggagttgtc tatccgtgga ttgacgttaa ttccctgact | 2280 |
| gccggcgaag ctctttcggg agtgagtcct gctcttgcca cttgctgggg tctaggtaaa | 2340 |
| cctgataccct gtgctgttcc cgccaagcac gagactggcg atgatgacaa ggactccaag | 2400 |
| tctgacgata gaccaagag agacaccgag tcggatgctg ccgatgatga aattgaaaca | 2460 |
| gtcagcacct ccaacgaaac cgccgttgaa accaccattg gaatgaagaa cacctccgag | 2520 |
| cccttccact tgccaacgg aacagggacg tcaacaaacg ccgccggagg agttggagga | 2580 |
| aacccatctc tctggaaaac cgtcgccacc gtgtctcaca ccatccgaaa cctcggtccc | 2640 |
| tatccaggag ccgcagtcac ccagatgtac attgccttcc ctcaggacga cattgattcg | 2700 |
| cctctcattc aacttcgggg atttgacaag actcgggttc tggacgtcgg agaactcgaa | 2760 |
| actaattcct acgacatctt gtggagagac ctggctgttt gggacgtggt catccagagc | 2820 |
| tggagagtcc agagaggaga gtacaagatc tacgtcggca actcctccag agactttgtt | 2880 |
| ctcatcgagt cctttactct ccagtag | 2907 |

<210> SEQ ID NO 34
<211> LENGTH: 2421
<212> TYPE: DNA
<213> ORGANISM: Artificial Sequence
<220> FEATURE:
<223> OTHER INFORMATION: YALI0_D19822g

<400> SEQUENCE: 34

| | |
|---|---:|
| atggaaggcg tggtggagaa cacaaacaag atcattacgt tgattggcga cggctggctg | 60 |
| gtggaaaagt cggcatttgg ggcactcaag gtggtggatg accgtctggc cattctggag | 120 |
| aagaatcaaa aggcctatga ggaggctttg agacagcca gttcgagaa ggagggccta | 180 |
| cctgtgtttg agattcgaga ggagctggac gacaagggaa atattgtaag ctcatctgtg | 240 |
| gaggagtttg ataccggtaa agctgctaat cttgagaggg ttatcaactc catgggagac | 300 |
| cggaagaaca tcagccatga cagcgacaag atggatgaag acgacgatga tggacacaa | 360 |
| aaggaggatg atctggacga cagcttcgac ggtgcatctc tgcctatgat ggagattaga | 420 |
| gaagagctag acgacgacgg gaacatcatc gagagtaaag tggaggaggc tggaaatgag | 480 |
| gacacaaatg agattgagaa gcatctgaag ctgctcaacg agctagccaa aaagaagttg | 540 |
| gatgcaaaga gtactacaga gcctgctgtc aaccccgaag ctgctaaatc taccaaacca | 600 |
| gaaactgcta aacccatcta tggtcctcct ccgccccca actatggtcg aaaggttgga | 660 |

```
ggcggcattt tcaagcccca agttactcct ggagtgctgc gacagcagag tcccaagatt    720
gaggaactta acgacgaaga agaacaagtg gaggacggca aggataacaa aaagactaca    780
gagcccgaaa aggagaagga caatagtcct acaatcaccg atgtcacgga agatgactcc    840
agtgactctc tttccagctt gcagtcgtct aactcgtcta tcacttctaa ccctgctgtt    900
gcgcccgagt cgcttcttga actggagctg ctagctgacg atgctatgga cgaagaggag    960
gacgatctgg aagccgatga cgacgactgg gactttgaag acgacgagtt agacgacgtg   1020
gaggccgacg aagacgacca tgggcgtacc cggggttcca tgttcccagg aatgtctcag   1080
gatcaactga gaagcattat ggagggcaga aaaaccgctg ctgctgagtc gagacctcct   1140
gctgcttcta tcgtgtctga tatcaccgaa tcaccccagc ccgtttcttc accagttcct   1200
actactgctg ctgttccaaa gagcagtttg aagtctgcat cttccaaacc caagtctgta   1260 tcgtttttcca acaatctaca tatcaaacga attcccaaca aggagaccat caagaaccag   1320
gaacgtcagg agatgaagaa gcagcagcaa cagagcagat tcaagcagga gctggcccgg   1380
aaggcccctg aacctgaaga tgacgacgat gaagatcata ttaccgtgcc tactgtctcc   1440
gatattgctg aacgagctgc cccagaagac cctgtgactg cccctgctcc tcccaagaag   1500
atgtcgcgat tcatgatggc tcgaatgggt aaagatgagg ctcttgcgcc caaacagtcc   1560
cgtgataccc aatcacatga tcagacaaac cccaaggatg gacgcgtcat aagaggcatc   1620
cccagtgttg gtgctacttt cccacctact cttgacaaag atattgctga ctacacagag   1680
tcaatgaagc tgacccccg accggcttct cagggacacg gccatgcaca tgggcatgtg   1740
agatcacgag caatttctgg gaatgtttct gagccagctc cagccgagga gaacgcccct   1800
tccaaggttt tcatcaaggc tccagtgtct ggacttgctc aaggcaagac taacgacgag   1860
cctcgacctc tgaccgatag cgacaaggag cacgatgacg ccatcatgaa ggaggtcatg   1920
tcgtatcttg ctgaaaatga ggatgaggag gctttcgagc agctgcatca ggacatggac   1980
gagtctaagc tggctgagga gctgtataga cagagggccc agaatcacaa tgctgctgtt   2040
cagcgagggc tcgaaagtat ggccgatgtt gacgtggatg atggagacga cgatgagatg   2100
gatttggacg atgatatggc tgatgctggc gacagagttg atgcggagaa cgacgagaat   2160
gcacaggtca tgaatgatat cgttgagaac gatattgatg atccttcgaa agacattatt   2220
cagggagatc tcgatatgga tcctgccgtg catcgacggg aggttgccga gcactactac   2280
cggctgcgaa acaacatggt tgccaagaat ggcgggttta tgaaatccga cggtgaaaag   2340
gccgccgagg agtgcgatga aatgccgct cccatcaaaa tgtctcgatt caaggctgcc   2400
agaatgaacc gagggcagta a                                              2421
```

<210> SEQ ID NO 35
<211> LENGTH: 1493
<212> TYPE: DNA
<213> ORGANISM: Artificial Sequence
<220> FEATURE:
<223> OTHER INFORMATION: YALI0_D20064g

<400> SEQUENCE: 35

```
atgtcacggt tcgatatcga cgaaacaaaa tccaaaacag acgactccaa cggctcccag     60
cctctgtggg gggggactgg agcacatgga gaaagcaggt gaacttcgcc tttgtcgctc    120
tcttcactct cacatctttt gcaacaatgt gtcaagcatc cgttgtctgg gaccccagda    180
caagggatct gggctggcag tttgaacagc tcaacagagg ctacgctttt agcatagctg    240
```

```
gccagggttt ggggtgtctt ctgatgatcc ccgtggccat caaattcgga agacggccgg    300
tctatctctt tggtgtggct ctgtcattgt gcacttcgct gtggcaggcg caaatgacgt    360
ctctccatga gctgtacaca gtttcgtttt tagaaggcat ggctgccagt ttgaccgagg    420
cgtgtgtcca aatgacgatt gcagacctat tcccggtcca gagcagaggc acctacaacg    480
gcatgtacat cattgcagtt tcggtgggca actttctcat tctggtgcct gctggagcca    540
tagtcaacca gtggggctgg agagctgcgt actgggcgat tggcctgttt cagatggtcg    600
agttggttgc atctttgttt ctgtttgaag aaactaaacc tggccatgtg tctggtcaaa    660
agttgagcat atatcctcgg tcatcttcaa agagtgacga agaggagaga gaaacattgg    720
ttaacgacat ggaaagacac aactcgtatg ataccgagag aagcgcgtcc agaggatgca    780
tcaagtgcac cgactcgttt ccacatatcc cgttggtcac agttactcct ggctggtcga    840
gtttcttcaa gtcttcctac actccgtttg tcctactggc ttcgcccatt gtcgcgtttg    900
ccgcaatcac ctatggattt tgctgctggg ctctgtcaat gtcgtcggta gtgacttctc    960
tcaagtttgc agaagccccc tatagcatga gtccctggtc cattggtctg gtgttcattt   1020
ctccgtttgt gggcatgacc atgggctcct ttttcggcgg gtacttgtct gactgggaca   1080
ttgtgcgaag aacaagactc aacagtgcg tctacagtcc acagatgcga ctgaaactca   1140
tctacccagg tctattggcc gtcacggcag gtctgctaac ttttggcatc tcggtgtcaa   1200
gaggagttca ttgggtggtg ccaactcttg cgtttggagc tgtttctttc ggatttggaa   1260
gcgtgggatc catagtattg acctatctga tcgactacaa ggagtctctg gctgctcagt   1320
ctctggttgc tgttgtggtg gtccgaaact ccatctgtat ggtggagtcc ttctccttgt   1380
ctccgtgggt ggattcggtt ggggttgaca atgtgttcat cacagcgggc tgtttctcgc   1440
tgatccccat cttttggcca ttggcgattg agctgtttca tcgcaagtct tag          1493
```

<210> SEQ ID NO 36
<211> LENGTH: 619
<212> TYPE: DNA
<213> ORGANISM: Artificial Sequence
<220> FEATURE:
<223> OTHER INFORMATION: YALI0_D20526g

<400> SEQUENCE: 36

```
atgtctcagg gtgagtattc agatggagag tgaagcgtgg gttggatacc tagaaacctc     60
tgagagcctg agagcctgag agcctgagag cctgagagcc tgagagcctg agagtcatca    120
acagactagc gtccttggct ctgacaggtc cattccatcg tcagacgggc gattcggaga    180
cagccacaga ctcctgtctg atgtccgctt tagaccatgt actaacctag ccggccgaaa    240
agatttcact gacaagctct ccgagggcgt gaccccccgac tcccagaagt ccactggcga    300
gaagctctcc gagaaggcca ccgacgccta cgacaaggtt gccaacgccg ttgatccacc    360
ggagcccgag tcccagaagt ccaccaccca gaaggtcggc gacaagttcg agtccgacac    420
ctccaaggcc aagtccgaca tctccgacga gaagaacaag ctcgagaagg agggcgagtc    480
ttacattgat caggccaagg acttcatcaa ctccggcaag cccaggagt acgttgacca    540 ggccaaggag tccatcaaca acttcccttgg tggaaactcc ggctccaccg gctccaccgg    600
caccggtgct accaaataa                                                   619
```

<210> SEQ ID NO 37
<211> LENGTH: 2883
<212> TYPE: DNA
<213> ORGANISM: Artificial Sequence
<220> FEATURE:
<223> OTHER INFORMATION: YALI0_D20790g

<400> SEQUENCE: 37

```
atgagtgata aagaacgcga acgtgaaagg agtcaatcac gtgaaagtag ccgaacacgt      60
gaaaggagcc gaacacgtga aaggagccga acacgtgact cgaagcgtga ccattccgat     120
tctcgatccc tccggagacg cagttatcgt ggcgacagat cgagaagccc gtcacgatct     180
cggtccaggt catattctcc atctcggtcg ccccgaagga agcggcgccg acacagaacc     240
agtcgcagaa gccggaggtc acgaagggaa ggtgatggac gacgcaaaga tggccctaga     300
ggccatgatg acagaagccc cttggcccct agggaggtgg aggatgtgac tgtcaagagg     360
gaggatagca cgaacgacaa ggaaagtact cacgacaagg aaagtacaaa cgacaaggaa     420
cgcaatgtct cgatggagga caggaaggat acttctgagg atgttgtgga ggatgtggag     480
gaggggatc cttctgaaga ggcactggaa aaaaagtaa agaacccaga agatgacttg     540
gaggcagcgg cagaagagct caagaaactc atggagctaa agtctggagg ccgatacgtt     600
cctcctgcta aaatcagagc gcttcagaag ctgctggtcc aggataagac gtccaaggag     660
ttccagaaga tccagtttga caatctcaaa aaggcaatca actcgctggt gaacaaggtc     720
agtgctcaga acattcgaga tattgcgggg gagattttca ctcataatct catccgagga     780
cgtgggctgt tctgtagaag tgtcatgacc gcccagagtc ttgctctgcc ctatacgcct     840
gtctacgcct gtctgacggc cattgtcaac tccaagctac ctcaggttgg cgagctgctt     900
gtgcgacgac tcattctgca atttcgacgg ggctacaagc gtaatcagaa ggacgtgtgt     960
ttgtcaagtg tgacgtttct ggcgcatttg tgcaattacc atgttgctca tgaggttcta    1020
gtgcttcagt tgctgcattt gttgcttgag accccccacag atcactctgt cgaggttgct    1080
gtagctttca tcaaggagtc cggtgccttt ttggccgaag tttcgcctgc tgccaacaac    1140
ggagtatttg agcgtcttcg agctgtgttg catgatggcg agctggaaaa acgaacgcag    1200
tacatgatcg agacgctgtt ccagatcaga aaagacggct acgaaaacta ccctgtggtt    1260
caagaagaac tggacctggt agacgaggag gactatgtga cacatatgac gggtttggac    1320
gacaagttta cagatgataa gctgctcaac tactttgtta tggaccctga ctacgaggcc    1380
aacgaggaga agtacgattt gctgaaaaag gagatcctgg agactctga cgacgaagag    1440
gaagatgata gtgaagccga ggaagaggca gatgatgaag aggaggagga ggggatgaa    1500
gaggaggagg ctcaagcctc tacctcggct gtgcgagacc tcacgggtac agagcttgct    1560
acgttgcgaa agaaaattta tctgacggtc atgtcgacca tgtcgatcga cgaaatcgtt    1620
cacaagcttg tcaagctgtc tcgaacggtt attgagatcc ctgagggtct ccccgaagac    1680
caggctctga ttctgcgtct caagcggacc caggaggtga cgaacatgct tgtggagtgt    1740
tgtgctcaag agaagattta taacaaaatc tacggaggta caggagagcg gcttctgaga    1800
ctgtcgcgga aatggagaac caactttgag aacacctttg ggttctttta ctcggttatc    1860
cacagatacg agcccaatca gatcagaaac attgccacgt tctttgggta cctgttggca    1920
tcagattctc tgtcgtggaa ggttttggag gctgtttctc tgactgaaga ggactcgaac    1980
ccctcgaacc gtatctttct caagattatg ttcaccgaga tgcgtcagga gctgggaatg    2040
gatctgttga aggagcgact ttccaagccg tttgtgcagc agtacattgc cggtatgttc    2100
cccaagacga atgcttctca tgttcggttt gccatcaact atttcactgc cattaatctt    2160
ggtcctttga cagatggtat gcgggagatt cttcctggtc tggtggagga ggaggagagg    2220
```

```
ctgaagaagg aggaggaaga gcagaagcga gagtacgaca gttacgattc atacgacagt    2280
tatgactcat acgactccta cgactcctac gactcctacg actcctacga ctcctacgat    2340
agttacgact cctacgatag ttatgactcc tatgactcct atgactccta tgactcagtg    2400
tctgaggatg atcggggggcg acgacgacga cgaggtgtag gaagtagaag gcggtcgcta    2460
actcggtctc ctggttcgcg gtcacggcca cgatcccggc cacgatcccg gtcacggtca    2520
agatctctat ctcgggatag aaccggttct ccgcctcgtg gtcgacggcg gtctcgatct    2580
tattcccgtt cgccttcgcg gtcatactct cgttcgagat cttattcccg atcgccatct    2640
ccgagaccta aatctaaagg ggctaaaggc cggagcagtt accgggccgc cagttattcg    2700
cggtcgagat ctccggtcag acgagttggt tattctagaa gcaggtctcc aagcgtgtct    2760
ggaggttcct ctcgaagtcc ttctagaagt ccttgtagaa gccccaacaa gggccgtgct    2820
cctactccgg agaaaggtct ttcgccgcct cgaaagcgag tgcgcgccag tgatttgttc    2880
taa                                                                 2883

<210> SEQ ID NO 38
<211> LENGTH: 633
<212> TYPE: DNA
<213> ORGANISM: Artificial Sequence
<220> FEATURE:
<223> OTHER INFORMATION: YALI0_D24563g

<400> SEQUENCE: 38
atgactgaac aggacgacaa ggcgctgaag ctggccaaga aggaggccaa ggaggccaag      60
gaggccaagg aggctaagaa ggaggctaag aaggagaaga aggagaagaa ggagaagaag     120
gagaaggaaa agtccaagaa gcgatcggct gaagatgatg atgtcaagga gatcaagaag     180
gccaagaagg acaagaagga aagaaggaa aagaaggaaa agaaggaaaa gaaggaaaag     240
aaggaaaaga aggaaaagaa ggaaaagaag gaaaagaagg aaaagaagga aaagaaggaa     300
aagaaggaaa agaaggaaaa gaaggaaaag aaggaaaaga aggaaaagaa ggaaaagaag     360
gacactgaaa aggaaaacac tccatctctc gcctcccccg cattcctcgc ctcccccgca     420
gcaacctcaa ccccaaaaac catagccgtg gatggcctgg actccgccca acaaaacaag     480
ttcctgcgac tgatgggagc ctccaaaaac aaggtgaccg tcaccaccaa ctccacctca     540
gaccactccc agagagaaaa agatctgatg aaacaattca ccagggcgt gaatctcaag      600 acgggtggaa agaaagccgg tatcggaaaa tag                                 633

<210> SEQ ID NO 39
<211> LENGTH: 270
<212> TYPE: DNA
<213> ORGANISM: Artificial Sequence
<220> FEATURE:
<223> OTHER INFORMATION: YALI0_D24849g

<400> SEQUENCE: 39
atgatacatc agtcagctga caccagtgaa cacagccaac tcagcaactc agcaactcag      60
tcgttcagca actcagcaac tcagtcatcg accaactcac caactcacca actcaccaac     120
tcactgactc accaactcac caactcactg actcaccaac tcaccgactc accaactcag     180
tcttccgcta atcaccaatc acatgactgt ggcttactac tcatttccct accacttgac     240 cactttttttt tcgttttcac acggtgctaa                                    270

<210> SEQ ID NO 40
<211> LENGTH: 1533
```

<212> TYPE: DNA
<213> ORGANISM: Artificial Sequence
<220> FEATURE:
<223> OTHER INFORMATION: YALI0_D25014g

<400> SEQUENCE: 40

```
atgcacctgt ccacctccgt tctcggtgcc ctgttggctc tgggccacgc cctgcctttt      60
gatacctcca gtgtcgctgc caccgacgcc tttgctgcca ccaacgccac ggccctcgcg     120
gccaacggca ctctcaccaa tggcaccttc agcaaccaca ctgcccccctc cgcaacctcc    180
cagcttgcct cactcactca gctgaccagt gataccccccg gcgaagccac cagtgccgcc    240
gtttctgccg ccgcagcaga ctttgccgca gccgccgtga ccgtgaccgt gaccgccccc    300
gccaacaccg tcaccgtcac cgagactcct gctccccaga ccgtgaccgt gtccgtctcc    360
tactgtccca cccccgcgcc tactggtgag gctgccgccg gtgcttccga caacaccgcc    420
gccgccgcag ctggaacccc ctccaacaag caggccggcc agaacttcaa cgccaacgag    480
gacgccgcta cgccaactc tggctcgag cccgctggcg ccaactctgg ctcggagccc      540
gccggcgcct ccgattcctc cgacgaagaa aacacaactg tcttcctcac ccagaccaag    600
ttcctgacca gaccctctc ccagtacgga gtcaccacca ccgttcccac cgccaccgtc    660
acctctgcta ttgtcaccaa ggccaatgag gagaacgccg ccgccgcctc ccccattgtg    720
actgacatca ccgagaccct gaccgaggtc gagaccgttg cctctgagga acctcaggga    780
acgtctactc gaactcatta catcaccaag accaacacca ttacccgggt gagatcgtcc    840
actgcccagc ccgagacttc caccgaagct cctgaggctg ctgccggagc ctcctcttcc    900
atcgagacct cctccgaggc ctcctccgag gcctctgtgg aggccaccgc ttcggtcgag    960
ccttccaaca cgtcatccga ggttgccgcc gaggccccca cctccgctcc ccacaacgca   1020
accttcaatg ctactcaggc tcccgttgag acctcctcca ccccccgtgct gtcgaccact   1080
tctcttgtgg cccccaccaa cgccaccgaa gccggagccg ctgctcccct cacctcttct   1140
tccgagcccg agggaacctc caccacctac gtttcctcca ccgtggtcgc tactctggcg   1200
cccaagacct cgtctatccc cgagggcgct gccggagccg agtcttccgg agtgtcttct   1260
gaggcctctt ctgagctccc ctcttcagtt gcttcttcct cggctcctgc ttccaccacc   1320
gctcccgaag cgctcctga aggagctgct gccgtctctt ctaccgcgga ggcctctgct   1380
gaggcttctt ccccggctcc ttcctctgcc cctgtctctg ctgaggccgg agagtctgcc   1440
gttcccctt ccgaatcggc tcccatcccc tcccctgccc cacagttgc ccccaccggc     1500
tttgccgcta acggcacctt cacctctgcc taa                                 1533
```

<210> SEQ ID NO 41
<211> LENGTH: 1638
<212> TYPE: DNA
<213> ORGANISM: Artificial Sequence
<220> FEATURE:
<223> OTHER INFORMATION: YALI0_D25058g

<400> SEQUENCE: 41

```
atgtctacga ctgaattcga cggcatctat ctcaatcaga gcaaggcaca cggccgtctg      60
cggatggttg agacgggcct gggctggaag gcagtgcaga gacgtcaat gggcggatcg     120
aaggagacca agaaggacga gccgtttcta cttggaaagg aggagctgct ggcggcgttt    180
tggagtcggg gctctcgggg attcgagatg aagatccaga cgaaaaaccg cggggccgcc    240
aactttgacg ggtttgaaca ggacaacctg gaggagctga agaacgtgat gaagcgcaac    300
```

```
tatggcattt cagtggagca gcgcgagcac agcgtcaagg gttggaactg gggcaagacg      360
gactttgagc gatccgagct ggtcttttcc gtcgccaaca agcccgcatt cgagatcccc      420
tacgccgaag tggccaactc caacctggtg ggcaaaaatg aggttgctct ggagttccag      480
cagcccgccg atggacgggc aggcgacgag ctcgtcgaaa tgcgattcta cgtgcccgga      540
gtaacttctg tggaaggtga tgagaacccc aagaagaagc agaagacgga gaagaaggag      600
ggagaagaag gcaaggaagg agacgacgac gccgacgccg acgacgaatc agaagaggag      660
gtccagtcca ccgcccagat cttctacgac accctcaagg aaaaggccga cattggagcc      720
gtggcaggta cggctgtggt gtctttgtcg gagatctacc tggtcatccc ccgaggacga      780
tacgatatcg acatgtacgc caacttcatg cgacttcgag gaaaaacata cgattacatg      840
gtgcagtaca agcacgtgca gcggctcatt gtgctgccca agcccgacga tctgcacaac      900
attctcgtgg tgcagctgga tcctcctctc agacagggcc agactcggta cccgtttctg      960
gtgatgcaat cctgcgtgag ggccgaaatc aaagtcgagc tcaatgtcga cgacgccgag     1020
tttgccgaaa agtacgccga caagggtctc aagcagtcgt acgacgagtc tgctcaccag     1080
gtggttggat ctattttccg cggtctcact ggccgaaaac tgaccgtgcc aggctcgttc     1140
aagaccgtgc atggccatgc tggtgtctcc tgttcgctca aggcgtctga gggccatcta     1200
taccccctgg aacgaaattt cctgtttctt ccaagcccg ttttcattcc ctttgccgag     1260
attcaagata tcactctgtc tcgagtgggt cttcggtaa ccacctctcg aacgtttgac     1320
atgactctca agctgcgaaa cgcccagggt gagtaccagt tctccaacat ctccaaggaa     1380
gagcaggagg gtctcgaggc gttcatcaag tccaagggca ttcgtcttaa gaatgatctt     1440
gctgaggaga aggcgctgct ggctgccact ctggctgagg tggacgatga ctctgatgat     1500
ggaggagagt ttcgaggctc ggctgatgag gatgacgaga gtcctgatga ggactttcat     1560
gccgagagtg atagtgaggt ggcggaggag tttgactcga atgccgagag cagttcggga     1620
gaggaggatg acgagtga                                                  1638
```

<210> SEQ ID NO 42
<211> LENGTH: 1971
<212> TYPE: DNA
<213> ORGANISM: Artificial Sequence
<220> FEATURE:
<223> OTHER INFORMATION: YALI0_D26257g

<400> SEQUENCE: 42

```
atgaagttcc caatcgccac cctggcagct gttgcagctg tggtttccgc tcagtacaac       60
ctgtacaatg cgaccaatgg cacgactact atttcttctt cagcttctcc ttcgaccaac      120
tactctgcct cttttgaccac ctcttcctct tggtctgatg atggtaccca taccactctg      180
cccatttggt ccgaactcat gtcggacatt tcttctctgg agtcaatgtg gaacaacagg      240
accacttcgg ccgagtctgt tggtcccacc acctattacg tcgacagctc cactccggtg      300
gaatcttcta cgttctcctc agcttcttct gcttggaaca cttccactgc gatcttgacc      360
gcttccaaca cctcgaccat tgcgtatcct actaatgttg aacgagctgt tccagttccc      420
accgggtttg aggacggcga cgagtatgac tatgatgaag acacagagga cgaggacgat      480
gacgaagatg aggaatactg gtactccacc tctgctctgt ggaacacctc taccgctcag      540
gctacaccta ctcccatttg gaacacgtct acctcctcca ccactctctg gaatacctcc      600
actgtcgtgt ggactgagac tgctacctcg tctaccctg cctggaactc tttcaacctg      660
tggaccgagt ctgagacgca gacttccacc gcttggaaca catccatttg gtggacttct      720
```

```
tcttcttctt cttctgcttc ccccactact ctctggaaca cttcttcttc agccactcct      780
acgcccattg tgaacacctc ttcctgggtc tggagctccg tcgagtcctc agctagcccc      840
acctcgatct ggaactcttc cactactgct cccatctatg agcgagactt tgacactacc      900
tcgtcttctt ccatgaactg gacctcctgg taccaccaca ctgtctcgac ttcttcctgg      960
tattctggag accccgagtc cacctccaag gccgtgacca cctctcacgc tacagccaca     1020
tcttctgtct ggtccaactc ttccaccgag acgaagtact ctagctccac ctggtacaac     1080
tcttctactg ctgcctaccc cacgagctct tctatttccg agaacagcga gtactggaat     1140
cccgttcccg tcaactccac catcatttcc cctccatacc agcgacaccg acagaacacg     1200
tctacctggt ctgagtctgc acccacttct tcgtacgtgt ccaacacaag gaactcctcc     1260
accgcctatc ctactacctg gtacaactca tccaccctct ggtcctccat ccccatcagt     1320
gtccccactg gtatcttcaa catcactact cctctgacca cagctgctcc cactactccc     1380
tcgtacaata cctctctggg tttcgaggag cgagactatg agactgacga cagctactgg     1440
gagtccgaat atgaggaata cgaggactgg gaggacgcgt cgactgagta ctcctggacc     1500
accagcagca gcaatttctc caccgcctgg ccttcttctt catcctcttc cacctggtgg     1560
acttcttctt cggccttcaa ctcttccact cctgtgactt cttacatctg gcccacctct     1620
ttggtcaaca cctctaccat ctggtcttcc agctatgtgg ctaacaccac caccaccgtg     1680
gccttctcca ttcctaccac caactcttct cgatctaccc gatctgcccg atccaggtac     1740
tcttcctctt ccttctctac tccctcgacc acttctactg atatccggac ctcttgggcc     1800
cccgaggatc tcatcgagca gcctgagccc actaccagct cctcccactt tgacgatgct     1860
ccgttcccta ccgccccact gcctcccctt gagtctggag acgaagcacc tctggaaatg     1920
cagtaccctg actcctttat cgatctcccc tgggttgatt acgagagtta a               1971

<210> SEQ ID NO 43
<211> LENGTH: 1838
<212> TYPE: DNA
<213> ORGANISM: Artificial Sequence
<220> FEATURE:
<223> OTHER INFORMATION: YALI0_D26510g

<400> SEQUENCE: 43
atgtcgaagt ccatcgtccg ttccatcaag aacgtcacga acggatacac ctcggcccag       60
gtgaaggtcc gaaatggtga gtatacaatt ctcccctctc tactattgca caatcccctt      120
ctcatcacca ccgttttttt ttctcgctct actaacatct agccacatcc aacgacgctt      180
ggggtccgtc cacgtttgac cttgaggaaa tcgccagact cacccactcc aaccaggagc      240
ttttcgaggt gatggacatg atcgatcgac gactcaacga caaggcaaa aactggcgcc       300
atgtcatcaa ggccctcaat ctgctggact actgtatcca ctgtggctcg gagaacgttg      360
ttctgtggtg caaggacaac ctgtacgtgg ttaagaccct gcgggagttc cattacatcg      420
atgagaacgg ccgagaccag ggtgccagca tccgttcccg agcaaaagaa atcacctcat      480
tgctgctgga cgatgagcga ctacgaaacg agcgggccaa tcggtcctcc tggaagaagg      540
gacgacgggc tcagggagac gactacgcct ctgacgagga gagtggaatt gtctcttctc      600
gaaccagaac cgccgacgac cgacgagacg accgacgaga cgaccgacga gattctcgac      660
gagattctcg acgacccctcc agacgaggat ccacgccaga cgatgaccta gcccgtgcgc      720
ttgccgagtc gcagcgaacg gccgacgagg aggcccgaat gcgacagaac ggaggagccg      780
```

```
aggacgaggc tctgagaaag gccattgctc tgtcggagga ggagcagaag aatcgagatc    840
tcggtggcgg aatggcccag ggaaccgcac agcccatcaa cctcatcgac acagacagct    900
ttcccactca gttccagcca cagcagcagc agcagcagat gcagcccact ggctatgatc    960
tgtttggcaa cgccatctac ggccagcagc agcccaccat gaacactgga gtgctccaga   1020
acgcatacgc cactggaggc atgttcgacc agcagcccaa ccagttccag cagcagcagc   1080
agcagttcca gcctcagcag cagcagtaca ccggattcca accccagcag cagccccagc   1140
aacagcagta cactggtttc cagcagcaaa cgacttctc tcagtccttc cagcagcagc    1200
agcagcagca gcctgctgag cccctccagc tctcaaaaac tggctctaac aaccccttg    1260 caaagcatga ttctacaaac ggctcttaag cttccactgg tccctccctc aacttcatgg   1320
cttctaacaa catgaccacc caggcacatc ccaaccacca acagcagcag cagcagcagc   1380
agcagcaaca gcaaccggca cccaagcagc gtgcgcaggt cactggcggt gctcatcccg   1440
aactcaacaa cctgctcatg accggagacg gagtcgacac ctttggaaac actggcgaga   1500
cccgaatccc cgcacagcac acccgagaca cgttcatgaa cgctcgtctg cagccccagg   1560
ccacagccaa caacaacccg tttgtgggcc agcagtacac cggtatcccc agcactcaga   1620
tccagcctgc agtgaccggc tacggttttg caacgcgcc acagcagacc ggcatgcagc    1680
agagcaacgg acagcagcag tacggacagc agcagtacgg acagcagcag aaccagcagc   1740
agtatggtca acagcagtat ggccagtttg gacagcagca gcctcagcag caacagtacg   1800
gcggaggagc accccagcaa tcgctgatag atttgtaa                           1838

<210> SEQ ID NO 44
<211> LENGTH: 1847
<212> TYPE: DNA
<213> ORGANISM: Artificial Sequence
<220> FEATURE:
<223> OTHER INFORMATION: YALI0_D26620g

<400> SEQUENCE: 44
atgtcgaagt ccatcgtccg ttccatcaag aacgtcacga acggatacac ctcggcccag     60
gtgaaggtcc gaaatggtga gtatacaatt ctcccctctc tactattgca caatcccctt    120
ctcatcacca ccgttttttt ttctcgctct actaacatct agccacatcc aacgacgctt    180
ggggtccgtc cacgttttgac cttgaggaaa tcgccagact cacccactcc aaccaggagc   240
ttttcgaggt gatggacatg atcgatcgac gactcaacga caagggcaaa actggcgcc    300 atgtcatcaa ggcccctcaat ctgctggact actgtatcca ctgtggctcg agaacgttg    360 ttctgtggtg caaggacaac ctgtacgtgg ttaagaccct gcgggagttc cattacatcg    420
atgagaacgg ccgagaccag ggtgccagca tccgttcccg agcaaaagaa atcacctcat    480
tgctgctgga cgatgagcga ctacgaaacg agcgggccaa tcggtcctcc tggaagaagg    540
gacgacgggc tcagggagac gactacggct ctgacgagga gagtggaatt gtctcttctc    600
gaaccagaac cgccgacgac cgacgagacg accgacgaga cgaccgacga gattctcgac   660
gagattctcg acgaccctcc agacgaggat ccacgccaga cgatgaccta gcccgtgcgc    720
ttgccgagtc gcagcgaacg gccgacgagg aggcccgaat gcgacagaac ggaggagccg   780
aggacgaggc tctgagaaag gccattgctc tgtcggagga ggagcagaag aatcgagatc    840
tcggtggcgg aatggcccag ggaaccgcac agcccatcaa cctcatcgac acagacagct    900
ttcccactca gttccagcca cagcagcgat gaggacgaca gcagcagcag atgcagccca    960
ctggctatga tctgtttggc aacgccatct acggccagca gcagcccacc atgaacactg   1020
```

-continued

```
gagtgctcca gaacgcatac gccactggag gcatgttcga ccagcagccc aaccagttcc    1080
agcagcagca gcagcagttc cagcctcagc agcagcagta caccggattc caaccccagc    1140
agcagcccca gcaacagcag tacactggtt ccagcagca aacgacttc tctcagtcct      1200 tccagcagca gcagcagcag cagcctgctg agccctcca gcctctcaaa actggctcta    1260
acaaccccct tgcaaagcat gattctacaa acggctcttc ttccactggt ccctccctca    1320
acttcatggc ttctaacaac atgaccaccc aggcacatcc caaccaccaa cagcagcagc    1380
agcagcagca gcagcaacag caaccggcac ccaagcagcg tgcgcaggtc actggcggtg    1440
ctcatcccga actcaacaac ctgctcatga ccggagacgg agtcgacacc tttggaaaca    1500
ctggcgagac ccgaatcccc gcacagcaca cccgagacac gttcatgaac gctcgtctgc    1560
agccccaggc cacagccaac aacaacccgt tgtgggcca gcagtacacc ggtatcccca    1620
gcactcagat ccagcctgca gtgaccggct acggttttgg caacgcgcca cagcagaccg    1680
gcatgcagca gagcaacgga cagcagcagt acggacagca gcagtacgga cagcagcaga    1740
accagcagca gtatggtcaa cagcagtatg gccagtttgg acagcagcag cctcagcagc    1800
aacagtacgg cggaggagca ccccagcaat cgctgataga tttgtaa                 1847
```

<210> SEQ ID NO 45
<211> LENGTH: 2172
<212> TYPE: DNA
<213> ORGANISM: Artificial Sequence
<220> FEATURE:
<223> OTHER INFORMATION: YALI0_D27016g

<400> SEQUENCE: 45

```
atgaaggtgg gcgatggagg agaagtcttc tttgtgttcg agaccgacgc agacgtgccc      60
gaagagctcc tgacatcccc cgtcatttct ccctcttcgt cgccatcctg gggccaggag     120
gaaggcgggg atggtgagcc ggactacctt gctctgaacg actctaaaca gggtggcgac     180
agcaagcacg gcagatcgcc ctcggagggc ccaccattca gatcaccttc ggcggatcac     240
ttacatgaga tgggcagctt cgatgatgag aatgaccctg aggtgaacag aagcaacgt      300 gcgagcacgg cagctccaga gcctgttcct ggttcgttga acacccagc cactatctcg     360 gaaggcatct cttcggcctc gttttccaac agcgatactg atcgaacaga cacttctgga    420
cccacagaga cagaacccac agagcccaca gagcctacag agcccacaga gcccacagag    480
cctctggatc ttgagcagag tctccaccgg gctgccactt ctcccgcccc ttcgtccgag    540
gagatttggg agaaggcccg tgcactgtcc aagaaactca catcagaaaa cattcagagt    600
aaaatctccg acaacggaga cattattctg gatatgactg gttacaagta cgaccacgag    660
gacgtgagtc gatcagagga gctggtcaag aaaatcctcg ctgaggaact gggagaagac    720
agagacctgt cccacatcct ggttgaagac gaggagggta accttgtgat tcagagcgct    780
ggagacagcc accatcacga gcatatgagc tcgcccgagt ctctggccca ctcccctcag    840
cccctccctt cttctaacct tccgtctcag gcctcggaca caagcacta cgccaagacc    900 atccgtttga cgtctgacca gctcaagtct ctggatctca gcccggcaa gaacgaggtc    960 acctttgctg tcaataacgg caagacgtcg tgttcggccc agctgttcta ctggaagtac   1020
gacattcctg ttgtcatttc cgacattgat ggcacgatca ccaagtccga tgctctgggc   1080
catctgctca ccatgatggg ccgagactgg acccacaccg cgtgggccaa gctctttccc   1140
gatatcagag ccaacgggta taatatcatg tatctgacag cacgatcagt gggacaggca   1200
```

```
gatgcaacca gggcatatct aggcggtgtt gaccagtttg gcttcaagct gcctccagga   1260
cccgtcatct tgtcgcctga tagaaccctg gcggctctca agagagaggt gattcttaag   1320
aaacctgagg tattcaagat ggcgtgtctg cgggacatta agtcgctgtt tggcgagacc   1380
gaagacgcca ccaatccatt ctacgctgga tttggcaacc gaatcaccga cgcgttgtcg   1440
tatagatctg tcggtgtgcc gtcgtctaga atcttcacaa tcaactcgaa cgccgaggtc   1500
catatggagc tgcttgaact ggctggctac aagtcctcgt atgtccacat tgccgatctt   1560
gtcgaccact ttttccctcc ggaaagcgag ttcacgacca ttcaggagga aaaatacacg   1620
gacgtcaact actggcgaga tcccattatt gacctgtctg atctgaccga cgacgagctg   1680
actgacgatg atgagctctc caagtcgccc aagtcgccca gatctcctag aagcccgcgg   1740
gccggttcgg caggctccag cgcggctccc tcaggctcgg gcgccgaccc tgccggaccc   1800
tccgagccga aggactccgc gaacccgtcg aagttcagct ataagaaggc tcctacgaac   1860
tctcgattcc agcccgtttc gtacgatctt gatcttgacg acggatacga gtacgacgat   1920
gacgatgact atgatgacga tgaggagttt gtggacgctg agcgacgc gctggaggag   1980 gatgacgacg atgatgatga cgtcgaccta gacaacgact ctgaccactc ccctgtcaag   2040
ccgccctcgc agatgcagcg agtcatcaac aagactattg aggacaacaa gggcctgcac   2100
atggatgagg atgacgttca aaaagccatg aaggccctga gatggaacg agcaagcatc   2160 aatcctgagt aa                                                      2172

<210> SEQ ID NO 46
<211> LENGTH: 687
<212> TYPE: DNA
<213> ORGANISM: Artificial Sequence
<220> FEATURE:
<223> OTHER INFORMATION: YALI0_E07832g

<400> SEQUENCE: 46
atgaagttct ccgttgccac cgtcgccgcc cttgccgccg ccgcctacgc tcaggtttcc     60
aactccaccc tcgccaccac cgaggctccc gtcacctccg ctgctcccat cgagtctgct    120
gagaacaacg gtaccgagct caccaccggc actgtctcca tcatcaagac cgagaccaac    180
gttgtcaccg cctacaccac ctactgcccc taccccaccg agattgttga gggcaacaag    240
acctacaccg tcaccgaggc caccaccctg accatcaccg actgcccctg cactcgaacc    300
actaccgttg ttaccgagac catcaccacc tgccccgtct ccgagttccc caccgagccc    360
atcactgagg gccccaagcc caccgagtcc aagcctgctc cttccccaa gcccgaggag    420 tccaagcctg ctccttctcc caagcccgag gagtccaagc ctgctccttc tccaagccc    480 gaggagtcta agcccgctcc caagcccccc gcttccaagc ccaccgcttc caagcccacc    540
gcttccaagc ccgagcagcc cgccgcttct actcccgtcc agacccagca gcccgctatc    600
tcctccggcc ctgagcaggc ttcttctgcc aacagggtca ccgtcggtgc cgtcgctgcc    660
attgctgccg ctgcctacct tctgtaa                                        687

<210> SEQ ID NO 47
<211> LENGTH: 1392
<212> TYPE: DNA
<213> ORGANISM: Artificial Sequence
<220> FEATURE:
<223> OTHER INFORMATION: YALI0_E08008g

<400> SEQUENCE: 47
atgaagctgt ctctcgctac cattgttgcc ttctctgccc ttgttgtggc tcagaacccc     60
```

```
agtcctgaga ccgtgtccag tgatattgct accggcaccc cctccaccct gtctcctgga    120
tccacctccc aggctgcctc cggtacccct gccgctccca ctgccacccc tacctccact    180
gccacttccg ccaacctctc tgtgctcgac aatgtgctca gcgaggttca ggccgttctg    240
gctgacgttc tggccgagct ccccgacatt ccagagctgc aggctctgat tgccaccgtg    300
aatgcctccc tgacagacat tcttgcccgt ctccctgctc tggaggcagg tcagtcggct    360
tcttcggccg ctgccgcttc ctccactgct tcagcctctc cctccagcaa cttcaccaac    420
cctctgctcg tccgacaagt tcgccgggtg gtcaagcttg ttgcccgaga ttccattgcc    480
gaactttccg acgacgtcag cactctagtg ggcaaccttc aggccattgt cgccatcatc    540
gagggcgttg agccccgatc cgactctctt caggctgccc ttgaccaaat tctggccatt    600
atcgctcgac ttgagaactg gttagctgag accaacggtg aggaggtccc cacttcctcc    660
gccggctctg ccatttccgg ctctgcctct gtcatttccg gttccgcccc tgccacctcc    720 acttctcccct tgtcaccac tctgagcatc tcttctgctt ctgcttctgc ttctgtttct    780
gctggttccg atggctcttc ctcttcctct tcctcttcct cttcctcttc ctcttcctct    840
tcctcttcgt ccactgaggt caccattgtc tacgtcaagg agtgcggctg ctacaagcac    900
aaggacggct ctgttgctac ccatgaggag gtcgaggccc acgaggctgc gcattcccag    960
tccaagggag ataccgagtc caagggagat accaagggcc cctcttccgg aggtaagact   1020
acttactcca ctgactctgc ctcttctgga tccagctcct ccggttcttc ctcttccggc   1080
tccagctctt ctggatcagc ttcccacgcg ggatcttcct tctctggagc ttcctctcca   1140
ggctctgctg tttccgactc ttccagctct tctagattag ctgcccacgc tggatcttcc   1200
tcctcttccg gttcatcttc cagctcttcc cccgcagctg ctgccggcgg atcctctgcc   1260
cctggctctg ctcccgctgc cggacccgct cttcgcctg ctggagagca cgttgcccag   1320
gccaacggtg cctctgccat gtctgtcggt accgctgctc ttgctctgcc cttcatcatg   1380
gctctctttt aa                                                       1392

<210> SEQ ID NO 48
<211> LENGTH: 1121
<212> TYPE: DNA
<213> ORGANISM: Artificial Sequence
<220> FEATURE:
<223> OTHER INFORMATION: YALI0_E11363g

<400> SEQUENCE: 48
atgcatgaac taaaaagatt caccatccag aagaaagaaa aaaccacac acacacacac      60 acacacacac acaaacaaca acacacagca tgagctgctc catctgtcag caggagagca    120
aatacagatg cccagcatgt tcggcgcgca cgtgttcgct ggcatgctca agcaacaca     180 aagcctccga gaagtgctca ggactccctg atcccacaaa gtacctgaac cgagaggctc    240 tcttttacaga cacatctgtt aacagagact accggtttct caagcggctg agcgagata    300 ttgtagtgcg caaacaggat ggcgaaagca tgccgatttt caagcgggct cgatacaacc    360
agaacagaaa agacggcaag gatggcagtg tgatggagcg aaacggagtc aagatacaca    420
aggtggctca aggatggga cggcagaagc ggaaccatag cagatgggat cctaacatca     480
agcagttttg ttggactgtc gaatgggtga atgttgacac taacgagacc atgactgtgg    540
acaaggtaaa ccctgtgcag tcacttctcg agtgtttcca gaagagaggc agtgagaagg    600
gtgggaatgg tgataataag ggtgaacgga aggtcgagaa gaacgacacc gagcaaacag    660
```

| | |
|---|---|
| agatgaaaga tgaacattca aaacagaagg atggcgacaa gaaagacgaa gaaaagaag | 720 |
| tggtcccgtt aacacctaga tcattctaca tgaagagaat caagtcgaag aacacatctc | 780 |
| caattctgtt agatccctca aagcctctgt ctgaaaatct gaaagacaaa tctgtcgtgg | 840 |
| aatatcctac catctactac accaacgaag agattgttgc gagtgacagc gatagtgaca | 900 |
| gtgacagtga ttccgacagc gacagtggtt ccgatgattc ggacgattcg gacgattcag | 960 |
| atgacgactc tgatgatgac tctgactcag ctcctgaaga ggagagtgct cgacaaccag | 1020 |
| agatgcctga cattgtcaaa acattggccg actcagctgt caacgacatg gccggcctag | 1080 |
| aggacgcctt cgaaaaagca caagaggaag gaaagcaata g | 1121 |

<210> SEQ ID NO 49
<211> LENGTH: 2157
<212> TYPE: DNA
<213> ORGANISM: Artificial Sequence
<220> FEATURE:
<223> OTHER INFORMATION: YALI0_E13596g

<400> SEQUENCE: 49

| | |
|---|---|
| atggaggtgg ccatggatgg aagccacaat gggcgccgga aatgcgctcg gcgaagctcg | 60 |
| tctgccgagc tgctcgaaaa accggagtcg gaccttttga cacaaatgta ccacatgcgc | 120 |
| aacgacgact cgctggccga cgctctcacc aacaacgaaa gcgagcattc caacgtgtcc | 180 |
| acttcgtcgg cagcgtcggc gtcgaccgcc gcaacctcgg cctcgatgat ggactcccag | 240 |
| gtgtacacaa acaagcaaaa cacagccgcc aacaacgtga ccccggcgcc caataacaca | 300 |
| gacatgcggc ctcccgagtc gccgggcccg ggctcgtcgg cgtcgcgaaa cgcaaggca | 360 |
| ccaatggcgt cgtcggagga atcgacgca gagctgcgca gagccgcaga gcaactggtg | 420 |
| ggcctgccaa ttgaagatat tgtggaaacc ctgcgtcgac aggactcgcc cgccggcaga | 480 |
| ggccatggca acgagcgcac caagcagacc tttggcatgg cctggctcat gaagttctgc | 540 |
| gagctcaatg agcagtcgtc ggtcctgcga tcccgcatct acgcccgcta cgtgaccatg | 600 |
| tgttcgcaac acaatgtgcg gcccatgaac ccggcatcgt ttggcaagct cgtgcgcgtc | 660 |
| atctaccccg acctgaccac gcgacgactg ggagttcgtg gccagagcaa gtaccattac | 720 |
| tgcggcatcc ggctcaccgg cgaggccgag gagatctcta ccccgggcc tggatcgcct | 780 |
| gatcgggcct tcaccccga attgactccc ttcgactcgc cctacgggtt ccgtggcaag | 840 |
| actgagactc ccgactacgc gctgggcctc aactccatga tggcgtccca gcccggcacg | 900 |
| ccacagcagc atatccaaaa tcatcagcag cagcatctgc aacaaatca ccaacagcat | 960 |
| catcaacagc aacagcagca gcagcaacat caacaacatc aacaacagca gcagcaacag | 1020 |
| caacaacaac aacaacaaca gcaacagcaa cagcaacaac aacagcaaca acaacagcaa | 1080 |
| cagcaacagc aacacataat gggaaccccc caaccaggcg tacccgacct tcgtttcgtg | 1140 |
| tcgaacctaa cggaagtgtc actatcagaa ggctacgact ccctcatgct gccctcgatg | 1200 |
| gagccgtacc ttcctctggg cactgacagc gacaccgcca acacgctagc ggcgctctac | 1260 |
| aaggcccact gccagtcgct ggtcgaatcg ctacggttca tgcatatcag aaaatttctc | 1320 |
| cacattcatg gagctttcat tggggcctg acatccacag ttcaaaagct gtatcgacat | 1380 |
| gagtcgctgc agccgtgggt ggccaaggcc gactggatta tgtacaagga catggtccag | 1440 |
| atgctgtcgc ctttggcgct gcaggagatt cctccacagg tcctgtcggg tctcaagagc | 1500 |
| ttgtcgcaat acttgcccga gtacctcaag tcgtctttgt gcaagacgtc gccggggttt | 1560 |
| gtggagacca agctcaagcc cgcgcgggcg tttgcatcac tgctgatgcg gctggtgcgg | 1620 |

-continued

```
gtgtcggagc tggctctcaa cgccggcaag ctgctggcgt ccgaccacga ccgagcggtg    1680
atgaaaaacg attggatcaa gtacgtggac agcgggctga tagtggctcg agacgttccg    1740
tgctcatcac aggaggtgac caagattctc gacgtcgacc ttccgcagct gctggactac    1800
aaggatccgg tggcgtcggc tatagtggag cactgggcaa tgtacctgat gactcttccg    1860
tcgcggttca ccaacgtgta ccccatatg tttctgcttt acatgaacgc tgtgtttaca     1920
gccgcactac gggagatttt tctcaacgga ggagacgggt ttggagcgtg atggtggtt     1980 cggtgctggg tggatgaatg gatgggatgg acggccgaac agggcacgtt tctgtctgcc    2040
gaccacaaca aggaggtcaa caagcatgag aacaaggaag gacgcccca tggcaacccc     2100 gccaagtttc tcgacatgac tgtggggttg ctcaagccca cccacaagga tgcatag       2157
```

<210> SEQ ID NO 50
<211> LENGTH: 4466
<212> TYPE: DNA
<213> ORGANISM: Artificial Sequence
<220> FEATURE:
<223> OTHER INFORMATION: YALI0_E14388g1

<400> SEQUENCE: 50

```
atgaccggcc ttgcagagga atggtggttc gacagtggta gggccgctct gggcgcagac    60
gccagagatt ggaagaaatt cacccaggcc ctcgagagcc gattcactcc ctcgacttac    120
gccatgaaca tggaggagga ctggagcaat ctgcaatgtg ggcccaacga gtcatcctat    180
tcctatgaga cacgcttccg agcggcacga caccacctgt ccagagaggc cgccccagag    240
gaggcctggt tacggctgac cagtggtatg aaggacatgt ggcgacgtga gatcatgaag    300
cagggcccca tactgcagaa caacgtcgag gagaccctgc gtcatatgca cattgtggca    360
ggcgcagaat acttcccagg agctcacgcc cagacacccg cggccgcacc tgtggccaca    420
cctacatcca ccagccagta cggtcctgga ccgatggagg tggacaacgc ggtgctgctc    480
aaggctatga tggaatcgca ggaggccagc cagaagcgaa tgatggaaca gcagacccat    540
atggttgaac tgatggcaaa cgccattgga cgagctaaca acaacggctc ccaaaacggc    600
cgcaacaacc gtggtggccg tggtaactac tacaaccagc gaacctctcg tgagtgctac    660
acctgcggca agattggcca cctggctcgt gactgccgac atcgtgaacg tgttcaggaa    720
ctgattcaac aggaccaggg aaatgtgcga cagcagtaat gaccgagacc attactgctg    780
agccactcga agatctcgaa tcggtgagtg tgccacctgc ggagtatgat ataatcaata    840
aatccaactt gtagaggac actaccgag aaccggagga tgcaggggta gaggtgcatc     900
tggaggaaga gcaaacggag gaaccaatgc agctggagga agaacaagtg ggggaacaag    960
tggaggaacc actgattgct gcacgagttg aggtggtaga tggtaagcgg cgacgagcct    1020
tgatcaaggg cgaccgacca ccgatctcga tcccgtactg ctacaacggt accacagtgc    1080
aggcgttgtt ggactgtggc gcgagctcgt gcttcattag caggaacctg gctgagaaat    1140
taggcctgaa aatgacgccc tgcaaaccac gacaagtcca gtccgtgcat agcatggaga    1200
caaccaacta tactgtggaa gtaccggttg agctgggtaa gtggggttgc gacgtgtttg    1260
cgtacgtctt accccagatg gtcggacaag agctactatt aggcatgccc ttcttcgaag    1320
agtatcatga agccgtggat ttcaaagctc gaacgttcac acccgacggg tacgaggtac    1380
cggcatggcc agctaacgag tcaactacgt gggacaaaca cggccacatc aagtcgtgct    1440
cactagagaa agctacgcag ctggccgaac accacggtgc gcagctgttc ctctacatgg    1500
```

```
tacgggagaa gccagagggg gaggagcatg agccggatgt cgatacccga gaggtgctgg    1560
aggagtatgc agatgtgatt gttgacaaaa tgccaatgga gctacctccg aaacggagcg    1620
tagaacatac catcgactcc gatgagacgg cacgacctcc agccagggca tcgtatcgac    1680
ttacccgatt cgaatgggct gaggtcgaca agcaggtaaa cgacttgttg gagcgaggaa    1740
tcatccgacc atcgaagtca ccttacagcg caccgttagt gattgtaaaa aagaaaggag    1800
gtgaacttcg tatctgcaca gactatcgcg ccctcaacga gcttaccacc aaggatcgat    1860
ttccgctgcc ccgtatcgat gacattctgg attgccttga cggcgccgac accttctcca    1920
agttcgatct tttgtcgggc tactggcagg tgttggtaaa agagtctgat gtacacaaga    1980
cggccttctc gactcgatcg ggacattatg agtacctggt aatgccgttc ggtctatgca    2040
acgctcccgc caccttccag agattgatga atgacgccct acgaccattc cttaacaaga    2100
cagtctgtgt gtatcttgac gacatcatcg tgttcagccg aaaccgagag gaccacaaac    2160
gacacgtgag ggaagtcttg gacgccctga gagcacagaa gttctatgcc aagaagtcga    2220
aatgtgagtt attcaggaag aagatgggat tcctgggcca cgtggtgtct gcggcaggag    2280
tggagccaga ccctgagaaa gtgaaggttg tggaagagtg ggtacctccc aacacgccga    2340
aaggcctctt gagctttcta ggactgactg ggtattatcg acggttcatc gaagactacg    2400
ctaaaatcgc cgccccactc acagacgctg ccacattgtc gccaactgac tttaaatgga    2460
ctgaggcatg ccaggtggcg tttgaacaga tgaaggcgaa gctagtatcg aacgaggtca    2520
tgatcatacc gacgatggag gacacgttca aggtgagcac ggacgcgtgc gatattgcga    2580
tgggcggagt actacagcag tggagtccca aggaccaaga gttccgacct gtggcatatg    2640
agtccacgaa gttcaagaaa cacgagatga actacccgac gcgtgagaag gaattctatg    2700
ctatcatcca tgcccctacgg aagtggcgac actacctact tggccgaccg ttcttgattg    2760
agacagatca tcagtctctg agttacttta cgtcccagac acaccctccc agtggacgac    2820
tgagtcgatg gctcgacttc ctagcggaat acgactttga gatcaagtac gtgccgggca    2880
aagacaacga cgcagccgac gggttgtctc gtatgttggc acagacagcg atggtgttcg    2940
agccggacga ctcgttgcta gacatcatca agcagggcta tgagtcggac gagtacttta    3000
aggacgtctt caaggtactg gccacggaac cggtggtcat ccccaaagag atgcacaacc    3060
acgcccgcca tttccgatac gacaagaaca caggactgct gtatttcgcc tccgtttaca    3120
agggggaggg agagcgactc tgcgtgccaa gaggtaaggc cagaaaaatg ctgatgaagg    3180
aggctcatga cgcaccccctt gctggtcact acggatactt caaaagctat gaaaggctgg    3240
cgagggctta ctactggcca cgaatgatag accacatgcg caaccacacc agatcctgtc    3300
tgatctgcca gaccacgaag gccagacgag caccaccccca gggcttgctg aagcagctgc    3360
cggtaccgac gggaaattgg caggagatca caatggactt cattggaggc atcccaacga    3420
cccatcgagg ccacaacaat atctgggtca cggttgatag gatgtcaaag atggtacatc    3480
tgattccttg caagacgagc acggatggag aagagttggc ggacatgtac attgaccgca    3540
ttgttcgata tcacggagta cctcgttcga tcgtgtcgga cagggacaag ctattcacag    3600
caaagctatg gcagacgtta cagacacgtc taggcacaga gttgaagttt tccacagtca    3660
atcaccccca gactgatgga cagtcagaac gagtgaacac cgagctgatt cgacagatga    3720
agcaacactt cgtcacggac aaaaactggg acctctggtt acctgtcatc gagtttgcga    3780
tgaattctgc aaagcattcg tccaccggat acgcacccctt cgaggcggtg tatggataca    3840
tcccagacgg accaacgtat gcctcgactc gagagctcac caaggtacac catcaaatgg    3900
```

```
acgcttggat ggacaaacta cgggctattt ccaattcgat gcacgaccga ttaatcgagc    3960
accaacgggt ccaggagaac agggtgaatc agcatcgagt gccagtcgcg tttcagatta    4020
acgaccaagt cttggtacat cggaaggcgt tctttgacaa ggccaagtac gcaaagatgt    4080
atgacgtcta ctttggacca tttcccatcg agaagaagat tgacaccaat gtctacaagg    4140
tgcagctacc atacgactcg actcgacaca agaatatcaa tgtacaacac ttgaagaagt    4200
tcatacctcg acctgagtat gacatcaacc cacccagtac ggagtactct caagaatgca    4260
gcctgcatca gatcaccagc ctggtgggta ttgatgacga ccgttacttc gtaacttggg    4320
aagattgtga ccccctctatt gcctcttcaa tttcgaaaga gatgttccac cgcatcccta    4380
aagacaaacg ggattcacta ttggatcaat ggaaccagtt cattaagacc cctgcggaaa    4440
gcgaggacta tgtggacatc tcctag                                         4466

<210> SEQ ID NO 51
<211> LENGTH: 3672
<212> TYPE: DNA
<213> ORGANISM: Artificial Sequence
<220> FEATURE:
<223> OTHER INFORMATION: YALI0_E16731g

<400> SEQUENCE: 51
atgaatacat ctgcagaagg agcagagcag ggcaggcaag atccccactg gacgtcgagg      60
acgaggatct ttggcatgga ggacgggtcc gagttctgga gtgggtcaac cctcacgccc     120
accaaacata ttgacaaggt ggtctttgga agcaacgcgg tctggcgcgc gtacgcaaag     180
agccatggaa aggttctctt ggttgatctg agctccggac gccaggatgg ccgggagttc     240
caacattgtg tgagctttgt tgcaaaggac gaagacggcg acaatgccta cctcgcgttt     300
ggatacatgc gaaacaagac gattgaggac ttcatgtggc tgtttgatat gatcaaggtc     360
cagttcaaac accactcggt gcctcttccc aagaccatct actccagcga gatgaaggag     420
tgctacgaga ccatcgaccg agcattcccc aacagtaaca tgcggttgtg gcttcgagag     480
atcaatcggg actttgtagc gcagtgccag catctggtgg tgcgtgactc tgatcgagtg     540
cttcacgaca aggtggatcc ttccagtttg accaaggacg aaaacatatg gcttgaaatg     600
atgtccgact ggtcggagat tctggaatca gacagcaaga accatttcaa ggaacaatgg     660
gacgagttcc gcgccactta caagaagagc caccccgaag ttgtttcgta tctcagaaac     720
caatggatca agccgcacaa gcgcatcttg acgggcttgt ggacaaacaa tgaagaggga     780
catgtgtttg atcagaatgc atacatggag ggtgctgcaa agttttttgga gagagccgcg     840 ggctgtcatg gcctggaaga ccgtctggta gctattcaga ctgcctacag agaaaatcat     900
cttactgagg gcagctctgg aaagcgacca agcgatgagg atgagtatca ggaggatgtt     960
gatgatgcaa caagtagaat tatgagcatt cttcgtggag gagagaacga ggagaagtcc    1020
ggaatctctg gaggactctga ggaagtggaa gtagtggagg atggtgagga agtggacgag    1080
ggtgagaagc aggaggtttc tgaaaaggat acatcggtag aggaggagga ttctgaagtg    1140
aaagaggagg aagagcatga ggaggcagaa atggaggtat ctgaggtggg ttctgaagag    1200
gaggactctg aagaagactc tgcagatgcc tacgaagagg agaggactga cgagtcgggc    1260
gagagtgatg ttgaagacac aaagaaatct gcaactcggg ctgtgaaaac tgtgaaccac    1320
ccgactactc ctcgaaaagc tactgtacaa gcaggcgctc caaccttgat aggtcacctc    1380
cccctcgcac tggtttctcc tacagccacg actttgatgc ctcccaggat gacaccactt    1440
```

-continued

```
ggagaggtat tccttcacgt tccgggaatt ggctatttgc ctgaatggcg tgctctagag    1500
ttacagaaag aatttgaaga agctaagaga aagcaggatg cggagagaga ggaagatgtg    1560
gtgatgttgg atgtccatga cttggaaaag gaaaagagg aggaagagga ggatgaggag    1620
gatgaggagg aagagtagga tgaggagtaa gaggaggaag aggaggaaga ggaagaggaa    1680
gaaaactctg gctttgatcc tgattctggt aaaccttgt cagagagtga agggagcga    1740 ataaaggcgg tcagaagaaa tttgcgtctg gaaggatccg gtacggaact tgaaaggttg    1800
ctaaattcta acaagcgttc aagaagtggg agatcacgtc catctctgga tggaaccagg    1860
aagagcatta ctgagatccc taatgaaggg aaaggcggtg ttgcatccga tacttttgtt    1920
gcagatgtcg acgggtcgtc agccagcaaa cgatcgagaa gaggtcagca gcgagcgtct    1980
tctacggttg ctacgctaaa gacgcccaaa cccaagaaca agactcaaga aaagagtgct    2040
gagtcggagc agcctgtaaa gcggggacca ggaaggccac gaaaacaccc tctcggtaag    2100
gagcctaagg cggctgtaat aaagcgggga ccacgagggc cgtataaaaa acgtgtcctg    2160
tccgcagcta cggtttatga ttctgattcc ggggatgctg ccgagccgaa gacgtctgga    2220
atgaaaagct ctgacactcc tacgaaatcc agaggtcgaa cgcgagctgc acgacgttca    2280
acgatggttt ctgaggatga ggaagagaag gacaggggaga agaaagattc agtgagagat    2340
tctcctgcag atacagtgag ctcttcttct gaggacgagc ctgtggtggc agttccaaag    2400
aagagtccaa ggagtatcag cgtcaacccc accaccaagc ctaccgcgaa gaagactact    2460
gcagcagcct ctaattccaa gtcatctccc acccagacta gaactcgcag atcgatggcg    2520
tcaaaggaga actctacagg agttttaaca gaaaccccca ccgcagtttc caagacggtg    2580
actccacgag ttgctagtgc aaagtcgaca ccgatacaaa ccagccagtc tcccatccag    2640
actagaactc gcagatcgat ggcgtcaaag gagaactcta caggagtttc aacagaaacc    2700
cccaccgcag tttccaagac ggtgactcca cgagttgcta gtgcaaaatc gacaccgata    2760
caaaccagcc agtctcccat ccagactaga actcgcagat cgatggcgtc aaaggagaac    2820
tctacaggag tttcaaaaga accccccacc gcagtttcca agacggtgac tccacgagtt    2880
gctagtgcaa agtcgacacc gatacaaact agccagtctc ccatccagac tagaactcgc    2940
agatcgatgg cgtcaaagga gaactctaca ggagtttcaa agaaaccccc accgcagtt    3000 tccaagacgg tgactccacg agttgctagt gcaaagtcga caccgataca aactagccag    3060
tctcccatcc agactagaac tcgcagatcg atggcgtcaa aggagaactc tacaggagtt    3120
tcaaaagaaa ccccaccgc agtttccaag acggtgactc cacgagttgc tagtgcaaag    3180
tcgacaccga tacaaaccag ccagcccaca tcaaactcga cctcaggcac ttcgagttcc    3240
aagcagaatc ggttgtcttt tgcttccaag tcgactccag ggcccaagag gaccccagag    3300
aatgcacctt cgaattcgac tccaaagtcg tcttcgcaga cttcttcgaa gacagtcact    3360
gagtcaccta ctcagaagac tacaccaagg ccagcttcca aggcgacgtc caaggcgacg    3420
tccaaggcga cgtccaacgg cactccgaag tcagtctcct ccaagacgac ccccaaatca    3480
accccgtcag attccatgtc tcggaaacga ccgactgagg aggctggatc tgggtctggc    3540
cggaagggca agaagcagcg caagtctgat gtcactcaga acgagtgtc caaggccgat    3600 acacccacca agagaaaaaa cagccagtct cgtccttcgc tgggtcagag aattttggga    3660
ttcttcaaat ag                                                        3672
```

<210> SEQ ID NO 52
<211> LENGTH: 933

```
<212> TYPE: DNA
<213> ORGANISM: Artificial Sequence
<220> FEATURE:
<223> OTHER INFORMATION: YALI0_E18073g

<400> SEQUENCE: 52
atgcagttca agaacattgc cctcgttgcc tttctcggtt tgttgccgc ctccgagtcc      60
gttcccgagt ctgtggacga cactcccgtg aacctcgacg atctgacagc cgaggaggct     120
gccttcttca tggacaagct caagaacaag tgtccgatga tgaagcagcc ccaggagtcg     180
tgccctaagc agtcgtgtcc caagcagcgt cagcagtcgt gtcccgcttg ccccaagcag     240
cagtcttgcc ccaagcagca gtcttgcccc acgcagcagt cttgtcctaa gcagcagacc     300
aagacggtca caaagaccat gagcaagcag ggagcggccc agaccaagac cgagacctct     360
acccaggtcc agttccagac tctgaccgag actcagaccc tgtatgagac tcagtggcag     420
actcagtggc agaccgagta ccagacccaa taccagactc tgtacgacac ccagtggcag     480
actcagacgg ttcaggggcc cactcagtac gtgaccgaga cccggactgt tcagggcgct     540
cctcagtacg tgactgagac tcagacggtt cagggtccca ctcagtacca gactgagtat     600
gtcaccaaga ccacccaggg agctcctcag tacatcaccg tcagtggagc tcctcagtac     660
cacaccgtca ccaagactgt tcagggccag aaccagtacg tcaccaagac tgttcagggc     720
cagaacaagt acatcaccaa gactgtgcag ggccagaaca agtacgtcac caagacggtg     780
caggcgcccg cccagaccat cacccagacg gtccgtggtg ctccttcgct ggtcaaggtt     840
cctgagtatg ttactgtcac ctccactgtc actgttggca agaagcacca gcaccagccc     900
aagaaggatt gcaagaaccg aaactgccag tga                                  933

<210> SEQ ID NO 53
<211> LENGTH: 960
<212> TYPE: DNA
<213> ORGANISM: Artificial Sequence
<220> FEATURE:
<223> OTHER INFORMATION: YALI0_E18216g

<400> SEQUENCE: 53
atgaagttgg aaacatttt gaatgaggca tcaagagaaa agtccgaggt tccaggtccg       60
gatgccactc aggctgagga cgggtccaag cgcgacggca agctgcctgc acacgaccac     120
cacccccaac gcagaccctc ggtccattcg cccaccagca ccagtacagc tgccggccag     180
gtggttgcac cgagtggaca acagggacca gtggaccta gtgggccgag cgtacaagcg     240
ccgagtggcg cacaaaccac gtccaaccag attgcggctc ccggacaaat gtctcgtcct     300
ccgagcacgg gccactttgg aatgcagccg gttccacaac cacacgaatt cattccgggg     360
ccattgcacg cgccccagcc ctattatccg catcatctac aacaccaggg ccactttccg     420
cccctgcaac cgatccagat cccccagtgg accgctccgc accacggcca tcatcccagt     480
ctgacccctg ggccctcgcc gaccgccacg gcccctgaac atcgtcacag acgcaactcg     540
tcggtctact cgccgtatca gcggcctcgt ggcggctccg tgggccatct ggggcccgtg     600
cccaccacca gctcacattt gccgcctcca gccacagtca cgtttgctcg gggcggcttt     660
gaagacaaga ccagcgacgg cagccaacgg aaacgcagca aggcgcccaa cagcacgtgg     720
accatggagg acgacaaccg gctgctggac ctggtgctgg ccacgttacc gcggcaggac     780
tacgccgagt acgcccgtct gctcaacaaa cgggacagtc agacggtgcg gtaccggtgg     840
aaggtgttgg ttcgacgggc acggggcgag ggagagcagc aacagcagca gcaacaacag     900
```
caacaacagc aacagcaaca gcaacagcag cagcagcagc agcagcagca ggacaggtag    960

<210> SEQ ID NO 54
<211> LENGTH: 1470
<212> TYPE: DNA
<213> ORGANISM: Artificial Sequence
<220> FEATURE:
<223> OTHER INFORMATION: YALI0_E20449g

<400> SEQUENCE: 54
atggatctgg cgaaaatcac cgacggcttc gtcaagcacg agacctcgtc gtcgtcctct     60
tcttgctcca ccaccaacac agggcccacc ccagacttgt ctccagtgac gccctccaag    120
gaatgtgaga agcggccacg agaggacgac cctgaagagt cgcacgacac gagcgccggc    180
gccaacagca acaacaacgc tagcgtgtct ctcatgtcca ccccagagcc caagtcgtcg    240
tctccccccg gactgtcgca tttcgcacac ctgatgcaaa agtcggacac catgtaccga    300
cagaacctca actcggacca gtacatctac tcggacgagg agaaggagaa ccacaagact    360
tcgggcaagc cccacacccc ccaggtgcct catacgccct ccagtgtgcc gacacaacaa    420
ccccaatatg catttatttc acattccatc acctcgtacc cgtcgaacga gcctcagatt    480
gacaacgcac ggctggcgcg ccgaaaacga cgccgaacgt ctcccacgga actcgcgctg    540
ctggagcagg agtttgcccg caaccagaag cctcccaagc acattcgcgt cgacattgcc    600
cgccgagtcg acatgactga aaaggctgtg caggtgtggt ccagaacaa gcggcagagc     660
gtgcgaaaga gcatgaacaa gagcatgacc gatgacacct ctttcgccga ctcttcgttc    720
gctgaaacta cctttgacga dagacggt aactccacat tcctgtccaa ttccaacgtc    780
agcaccagcg taagcaacaa gtcaatcact tcttccatca cagacaacaa gtcgcccctg    840
gcacagtcaa ccaccgccga ctctgttgcc aacgccaacg ccaacgccaa cgccaacgca    900
aacgccaaca caacaccgc atccacttcc tccacaaacg actccgaaat tgcatccgtc    960
gccccaaaa caaacggcag ctcattctct gttttcgaag ataccccga gactcccgcg    1020
aaaaagaaac ccagtgctcc gcgactgtcc atgcgtggtg ggaaggctac tgttatctac    1080
gccggcaagc ccaagggtgt cacgctgtcc tcgggaagac gtcttggggt ccctgccaca    1140
ccctcctctc ccgccaacaa caatcttggc ctgggaggct cgcctctggc cacatcgtct    1200
cctatgaccc agcggaccgc gtcgcaactg aaccaggcat ctgcatcttc tcccctatcg    1260
gctgttaagt ccaagtcttt tggaactgcc gaggaaagcc tggctgcgac gctcaagaag    1320
cggcttccgt ccatgcacta cgacctgccc gtgaccaaca agacgtcgtc tgtgcgccat    1380
ggcgtgagct ctcccgtggt cgacgccggc agccgtgagg ccgagtgtat ttccaatctc    1440
ctctctcttc gaaacggagg acgatggtaa                                    1470

<210> SEQ ID NO 55
<211> LENGTH: 1185
<212> TYPE: DNA
<213> ORGANISM: Artificial Sequence
<220> FEATURE:
<223> OTHER INFORMATION: YALI0_E21109g

<400> SEQUENCE: 55
atggcccccg ccgttactgt caccgctggc caggaacctg ctcctgcccc cgctccccag     60
cccgagccta cccccgctcc tgctcccgcc cctgctcctt ccctgcccc tgctcctgga    120
cctgaatctc aggttcctcc tgctcctgct cctcaaccta ctgagcccgc ccctgcccct    180
cagcccaacc ccgttgagtc ctctcctgct ccccagccca cttcccaagc cccgcctgcc    240

```
cctcctgccc ctcctgcccc tcagactacc tctgacgctg cccctctcc ccagcctgcc      300 cctaccacct tttccacttc tgttatcgag ccctcttcca cctcttcttc tgctgcggag      360
gccactccca ctttcacgcc caacggaatt ctgccctact cgctcaccta ctcgccctac      420
aacgacgact cgtcctgcaa gactatggac gaggtcatga aggacctcaa ggagatcgtc      480
gccaagggta tcaaggtgat ccgtgtctac ggcactgact gcggctctgt ccagaccatt      540
gaacctgccg ctaagcagct tggtctcaag atcaaccagg gtttctggat cggaccagac      600
ggagtcgact ccattgactc tggtgtccag gagttcatta actgggtcca gcagaaccag      660
gcctggggta tgattgactc tatcactgtt ggaaatgagg ctatcattgc cggctacgtc      720
agcccccagc aactccttgg aaagatcggc caggtcaaga gtcagctcaa ggctgctgga      780
taccagggac aggtcaccac cgccgagcct gctgtctcct acaccaccca ccccgagctg      840
tgcactggcc ctgagctcga ctacgttggg atcaactctc acgcctactt caacccccaa      900
cagtctcctg agaccgccgg ccagtttgct ctggacgaga tggctcttac tcagaagact      960
tgtaacaaca aggttgtttt tgtcaccgag acaggctacc cttctgctgg taacaccaac     1020
ggcaacaatg ttcctactcc ccagaaccag gaaattgcca tcaactcttt gctcaaggcc     1080
ctcaatggct acggcacctt tttccaccatg tacaacgact tctggaaggc cccggtcct    1140 tacaacgttg agcagcattt tggtatcatt aacattcttc agtaa                   1185

<210> SEQ ID NO 56
<211> LENGTH: 1146
<212> TYPE: DNA
<213> ORGANISM: Artificial Sequence
<220> FEATURE:
<223> OTHER INFORMATION: YALI0_E23969g

<400> SEQUENCE: 56
atggtcgccg caaaaatcgt cttttccaca gcgctgctgg cgctagtggc cggcgccgcc       60
accgatgcaa cctccaacaa cgttgcagac ctcatgcaga aaattgtcga gaaggacgct      120
gtccccacca tcacagacca cagagagccc ccgttcgtgg ttgttgagaa acgacaattc      180
cagggcaacc agggtaacca gggtaaccag ggtaaccagg gaaatcaggg aaatcagggc      240
aaccagcaga acaacgccac ctcctccatc cccaccaact cgggctcttc ccaggcagga      300
ggcttttctt ctagctcatc cccgggcttc ttttcatcca cggagatttc ttccaccgag      360
tctagctctt cgccgagtc cacttcctcc gagtcctcct cccggtttgt gccctcatcc       420
acctcgacct cctcggagag ctccagctct gagatctcta cgtcgacctc ctctgagagc      480
tcctctaccc ccgagtcctc taccaccgag tcctctacca ccgagtcctc caccaccgag      540
tcctccacca ccgagccctc ctccaccacc gagtcctcaa ccactgagag ctccacgtct      600
gcatttgtcc ccgtgcctac cacggagtca tcctctgagg cttcttcctc tgcttctccc      660
tctcctacct cgacagagtc ctcggcctcg ccttctccct ccaccacaga aggcccctcg      720
tcagagtctt ccactgaagt cacttccgac gccgtggtgt cgtccaccct aatcgacgcg      780
tccggcggcc gaaccaccgt tatcatgacc ctcacaaaca caaaggtgac ctacgtcggg      840
tccacaacca ctctgcctgt ggagaccccc accgcaagcg gagtcactgg caacaacaac      900
aagtctacgg gctcgacctc ccacacgggc cgaaacgtcg gtatcggtgt gggagtgggt      960
gttggtgtac ctgttgtggc agccgtcatt ggaggtctgt ggtggtggcg acgaaagcga     1020
ggaggagaca cccccatgta cgacaaggac gatctcatca gcggaggcga ggactccaac     1080
```

```
gtgtttcgat ccaacattga ccagtaccat gcgcctaacc gggccaactc cgcagcgaac    1140
ttttaa                                                               1146

<210> SEQ ID NO 57
<211> LENGTH: 3228
<212> TYPE: DNA
<213> ORGANISM: Artificial Sequence
<220> FEATURE:
<223> OTHER INFORMATION: YALI0_F04906g

<400> SEQUENCE: 57
atgcagtgtg aacccaatcc gatattttg ttatcttcct ccacacaact cagctctgga      60
atggcatttt ctggctggca gaacagtccc ggtgggcatt ccgtcggcgc caagctggtg    120
gctcgtgccc agaacgaaaa cgaacaggtg gtgcccggca cggtcttttt gtcgtaccat    180
ggcgagggtc agccctgggg ccggaccctg tctgacgcca acgagaagat tagcaccaag    240
cggttggacg acattgatcg gatttgcatt gagatgattc tcaacattga aggacacgt     300 ggcccgattg ttcccagcct tcaggagtct cctacgagct gttccgtgga actgactcgg    360
aaggagctgg accacatgat cgagactcct gctttcgagc tggaccgtcc cacggtcgac    420
agcgactggg gcggcaagtt cccacgtgcg agagcgctgg aaattgaggc actgttatac    480
aatgagttct tcaaggagaa ccaacacagt gtgacctctc ctgcacgcag acgtcgtgac    540
caaaagtaca gacaaaagta ctaccagccg tttgtggacc ccggcgtggg ccccagggag    600
acagacaggg agtacagaaa gtttcttgcc gctcagcaga gggatgccga gaccagaggc    660
aagcccgaga gggaagagga cagcaaagga gaaggactgt tttccgacaa gtttttattct    720 gccaacgata tcgaggagga ggctcagcgc gacaacgaca ccgaagatgc agttactggt    780
actatctgga gcgaaaacga gaaggaacac ttcttctctc ttctaggacg agtggggaga    840
caccgactgg gcgagattgc cgacgcaatg gactccaagt cacttgccga ggtcgaggag    900
taccacgatc tgctgtttac cgcgtctgag caccagaagg aaatgttcaa tgtccgagta    960
aatgctgggg aggagttcat tccggaaaaa gaccgaccgg tttcgttcaa ggagatccca   1020
gctgcttgtg aaatgtccga caagtggatc gctctggagg agtcgtttgc tcacggtatc   1080
gccaagtggg aagatgagca tatggctaaa ggggaggagc cgttttgttc gatgagagtt   1140
ggggacgaga cgaaagagaa cgcgtctgag gacttactca aaaccgaggc gttggtgtct   1200
cttgctgcag aaatcttcta ccccaatcct gccaatggta tggatattca aagcaaggag   1260
tacaacactg acttgcctgt gtttgagggt attgagggag atgcaatcaa ggagttgttg   1320
attagaatcg tcgacaagac ccgcgaatta ttccgcaact acatggaagt tgataaaact   1380
acgtatgctc gaacagacag caccatgtct accggaaata tgctgtttgt tcaagggctc   1440
aggtacaaca aattgtctcg ttttcttccgg agctactggg agagaagtgg atctgagtac   1500
gtggatgaga gatcggaggt tccgttcccg gagtcacttg ttacacccgg aacaactgaa   1560
gaacagcaca agaagatttt cggagaaatc aaggatgccg cacttccaaa gctgtacaca   1620
aacacaggtc tgcttgctgc gagtgtgaag agcatgtcca agctggacaa ggtcaaattt   1680
ttggacgtca aggagcagga gaggttgaat ggtatgattg aggaggaaaa aaagtacaag   1740
cgtgaacttg aggagggaaa tctagagtgg gatttcaccc ctgaagcacc aaagaaaccg   1800
tacaaaaccc gttccgaaag gaatctatcc gagattctca tggaaaagag agaccaagtt   1860
gataccgatt acttgtaccc cttcaagagc gcccatgtcc ccgtgtttct cgatattatg   1920
cacatggagg agaccggtat gcttgagaat ttggatgagc gcaattctaa gattatggag   1980
```

```
gccggtctga ctcgcttgct tgcaggtgct gctccataca catacecag gatcactact    2040 caggttaaca agctcatgta tgagcaggac aagaagctgg aggaaagatt caaggagaag    2100
atgctgcggt acaaatacga cggcgagggg aaggagatca atatgtggaa gcaggatctg    2160
cctcatgtga gggaggagat gataagacga ccacaagacg tcctctggaa ggctagagat    2220
gaatatgttt acgtctccc ctggtataac cccggtacga gaggtcccgg aggcggtttg    2280
aaccagccag aaaactctta ccctcctagt gttccgtatc cttcttctga tgatcctgtc    2340
caggatagga caagatacat atatcctgac ggatccttat acgacgaata tagccgacag    2400
gtattccagt ttcgccgcgc gcgcccgttc tttgagctca cccattctcc ctacattgag    2460
attggcaggg gtatgctgag tgagtggatg gaccatgatg atattgagaa gggaactcgg    2520
gaccatgtga tgggcatgag gcaatacttc cacaacttta ccgacacacc gccaactaac    2580
ccgtactctg tgtactacga ggaggagcgt ccgaaatatg aaactgcaga ggatgcggaa    2640
tatgagatta agatgagaa agatgcagcc gctgaccccc ctcttgctgt gttggggtg    2700 gaggaggaga agaaggagga ggagaagaag gaggaggatg aggtggtgga acagtcgccg    2760
ccgccgaaac acttgtcctt gtatctttcg aagcagcagc gacaagatat gcaggaacgg    2820
atgcggcagg agtatcagga tgtggtggat aagctggcac agagtggata cgaaaacgtg    2880
gagagatttg gcatatcgcc gttcgatctt aaccccattt atggccactc tggtttgttg    2940
cttcaatatg acaccctgaa cttccgatcc gacgatattc ctggtcggtt catggtgcag    3000
cagcgggaat catacaatca aatgcatatc cggcagccac aagacaatga ctatgtggac    3060
cctaacgaat acacaccggg ccgtggtcta aaacgcaaag ctcgtaacca cgaggaggac    3120
acaaggccgt ctaagatgcc caggttggaa ggcagcgagg tgcggaggct ggaggagatg    3180
tccatgacga acaatggatc ggaggatcct gtttgcagag ttagttag                3228
```

<210> SEQ ID NO 58
<211> LENGTH: 2424
<212> TYPE: DNA
<213> ORGANISM: Artificial Sequence
<220> FEATURE:
<223> OTHER INFORMATION: YALI0_F12221g

<400> SEQUENCE: 58

```
atgactgcgc gagcgccccc tgccaaccgc aagctcagca acatgctgat ggcggacttc     60
aagcagtgtc tgactctgta cgaaaaaaag gagtacgccg aagccatcaa acgggcggat    120
cacattctga ctcagaagcc ggatcatggc gagactctgg cggtcaaggg tctgtgtcgg    180
taccatcagg actcgcccgt ggagggccga tcgctgatca acgccggaat gaagaacgac    240
cccgagtcct acatcatctg gcacgtgctg gctcttctgg agcggtcgga aaaaactac     300 cacgcggccc tcaaggcgta ccaaaagtcg ctgaccatcg accgtccaa ccagaacgtg    360 ctgcgggacc tgtcgttgat gcagatccag cccgtgagt acgagccgct ggtgatcacc    420
cgacggaaac aactgaccga caagccggag atccgggcca attggaccgg gctggcggtc    480
gcgctgtttc tcaagggcga ctacgccacc gccgcacgaa ccctcgcggc atacgaggaa    540 agcgccccg aaaaggaacc caaggacaag acccagtcgg acgacattga aaactgcgag    600
ctggcgctgt tccgaaacaa gtgcctgatc gaggccaagg aatacgactt ggcgctcaag    660
gatctcgagg agctggaaaa taaaacctcc aagcgcccata tccccgacca gcagtccatt    720
ctcgaacatc gatgcgacat ttacatccga cagggcaaaa ccaaggacgc ccagagactc    780
```

| | |
|---|---|
| acccgagtgc tgctgcgacg aaaccccccat gaccgggctc tctaccgaca gctggagaag | 840 |
| gtgctcggca tccaggacaa caaccagctc aagtctgtca tgtacaagaa gctggctcaa | 900 |
| aaataccccc ggtccgactg tcctcgatcc atgcctctgg agttcctcga gggccaggcg | 960 |
| ttcgacgagg ctgccgacgc ctacgtgtcc accctcatcc atcgacgggt cccctcggcc | 1020 |
| ttcatgaacg tcaagcacct gtacaagaac cccgccaagg ctctttctat cggcgccatt | 1080 |
| gcccaacgga tctttgatgg cgccactgaa gatctttctg cgcctcgga ttttctgtgg | 1140 |
| tccgcctgct ttctggccca gcactttttcc aagctcggcg accagaacaa ggccctcaag | 1200 |
| ttcattgaca atgccattga gcacacccca accctggtgg agttgcatct gacccgagcc | 1260 |
| aaaattctca gcgaatgggc gcggtcaac aagggtgctg aggccgccaa tgccgcccgg | 1320 |
| gaactcgatc tccaggaccg ttatctcaac accaaggccg ccaagtacac tttgcgggcc | 1380 |
| aacaacgcgg acgacattga gcaggccatc aagctcatct ccatgttcac gcgaaatgac | 1440 |
| acctccggta ccggcgttca ggacctgcac gatatgcagg gctactggtt cctgtccgag | 1500 |
| ctggcccgac gacagcgacg aaacggagac ggccccttgg ctctcaagcg acacaaggcc | 1560 |
| gcgctcaacg tgttcagcga gtttgaacac gagcagctgg acttccatct gtacgcgctt | 1620 |
| cgaaagggaa ccatgaacgc gtacattgac atgctgcagt gggaggacaa gctgtacaag | 1680 |
| agtaagaagt ttatccggtc cacccgggt atcattgaga cttacattgc gctgtgggat | 1740 |
| accaagcccg actgtggctg tggagcagtg attccgggct cttcccctct taaggcggtc | 1800 |
| gactacaacg cctccaccac ggtcaagaag aagaagaaga agaccaacga gggttctgcc | 1860 |
| gaggccaaac agaaccctaa cggtctgcct accccgaac atcgacacga tgccgatccc | 1920 |
| gagggtctca agctcgtcaa gaacgtcgat ctgctggaaa ctgcccttgt tcatgcgaaa | 1980 |
| aagctcgccg aggtcggcga cagcctcggg cttgtgttcc aggccgagat ttatctgcga | 2040 |
| cagaacaagt acatgcttgc tcttcagtcg ctcaacaagc tcaaggcctc cgacgccgca | 2100 |
| tctcctacg cctctgtgct ggccaaggtc gccgaggccc agcttaatgg cgatgatagc | 2160 |
| accgcccaga acctcaagga tatgactctc aagatgcttc ccaagctgtt caacgagaca | 2220 |
| gagtccgatg ccgtggccac cgctcgactg gccttttccg tgccctctta caaggagcta | 2280 |
| gctggagaat tgctcaaggg tctggtctcg gagaatgcca ccgctgccgc tctagcagtt | 2340 |
| tgggctgcca attcgcttgg tctggagctg gaggatctgg ccaaggagca gtatcccgag | 2400 |
| ctggaggttc ctcttcccaa ctag | 2424 |

<210> SEQ ID NO 59
<211> LENGTH: 4308
<212> TYPE: DNA
<213> ORGANISM: Artificial Sequence
<220> FEATURE:
<223> OTHER INFORMATION: YALI0_F12793g

<400> SEQUENCE: 59

| | |
|---|---|
| atggaacgac tcagccatgg aggcggcgga tcgctcgccg tggtgacgca gtcgccgccg | 60 |
| ctcaaccgcc ggctgtcggc agagccccca acctcgcccc agacgtcggc ctcccccaac | 120 |
| cgcatccaac cgcaatcgcg tgccgtggcc caagagatca cgccatcca gacgctcaag | 180 |
| cggctgtcta tcggtgccgc gctgaccacc gacccggacc tgccggacgc ctaccactcg | 240 |
| taccacgtgg cgcaggcgct gggcattgac atggacacgg acgagttcca tgatgcagct | 300 |
| gagacgacag acgtggtggg agtgggccgc tcgcggtctg cggagcgggg agccgctact | 360 |
| tcgcccacgc ccccggcacg cacactcgcc agacacacgt cactggacac ccccaccaca | 420 |

```
ccgcccgac ggcgctcctc cgcccgcaag tcgtcgtctt cctcaagctc gtccccagac    480
cgaaactcgc tgctgtgggt cccagcgtct atccatccgg agctggctcc gcaggagtgg    540
aagacgtttg tggaaaacaa ggtggcgggc atggatgagg agacagacac gcgccggctg    600
tcggcgtcgt cgctgtcaag cttgtcacga tctccgtcag ccacatacac ccagactgac    660
gtgggagagg ccaacgtgga acacaagcgc aagtcgggcc tgcaacgctc aaactctcga    720
ctctcaaaac aaatccgcga ccaggaggac tacacagacg gctccgagat tctggagaac    780
cgacgcagat cgtcgctatt gtccacctca acgctcggct ccgtcaccat cgaggagctg    840
tccacgcagc tgtcccagtt gactacacag cagacgaacg cagatccgtt cacactggca    900
cgttcgctgt cggtgtcacg agatggacaa acgtcgcccc aaaagctgca gcgcaaaaag    960
actctggact cgtctccggg agtggactcc atccaggagg aggaagaatc caacacgccg   1020
ctcatgggtc tgcgacgggc caagcggacc aactactcca agccgagtag cattcgtcgt   1080
gctagggccg agtctgccgc tcgagatcgg aaccccttg atgctgattc gccctctcag   1140
actcagactc agacaccatc acaatcacag gttgcggatc cgccattga tcccgctgat   1200
cctgtttcta caatcgtgga tactgcggac tctcttcctc ctactccccc gcctaaggag   1260
gacaagtatc tgcaggacaa acagctgcac gtggatgttg ctgttgacaa gccgccattg   1320
atggctcccc tcgatggctt ggacaaaccg gtgccttctc ttccgccacc agcagcggga   1380
gaagacttgg acgtgaatgt aaacgtggac aagcccatgc ctccaattcc tggaggagtc   1440
gtgggagcag ttggagcggt ggacgacggg gaggtctcac caaactctcc ggtgcaagcc   1500
gttgagcaga tttctcccaa gcagcagatt ccgcccgaac aggtgtctcc tactcaggtt   1560
tcgcccaaac atgtggttc aaggagagt gagccagaat tggtgtctca tactgtgaca   1620
gtcactgctc cggctttgga caagccgctt cccgacggaa agcctccgca tgctgctcag   1680
gctccttctc ctgcgcctcc aacagttcct cttcctgctg ctcccgaaga cgacaacggc   1740
ttctcgtttg aagacgacgt taagcagaga agacgaggtg ctcctggcgg tcctcctccg   1800
ggcccgacac ctgttccggt taccagctcc gtccctggcc cttcctctgg ccctggccct   1860
ggccctggcc ccaggccgga tatggctgcc cctcctcctc caggacaggt acagggtcct   1920
cgagatggtc ctatgccccg agatggaccc cgagatggac ccgagatgg accccgagat   1980
ggaccccgag atggaccccg cgatggactc cgagacggtc ctcgggacac tcacggacct   2040
ccccaccacg gataccacgg tggccagccc atgcaccgac aacattcaca tcccccgcat   2100
caacaaccac attctcagca tccccagcaa cagcatcccc agcagcatcc ccggcagcat   2160
ctccagcagc aacaacatca acagcaccag ggcccccctc ctggttataa tggacctcct   2220
ccgaaacaca agcgtcgaga tcgtccacat ggccaaggtc atccacagca gcagggcccc   2280
tatcccgcgc cccagggaca gcagcagggc ccgtaccctg gaccttctgg gcaacacccc   2340
gctcctcacc agggtcacca gggaggtccc taccctcccg cacatcggtc cagaggccat   2400
gcccagggcc aacatgggct ggcgcatgga cctcagaacc atgtccaggg tcacgggccg   2460
aaccacggac cgaaccatgg ccccagggt gggcacgggg gtaatagccc caggcggga   2520
cacggtcaca gccggcccca gcagcgtcct ccaggacgag gcaagccggg aactcatggg   2580
ggacctcctg gaccgtacaa gccgggccac aagtcgagcc acagccacag tcccgagctg   2640
aaaagtcatc ccgacttccc ctcgacttca gggtcctccg cggcatccag agacccgtct   2700
catgctcgag atggaagcac ggcgtcggag cccaccccct ctactgttga ctcgccggac   2760
```

```
caacacgcgc ctccctcacc gcctcagcct ctgcacaagg agctgagtta caaggagctt    2820
cccatcaaca aggaggcgcc agtggtctac cgtatcacgg acgagcagct gattggcgga    2880
tcatcgttca actcgccatc gatgatgggc cagacgactg acgtgctttc gtcgattcca    2940
ccgtcagagc agctatacgg ccgagggcgc tccaacacgg ctcccagcag cgacgccggc    3000
tacgactcgg atggcgaggt gaccaagacc aagtccaaat cgaagaagag cacgtggggc    3060
tggctactag cgacaagga caaggacggc aaggacaagg atggaggaaa ggacgccagt    3120
aacgccgagg acgaggtaca cgcgccggcg cagtcttcca acctcatcaa gcgcaaggtc    3180
aagggcaaga aggacgcagc gaccctgatc acgtcgtttt tcaagaaaga caagaagggc    3240
gacgacgaca ttaacacagc aggagaggac aagcgggagg acaagaagga ggtggaccag    3300
agagagcaga gagagcagag ggaacagagg cgagagccag agcttccagt cgacgtgcag    3360
cagcaggcaa caaactctcc tgttcaggcc gtccctgtgc tggctccctc ctcatcgcaa    3420
ccatcgcaat ctggacaacc cggccgtcga ggaacagcac ctgcagctgc ttcgtcggct    3480
cccgaggacc ggtcccgatc tcagtctccg tctcagcgtc gacggatcca aaaggcacgc    3540
aactccaaga gccccaccaa gcgacgacgc gacaagaaca agtccaagtc tgagcacgtg    3600 cgagccagc tggagcgaca ggacgaccac atggacgtgg atcggaccgt ggtgggccct    3660
ggctcaaagg atatggagga cactgttccg tctgagtcca gtgatggata catggaccct    3720
gcgcagcagc agcagcccat gtactcgccc atcgatccgg ctctgttcga tctgccgtcc    3780
acttacatga agcccaacat gatgacagtg atggactacg agactccgat tttctactcg    3840
ggtcccgcag ttctggtgcc tcccggtgcc ggacgggcca tggtcatgta ctaccatcgg    3900
ttcccgctgc acattgagcg ggccatctac cggctgtctc atttgaagct ggccaaccct    3960
cgtcgcccac tggtgcagca agtgctgctg tccaacttta tgtacgcata tctggatctc    4020
atcaaccagg gctaccagca gcagcagcag cagtacgagg caggggctgg tcaactgggc    4080
gccggagccg gagccggagc tggagctgga gctgatggag ctgcaggaga aaccaccgag    4140
tctgtcgagg ccgacgacta cttctctgaa ggcacctatg accagatggt ggagcagaat    4200
gcgtacgctg ccgttgtgga cgatgacgcc atgggcagtc ctgtaagcac cagcagttcc    4260
agcagtagct ccagcaacga ggagtactgg cacgaggagg gacattag                 4308
```

<210> SEQ ID NO 60
<211> LENGTH: 1171
<212> TYPE: DNA
<213> ORGANISM: Artificial Sequence
<220> FEATURE:
<223> OTHER INFORMATION: YALI0_F16577g

<400> SEQUENCE: 60

```
agtgagtacg aactctggaa tctggtccgt tggaataatt ttttggttgc gattgtgaac      60
actgctgggg ctaccacccg tatagcactg ctctgcactc tcatggcatg tacaagaccc     120
ctctacttga tactgcctca cagcgaacac tagccagcca cattgattgc ttttttttct     180
tgatatttca tggtattggc agcaatcatc atgtttccat ctcattagag ccctgtcatc     240
aagcaactca cctaacacag tgaccctcga atcttcgctt cacctcctca cacctgacca     300
gctttcgtct ctggcccatc tgcaaatttc cgtccccgag ctctgcaaga ctgcccatta     360
tgccgagatt tacggtcacc atttacttcc agatcagaaa tgccccggaa gatactctga     420
gaaggccaga gatgtgattc tgctgaaagt gttggaatcc gaaaactacg acgctactaa     480
ggcaggagac aaactactaa cggtgctgag atggagaaag gactacaagc ctatggatga     540
```

| | |
|---|---|
| agacagagac ctaccagtgt tggatggtca cgttactaca gttgctgcta ccaatctgcc | 600 |
| tcagaccaca ctctggcatc gctcttcggc aactcacatt cccaactcga tctacattcg | 660 |
| atggaaggtt ggattgattg agcaagctat cagtactctt gacttcagct ctcccgacaa | 720 |
| ctcttccaag ctcacatgtg tcgaggactt caaccacaac atgtacgatg aagttctatg | 780 |
| gaagcagctg agcaccctga gagagttcct cctctatcct ggaattttcg acaagacctt | 840 |
| ttttgtcaat gttcctctga gtctcagaat tggactgaga ttcttcaaca agtccaaccc | 900 |
| cgtgtacaac cgtcgaaact ccgtcattct cggcaagggc aaggagttga gaagcacct | 960 |
| tggtaactgg gtgcctcgag aatatggcgg agaaggacca ggacttgaga tccaaggaag | 1020 |
| aaatgtccgc ggttattcag cttatgaaca ccacgctttg cgacatgttc tgaccacttc | 1080 |
| tcctacacaa tacagtcatg cgaagggaga cgcataccga gacagctatg cccaccaga | 1140 |
| cgatgacgat gttcctcctt attaccatta g | 1171 |

<210> SEQ ID NO 61
<211> LENGTH: 3414
<212> TYPE: DNA
<213> ORGANISM: Artificial Sequence
<220> FEATURE:
<223> OTHER INFORMATION: YALI0_F17468g

<400> SEQUENCE: 61

| | |
|---|---|
| atgaacgact ttgaagacga ccagaaacat aaggcaagaa ccgagccctc gggccagccg | 60 |
| cccaagaaac ggtcaagagt cacattttcg tgtcttattt gccgtaaacg aaagatgaag | 120 |
| tgcgaccgca atctgccgtg ctccacctgc aaggccgcca cgccgccca tctctgtcgc | 180 |
| tatgacatga accgcagcgc gtcgccccag gacagagaca tgcccatccc cagcgacgag | 240 |
| tccatggtgg caccaacgag cgctcctgga ggaggaagcg cggccaactc gggctccaag | 300 |
| aagccccgtg gccggcccaa gaagtctgtc gccgagctca ccaagatgca ccagcaactg | 360 |
| ctggaacaga acgagctcaa gggcgagacc aaagagctga aggacgtggt caagcaggag | 420 |
| ttccagtctc ttcctccca gcaacagcaa cacatccccc aacagcagca gcagcagcag | 480 |
| cagcaccacc aacagcaaca aaccatgcga catgtcccc agcaacagca acagcacatg | 540 |
| ccccagcaag cacatcaaca acagcagttc cacgcgctca accaacatca acaccagcac | 600 |
| ctgcaacagc agcaccacgc tcagcagcat cacaagccca acggcctaac catcaataca | 660 |
| aacgaccctg ctacgcccgt caaccaagcg gtgcgaaaat cgtccgcagc ctcagccact | 720 |
| ccgggcagaa cgccccccaa cgaaaactcg cctcgacgtg gatcggccaa gaaacacctg | 780 |
| ccgccgatcg gagatacgcc ctcaccgtcc atgtcgtcgc cgtcctccgc attcaaatcg | 840 |
| tcggctgaca tgctgcacca ggtggtcacc cggaccgcca cagacaccaa atatattggc | 900 |
| atttcgtcga aattctcgct gtgcatgaag cccgcgcgcc agcagttgtt tggacccttc | 960 |
| tcgtccatgt ccttctttc ggaaaacgag cacctgcagc ggttctccaa acaggtgtac | 1020 |
| gaggccaaga acaaaacta catcaaggac aagaacgcac ctgtgcttat gcgccacaaa | 1080 |
| aacatatttta ccgacttgcc gcaaaagtac cgggtcggcc gaggctcgtt tgtaggggct | 1140 |
| ggcagccatt acggaggcac cagtgcgccg ggaagcacaa acagccacgc caatggcggc | 1200 |
| ggtgctttca atgcggctgc gtcgccatg acaagactc cggcctccac ctcgtcatct | 1260 |
| tgctcgacca tggactgtgg agacatttcc aagtctttcc catttgactc gccgaacggt | 1320 |
| atctacgagg tactggagct agtccctccc aagccctga cgtactttct ggtcgacaag | 1380 |

-continued

```
tatatgaact cggtcaaccg gttcttctac acggtcattc ccaaatcctt ctacgagtgt      1440
ctcgacgagt ttttcatcca gaagcagcgc attctgaacc gagagatccc cgccactgtc      1500
aagactgtcg atctgcgaca ggtggcccag attttgctga ttctgcgtct ggctcgaatt      1560
acgctccctt ttgactgggt ggttcccgag tacctggtag gtggcaactc taacagcaca      1620
actggcggtt caaacaatga cggctcctcc gcctcgtctc ctcctgcctc ggcagacacc      1680
tcggacgtgt accttggagc cgggcttttct cagattgccg aaaactgcct caaccacatc      1740
ggctatctgc gaaaggccaa cctgcgggta ctccaggtgc tatgtttgct caaaatcacg      1800
gccatgtgcg atcccgacgc cggcgactcg gccgacggct gcgactcgtg caacctcacc      1860
ggtctgatca tccagatctc aatctctatg gggctgcata tggaccccag ccacttctcc      1920
aaggtgtccc caaccattgc tcatctgtgg agaatgctgt ttggtttcat tgtcactctg      1980
gacgcccatc gatccatgga gctggctctg cctccctctc tgcctctgga gtgttcggat      2040
accgacattc tgttcgagcg acactctctg cccgatgacc tgctgtcacc cggcgaggag      2100
cagcacattt accatcgacg aaagcagctg cgatgggcct tcatttctct agatgtggtt      2160
cggggactgc tgcgaacaac agtgcatgtt actcccgatg gaatgggcac ctctccacag      2220
gccatgggca aggagtactt cgatgccatt gagcgcaagc tggaagcatt tgagaacgac      2280
atgaacccctt actacgagga gatcctgtcg gctctacagg cacccgagtc ccgagacagc      2340
gactaccgca ccgtgacgg ccatgctgcc gcccagcggc tgtctctgta catgacacta      2400
gtgcgtctcc gtcttggcta ctacctgtgt gccggcaact ttatggacgc cgccgaggtc      2460
aagaccaagg tggttacgtg tgctcttaag atgtgcgata tcatgcaggc tgctatggag      2520
cgacctcatc tcttctctgg gttcatgtgg tatgtgcatt tcgtcaacct gcgaaacttc      2580
accttctcgt ttggtacttg catttctgca tacctgaacg agatcaacac tcgacgagcc      2640
gagcgcgaca tgcccatcat tactcctgcc gtcaaccgaa agtacaatga catgacgttt      2700
gactattcgc ccgacaagat ccgagatccc aagcggttga ttcaggctgc catcagaact      2760
caccgatggg tccgatctct ttcgcagcgg tactatgttg cctggaagtg tcatgccgtc      2820
attgtcggtc ttcttcgagg tgctcgtctg gaggttctcg cccagtacat tgacgctcaa      2880
gagtacaagc ggctggagaa ggagggccac cgggacaaca cgtttgtggg tccttacgcg      2940
cctcaaaatgc gagagcccac aaccatgtcg gttaccaaaa acgactgggg tcgagacatc      3000
acgtcggaga actacgaccg agagcagagc gaacttcgag ctgccgagga gcgtgccaac      3060
cgccaaggtc aaggcccgga gtctatgtct gctcctgcag cgcagtctca ggaccagatt      3120
ggccagggca accagcagca gcagatggag tggcagggtg acaacaacat gtttcagaac      3180
aacggtctga tggagcctcc ctttctagag gacccgatca ttgacgaccc cacctttgat      3240
accctgggct cgactctggg gcttccgtcg cttattgccg aagagtgggc caacattgag      3300
gactcgctct ttgatgatct taactcgtcg cggttctaca tgtccatgga ccagaatttt      3360
aacaacaccct ccaccgccac tgacaactat gaggtaactt cgccctccag atag           3414
```

<210> SEQ ID NO 62
<211> LENGTH: 2490
<212> TYPE: DNA
<213> ORGANISM: Artificial Sequence
<220> FEATURE:
<223> OTHER INFORMATION: YALI0_F19030g

<400> SEQUENCE: 62

```
atgaagttct ctgccactct tctcgctgct gcagtcagcg ttgctgtcgc cgaccctatc        60
```

```
ctcggaaagg gacccgaccc caacactttc tggttctccc agccctctac tcccggagcc    120
cccgctcctt ccaaccctcc tgccgctccc gctcccaagc ctaaccccgg cggagttgac    180
cctaacactt tctggttctc gcagtccagc actcctaccc ctgctccccc tgctcccgct    240
cccagcaccc aggctcccgc ccccctgct tcttctcccg ctcctcccgc ttcttcggct     300
gccctgccc cccagcctga ggagacctgt atcgcccccg ccggcgctca ggagaagcga     360
tctctggccc tcctgtccca ggtcttctgc tccaccaagt gcttcaagct ctctttcggt    420
ctgcagacct gccagggtct ccagtcctgc gagtgtcagt tccttgatgg cttcgcctgg    480
acccagaagt gtctgtcttg tgctcaggct taccccagt acggcatgca ggagatcgac     540
gacgtcatta agaagtgcca ccccaggcc acctcttctg tcgctccccc tcccgttgtt     600
gtcaccacca ctccccccga tgttaccagc tctcttcccg agtgtgaggt tcctcctccc    660
acttgtaccc ccgagccttc tcaccccgct tctcttgata acatgcttaa caagcgattc    720
aacctgatcg gcaagctcac ctgcaagaag acctgtaaca ccgttgttgc tgacatcaac    780
tcctgtggcc aggatgccaa gtgcatctgt gacaagatca agtccaccca gtctgctgtt    840
gaccagtgca cttcttgtgt ccagcagtac aacatgtggc cttacttcaa cgtcgacaag    900
cagctcctcc agtacgttga ggcttgcaag gctgtcgcca ccccactgc caccccact     960
cccatcatcc ccgtctgccc taccgagggt gccaccactg agcccgctcc ttcttccacc    1020
cctgcctcct ctacccctgc ctcctctacc cctgcctcct acccctgc ctcctctgcc     1080
cccgcttctt ccaagcccga ggagtcttct gccgtcccca cctccgctcc cgttgctccc    1140
accaacgcca ccgagtcttc tgtcgctccc tctaccactg aggctgctac ttcccctgtc    1200
cccaccaacg gaactgtttc ttcctcttcc gttgcttctt ggactaccaa gactctgacc    1260
tctaccgttc cttgccacga gtgcgagcac ggcggcaaca agactgtcat cgtgactgtc    1320
actgagcctt gctctactga ggtccctact accgccgatg ttcctactac ctccgaggtt    1380
cctaccacct ccgttgaggc tgtccctacc tccgaggctc ccgtccagaa caccacccag    1440
actgtcactg aggagtgtga gacttgcaag cactcttcta ctgctgctcc ttctctcacc    1500
accaagacca ccgtcattga gggtaagact gtcaccatca ctgagccctg ctccactgag    1560
gcccccaccg aggcccccga ggctacttct gcccccgtta ccaccaaggt caccgttgtt    1620
gagggcaaga ctgtcactct cactgaggag tgtgaggagt gcaagcacca ctctaccgag    1680
gcccccaagc ccaagcctac ctccgagtac cccgagggag tttctctcac taccaaggtc    1740
actgtgatcg agggagttac caagactgtt accgttcctt gcgatactac cactgaggct    1800
cccgtcccg agacttctgc ccctgctccc aagcccgagt cttctgctcc cccgctcct    1860
gccctgctc ctgagtcccc cgccggcaag cccgagccta cccccgctcc tgctccctct   1920
tctgctcctg ctcccgctcc caagcccgag tcttctgctc ctgctcccgc tcccaagccc   1980
gagtcttctg ctcctgctcc cgctcccaag cccgagtctt ctgctcctgc tcccgctccc   2040
aagcccgagt cttctgctcc tgctcccgct cccaagcccg agacttctgc tcctgctccc   2100
gctcccaagc ccgaggattc tgccctgct cctgctccca gcctgagga gtctgcccct    2160
gctcccgctc ccaagcccga gtcttctgct cctcccgctc ctgctcctgc tctgagtct    2220
cccgccgtca agcccgagtc taccccgcc ccgcccctg cccccgctcc tgctcctgct    2280
cctgagtctt ctgctcctcc cgccctgcc ccaagcccg aggcttctgc tcctcccgct    2340
ggcaagcccg aggttcccca ggctcagcct tccacccccg agcaggctcc ccaggctccc    2400
```

| | |
|---|---|
| tcttccggcc ctgcccaggc taacggcgct gcctccaacg gtatctccgc cgctatcctt | 2460 |
| gccgctgctg gtatccttgc tcttttctaa | 2490 |

<210> SEQ ID NO 63
<211> LENGTH: 3339
<212> TYPE: DNA
<213> ORGANISM: Artificial Sequence
<220> FEATURE:
<223> OTHER INFORMATION: YALI0_F23287g

<400> SEQUENCE: 63

| | |
|---|---|
| atgctccgag acgtgagcaa gtcgactctc aacattatgg aagcaggtgc cacggacacg | 60 |
| tgtgggcgcg acggcgacgg actccacgac gctcgctcgc aggtcgagcc acaacacgtg | 120 |
| gactacgcca tcaacgacga ctcggtgata cccgactcgg agtgcgagca ggaggtgctc | 180 |
| aacacggact acgtcggcgg cgtgagcaag tcccacagac agggccatca aggggggtgtg | 240 |
| gtggaagaca ccacgttcag cgatcttctg gaaatgaaca tcaactttgc cccgggatcc | 300 |
| atggaggtgg gcgagttgcg gacggaggaa gtcacgcccg aggtggagga gtgttttcgg | 360 |
| ggttttgagc gccaaatgat gagccacgtg agccacagca acgtgagcca cagcaacgtg | 420 |
| agccacagca acgtgagcca caactccatg ctcggaagct atccgatcca gagccactgt | 480 |
| ggatccatag ccagagcct agggtatttc gccagtgagg aactgactga ggtggaaaaa | 540 |
| gggaccattc atgatgagcg ggagcaggaa cagaagcaag agcaggaaca gaagcaagag | 600 |
| caggaacagg aggagcagat ggaggagggt aatgaagaac agagcaacga acagcccgtg | 660 |
| actgaacagt cggagtctgt tagtggaagc gaggagggtc aggaggttga ggcaagtgaa | 720 |
| gctggtgttc tagctgtcat tgaagatgaa gttggagaga atggcgagcc tggtggagcg | 780 |
| ggcgattctt ctcatgccat tgaaatcaca tctactagtc cttccaagat cgagattgct | 840 |
| attgaagatg aagatgaagg tgaagatgaa gatgaagatg aagatgaaga tgaaggtgag | 900 |
| gctgaagtag acgaagaggc agaagaagtc gaagacgagc tagaagccga gtcagagact | 960 |
| acgccaaagg tttctgcgtc cgaaaacgag ttctcacaca catcgcactt tgaaactcca | 1020 |
| gcagctgaga caccaaaaca cgacgaggag gttatcgcag ttgaagccga tcaagacgtg | 1080 |
| tccatgatga acgtgagcat ggaccgaacc aaccacgatg tgagcatggc agaaacaact | 1140 |
| gcagtggtca acaccactag tggagatact actgtcacag acgaagcttc tacagctcta | 1200 |
| acagcaccca ctacacacac acatgcagaa gacactgcat cgcaggctac tgtttcgcgt | 1260 |
| gagtcgtcag cccaagttgg agcaactctc ggaacaagtg ctaagcccga gaaacagaa | 1320 |
| ggagatacaa cagtcactgt gacggcctct gctactccag agaacacagg tatggacgag | 1380 |
| ggtcctcctg tcctatctct cttggacgta gatggtgatg tccatatgga gatgcaagag | 1440 |
| gccaatggtg aggttaatga gcgcgataca catggggagg atacacatga ggaggaggag | 1500 |
| gagatgacag gggaggacgg cgacgagctg cagatggcg aagactacga tatggcaggc | 1560 |
| gaagcagacg agcaaccaca gaaacagact attacagaga ctgctccaac agtgtcaccg | 1620 |
| gttgcatctt tcccagcact tcccatgaac acagctagac ttactcggga acacaagacg | 1680 |
| attcccggtg aggtaacacc agaagccaaa ttgattccag gtgaagttcc tggtgagaag | 1740 |
| cgtctcattc ctggtgagaa gctgttgcc ggttctacga agaagcccat cccaggagag | 1800 |
| attctatctg ccaaacgacc tcttcttgac gagactcccg tgtctcgatc agctcccact | 1860 |
| gttgccacat ctaaactcat tcctggagag gttcctcgaa acacatcatc atcatcatcc | 1920 |
| tctgcatcga agattcttca gccgacacca cgagtggcat tgtcaatgaa gcctccggag | 1980 |

```
tcgctggttt cgagtgttcg agcatcgtct cagcctcctc gtcagctgac tcccattccc    2040
aatctttcgc attccgacgc tcttccagaa gaccctaccg accaggctcg acaggctctg    2100
gctcgaaaaa gacctctccc caagcgtccc cagggccgta agatctctca cgagaccact    2160
ctggagctgc agaacttcga gttgtcttgc aagggtcttt ctgatcacta tcggcttctg    2220
gacaaggttg gcgagggtac tttctcctca gtctaccttg ccgaagacat tcattacgac    2280
ctcaagcgtg aatttgctgc tcggaagaag cagaaccagt cgtccagcca ctggaagtct    2340
ccccctttga actccaagaa gcggattcga ttgctggagc gttcaaacac agatatccat    2400
cggggtccac ttgtggccat caagcgcatc tacgtgacgc cttcgcccaa acgaattctt    2460
aacgaaatca gattcttga cgcgctctca ggctacgaca atatatcgcc actgttaaag    2520
gtgatgcgcc atgaggacca aattctcgcg gtactgccgt actttgagca tcaggatttt    2580
cggtcgctgt acaaaaccgg ctccaagacg gacatccgta tttatattac ccagctgtgc    2640
caggccctca gtttgtgca ttccaaggac atcatccacc gagacatcaa gcctaccaac    2700
ttcctctacg accgtcaccg acggtacggg gtgctggtgg actttggact ggcagaagtg    2760
cagtcatttt cgacgtccaa tccctgtgtg tgtgtttctc aggaaaacca gaaacgtatt    2820
ttgggctcgg cgtgggagct caagcccaag ggctcatacg agaagaacga cgtgcggtct    2880
ggccggcgaa gcaaccgagc aggtactcga ggctttcgag ccccgaggt gctgttcaag    2940 tgcacctgcc agacgaccca gatcgacatg tggtccgtgg gcgtgatctt gctgtcattc    3000
ctgtgcaaga ctctgccttt cttcatgtcg cacgacgatg ctgatgctct ggtggagcta    3060
tgcagcattt ttggccgcca ggctatgcac cagacgggtc ttctacatgg tgcttttctt    3120
gagctccaga tccccaaact gcgaagtaca ggcctgccgt ttgagcgggt tctgttacag    3180
gctggatgcc ccgaggagtg ggctcgagat ccggtggtga ttgattttct cagcaacacc    3240
atgaagctgg atcaccacca tcggttttcc gccgagaagg cttggcccca tgagttttgc    3300
cagcgtgcct atgaggagga tgattacgta gacgtataa                          3339
```

<210> SEQ ID NO 64
<211> LENGTH: 15
<212> TYPE: DNA
<213> ORGANISM: Artificial Sequence
<220> FEATURE:
<223> OTHER INFORMATION: Synthetic

<400> SEQUENCE: 64

```
tcctctaccc ccgag                                                       15
```

<210> SEQ ID NO 65
<211> LENGTH: 15
<212> TYPE: DNA
<213> ORGANISM: Artificial Sequence
<220> FEATURE:
<223> OTHER INFORMATION: Synthetic

<400> SEQUENCE: 65

```
cctccaccac cgagc                                                       15
```

<210> SEQ ID NO 66
<211> LENGTH: 12
<212> TYPE: DNA
<213> ORGANISM: Artificial Sequence
<220> FEATURE:
<223> OTHER INFORMATION: Synthetic

```
<400> SEQUENCE: 66
gaggtcaagg tc                                                         12

<210> SEQ ID NO 67
<211> LENGTH: 13
<212> TYPE: DNA
<213> ORGANISM: Artificial Sequence
<220> FEATURE:
<223> OTHER INFORMATION: Synthetic

<400> SEQUENCE: 67
gagctgagat gac                                                        13

<210> SEQ ID NO 68
<211> LENGTH: 18
<212> TYPE: DNA
<213> ORGANISM: Artificial Sequence
<220> FEATURE:
<223> OTHER INFORMATION: Synthetic

<400> SEQUENCE: 68
aggaggaggc taagaaga                                                   18

<210> SEQ ID NO 69
<211> LENGTH: 12
<212> TYPE: DNA
<213> ORGANISM: Artificial Sequence
<220> FEATURE:
<223> OTHER INFORMATION: Synthetic

<400> SEQUENCE: 69
gacagtcagc ac                                                         12

<210> SEQ ID NO 70
<211> LENGTH: 45
<212> TYPE: DNA
<213> ORGANISM: Artificial Sequence
<220> FEATURE:
<223> OTHER INFORMATION: Synthetic

<400> SEQUENCE: 70
ctcccgagtc tctgctgag cctaccagcg aagagacttc ttccg                      45

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71
aaaaagtggt cgaaaaagtg gcca                                            24

<210> SEQ ID NO 72
<211> LENGTH: 21
<212> TYPE: DNA
<213> ORGANISM: Artificial Sequence
<220> FEATURE:
<223> OTHER INFORMATION: Synthetic

<400> SEQUENCE: 72
tggccgaaaa agtggccaaa a                                               21

<210> SEQ ID NO 73
<211> LENGTH: 15
```

<212> TYPE: DNA
<213> ORGANISM: Artificial Sequence
<220> FEATURE:
<223> OTHER INFORMATION: Synthetic

<400> SEQUENCE: 73
cccacccgca aaccc                                                    15

<210> SEQ ID NO 74
<211> LENGTH: 15
<212> TYPE: DNA
<213> ORGANISM: Artificial Sequence
<220> FEATURE:
<223> OTHER INFORMATION: Synthetic

<400> SEQUENCE: 74
cctctcacca actca                                                    15

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cacgtgaaag tagccgaa                                                 18

<210> SEQ ID NO 76
<211> LENGTH: 27
<212> TYPE: DNA
<213> ORGANISM: Artificial Sequence
<220> FEATURE:
<223> OTHER INFORMATION: Synthetic

<400> SEQUENCE: 76
ccgctagcgc caactctggc tcggagc                                       27

<210> SEQ ID NO 77
<211> LENGTH: 12
<212> TYPE: DNA
<213> ORGANISM: Artificial Sequence
<220> FEATURE:
<223> OTHER INFORMATION: Synthetic

<400> SEQUENCE: 77
cgatgaggac ga                                                       12

<210> SEQ ID NO 78
<211> LENGTH: 30
<212> TYPE: DNA
<213> ORGANISM: Artificial Sequence
<220> FEATURE:
<223> OTHER INFORMATION: Synthetic

<400> SEQUENCE: 78
ccaagccccc cgcttccaag cccaccgctt                                    30

<210> SEQ ID NO 79
<211> LENGTH: 30
<212> TYPE: DNA
<213> ORGANISM: Artificial Sequence
<220> FEATURE:
<223> OTHER INFORMATION: Synthetic

<400> SEQUENCE: 79
ctcttcctct tcctcttcct cttcctcttc                                30

<210> SEQ ID NO 80
<211> LENGTH: 18
<212> TYPE: DNA
<213> ORGANISM: Artificial Sequence
<220> FEATURE:
<223> OTHER INFORMATION: Synthetic

<400> SEQUENCE: 80
caacaacaac agcaacaa                                             18

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81
tgaggaggaa gagtaggatg aggagta                                   27

<210> SEQ ID NO 82
<211> LENGTH: 18
<212> TYPE: DNA
<213> ORGANISM: Artificial Sequence
<220> FEATURE:
<223> OTHER INFORMATION: Synthetic

<400> SEQUENCE: 82
ccccacgcag cagtcttg                                             18

<210> SEQ ID NO 83
<211> LENGTH: 18
<212> TYPE: DNA
<213> ORGANISM: Artificial Sequence
<220> FEATURE:
<223> OTHER INFORMATION: Synthetic

<400> SEQUENCE: 83
cctactaccg ccgatgtt                                             18

<210> SEQ ID NO 84
<211> LENGTH: 4
<212> TYPE: PRT
<213> ORGANISM: Artificial Sequence
<220> FEATURE:
<223> OTHER INFORMATION: Synthetic

<400> SEQUENCE: 84

Arg Gly Gln Gly
1

<210> SEQ ID NO 85
<211> LENGTH: 6
<212> TYPE: PRT
<213> ORGANISM: Artificial Sequence
<220> FEATURE:
<223> OTHER INFORMATION: Synthetic

<400> SEQUENCE: 85

Glu Glu Ala Lys Lys Lys
1               5

<210> SEQ ID NO 86
<211> LENGTH: 4

```
<212> TYPE: PRT
<213> ORGANISM: Artificial Sequence
<220> FEATURE:
<223> OTHER INFORMATION: Synthetic

<400> SEQUENCE: 86

Thr Val Ser Thr
1

<210> SEQ ID NO 87
<211> LENGTH: 15
<212> TYPE: PRT
<213> ORGANISM: Artificial Sequence
<220> FEATURE:
<223> OTHER INFORMATION: Synthetic

<400> SEQUENCE: 87

Ala Pro Glu Ser Ser Ala Glu Pro Thr Ser Glu Glu Thr Ser Ser
1               5                   10                  15

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Lys Lys Trp Ser Lys Lys Trp Pro
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic

<400> SEQUENCE: 89

Trp Pro Lys Lys Trp Pro Lys
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic

<400> SEQUENCE: 90

Pro His Pro Gln Thr
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic

<400> SEQUENCE: 91

Pro Leu Thr Asn Ser
1               5

<210> SEQ ID NO 92
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 92

Arg Glu Ser Ser Arg Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Ala Ser Ala Asn Ser Gly Ser Glu Pro
1               5

<210> SEQ ID NO 94
<211> LENGTH: 4
<212> TYPE: PRT
<213> ORGANISM: Artificial Sequence
<220> FEATURE:
<223> OTHER INFORMATION: Synthetic

<400> SEQUENCE: 94

Asp Asp Glu Asp
1

<210> SEQ ID NO 95
<211> LENGTH: 10
<212> TYPE: PRT
<213> ORGANISM: Artificial Sequence
<220> FEATURE:
<223> OTHER INFORMATION: Synthetic

<400> SEQUENCE: 95

Lys Pro Pro Ala Ser Lys Pro Thr Ala Ser
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Ser Ser Ser Ser Ser Ser Ser Ser Ser Ser
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: Termination site in between these two amino
      acids
<220> FEATURE:
<221> NAME/KEY: misc_feature
<222> LOCATION: (8)..(8)
<223> OTHER INFORMATION: Termination site after this amino acid

<400> SEQUENCE: 97
```

```
<210> SEQ ID NO 98
<211> LENGTH: 6
<212> TYPE: PRT
<213> ORGANISM: Artificial Sequence
<220> FEATURE:
<223> OTHER INFORMATION: Synthetic

<400> SEQUENCE: 98

Asp Glu Glu Glu Glu Asp Glu Glu
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic

<400> SEQUENCE: 98

Pro Thr Gln Gln Ser Cys
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic

<400> SEQUENCE: 99

Ser Ser Thr Pro Glu
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic

<400> SEQUENCE: 100

Ser Thr Thr Glu Pro
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic

<400> SEQUENCE: 101

Pro Thr Thr Ala Asp Val
1               5
```

YEAST STRAIN WITH XYLOSE UTILIZING CAPACITY

REFERENCE TO SEQUENCE LISTING SUBMITTED VIA EFS-WEB

This application includes an electronically submitted sequence listing in .txt format. The .txt file contains a sequence listing entitled "2020-11-18 5398-0114PUS1_ST25.txt" created on Nov. 18, 2020, and is 203,908 bytes in size. The sequence listing contained in this .txt file is part of the specification and is hereby incorporated by reference herein in its entirety.

CROSS-REFERENCE TO RELATED APPLICATION

This application claims priority to Korean Patent Application No. 10-2018-0117860, filed on Oct. 2, 2018, and all the benefits accruing therefrom under 35 U.S.C. § 119, the contents of which in its entirety are herein incorporated by reference.

BACKGROUND

1. Field of the Invention

Disclosed herein are a yeast strain capable of utilizing xylose as a carbon source and a method for producing lipids using the same.

Description about National Support Research and Development

This study is made by the support of the development of core technology for novel and renewable energy business of the Ministry of Trade, Industry and Energy under the supervision of the Korea Institute of Science and Technology, and the subject name thereof is Development of efficient lipid producing yeast from lignocellulosic biomass derived carbon (C6/C5) sources Subject Identification No.: 1415154268).

2. Description of the Related Art

In order to cope with the increasing demand for biodiesel, technologies for improving the economic feasibility and sustainability of biodiesel by producing high density lipids, which are raw materials of biodiesel, from biomass using yeast strains that produce lipids have been developed as new technologies for biodiesel production that can overcome the limitation of the existing biodiesel production methods which are based on vegetable oil or microalgae.

*Yarrowia lipolytica*, which is a type of yeast, is a representative lipid-producing yeast strain. It has been reported that when transformed *Yarrowia lipolytica* strains are cultured in a glucose-based medium, they produce lipids until they account for up to about 90% of the dry weight of the cells. However, the strains cannot utilize pentose (xylose), which is a representative hydrolyzate of lignocellulosic (woody) biomass, and thus have a limitation in utilization of carbon sources. Thus, there is a need for development of a lipid-producing yeast strain capable of metabolizing xylose for more economical production of biodiesel.

The process of lipid production using a yeast strain is an economical process that can easily convert biomass into biofuels. However, when nonedible biomass such as lignocellulosic biomass is used as a raw material in the process, only biomass-derived hexose (the representative example is glucose, which accounts for up to 50% of biomass) is used without utilizing pentose (the representative example is xylose, which accounts for up to 25% of biomass), resulting in inferior conversion efficiency. It is expected that, if this problem is overcome, it will be possible to significantly increase the maximum conversion rate of biomass from 50% to 75%. Accordingly, the development of xylose-converting strains is underway.

Yeast inherently has the xylose metabolic pathway based on oxidoreductase, which can utilize xylose, but the expression of the related gene is low, so that a wild-type yeast cannot metabolize xylose. Development of a transformed strain in which the xylose metabolic pathway based on oxidoreductase has been introduced to impart xylose utilizing capacity to the yeast has been reported. However, a satisfactory level of xylose utilizing capacity has not yet been achieved. In particular, the xylose metabolic pathway based on oxidoreductase not only has a problem of cofactor imbalance, but also consumes NADPH, which is a cofactor that requires high consumption, in the process of lipid production, resulting in decreased lipid-producing ability. Therefore, the present inventors intended to develop a yeast strain that metabolizes xylose based on xylose isomerase, which does not have cofactor problems, and thereby to develop a transformed strain capable of producing lipids from lignocellulosic biomass (the available carbon sources thereof contain up to 50% of glucose and up to 25% of xylose) at a high yield. As a result, the present inventors have developed a transformed yeast strain with improved xylose utilizing capacity by introducing the xylose metabolic pathway based on xylose isomerase into an adaptively evolved yeast strain through metabolic engineering and evolutionary engineering, and a method for producing lipids using the same.

3. Citation List

Patent Literature

Patent Literature 1: U.S. Pat. No. 9,096,876 B2

Non-Patent Literature

Non-Patent Literature 1: Rodrigo Ledesma Amaro et al., Metabolic engineering of *Yarrowia lipolytica* to produce chemicals and fuels from xylose, Met. Eng., 2016, 38, 115-124

Non-Patent Literature 2: Gabriel M. Rodriguez et al., Engineering xylose utilization in *Yarrowia lipolytica* by understanding its cryptic xylose pathway, Biotechnol. Biofuel., 2016, 9:149

Non-Patent Literature 3: Haibo Li et al., Enabling xylose utilization in *Yarrowia lipolytica* for lipid production, Biotechnol. J., 2016, 11, 1230-1240

SUMMARY

In one aspect, an object of the present invention is to provide a transformed and adaptively evolved yeast strain, comprising the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, and YALI0_F17468g, comprising at least one gene selected from the group consisting of a gene encoding an enzyme that interconverts D-xylose and D-xylulose and a gene encoding an enzyme that produces D-xylulose-5-phosphate from D-xylulose, and capable of utilizing xylose as the sole carbon source:

147G>A mutation in the YALI0_A15642g gene;
567_568insACA and 576T>G mutations in the YALI0_A15796g gene;
1523T>C mutation in the YALI0_C11165g gene;
T1412A, G1441A, A1513G, A1534G, G1535T, T1544A, and C1847T mutations in the YALI0_C16247g gene;
103G>A mutation in the YALI0_D24849g gene;
446T>C mutation in the YALI0_D27016g gene;
2525C>G, 2531T>G, 2534A>G, and 2558T>C mutations in the YALI0_E14388g1 gene;
480_481insTCCTCTACCCCCGAG (SEQ ID NO: 64), 526_527insCCTCCACCACCGAGC (SEQ ID NO: 65), and 497A>C mutations in the YALI0_E23969g gene;
2702T>A mutation in the YALI0_F04906g gene; or
482_483insGCACCA mutation in the YALI0_F17468g gene.

In another aspect, an object of the present invention is to provide a transformed and adaptively evolved yeast strain, comprising the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, YALI0_F17468g, YALI0_A00891g, YALI0_A00935g, YALI0_A02002g, YALI0_A02497g, YALI0_A07997g, YALI0_A13849g, YALI0_A16863g, YALI0_A17578g, YALI0_A17776g, YALI0_A17853g, YALI0_A19646g, YALI0_B00748g, YALI0_B08800g, YALI0_C06424g, YALI0_C07172g, YALI0_C08437g, YALI0_C09031g, YALI0_C09614g, YALI0_C13728g, YALI0_C14476g, YALI0_C15532g, YALI0_C16148g, YALI0_D15752g, YALI0_D17820g, YALI0_D18381g, YALI0_D19822g, YALI0_D20064g, YALI0_D20526g, YALI0_D20790g, YALI0_D24563g, YALI0_D25014g, YALI0_D25058g, YALI0_D26257g, YALI0_D26510g, YALI0_D26620g, YALI0_E07832g, YALI0_E08008g, YALI0_E11363g, YALI0_E13596g, YALI0_E16731g, YALI0_E18073g, YALI0_E18216g, YALI0_E20449g, YALI0_E21109g, YALI0_F12221g, YALI0_F12793g, YALI0_F16577g, YALI0_F19030g, and YALI0_F23287g, comprising a gene encoding an enzyme that interconverts D-xylose and D-xylulose and a gene encoding an enzyme that produces D-xylulose-5-phosphate from D-xylulose, and capable of utilizing xylose as the sole carbon source:

147G>A mutation in the YALI0_A15642g gene;
567_568insACA and 576T>G mutations in the YALI0_A15796g gene;
1523T>C mutation in the YALI0_C11165g gene;
T1412A, G1441A, A1513G, A1534G, G1535T, T1544A, and C1847T mutations in the YALI0_C16247g gene;
103G>A mutation in the YALI0_D24849g gene;
446T>C mutation in the YALI0_D27016g gene;
2525C>G, 2531T>G, 2534A>G, and 2558T>C mutations in the YALI0_E14388g1 gene;
480_481insTCCTCTACCCCCGAG (SEQ ID NO: 64), 526_527insCCTCCACCACCGAGC (SEQ ID NO: 65), and 497A>C mutations in the YALI0_E23969g gene;
2702T>A mutation in the YALI0_F04906g gene;
482_483insGCACCA mutation in the YALI0_F17468g gene;
11_16delACGGCC mutation in the YALI0_A00891g gene;
202_203insGCTC mutation in the YALI0_A00935g gene;
1255_1256insGAGGTCAAGGTC (SEQ ID NO: 66) mutation in the YALI0_A02002g gene;
132_137dupCAACTC and 331_332insCCCACT mutations in the YALI0_A02497g gene;
2846_2847insGGAGCAGGA and 2869_2870insAGGAGGAGG mutations in the YALI0_A07997g gene;
165_166insCAAA mutation in the YALI0_A13849g gene;
888_889insGAGCTGAGATGAC (SEQ ID NO: 67) mutation in the YALI0_A16863g gene;
432_433insGCGGAGCCG mutation in the YALI0_A17578g gene;
959_960insACAGCAGAT mutation in the YALI0_A17776g gene;
1940_1942delAGG, 1990_1991insAGGAGGAGGCTAGAAGA (SEQ ID NO: 68) and 2817_2818insTCTGAG mutations in the YALI0_A17853g gene;
1462_1463insGGG mutation in the YALI0_A19646g gene;
525_526insCCCGAC mutation in the YALI0_B00748g gene;
152_153delGT mutation in the YALI0_B08800g gene;
1370_1373delACTT mutation in the YALI0_C06424g gene;
308_309insGCAGCGACA mutation in the YALI0_C07172g gene;
1592_1593insGACAGTCAGCAC (SEQ ID NO: 69) mutation in the YALI0_C08437g gene;
1789_1790insCTCCCGAGTCCTCTGCTGAGCCTACCAGCGAAGAGACTTCTTCCG (SEQ ID NO: 70) mutation in the YALI0_C09031g gene;
1620_1622delACA mutation in the YALI0_C09614g gene;
99_100insAAAAAGTGGTCGAAAAAGTGGCCA (SEQ ID NO: 71) and 129_130insTGGCCGAAAAAGTGGCCAAAA (SEQ ID NO: 72) mutations in the YALI0_C13728g gene;
778_779insTGC mutation in the YALI0_C14476g gene;
1611_1616delCAGCTT mutation in the YALI0_C15532g gene;
961_969delAGCAGCAGT mutation in the YALI0_C16148g gene;
1038_1039insCAG mutation in the YALI0_D15752g gene;
619_620insCCCACCCGCAAACCC (SEQ ID NO: 73) mutation in the YALI0_D17820g gene;
114_115insCCTCTCACCAACTCA (SEQ ID NO: 74) mutation in the YALI0_D18381g gene;
310_315delAAAGAG mutation in the YALI0_D19822g gene;
67_68insGGGGGGGG mutation in the YALI0_D20064g gene;
354_355insTCCACCGGA mutation in the YALI0_D20526g gene;
37_38insCACGTGAAAGTAGCCGAA (SEQ ID NO: 75) mutation in the YALI0_D20790g gene;
84_85insGCT mutation in the YALI0_D24563g gene;
484_485insCCGCTAGCGCCAACTCTGGCTCGAGC (SEQ ID NO: 76) mutation in the YALI0_D25014g gene;
592_594dupAAG mutation in the YALI0_D25058g gene;
1478_1480delAGA mutation in the YALI0_D26257g gene;

1287_1288insAAG mutation in the YALI0_D26510g gene;

926_927insCGATGAGGACGA (SEQ ID NO: 77) mutation in the YALI0_D26620g gene;

499_500insCCAAGCCCCCGCTTCCAAGCCCAC-CGCTT (SEQ ID NO: 78) mutation in the YALI0_E07832g gene;

794_795insCTCTTCCTCTTCCTCTTCCTCTTCCTC-TTC (SEQ ID NO: 79) mutation in the YALI0_E08008g gene;

74_77delCACA mutation in the YALI0_E11363g gene;

1053_1054insCAACAACAACAGCAACAA (SEQ ID NO: 80) mutation in the YALI0_E13596g gene;

1622_1623insTGAGGAGGAAGAGTAGGATGAG-GAGTA (SEQ ID NO: 81) mutation in the YALI0_E16731g gene;

266_267insCCCCACGCAGCAGTCTTG (SEQ ID NO: 82) mutation in the YALI0_E18073g gene;

930_938delACAACAGCA mutation in the YALI0_E18216g gene;

899_900insAAACGC mutation in the YALI0_E20449g gene;

228_229insGCCCCGCCT mutation in the YALI0_E21109g gene;

1825_1827delAAG mutation in the YALI0_F12221g gene;

1855_1860delTCTTCT mutation in the YALI0_F12793g gene;

807_808insCCTCCT mutation in the YALI0_F16577g gene;

1344_1345insCCTACTACCGCCGATGTT (SEQ ID NO: 83), 2065T>A, 2098A>G and 2099C>A mutations in the YALI0_F19030g gene; or 1919_1920insCTC mutation in the YALI0_F23287g gene.

In one aspect, the present invention provides a transformed and adaptively evolved yeast strain, comprising a mutation in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, and YALI0_F17468g, comprising at least one gene selected from the group consisting of a gene encoding an enzyme that interconverts D-xylose and D-xylulose and a gene encoding an enzyme that produces D-xylulose-5-phosphate from D-xylulose, and capable of utilizing xylose as the sole carbon source.

In another aspect, the present invention provides a method for producing the transformed and adaptively evolved yeast strain.

In another aspect, the present invention provides a method for producing lipids, comprising the step of culturing the transformed and adaptively evolved yeast strain in a medium containing xylose as a carbon source.

In another aspect, the present invention provides a method for producing biodiesel, comprising the steps of: culturing the transformed and adaptively evolved yeast strain in a medium containing xylose as a carbon source to produce lipids; and transesterifying the produced lipids to obtain biodiesel.

DETAILED DESCRIPTION

Figure 1:
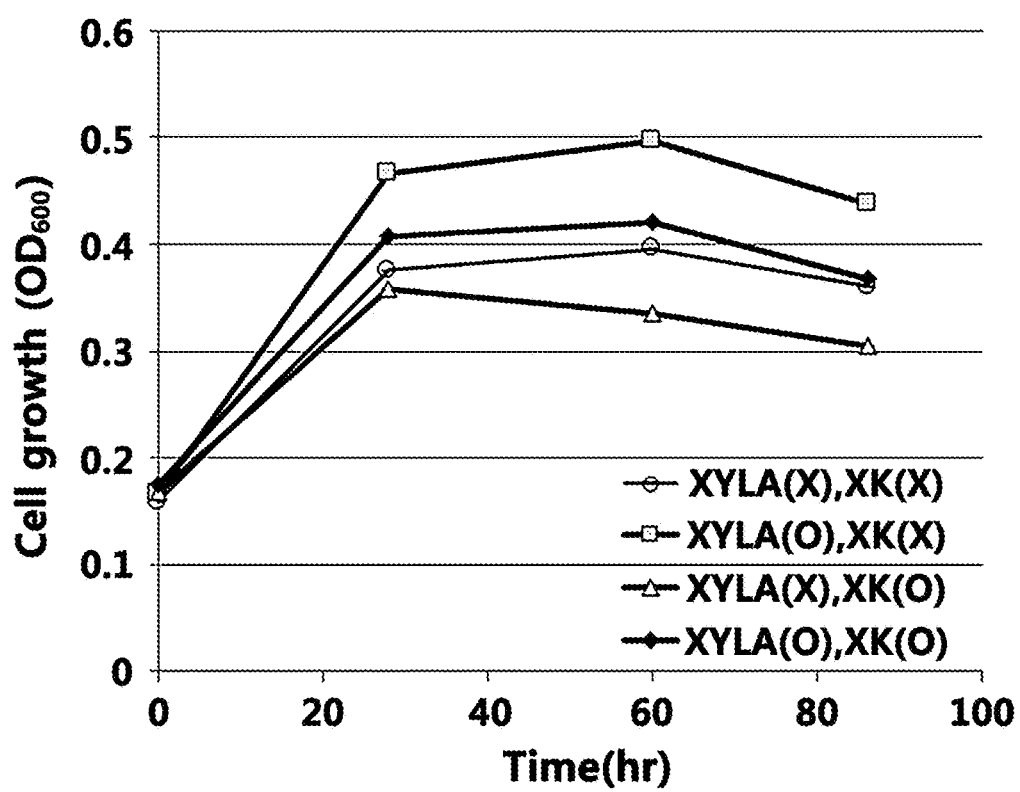
FIG. 1 shows the growth curves of a strain (XYLA(O), XK(X)) obtained by introducing only the xylose isomerase gene into a wild-type Yarrowia lipolytica strain (XYLA(X), XK(X)), a strain (XYLA(X), XK(O)) obtained by introducing only the xylulokinase gene, and a strain (XYLA(O), XK(O)) obtained by introducing both the xylose isomerase gene and the xylulokinase gene, in a medium containing xylose as a carbon source.

Hereinafter, the present invention will be described in detail.

The present invention relates to a new technology for biodiesel production capable of overcoming the limitations of conventional biodiesel production methods based on vegetable oil or microalgae in order to cope with the increasing demand for biodiesel. It relates to a technology for improving the economic feasibility and sustainability of biodiesel by producing high density lipids, which are raw materials of biodiesel, from biomass using a yeast strain that produce or contain lipids, specifically a Yarrowia lipolytica strain.

Yarrowia lipolytica strain as used herein is a representative lipid-producing strain. The lipids produced by the strain can be used as biodiesel after going through a simple chemical reaction, and biomaterials (raw materials for cosmetics, etc.). However, it is known that the wild-type Yarrowia lipolytica strain cannot utilize xylose as a carbon source. In order to increase economic feasibility and sustainability in the production of biodiesel and biomaterials, lignocellulosic biomass may be used as a raw material to produce lipids, instead of refined sugar. The "lignocellulosic biomass" is a raw material that provides a carbon source necessary for a lipid-producing strain to produce lipids and encompasses herbaceous biomass and cellulosic biomass. It is the most abundant carbon source which accounts for at least 90% of the total biomass produced on earth and is an environmentally friendly, renewable resource. Also, biofuels produced from lignocellulosic biomass have a better carbon reduction effect than fossil fuels and first-generation biofuels. The lignocellulosic biomass includes waste wood, agricultural and forestry by-products, and energy crops. Among the available carbon sources in lignocellulosic biomass, the carbon source that yeast strains such as yeast can utilize is glucose, which accounts for about 50% of the total lignocellulosic biomass. If a yeast strain that can also utilize xylose, which accounts for up to about 30% of lignocellulosic biomass, is developed, it will be possible to utilize up to about 80% of the available resources in lignocellulosic biomass, which will greatly improve the yield of lipid per unit biomass and thus the economical feasibility and sustainability of the production of biodiesel and biomaterials using lignocellulosic biomass. Accordingly, the present inventors have developed a yeast strain, specifically a *Yarrowia lipolytica* strain, capable of utilizing xylose as a carbon source.

In one aspect, the present invention provides a transformed and adaptively evolved yeast strain, comprising the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, and YALI0_F17468g, comprising at least one gene selected from the group consisting of a gene encoding an enzyme that interconverts D-xylose and D-xylulose and a gene encoding an enzyme that produces D-xylulose-5-phosphate from D-xylulose, and capable of utilizing xylose as the sole carbon source:

147G>A mutation in the YALI0_A15642g gene;
567_568insACA and 576T>G mutations in the YALI0_A15796g gene;
1523T>C mutation in the YALI0_C11165g gene;
T1412A, G1441A, A1513G, A1534G, G1535T, T1544A, and C1847T mutations in the YALI0_C16247g gene;
103G>A mutation in the YALI0_D24849g gene;
446T>C mutation in the YALI0_D27016g gene;
2525C>G, 2531T>G, 2534A>G, and 2558T>C mutations in the YALI0_E14388g1 gene;
480_481insTCCTCTACCCCCGAG (SEQ ID NO: 64), 526_527insCCTCCACCACCGAGC (SEQ ID NO: 65) and 497A>C mutations in the YALI0_E23969g gene;
2702T>A mutation in the YALI0_F04906g gene; or
482_483insGCACCA mutation in the YALI0_F17468g gene.

In another aspect, the present invention provides a transformed and adaptively evolved yeast strain, comprising the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, YALI0_F17468g, YALI0_A00891g, YALI0_A00935g, YALI0_A02002g, YALI0_A02497g, YALI0_A07997g, YALI0_A13849g, YALI0_A16863g, YALI0_A17578g, YALI0_A17776g, YALI0_A17853g, YALI0_A19646g, YALI0_B00748g, YALI0_B08800g, YALI0_C06424g, YALI0_C07172g, YALI0_C08437g, YALI0_C09031g, YALI0_C09614g, YALI0_C13728g, YALI0_C14476g, YALI0_C15532g, YALI0_C16148g, YALI0_D15752g, YALI0_D17820g, YALI0_D18381g, YALI0_D19822g, YALI0_D20064g, YALI0_D20526g, YALI0_D20790g, YALI0_D24563g, YALI0_D25014g, YALI0_D25058g, YALI0_D26257g, YALI0_D26510g, YALI0_D26620g, YALI0_E07832g, YALI0_E08008g, YALI0_E11363g, YALI0_E13596g, YALI0_E16731g, YALI0_E18073g, YALI0_E18216g, YALI0_E20449g, YALI0_E21109g, YALI0_F12221g, YALI0_F12793g, YALI0_F16577g, YALI0_F19030g, and YALI0_F23287g, comprising at least one gene selected from the group consisting of a gene encoding an enzyme that interconverts D-xylose and D-xylulose and a gene encoding an enzyme that produces D-xylulose-5-phosphate from D-xylulose and capable of utilizing xylose as the sole carbon source:

147G>A mutation in the YALI0_A15642g gene;
567_568insACA and 576T>G mutations in the YALI0_A15796g gene;
1523T>C mutation in the YALI0_C11165g gene;
T1412A, G1441A, A1513G, A1534G, G1535T, T1544A, and C1847T mutations in the YALI0_C16247g gene;
103G>A mutation in the YALI0_D24849g gene;
446T>C mutation in the YALI0_D27016g gene;
2525C>G, 2531T>G, 2534A>G, and 2558T>C mutations in the YALI0_E14388g1 gene;
480_481insTCCTCTACCCCCGAG (SEQ ID NO: 64), 526_527insCCTCCACCACCGAGC (SEQ ID NO: 65) and 497A>C mutations in the YALI0_E23969g gene;
2702T>A mutation in the YALI0_F04906g gene;
482_483insGCACCA mutation in the YALI0_F17468g gene;
11_16delACGGCC mutation in the YALI0_A00891g gene;
202_203insGCTC mutation in the YALI0_A00935g gene;
1255_1256insGAGGTCAAGGTC (SEQ ID NO: 66) mutation in the YALI0_A02002g gene;
132_137dupCAACTC and 331_332insCCCACT mutations in the YALI0_A02497g gene;
2846_2847insGGAGCAGGA and 2869_2870insAGGAGGAGG mutations in the YALI0_A07997g gene;
165_166insCAAA mutation in the YALI0_A13849g gene;
888_889insGAGCTGAGATGAC (SEQ ID NO: 67) mutation in the YALI0_A16863g gene;
432_433insGCGGAGCCG mutation in the YALI0_A17578g gene;
959_960insACAGCAGAT mutation in the YALI0_A17776g gene;
1940_1942delAGG, 1990_1991insAGGAGGAGGCTAAGAAGA (SEQ ID NO: 68), and 2817_2818insTCTGAG mutations in the YALI0_A17853g gene;
1462_1463insGGG mutation in the YALI0_A19646g gene;
525_526insCCCGAC mutation in the YALI0_B00748g gene;
152_153delGT mutation in the YALI0_B08800g gene;
1370_1373delACTT mutation in the YALI0_C06424g gene;
308_309insGCAGCGACA mutation in the YALI0_C07172g gene;
1592_1593insGACAGTCAGCAC (SEQ ID NO: 69) mutation in the YALI0_C08437g gene;
1789_1790insCTCCCGAGTCCTCTGCTGAGCCTACCAGCGAAGAGACTTCTTCCG (SEQ ID NO: 70) mutation in the YALI0_C09031g gene;
1620_1622delACA mutation in the YALI0_C09614g gene;
99_100insAAAAAGTGGTCGAAAAAGTGGCCA (SEQ ID NO: 71) and 129_130insTGGCCGAAAAAGTGGCCAAAA (SEQ ID NO: 72) mutations in the YALI0_C13728g gene;
778_779insTGC mutation in the YALI0_C14476g gene;
1611_1616delCAGCTT mutation in the YALI0_C15532g gene;
961_969delAGCAGCAGT mutation in the YALI0_C16148g gene;
1038_1039insCAG mutation in the YALI0_D15752g gene;
619_620insCCCACCCGCAAACCC (SEQ ID NO: 73) mutation in the YALI0_D17820g gene;

114_115insCCTCTCACCAACTCA (SEQ ID NO: 74) mutation in the YALI0_D18381g gene;

310_315delAAAGAG mutation in the YALI0_D19822g gene;

67_68insGGGGGGGG mutation in the YALI0_D20064g gene;

354_355insTCCACCGGA mutation in the YALI0_D20526g gene;

37_38insCACGTGAAAGTAGCCGAA (SEQ ID NO: 75) mutation in the YALI0_D20790g gene;

84_85insGCT mutation in the YALI0_D24563g gene;

484_485insCCGCTAGCGCCAACTCTGGCTCG-GAGC (SEQ ID NO: 76) mutation in the YALI0_D25014g gene;

592_594dupAAG mutation in the YALI0_D25058g gene;

1478_1480delAGA mutation in the YALI0_D26257g gene;

1287_1288insAAG mutation in the YALI0_D26510g gene;

926_927insCGATGAGGACGA (SEQ ID NO: 77) mutation in the YALI0_D26620g gene;

499_500insCCAAGCCCCCGCTTCCAAGCCCAC-CGCTT (SEQ ID NO: 78) mutation in the YALI0_E07832g gene;

794_795insCTCTTCCTCTTCCTCTTCCTCTTCCTC-TTC (SEQ ID NO: 79) mutation in the YALI0_E08008g gene;

74_77delCACA mutation in the YALI0_E11363g gene;

1053_1054insCAACAACAACAGCAACAA (SEQ ID NO: 80) mutation in the YALI0_E13596g gene;

1622_1623insTGAGGAGGAAGAGTAGGATGAG-GAGTA (SEQ ID NO: 81) mutation in the YALI0_E16731g gene;

266_267insCCCCACGCAGCAGTCTTG (SEQ ID NO: 82) mutation in the YALI0_E18073g gene;

930_938delACAACAGCA mutation in the YALI0_E18216g gene;

899_900insAAACGC mutation in the YALI0_E20449g gene;

228_229insGCCCCGCCT mutation in the YALI0_E21109g gene;

1825_1827delAAG mutation in the YALI0_F12221g gene;

1855_1860delTCTTCT mutation in the YALI0_F12793g gene;

807_808insCCTCCT mutation in the YALI0_F16577g gene;

1344_1345insCCTACTACCGCCGATGTT (SEQ ID NO: 83), 2065T>A, 2098A>G and 2099C>A mutations in the YALI0_F19030g gene; or 1919_1920insCTC mutation in the YALI0_F23287g gene.

The type of the yeast strain or wild-type yeast strain of the present invention is not limited as long as they are capable of producing an intracellular product or lipid. Specifically, it may be a *Yarrowia lipolytica* strain or a wild-type *Yarrowia lipolytica* strain. The wild-type *Yarrowia lipolytica* strain may be a commercially available one or the one deposited in a reliable depository authority and for which the fact that it can be freely purchased through a catalog, etc. issued by the depository authority has been verified.

Descriptions of the mutations as used herein, including deletion (del), insertion (ins), frame shift (fs), duplication (duplication) and stop (*), are as follows. For example, an expression of a mutation of a specific gene, "A; B" such as "11_16delACGGCC; p.Asn4_Gln6delinsLys", means that "the amino acid sequence has been mutated into B due to the gene mutation of A". In addition, for example, an expression of a mutation of a specific gene, "11_16delACGGCC", means that "bases 11 to 16, ACGGCC, have been deleted". Also, for example, an expression of a mutation of a specific gene, "202_203insGCTC", means that "GCTC has been inserted between base 202 and base 203" of the gene. In addition, for example, an expression of a mutation of a specific gene, "132_137dupCAACTC", means that "bases 132 to 137 of the gene, CAACTC, have been duplicated". Also, for example, an expression of a mutation of a specific gene, "147G>A", means that "base 147 of the gene, G, has been substituted with A". Also, for example, an expression of an amino acid sequence modification (mutation) due to a mutation of a specific gene, "p.Trp49*", means that "the amino acid Trp has changed to stop (*). Also, for example, an expression of a mutation of a specific gene such as "T1412A" means that "base 1412 of the gene, T, has been substituted with A".

As used herein, the term "adaptively evolved yeast strain" may refer to a strain comprising the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, and YALI0_F17468g:

147G>A mutation in the YALI0_A15642g gene;

567_568insACA and 576T>G mutations in the YALI0_A15796g gene;

1523T>C mutation in the YALI0_C11165g gene;

T1412A, G1441A, A1513G, A1534G, G1535T, T1544A, and C1847T mutations in the YALI0_C16247g gene;

103G>A mutation in the YALI0_D24849g gene;

446T>C mutation in the YALI0_D27016g gene;

2525C>G, 2531T>G, 2534A>G, and 2558T>C mutations in the YALI0_E14388g1 gene;

480_481insTCCTCTACCCCCGAG (SEQ ID NO: 64), 526_527insCCTCCACCACCGAGC (SEQ ID NO: 65), and 497A>C mutations in the YALI0_E23969g gene;

2702T>A mutation in the YALI0_F04906g gene; or

482_483insGCACCA mutation in the YALI0_F17468g gene.

Also, the term "adaptively evolved yeast strain" as used herein may refer to a strain comprising the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, YALI0_F17468g, YALI0_A00891g, YALI0_A00935g, YALI0_A02002g, YALI0_A02497g, YALI0_A07997g, YALI0_A13849g, YALI0_A16863g, YALI0_A17578g, YALI0_A17776g, YALI0_A17853g, YALI0_A19646g, YALI0_B00748g, YALI0_B08800g, YALI0_C06424g, YALI0_C07172g, YALI0_C08437g, YALI0_C09031g, YALI0_C09614g, YALI0_C13728g, YALI0_C14476g, YALI0_C15532g, YALI0_C16148g, YALI0_D15752g, YALI0_D17820g, YALI0_D18381g, YALI0_D19822g, YALI0_D20064g, YALI0_D20526g, YALI0_D20790g, YALI0_D24563g, YALI0_D25014g, YALI0_D25058g, YALI0_D26257g, YALI0_D26510g, YALI0_D26620g, YALI0_E07832g, YALI0_E08008g, YALI0_E11363g, YALI0_E13596g, YALI0_E16731g, YALI0_E18073g, YALI0_E18216g, YALI0_E20449g, YALI0_E21109g, YALI0_F12221g, YALI0_F12793g, YALI0_F16577g, YALI0_F19030g, and YALI0_F23287g:

147G>A mutation in the YALI0_A15642g gene;
567_568insACA and 576T>G mutations in the YALI0_A15796g gene;
1523T>C mutation in the YALI0_C11165g gene;
T1412A, G1441A, A1513G, A1534G, G1535T, T1544A, and C1847T mutations in the YALI0_C16247g gene;
103G>A mutation in the YALI0_D24849g gene;
446T>C mutation in the YALI0_D27016g gene;
2525C>G, 2531T>G, 2534A>G, and 2558T>C mutations in the YALI0_E14388g1 gene;
480_481insTCCTCTACCCCCGAG (SEQ ID NO: 64), 526_527insCCTCCACCACCGAGC (SEQ ID NO: 65), and 497A>C mutations in the YALI0_E23969g gene;
2702T>A mutation in the YALI0_F04906g gene;
482_483insGCACCA mutation in the YALI0_F17468g gene;
11_16delACGGCC mutation in the YALI0_A00891g gene;
202_203insGCTC mutation in the YALI0_A00935g gene;
1255_1256insGAGGTCAAGGTC (SEQ ID NO: 66) mutation in the YALI0_A02002g gene;
132_137dupCAACTC and 331_332insCCCACT mutations in the YALI0_A02497g gene;
2846_2847insGGAGCAGGA and 2869_2870insAGGAGGAGG mutations in the YALI0_A07997g gene;
165_166insCAAA mutation in the YALI0_A13849g gene;
888_889insGAGCTGAGATGAC (SEQ ID NO: 67) mutation in the YALI0_A16863g gene;
432_433insGCGGAGCCG mutation in the YALI0_A17578g gene;
959_960insACAGCAGAT mutation in the YALI0_A17776g gene;
1940_1942delAGG, 1990_1991insAGGAGGAGGCTAAGAAGA (SEQ ID NO: 68) and 2817_2818insTCTGAG mutations in the YALI0_A17853g gene;
1462_1463insGGG mutation in the YALI0_A19646g gene;
525_526insCCCGAC mutation in the YALI0_B00748g gene;
152_153delGT mutation in the YALI0_B08800g gene;
1370_1373delACTT mutation in the YALI0_C06424g gene;
308_309insGCAGCGACA mutation in the YALI0_C07172g gene;
1592_1593insGACAGTCAGCAC (SEQ ID NO: 69) mutation in the YALI0_C08437g gene;
1789_1790insCTCCCGAGTCCTCTGCTGAGCCTACCAGCGAAGAGACTTCTTCCG (SEQ ID NO: 70) mutation in the YALI0_C09031g gene;
1620_1622delACA mutation in the YALI0_C09614g gene;
99_100insAAAAAGTGGTCGAAAAAGTGGCCA (SEQ ID NO: 71) and 129_130insTGGCCGAAAAAGTGGCCAAAA (SEQ ID NO: 72) mutations in the YALI0_C13728g gene;
778_779insTGC mutation in the YALI0_C14476g gene;
1611_1616delCAGCTT mutation in the YALI0_C15532g gene;
961_969delAGCAGCAGT mutation in the YALI0_C16148g gene;
1038_1039insCAG mutation in the YALI0_D15752g gene;
619_620insCCCACCCGCAAACCC (SEQ ID NO: 73) mutation in the YALI0_D17820g gene;
114_115insCCTCTCACCAACTCA (SEQ ID NO: 74) mutation in the YALI0_D18381g gene;
310_315delAAAGAG mutation in the YALI0_D19822g gene;
67_68insGGGGGGGG mutation in the YALI0_D20064g gene;
354_355insTCCACCGGA mutation in the YALI0_D20526g gene;
37_38insCACGTGAAAGTAGCCGAA (SEQ ID NO: 75) mutation in the YALI0_D20790g gene;
84_85insGCT mutation in the YALI0_D24563g gene;
484_485insCCGCTAGCGCCAACTCTGGCTCGGAGC (SEQ ID NO: 76) mutation in the YALI0_D25014g gene;
592_594dupAAG mutation in the YALI0_D25058g gene;
1478_1480delAGA mutation in the YALI0_D26257g gene;
1287_1288insAAG mutation in the YALI0_D26510g gene;
926_927insCGATGAGGACGA (SEQ ID NO: 77) mutation in the YALI0_D26620g gene;
499_500insCCAAGCCCCCCGCTTCCAAGCCCACCGCTT (SEQ ID NO: 78) mutation in the YALI0_E07832g gene;
794_795insCTCTTCCTCTTCCTCTTCCTCTTCCTCTTC (SEQ ID NO: 79) mutation in the YALI0_E08008g gene;
74_77delCACA mutation in the YALI0_E11363g gene;
1053_1054insCAACAACAACAGCAACAA (SEQ ID NO: 80) mutation in the YALI0_E13596g gene;
1622_1623insTGAGGAGGAAGAGTAGGATGAGGAGTA (SEQ ID NO: 81) mutation in the YALI0_E16731g gene;
266_267insCCCCACGCAGCAGTCTTG (SEQ ID NO: 82) mutation in the YALI0_E18073g gene;
930_938delACAACAGCA mutation in the YALI0_E18216g gene;
899_900insAAACGC mutation in the YALI0_E20449g gene;
228_229insGCCCCGCCT mutation in the YALI0_E21109g gene;
1825_1827delAAG mutation in the YALI0_F12221g gene;
1855_1860delTCTTCT mutation in the YALI0_F12793g gene;
807_808insCCTCCT mutation in the YALI0_F16577g gene;
1344_1345insCCTACTACCGCCGATGTT (SEQ ID NO: 83), 2065T>A, 2098A>G, and 2099C>A mutations in the YALI0_F19030g gene; or
1919_1920insCTC mutation in the YALI0_F23287g gene.

The mutation may be introduced by treating a microorganism with any chemical means and/or physical means known in the art to be capable of causing a mutation. Examples of the chemical means include chemical substances such as nitrosoguanidine (NTG), which is a guanidine derivative effective as a mutagenic substance (mutagen), methyl methanesulfonate (MMS), ethyl methanesulfonate (EMS), and benzopyrene. Examples of the physical means include radiations such as UV rays, X-rays, and γ-rays, although not limited thereto. In addition, the mutant genes may be introduced using a molecular biological method, specifically, genetic scissors such as CRISPR-Cas, although not limited thereto. The adaptively evolved yeast strain may be a mutant strain adaptively evolved to obtain xylose utilizing capacity by subculturing three times or more, specifically three times or more, four times or more, or five times or more in a medium containing xylose as the sole carbon source, although not limited thereto. Alternatively, the adaptively evolved yeast strain may be an adaptively evolved *Yarrowia lipolytica* strain. Also, it may be a strain having the accession number KCTC13615BP.

The transformed and adaptively evolved yeast strain of the present invention may be a strain obtained by transforming the adaptively evolved yeast strain. Also, it may be a transformed and adaptively evolved *Yarrowia lipolytica* strain. Specifically, it may be a strain transformed to comprise at least one gene selected from the group consisting of a gene encoding an enzyme that interconverts D-xylose and D-xylulose and a gene encoding an enzyme that produces D-xylulose-5-phosphate from D-xylose.

According to one embodiment of the present invention, the adaptively evolved strain (YSK), which is obtained by subculturing a wild-type *Yarrowia lipolytica* strain five times in a medium containing xylose as the sole carbon source and in which at least one gene selected from the group consisting of the genes shown in Table 1 below has been mutated as shown in Table 1 below, exhibited greatly improved xylose utilizing capacity as compared to wild-type *Yarrowia lipolytica* strains which express xylose isomerase, and thus was found to be able to grow utilizing xylose as the sole carbon source (Example 2). The sequence of each SEQ ID NO. listed in Table 1 below represents a sequence in which the respective gene has been mutated as shown in Table 1 below.

TABLE 1

| Gene No. | Gene Name | NCBI Reference Sequence no. | Mutations in Gene | SEQ ID NO. |
|---|---|---|---|---|
| 1 | YALI0_A00891g | NC_006067.1 (112988..114379, complement) | 11_16delACGGCC; p.Asn4_Gln6delinsLys | 5 |
| 2 | YALI0_A00935g | NC_006067.1 (121112..121432, complement) | 202_203insGCTC; p.Tyr68fs | 6 |
| 3 | YALI0_A02002g | NC_006067.1 (252726..254057, complement) | 1255_1256insGAGGTCAAGGTC (SEQ ID NO: 66); p.Gly418_Gln419insArgGlyGlnGly (SEQ ID NO: 84) | 7 |
| 4 | YALI0_A02497g | NC_006067.1 (316093..317005, complement) | 132_137dupCAACTC; p.Ser46Gly47insAsnSer, 331_332insCCCACT; p.Asn110_Tyr111insSerHis | 8 |
| 5 | YALI0_A07997g | NC_006067.1 (762324..766571, complement) | 2846_2847insGGAGCAGGA; p.Gly949Glu950insGluGlnGlu, 2869_2870insAGGAGGAGG; p.Lys957_Glu958insGluGluGlu | 9 |
| 6 | YALI0_A13849g | NC_006067.1 (1420547..1420819, complement) | 165_166insCAAA; p.Lys56fs | 10 |
| 7 | YALI0_A15642g | NC_006067.1 (1605399..1605629, complement) | 147G > A; p.Trp49* | 11 |
| 8 | YALI0_A15796g | NC_006067.1 (1616617..1619565, complement) | 567_568insACA; p.Thr189dup, 576T > G; p.Asp192Glu | 12 |
| 9 | YALI0_A16863g | NC_006067.1 (1743518..1744417, complement) | 888_889insGAGCTGAGATGAC (SEQ ID NO: 67); p.Val298fs | 13 |
| 10 | YALI0_A17578g | NC_006067.1 (1813242..1816943, complement) | 432_433insGCGGAGCCG; p.Pro144_Ser145insAlaGluPro | 14 |
| 11 | YALI0_A17776g | NC_006067.1 (1825648..1829883, complement) | 959_960insACAGCAGAT; p.Pro320_Gln321insGlnGlnIle | 15 |
| 12 | YALI0_A17853g | NC_006067.1 (1845367..1849173, complement) | 1940_1942delAGG; p.Glu648del, 1990_1991insAGGAGGAGGCTAAGAAGA (SEQ ID NO: 68); p.Glu664_Glu665insGluGluAlaLysLysLys (SEQ ID NO: 85), 2817_2818insTCTGAG; p.Asp939_Ser940insSerGlu | 16 |

TABLE 1-continued

| Gene No. | Gene Name | NCBI Reference Sequence no. | Mutations in Gene | SEQ ID NO. |
|---|---|---|---|---|
| 13 | YALI0_A19646g | NC_006067.1 (2112864..2114768, complement) | 1462_1463insGGG; p.Glu487_Glu488insGly | 17 |
| 14 | YALI0_B00748g | NC_006068.1 (102187..103176, complement) | 525_526insCCCGAC; p.Asp175_Ser176insProAsp | 18 |
| 15 | YALI0_B08800g | NC_006068.1 (1210467..1212137, complement) | 152_153delGT; p.Cys51fs | 19 |
| 16 | YALI0_C06424g | NC_006069.1 (852842..854389, complement) | 1370_1373delACTT; p.Tyr457fs | 20 |
| 17 | YALI0_C07172g | NC_0060697.1 (955882..958353, complement) | 308_309insGCAGCGACA; p.Gln103_Gln104insGlnArgGln | 21 |
| 18 | YALI0_C08437g | NC_006069.1 (1146546..1148330, complement) | 1592_1593insGACAGTCAGCAC (SEQ ID NO: 69); p.Lys531_Thr532insThrValSerThr (SEQ ID NO: 86) | 22 |
| 19 | YALI0_C09031g | NC_006069.1 (1232749..1236846, complement) | 1789_1790insCTCCCGAGTCCTCTGCTGAGCCTACCAGCGAAGAGACTTCTTCCG (SEQ ID NO: 70); p.Ser596_Val597insAlaProGluSerSerAlaGluProThrSerGluGluThrSerSer | 23 |
| 20 | YALI0_C09614g | NC_006069.1 (1309626..1312265, complement) | 1620_1622delACA; p.Gln541del | 24 |
| 21 | YALI0_C11165g | NC_006069.1 (1536684..1540028, complement) | 1523T > C; p.Val508Ala | 25 |
| 22 | YALI0_C13728g | NC_006069.1 (1885929..1886756, complement) | 99_100insAAAAAGTGGTCGAAAAAGTGGCCA (SEQ ID NO: 71); p.Pro33_Lys34insLysLysTrpSerLysLysTrpPro (SEQ ID NO: 88), 129_130insTGGCCGAAAAAGTGGCCAAAA (SEQ ID NO: 72); p.Lys43_Lys44insTrpProLysLysTrpProLys (SEQ ID NO: 89) | 26 |
| 23 | YALI0_C14476g | NC_006069.1 (1992000..1994063, complement) | 778_779insTGC; p.Lys260delinsMetGln | 27 |
| 24 | YALI0_C15532g | NC_006069.1 (2170451..2173659, complement) | 1611_1616delCAGCTT; p.Ser538_Phe539del | 28 |
| 25 | YALI0_C16148g | NC_006069.1 (2285288..2286607, complement) | 961_969delAGCAGCAGT; p.Ser321_Ser323del | 29 |
| 26 | YALI0_C16247g | NC_006069.1 (2295675..2299085, complement) | T1412A; Val471Asp, G1441A; Asp481Asn, A1513G; Asn505Asp, A1534G; Ser512Gly, G1535T; Ser512Ile, T1544A; Val515Glu, C1847T; Ala616Val | 30 |
| 27 | YALI0_D15752g | NC_006070.1 (1928726..1930150, complement) | 1038_1039insCAG; Pro346_Gln347insGln | 31 |
| 28 | YALI0_D17820g | NC_006070.1 (2203609..2206944, complement) | 619_620insCCCACCCGCAAACCC (SEQ ID NO: 73); Thr206_His207insProHisProGlnThr (SEQ ID NO: 90) | 32 |

TABLE 1-continued

| Gene No. | Gene Name | NCBI Reference Sequence no. | Mutations in Gene | SEQ ID NO. |
|---|---|---|---|---|
| 29 | YALI0_D18381g | NC_006070.1 (2301563..2304454, complement) | 114_115insCCTCTCACCAACTCA (SEQ ID NO: 74); Ser38_Thr39insProLeuThrAsnSer (SEQ ID NO: 91) | 33 |
| 30 | YALI0_D19822g | NC_006070.1 (2505960..2508386, complement) | 310_315delAAAGAG; Lys104_Glu105del | 34 |
| 31 | YALI0_D20064g | NC_006070.1 (2529127..2530611, complement) | 67_68insGGGGGGGG; p.Tyr23fs | 35 |
| 32 | YALI0_D20526g | NC_006070.1 (2604298..2604907, complement) | 354_355insTCCACCGGA; p.Gly118_Ser119insSerThrGly | 36 |
| 33 | YALI0_D20790g (Pre-mRNA-splicing factor CWC22) | NC_006070.1 (2636519..2639383, complement) | 37_38insCACGTGAAAGTAGCCGAA (SEQ ID NO: 75); p.Ser13Arg14insArgGluSerSerArgThr (SEQ ID NO: 92) | 37 |
| 34 | YALI0_D24563g | NC_006070.1 (3267394..3268023, complement) | 84_85insGCT; p.Glu28_Lys29insAla | 38 |
| 35 | YALI0_D24849g | NC_006070.1 (3309927..3310196, complement) | 103G > A; p.Ala35Thr | 39 |
| 36 | YALI0_D25014g | NC_006070.1 (3333236..3334741, complement) | 484_485insCCGCTAGCGCCAACTCTGGCTCGGAGC (SEQ ID NO: 76); p.Ala162_Ala163insAlaSerAlaAsnSerGlySerGluPro (SEQ ID NO: 93) | 40 |
| 37 | YALI0_D25058g (FACT complex subunit POB3) | NC_006070.1 (3340885..3342519, complement) | 592_594dupAAG; p.Lys198dup | 41 |
| 38 | YALI0_D26257g | NC_006070.1 (3490069..3492042, complement) | 1478_1480delAGA; p.Glu493_Thr494delinsAla; | 42 |
| 39 | YALI0_D26510g | NC_006070.1 (3533723..3535557, complement) | 1287_1288insAAG; p.Gln429_Gln430insLys | 43 |
| 40 | YALI0_D26620g | NC_006070.1 (3542396..3546277, complement) | 926_927insCGATGAGGACGA (SEQ ID NO: 77); p.Asp308_Glu309insAspAspGluAsp (SEQ ID NO: 94) | 44 |
| 41 | YALI0_D27016g | NC_006070.1 (3595010..3597181, complement) | 446T > C; p.Leu149Pro | 45 |
| 42 | YALI0_E07832g | NC_006071.1 (908935..909591, complement) | 499_500insCCAAGCCCCCGCTTCCAAGCCCACCGCTT (SEQ ID NO: 78); p.Pro167_Lys168insLysProProAlaSerLysProThrAlaSer (SEQ ID NO: 95) | 46 |
| 43 | YALI0_E08008g | NC_006071.1 (934849..936210, complement) | 794_795insCTCTTCCTCTTCCTCTTCCTCTTC (SEQ ID NO: 79); p.Gly265_Ser266insSerSerSerSerSerSerSerSer (SEQ ID NO: 96) | 47 |
| 44 | YALI0_E11363g | NC_006071.1 (1388910..1390034, complement) | 74_77delCACA; p.Thr25fs | 48 |
| 45 | YALI0_E13596g | NC_006071.1 (1643634..1645772, complement) | 1053_1054insCAACAACAACAGCAACAA; p.Gln346_Gln351dup | 49 |

TABLE 1-continued

| Gene No. | Gene Name | NCBI Reference Sequence no. | Mutations in Gene | SEQ ID NO. |
|---|---|---|---|---|
| 46 | YALI0_E14388g1 | NC_006071.1 (1723970..1728435, complement) | 2531T > G; p.Leu844Arg, 2534A > G; p.Gln845Arg, 2558T > C; p.Val853Ala, 2525C > G; p.Ser842* | 50 |
| 47 | YALI0_E16731g | NC_006071.1 (1979332..1982976, complement) | 1622_1623insTGAGGAGGAAGAGTAGGATGAGGA GTA (SEQ ID NO: 81); p.Glu541delinsAspGluGluGluGluTerAspGlu GluTer (SEQ ID NO: 97) | 51 |
| 48 | YALI0_E18073g | NC_006071.1 (2132735..2133649, complement) | 266_267insCCCCACGCAGCAGTCTTG (SEQ ID NO: 82); p.Cys89_Pro90insProThrGlnGlnSerCys (SEQ ID NO: 98) | 52 |
| 49 | YALI0_E18216g | NC_006071.1 (2171557..2172525, complement) | 930_938delACAACAGCA; p.Gln311_Gln313del | 53 |
| 50 | YALI0_E20449g | NC_006071.1 (2423925..2425388, complement) | 899_900insAAACGC; p.Ala300_Asn301insAsnAla | 54 |
| 51 | YALI0_E21109g | NC_006071.1 (2510568..2511743, complement) | 228_229insGCCCCGCCT; p.Gln76_Ala77insAlaProPro | 55 |
| 52 | YALI0_E23969g | NC_0060717.1 (2842397..2843512, complement) | 480_481insTCCTCTACCCCGAG (SEQ ID NO: 64); p.Ser160_Ser161insSerSerThrProGlu (SEQ ID NO: 99), 526_527insCCTCCACCACCGAGC (SEQ ID NO: 65); p.Ser176_Ser177insSerThrThrGluPro (SEQ ID NO: 100), 497A > C; p.Tyr166Ser | 56 |
| 53 | YALI0_F04906g | NC_006072.1 (750999..754226, complement) | 2702T > A; p.Val901Glu | 57 |
| 54 | YALI0_F12221g | NC_006072.1 (1609086..1611512, complement) | 1825_1827delAAG; p.Lys609del | 58 |
| 55 | YALI0_F12793g | NC_0060727.1 (1713697..1718010, complement) | 1855_1860delTCTTCT; p.Ser619_Ser620del | 59 |
| 56 | YALI0_F16577g | NC_006072.1 (2216900..2218064, complement) | 807_808insCCTCCT; p.Leu269_Thr270insProPro | 60 |
| 57 | YALI0_F17468g | NC_006072.1 (2332587..2335994, complement) | 482_483insGCACCA; p.Gln160_His161insGlnHis | 61 |
| 58 | YALI0_F19030g | NC_006072.1 (2541990..2544461, complement) | 1344_1345insCCTACTACCGCCGATGTT (SEQ ID NO: 83); p.Val448_Pro449insProThrThrAlaAspVal (SEQ ID NO: 101), 2065T > A; p.Ser689Thr, 2098A > G; p.Thr700Ala, 2099C > A; p.Thr700Asn | 62 |
| 59 | YAL10_F23287g | NC_006072.1 (3052893..3056228, complement) | 1919_1920insCTC; p.Ser640dup | 63 | del: deletion, ns: insertion, fs: frame shift, dup: duplication, *: stop

The transformed and adaptively evolved yeast strain of the present invention may comprise a gene encoding an enzyme that interconverts D-xylose and D-xylulose. Alternatively, the transformed and adaptively evolved yeast strain of the present invention may comprise the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, and YALI0_F17468g:

147G>A mutation in the YALI0_A15642g gene;

567_568insACA and 576T>G mutations in the YALI0_A15796g gene;

1523T>C mutation in the YALI0_C11165g gene;

T1412A, G1441A, A1513G, A1534G, G1535T, T1544A, and C1847T mutations in the YALI0_C16247g gene;

103G>A mutation in the YALI0_D24849g gene;

446T>C mutation in the YALI0_D27016g gene;

2525C>G, 2531T>G, 2534A>G, and 2558T>C mutations in the YALI0_E14388g1 gene;

480_481insTCCTCTACCCCCGAG (SEQ ID NO: 64), 526_527insCCTCCACCACCGAGC (SEQ ID NO: 65) and 497A>C mutations in the YALI0_E23969g gene;

2702T>A mutation in the YALI0_F04906g gene; or

482_483insGCACCA mutation in the YALI0_F17468g gene, or comprise the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, YALI0_F17468g, YALI0_A00891g, YALI0_A00935g, YALI0_A02002g, YALI0_A02497g, YALI0_A07997g, YALI0_A13849g, YALI0_A16863g, YALI0_A17578g, YALI0_A17776g, YALI0_A17853g, YALI0_A19646g, YALI0_B00748g, YALI0_B08800g, YALI0_C06424g, YALI0_C07172g, YALI0_C08437g, YALI0_C09031g, YALI0_C09614g, YALI0_C13728g, YALI0_C14476g, YALI0_C15532g, YALI0_C16148g, YALI0_D15752g, YALI0_D17820g, YALI0_D18381g, YALI0_D19822g, YALI0_D20064g, YALI0_D20526g, YALI0_D20790g, YALI0_D24563g, YALI0_D25014g, YALI0_D25058g, YALI0_D26257g, YALI0_D26510g, YALI0_D26620g, YALI0_E07832g, YALI0_E08008g, YALI0_E11363g, YALI0_E13596g, YALI0_E16731g, YALI0_E18073g, YALI0_E18216g, YALI0_E20449g, YALI0_E21109g, YALI0_F12221g, YALI0_F12793g, YALI0_F16577g, YALI0_F19030g, and YALI0_F23287g:

147G>A mutation in the YALI0_A15642g gene;

567_568insACA and 576T>G mutations in the YALI0_A15796g gene;

1523T>C mutation in the YALI0_C11165g gene;

T1412A, G1441A, A1513G, A1534G, G1535T, T1544A, and C1847T mutations in the YALI0_C16247g gene;

103G>A mutation in the YALI0_D24849g gene;

446T>C mutation in the YALI0_D27016g gene;

2525C>G, 2531T>G, 2534A>G, and 2558T>C mutations in the YALI0_E14388g1 gene;

480_481insTCCTCTACCCCCGAG (SEQ ID NO: 64), 526_527insCCTCCACCACCGAGC (SEQ ID NO: 65), and 497A>C mutations in the YALI0_E23969g gene;

2702T>A mutation in the YALI0_F04906g gene;

482_483insGCACCA mutation in the YALI0_F17468g gene;

11_16delACGGCC mutation in the YALI0_A00891g gene;

202_203insGCTC mutation in the YALI0_A00935g gene;

1255_1256insGAGGTCAAGGTC (SEQ ID NO: 66) mutation in the YALI0_A02002g gene;

132_137dupCAACTC and 331_332insCCCACT mutations in the YALI0_A02497g gene;

2846_2847insGGAGCAGGA and 2869_2870insAGGAGGAGG mutations in the YALI0_A07997g gene;

165_166insCAAA mutation in the YALI0_A13849g gene;

888_889insGAGCTGAGATGAC (SEQ ID NO: 67) mutation in the YALI0_A16863g gene;

432_433insGCGGAGCCG mutation in the YALI0_A17578g gene;

959_960insACAGCAGAT mutation in the YALI0_A17776g gene;

1940_1942delAGG, 1990_1991insAGGAGGAGGCTAAGAAGA (SEQ ID NO: 68), and 2817_2818insTCTGAG mutations in the YALI0_A17853g gene;

1462_1463insGGG mutation in the YALI0_A19646g gene;

525_526insCCCGAC mutation in the YALI0_B00748g gene;

152_153delGT mutation in the YALI0_B08800g gene;

1370_1373delACTT mutation in the YALI0_C06424g gene;

308_309insGCAGCGACA mutation in the YALI0_C07172g gene;

1592_1593insGACAGTCAGCAC (SEQ ID NO: 69) mutation in the YALI0_C08437g gene;

1789_1790insCTCCCGAGTCCTCTGCTGAGCCTACCAGCGAAGAGACTTCTTCCG (SEQ ID NO: 70) mutation in the YALI0_C09031g gene;

1620_1622delACA mutation in the YALI0_C09614g gene;

99_100insAAAAAGTGGTCGAAAAAGTGGCCA (SEQ ID NO: 71) and 129_130insTGGCCGAAAAAGTGGCCAAAA (SEQ ID NO: 72) mutations in the YALI0_C13728g gene;

778_779insTGC mutation in the YALI0_C14476g gene;

1611_1616delCAGCTT mutation in the YALI0_C15532g gene;

961_969delAGCAGCAGT mutation in the YALI0_C16148g gene;

1038_1039insCAG mutation in the YALI0_D15752g gene;

619_620insCCCACCCGCAAACCC (SEQ ID NO: 73) mutation in the YALI0_D17820g gene;

114_115insCCTCTCACCAACTCA (SEQ ID NO: 74) mutation in the YALI0_D18381g gene;

310_315delAAAGAG mutation in the YALI0_D19822g gene;

67_68insGGGGGGGG mutation in the YALI0_D20064g gene;

354_355insTCCACCGGA mutation in the YALI0_D20526g gene;

37_38insCACGTGAAAGTAGCCGAA (SEQ ID NO: 75) mutation in the YALI0_D20790g gene;

84_85insGCT mutation in the YALI0_D24563g gene;

484_485insCCGCTAGCGCCAACTCTGGCTCGAGC (SEQ ID NO: 76) mutation in the YALI0_D25014g gene;

592_594dupAAG mutation in the YALI0_D25058g gene;

1478_1480delAGA mutation in the YALI0_D26257g gene;

1287_1288insAAG mutation in the YALI0_D26510g gene;

926_927insCGATGAGGACGA (SEQ ID NO: 77) mutation in the YALI0_D26620g gene;
499_500insCCAAGCCCCCGCTTCCAAGCCCAC-CGCTT (SEQ ID NO: 78) mutation in the YALI0_E07832g gene;
794_795insCTCTTCCTCTTCCTCTTCCTCTTCCTC-TTC (SEQ ID NO: 79) mutation in the YALI0_E08008g gene;
74_77delCACA mutation in the YALI0_E11363g gene;
1053_1054insCAACAACAACAGCAACAA (SEQ ID NO: 80) mutation in the YALI0_E13596g gene;
1622_1623insTGAGGAGGAAGAGTAGGATGAG-GAGTA (SEQ ID NO: 81) mutation in the YALI0_E16731g gene;
266_267insCCCCACGCAGCAGTCTTG (SEQ ID NO: 82) mutation in the YALI0_E18073g gene;
930_938delACAACAGCA mutation in the YALI0_E18216g gene;
899_900insAAACGC mutation in the YALI0_E20449g gene;
228_229insGCCCCGCCT mutation in the YALI0_E21109g gene;
1825_1827delAAG mutation in the YALI0_F12221g gene;
1855_1860delTCTTCT mutation in the YALI0_F12793g gene;
807_808insCCTCCT mutation in the YALI0_F16577g gene;
1344_1345insCCTACTACCGCCGATGTT (SEQ ID NO: 83), 2065T>A, 2098A>G, and 2099C>A mutations in the YALI0_F19030g gene; or
1919_1920insCTC mutation in the YALI0_F23287g gene, and comprise a gene encoding an enzyme that interconverts D-xylose and D-xylulose. The gene encoding an enzyme that interconverts D-xylose and D-xylulose may be a gene encoding xylose isomerase. The gene encoding an enzyme that interconverts D-xylose and D-xylulose may be derived from *Piromyces* sp., specifically, a xylA (xylose isomerase) gene. More specifically, it may be a gene (xylA3*) obtained by mutating a xylA (xylose isomerase) gene derived from *Piromyces* sp. to obtain improved performance. More specifically, it may be a gene consisting of the sequence of SEQ ID NO: 1.

The transformed and adaptively evolved yeast strain of the present invention may comprise a gene encoding an enzyme that produces D-xylulose-5-phosphate from D-xylulose. Alternatively, the transformed and adaptively evolved yeast strain of the present invention may comprise the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, and YALI0_F17468g:
147G>A mutation in the YALI0_A15642g gene;
567_568insACA and 576T>G mutations in the YALI0_A15796g gene;
1523T>C mutation in the YALI0_C11165g gene;
T1412A, G1441A, A1513G, A1534G, G1535T, T1544A, and C1847T mutations in the YALI0_C16247g gene;
103G>A mutation in the YALI0_D24849g gene;
446T>C mutation in the YALI0_D27016g gene;
2525C>G, 2531T>G, 2534A>G, and 2558T>C mutations in the YALI0_E14388g1 gene;
480_481insTCCTCTACCCCCGAG (SEQ ID NO: 64), 526_527insCCTCCACCACCGAGC (SEQ ID NO: 65), and 497A>C mutations in the YALI0_E23969g gene;
2702T>A mutation in the YALI0_F04906g gene; or
482_483insGCACCA mutation in the YALI0_F17468g gene, or comprise the following mutations in at least one gene selected from the group consisting of YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, YALI0_F17468g, YALI0_A00891g, YALI0_A00935g, YALI0_A02002g, YALI0_A02497g, YALI0_A07997g, YALI0_A13849g, YALI0_A16863g, YALI0_A17578g, YALI0_A17776g, YALI0_A17853g, YALI0_A19646g, YALI0_B00748g, YALI0_B08800g, YALI0_C06424g, YALI0_C07172g, YALI0_C08437g, YALI0_C09031g, YALI0_C09614g, YALI0_C13728g, YALI0_C14476g, YALI0_C15532g, YALI0_C16148g, YALI0_D15752g, YALI0_D17820g, YALI0_D18381g, YALI0_D19822g, YALI0_D20064g, YALI0_D20526g, YALI0_D20790g, YALI0_D24563g, YALI0_D25014g, YALI0_D25058g, YALI0_D26257g, YALI0_D26510g, YALI0_D26620g, YALI0_E07832g, YALI0_E08008g, YALI0_E11363g, YALI0_E13596g, YALI0_E16731g, YALI0_E18073g, YALI0_E18216g, YALI0_E20449g, YALI0_E21109g, YALI0_F12221g, YALI0_F12793g, YALI0_F16577g, YALI0_F19030g, and YALI0_F23287g:
147G>A mutation in the YALI0_A15642g gene;
567_568insACA and 576T>G mutations in the YALI0_A15796g gene;
1523T>C mutation in the YALI0_C11165g gene;
T1412A, G1441A, A1513G, A1534G, G1535T, T1544A, and C1847T mutations in the YALI0_C16247g gene;
103G>A mutation in the YALI0_D24849g gene;
446T>C mutation in the YALI0_D27016g gene;
2525C>G, 2531T>G, 2534A>G, and 2558T>C mutations in the YALI0_E14388g1 gene;
480_481insTCCTCTACCCCCGAG (SEQ ID NO: 64), 526_527insCCTCCACCACCGAGC (SEQ ID NO: 65), and 497A>C mutations in the YALI0_E23969g gene;
2702T>A mutation in the YALI0_F04906g gene;
482_483insGCACCA mutation in the YALI0_F17468g gene;
11_16delACGGCC mutation in the YALI0_A00891g gene;
202_203insGCTC mutation in the YALI0_A00935g gene;
1255_1256insGAGGTCAAGGTC (SEQ ID NO: 66) mutation in the YALI0_A02002g gene;
132_137dupCAACTC and 331_332insCCCACT mutations in the YALI0_A02497g gene;
2846_2847insGGAGCAGGA and 2869_2870insAG-GAGGAGG mutations in the YALI0_A07997g gene;
165_166insCAAA mutation in the YALI0_A13849g gene;
888_889insGAGCTGAGATGAC (SEQ ID NO: 67) mutation in the YALI0_A16863g gene;
432_433insGCGGAGCCG mutation in the YALI0_A17578g gene;
959_960insACAGCAGAT mutation in the YALI0_A17776g gene;
1940_1942delAGG, 1990_1991insAGGAG-GAGGCTAAGAAGA (SEQ ID NO: 68), and 2817_2818insTCTGAG mutations in the YALI0_A17853g gene;
1462_1463insGGG mutation in the YALI0_A19646g gene;
525_526insCCCGAC mutation in the YALI0_B00748g gene;

152_153delGT mutation in the YALI0_B08800g gene;

1370_1373delACTT mutation in the YALI0_C06424g gene;

308_309insGCAGCGACA mutation in the YALI0_C07172g gene;

1592_1593insGACAGTCAGCAC (SEQ ID NO: 69) mutation in the YALI0_C08437g gene;

1789_1790insCTCCCGAGTCCTCTGCTGAGCCTACCAGCGAAGAGACTTCTTCCG (SEQ ID NO: 70) mutation in the YALI0_C09031g gene;

1620_1622delACA mutation in the YALI0_C09614g gene;

99_100insAAAAAGTGGTCGAAAAAGTGGCCA (SEQ ID NO: 71) and 129_130insTGGCCGAAAAAGTGGCCAAAA (SEQ ID NO: 72) mutations in the YALI0_C13728g gene;

778_779insTGC mutation in the YALI0_C14476g gene;

1611_1616delCAGCTT mutation in the YALI0_C15532g gene;

961_969delAGCAGCAGT mutation in the YALI0_C16148g gene;

1038_1039insCAG mutation in the YALI0_D15752g gene;

619_620insCCCACCCGCAAACCC (SEQ ID NO: 73) mutation in the YALI0_D17820g gene;

114_115insCCTCTCACCAACTCA (SEQ ID NO: 74) mutation in the YALI0_D18381g gene;

310_315delAAAGAG mutation in the YALI0_D19822g gene;

67_68insGGGGGGGG mutation in the YALI0_D20064g gene;

354_355insTCCACCGGA mutation in the YALI0_D20526g gene;

37_38insCACGTGAAAGTAGCCGAA (SEQ ID NO: 75) mutation in the YALI0_D20790g gene;

84_85insGCT mutation in the YALI0_D24563g gene;

484_485insCCGCTAGCGCCAACTCTGGCTCGGAGC (SEQ ID NO: 76) mutation in the YALI0_D25014g gene;

592_594dupAAG mutation in the YALI0_D25058g gene;

1478_1480delAGA mutation in the YALI0_D26257g gene;

1287_1288insAAG mutation in the YALI0_D26510g gene;

926_927insCGATGAGGACGA (SEQ ID NO: 77) mutation in the YALI0_D26620g gene;

499_500insCCAAGCCCCCGCTTCCAAGCCCACCGCTT (SEQ ID NO: 78) mutation in the YALI0_E07832g gene;

794_795insCTCTTCCTCTTCCTCTTCCTCTTCCTCTTC (SEQ ID NO: 79) mutation in the YALI0_E08008g gene;

74_77delCACA mutation in the YALI0_E11363g gene;

1053_1054insCAACAACAACAGCAACAA (SEQ ID NO: 80) mutation in the YALI0_E13596g gene;

1622_1623insTGAGGAGGAAGAGTAGGATGAGGAGTA (SEQ ID NO: 81) mutation in the YALI0_E16731g gene;

266_267insCCCCACGCAGCAGTCTTG (SEQ ID NO: 82) mutation in the YALI0_E18073g gene;

930_938delACAACAGCA mutation in the YALI0_E18216g gene;

899_900insAAACGC mutation in the YALI0_E20449g gene;

228_229insGCCCCGCCT mutation in the YALI0_E21109g gene;

1825_1827delAAG mutation in the YALI0_F12221g gene;

1855_1860delTCTTCT mutation in the YALI0_F12793g gene;

807_808insCCTCCT mutation in the YALI0_F16577g gene;

1344_1345insCCTACTACCGCCGATGTT (SEQ ID NO: 83), 2065T>A, 2098A>G and 2099C>A mutations in the YALI0_F19030g gene; or 1919_1920insCTC mutation in the YALI0_F23287g gene, and comprise a gene encoding an enzyme that produces D-xylulose-5-phosphate from D-xylulose. Alternatively, the transformed and adaptively evolved yeast strain of the present invention may comprise a gene encoding an enzyme that interconverts D-xylose and D-xylulose and a gene encoding an enzyme that produces D-xylulose-5-phosphate from D-xylulose. The gene encoding an enzyme that produces D-xylulose-5-phosphate from D-xylulose may be a xylulokinase. The gene encoding an enzyme that produces D-xylulose-5-phosphate from D-xylulose may be derived from *Yarrowia lipolytica*, specifically, a XK (xylulokinase) gene. More specifically, it may be a gene consisting of the sequence of SEQ ID NO: 2.

The adaptively evolved yeast strain or transformed and adaptively evolved yeast strain of the present invention is capable of utilizing xylose as the sole carbon source. Alternatively, the transformed and adaptively evolved yeast strain of the present invention is obtained by transforming the adaptively evolved yeast strain to comprise at least one gene selected from the group consisting of a gene encoding an enzyme that interconverts D-xylose and D-xylulose and a gene encoding an enzyme that produces D-xylulose-5-phosphate from D-xylulose, and is capable of utilizing xylose as the sole carbon source.

In one example of the present invention, a strain (YSX_xylA) transformed by introducing only the xylose isomerase gene into a strain, which is adaptively evolved by subculturing five times in a medium containing xylose as the sole carbon source, exhibited a growth rate of about 1.02 times greater than that of the control (wild-type yeast strain not subjected to adaptive evolution, $OD_{600}$ of about 0.88, strain growth rate (μ) of about 0.0158 $h^{-1}$). A strain (YSX_XK) transformed by introducing only the xylulokinase gene exhibited an about 1.49 times greater growth rate. A strain (YSX_xylA_XK) transformed by introducing both the xylose isomerase gene and the xylulokinase gene exhibited an about 12 times greater growth rate, indicating that it can utilize xylose as the sole carbon source (see Example 3).

The transformed and adaptively evolved yeast strain of the present invention may be transformed with at least one vector selected from the group consisting of a first vector and a second vector. Here, the terms "first" and "second" are only for distinguishing between the types of vectors, and do not limit the order or method of transformation.

The first vector may comprise a gene encoding an enzyme that interconverts D-xylose and D-xylulose. Specifically, it may comprise a UAS1B enhancer, a translational elongation factor (TEF) promoter, and a gene encoding an enzyme that interconverts D-xylose and D-xylulose. More specifically, it may consist of the sequence of SEQ ID NO: 3.

The second vector may comprise a gene encoding an enzyme that produces D-xylulose-5-phosphate from D-xylulose. Specifically, it may comprise a UAS1B enhancer, a translational elongation factor (TEF) promoter, and a gene encoding an enzyme that produces D-xylulose-5-phosphate from D-xylulose. More specifically, it may consist of the sequence of SEQ ID NO: 4.

The transformed and adaptively evolved yeast strain of the present invention may be a strain having the accession number KCTC13616BP. The strain having the accession number KCTC13616BP may be a strain obtained by transforming a strain adaptively evolved by subculturing five times in a medium containing xylose as the sole carbon source and which is adaptively evolved compared with, for example, wild-type yeast strains, with a first vector comprising a gene encoding an enzyme that interconverts D-xylose and D-xylulose. Alternatively, it may be a strain obtained by transforming the adaptively evolved strain with a second vector comprising a gene encoding an enzyme that produces D-xylulose-5-phosphate from D-xylulose. Alternatively, it may be a strain obtained by transforming the adaptively evolved strain with the first vector and the second vector.

In another aspect, the present invention may relate to a method for producing the transformed and adaptively evolved yeast strain, comprising the steps of: subculturing a wild-type yeast strain three times or more in a medium containing xylose as the sole carbon source; and transforming the subcultured strain to comprise at least one gene selected from the group consisting of a gene encoding an enzyme that interconverts D-xylose and D-xylulose and a gene encoding an enzyme that produces D-xylulose-5-phosphate from D-xylulose. Alternatively, the present invention may relate to a method for producing the transformed and adaptively evolved yeast strain, comprising the steps of: subculturing a wild-type yeast strain three times or more in a medium containing xylose as the sole carbon source; and transforming the subcultured strain to comprise at least one gene selected from the group consisting of a gene encoding an enzyme that interconverts D-xylose and D-xylulose and a gene encoding an enzyme that produces D-xylulose-5-phosphate from D-xylulose.

The step of subculturing may be subculturing a wild-type yeast strain three times or more, specifically, three times or more, four times or more, or five times or more in a medium containing xylose as the sole carbon source. The subcultured strain may be an adaptively evolved strain which comprises a mutation as shown in Table 2 below in at least one gene selected from the group consisting of the genes of Table 2 below or which comprises a mutation as shown in Table 2 below in at least one gene selected from the group consisting of the genes of Table 2 below and a mutation as shown in Table 3 below in at least one gene selected from the group consisting of the genes of Table 3 below, as compared with wild-type yeast strains. Also, the subcultured strain may be an adaptively evolved strain having the accession number KCTC13615BP.

TABLE 2

| Gene No. | Gene Name | Mutations in Gene |
|---|---|---|
| 7 | YALI0_A15642g | 147G > A; p.Trp49* |
| 8 | YALI0_A15796g | 567_568insACA; p.Thr189dup, 576T > G; p.Asp192Glu |
| 21 | YALI0_C11165g | 1523T > C; p.Val508Ala |
| 26 | YALI0_C16247g | T1412A; Val471Asp, G1441A; Asp481Asn, A1513G; Asn505Asp, A1534G; Ser512Gly, G1535T; Ser512Ile, T1544A; Val515Glu, C1847T; Ala616Val |
| 35 | YALI0_D24849g | 103G > A; p.Ala35Thr |
| 41 | YALI0_D27016g | 446T > C; p.Leu149Pro |
| 46 | YALI0_E14388g1 | 2531T > G; p.Leu844Arg, 2534A > G; p.Gln845Arg, 2558T > C; p.Val853Ala |
| 52 | YALI0_E23969g | 480_481insTCCTCTACCCCCGAG (SEQ ID NO: 64); p.Ser160_Ser161insSerSerThrProGlu (SEQ ID NO: 99), 526_527insCCTCCACCACCGAGC (SEQ ID NO: 65); p.Ser176_Ser177insSerThrThrGluPro (SEQ ID NO: 100), 497A > C; p.Tyr166Ser |
| 53 | YALI0_F04906g | 2702T > A; p.Val901Glu |
| 57 | YALI0_F17468g | 482_483insGCACCA; p.Gln160_His161insGlnHis | del: deletion, ins: insertion, fs: frame shift, dup: duplication, *: stop

TABLE 3

| Gene No. | Gene Name | Mutations in Gene |
|---|---|---|
| 1 | YALI0_A00891g | 11_16delACGGCC; p.Asn4_Gln6delinsLys |
| 2 | YALI0_A00935g | 202_203insGCTC; p.Tyr68fs |
| 3 | YALI0_A02002g | 1255_1256insGAGGTCAAGGTC (SEQ ID NO: 66); p.Gly418_Gln419insArgGlyGlnGly (SEQ ID NO: 84) |
| 4 | YALI0_A02497g | 132_137dupCAACTC; p.Ser46_Gly47insAsnSer, 331_332insCCCACT; p.Asn110_Tyr111insSerHis |

TABLE 3-continued

| Gene No. | Gene Name | Mutations in Gene |
|---|---|---|
| 5 | YALI0_A07997g | 2846_2847insGGAGCAGGA; p.Gly949_Glu950insGluGlnGlu, 2869_2870insAGGAGGAGG; p.Lys957_Glu958insGluGluGlu |
| 6 | YALI0_A13849g | 165_166insCAAA; p.Lys56fs |
| 9 | YALI0_A16863g | 888_889insGAGCTGAGATGAC (SEQ ID NO: 67); p.Val298fs |
| 10 | YALI0_A17578g | 432_433insGCGGAGCCG; p.Pro144_Ser145insAlaGluPro |
| 11 | YALI0_A17776g | 959_960insACAGCAGAT; p.Pro320_Gln321insGlnGlnIle |
| 12 | YALI0_A17853g | 1940_1942delAGG; p.Glu648del, 1990_1991insAGGAGGAGGCTAAGAAGA (SEQ ID NO: 68); p.Glu664_Glu665insGluGluAlaLysLysLys (SEQ ID NO: 85), 2817_2818insTCTGAG; p.Asp939_Ser940insSerGlu |
| 13 | YALI0_A19646g | 1462_1463insGGG; p.Glu487_Glu488insGly |
| 14 | YALI0_B00748g | 525_526insCCCGAC; p.Asp175_Ser176insProAsp |
| 15 | YALI0_B08800g | 152_153delGT; p.Cys51fs |
| 16 | YALI0_C06424g | 1370_1373delACTT; p.Tyr457fs |
| 17 | YALI0_C07172g | 308_309insGCAGCGACA; p.Gln103_Gln104insGlnArgGln |
| 18 | YALI0_C08437g | 1592_1593insGACAGTCAGCAC (SEQ ID NO: 69); p.Lys531_Thr532insThrValSerThr (SEQ ID NO: 86) |
| 19 | YALI0_C09031g | 1789_1790insCTCCCGAGTCCTCTGCTGAGCCTACCAGCGAAGAGACTTCTTCCG (SEQ ID NO: 70); p.Ser596_Val597insAlaProGluSerSerAlaGluProThrSerGluGluThrSerSer (SEQ ID NO: 87) |
| 20 | YALI0_C09614g | 1620_1622delACA; p.Gln541del |
| 22 | YALI0_C13728g | 99_100insAAAAAGTGGTCGAAAAAGTGGCCA (SEQ ID NO: 71); p.Pro33_Lys34insLysLysTrpSerLysLysTrpPro (SEQ ID NO: 88), 129_130insTGGCCGAAAAAGTGGCCAAAA (SEQ ID NO: 72); p.Lys43_Lys44insTrpProLysLysTrpProLys (SEQ ID NO: 89) |
| 23 | YALI0_C14476g | 778_779insTGC; p.Lys260delinsMetGln |
| 24 | YALI0_C15532g | 1611_1616delCAGCTT; p.Ser538_Phe539del |
| 25 | YALI0_C16148g | 961_969delAGCAGCAGT; p.Ser321_Ser323del |
| 27 | YALI0_D15752g | 1038_1039insCAG; Pro346_Gln347insGln |
| 28 | YALI0_D17820g | 619_620insCCCACCCGCAAACCC (SEQ ID NO: 73); Thr206_His207insProHisProGlnThr (SEQ ID NO: 90) |
| 29 | YALI0_D18381g | 114_115insCCTCTCACCAACTCA (SEQ ID NO: 74); Ser38_Thr39insProLeuThrAsnSer (SEQ ID NO: 91) |
| 30 | YALI0_D19822g | 310_315delAAAGAG; Lys104_Glu105del |
| 31 | YALI0_D20064g | 67_68insGGGGGGGG; p.Tyr23fs |
| 32 | YALI0_D20526g | 354_355insTCCACCGGA; p.Gly118_Ser119insSerThrGly |
| 33 | YALI0_D20790g | 37_38insCACGTGAAAGTAGCCGAA (SEQ ID NO: 75); p.Ser13_Arg14insArgGluSerSerArgThr (SEQ ID NO: 92) |
| 34 | YALI0_D24563g | 84_85insGCT; p.Glu28_Lys29insAla |
| 36 | YALI0_D25014g | 484_485insCCGCTAGCGCCAACTCTGGCTCGGAGC (SEQ ID NO: 76); p.Ala162_Ala163insAlaSerAlaAsnSerGlySerGluPro (SEQ ID NO: 93) |
| 37 | YALI0_D25058g | 592_594dupAAG; p.Lys198dup |
| 38 | YALI0_D26257g | 1478_1480delAGA; p.Glu493_Thr494delinsAla; 1480/1974; 1478/1974; 493/657; |
| 39 | YALI0_D26510g | 1287_1288insAAG; p.Gln429_Gln430insLys |

TABLE 3-continued

| Gene No. | Gene Name | Mutations in Gene |
|---|---|---|
| 40 | YALI0_D26620g | 926_927insCGATGAGGACGA (SEQ ID NO: 77); p.Asp308_Glu309insAspAspGluAsp (SEQ ID NO: 94) |
| 42 | YALI0_E07832g | 499_500insCCAAGCCCCCGCTTCCAAGCCCACCGCTT (SEQ ID NO: 78); p.Pro167_Lys168insLysProProAlaSerLysProThrAlaSer (SEQ ID NO: 95) |
| 43 | YALI0_E08008g | 794_795insCTCTTCCTCTTCCTCTTCCTCTTCCTCTTC (SEQ ID NO: 79); p.Gly265_Ser266insSerSerSerSerSerSerSerSerSer (SEQ ID NO: 96) |
| 44 | YALI0_E11363g | 74_77delCACA; p.Thr25fs |
| 45 | YALI0_E13596g | 1053_1054insCAACAACAACAGCAACAA (SEQ ID NO: 80); p.Gln346_Gln351dup |
| 47 | YALI0E16731g | 1622_1623insTGAGGAGGAAGAGTAGGATGAGGAGTA (SEQ ID NO: 81); p.Glu541delinsAspGluGluGluGluTerAspGluGluTer (SEQ ID NO: 97) |
| 48 | YALI0_E18073g | 266_267insCCCCACGCAGCAGTCTTG (SEQ ID NO: 82); p.Cys89_Pro90insProThrGlnGlnSerCys (SEQ ID NO: 98) |
| 49 | YALI0_E18216g | 930_938delACAACAGCA; p.Gln311_Gln313del |
| 50 | YALI0_E20449g | 899_900insAAACGC; p.Ala300_Asn301insAsnAla |
| 51 | YALI0_E21109g | 228_229insGCCCCGCCT; p.Gln76_Ala77insAlaProPro |
| 54 | YALI0_F12221g | 1825_1827delAAG; p.Lys609del |
| 55 | YALI0_F12793g | 1855_1860delTCTTCT; p.Ser619_Ser620del |
| 56 | YALI0_F16577g | 807_808insCCTCCT; p.Leu269_Thr270insProPro |
| 57 | YALI0_F19030g | 1344_1345insCCTACTACCGCCGATGTT (SEQ ID NO: 83); p.Val448_Pro449insProThrThrAlaAspVal (SEQ ID NO: 101), 2065T > A; p.Ser689Thr, 2098A > G; p.Thr700Ala, 2099C > A; p.Thr700Asn |
| 58 | YALI0_F23287g | 1919_1920insCTC; p.Ser640dup | del: deletion, ins: insertion, fs: frame shift, dup: duplication, *: stop

The step of transformation may be transforming the subcultured strain to comprise at least one gene selected from the group consisting of a gene encoding an enzyme that interconverts D-xylose and D-xylulose and a gene encoding an enzyme that produces D-xylulose-5-phosphate from D-xylulose. Specifically, it may be the step of transformation with at least one vector selected from the group consisting of the first vector and the second vector. The descriptions of the gene encoding an enzyme that interconverts D-xylose and D-xylulose, the gene encoding an enzyme that produces D-xylulose-5-phosphate from D-xylulose, the first vector, and the second vector are as described above.

In yet another aspect, the present invention provides a method for producing lipids, comprising the step of culturing the transformed and adaptively evolved yeast strain. Also, the present invention provides a method for produing lipids comprising the step of culturing the transformed and adaptively evolved yeast strain in a medium containing xylose as a carbon source.

The transformed and adaptively evolved yeast strain may be a strain obtained by subculturing three times or more, specifically, three times or more, four times or more, or five times or more in a medium containing xylose as the sole carbon source. Also, the subcultured yeast strain may be an adaptively evolved strain which comprises a mutation as shown in Table 2 below in at least one gene selected from the group consisting of the genes of Table 2 below or which comprises a mutation as shown in Table 2 below in at least one gene selected from the group consisting of the genes of Table 2 below and a mutation as shown in Table 3 below in at least one gene selected from the group consisting of the genes of Table 3 below, as compared with wild-type yeast strains. Also, it may be an adaptively evolved strain having the accession number KCTC13615BP. The descriptions of the adaptively evolved strain, the subculture, the mutant strain, the transformed and adaptively evolved yeast strain, etc. are as described above.

The "lipid" is an organic matter or organic compound consisting essentially of a fatty acid and glycerol, and may comprise at least one selected from the group consisting of acylglycerol, glyceride, and free fatty acid. The acylglycerol may be at least one selected from the group consisting of triacylglycerol (TAG), diacylglycerol (DAG), and monoacylglycerol (MAG). The glyceride may be at least one selected from the group consisting of monoglyceride, diglyceride, and triglyceride. Alternatively, the lipid may be at least one selected from the group consisting of butyric acid (butanoic acid, C4:0), caproic acid (hexanoic acid, C6:0), caprylic acid (octanoic acid, C8:0), capric acid (decanoic acid, C10:0), lauric acid (dodecanoic acid, C12:0), myristic acid (tetradecanoic acid, C14:0), myristoleic acid ($\omega$-5, C14:1), pentadecylic acid (C15:0), palmitic acid (hexadecanoic acid, C16:0), palmitoleic acid ($\omega$-7, C16:1), hexadecadienoic acid (C16:2), hexadecatrienoic acid (C16:3), margaric acid (C17:0), heptadenoic acid (C17:1), stearic acid (octadecanoic acid, C18:0), oleic acid ($\omega$-9, C18:1), linoleic acid (LA, ω-6, C18:2), alpha-linolenic acid (ALA, ω-3, C18:3), octadecatetraenoic acid (C18:4), nonadecylic acid (C19:0), nonadecylic acid (C19:1), arachidic acid (eicosanoic acid, C20:0), arachidonic acid (AA, ω-6, C20:4), eicosapentaenoic acid (ω-3, C20:5), behenic acid (docosanoic acid, C22:0), erucic acid (ω-9, C22:1), docosapentaenoic acid (DPA, ω-3, 22:5), and docosahexaenoic acid (DHA, ω-3, C22:6). Specifically, it may be at least one fatty acid selected from the group consisting of C16:0, C16:1, C16:2, C16:3, C18:0, C18:1, C18:2, C18:3, and C18:4.

The medium used for the culture may be appropriately selected according to the characteristics of the microorganism to be cultured. If the microorganism to be cultured is a yeast strain, specifically, a *Yarrowia lipolytica* strain, a Yeast Synthetic Complete (YSC) medium may be used. Also, the culture medium used for the culture may be a common medium containing at least one selected from the group consisting of a suitable carbon source, nitrogen source, amino acid, vitamin, etc., and which satisfies the culture conditions of yeast strains according to an appropriate method with adjustment of the temperature, pH, etc. Examples of carbon sources that may be used include sugars and carbohydrates such as glucose, xylose, sucrose, lactose, fructose, maltose, starch, and cellulose, oils and fats such as soybean oil, sunflower oil, castor oil, and coconut oil, fatty acids such as palmitic acid, stearic acid and linoleic acid, alcohols such as glycerol and ethanol, organic acids such as acetic acid, and volatile fatty acids (VFA) such as acetic acid, butyric acid, isobutyric acid, propionic acid, valeric acid, isovaleric acid, and caproic acid. These materials may be used alone or as a mixture. Examples of nitrogen sources that may be used include inorganic nitrogen sources such as ammonia, ammonium sulfate, ammonium chloride, ammonium acetate, ammonium phosphate, ammonium carbonate, and ammonium nitrate; and organic nitrogen sources, such as amino acids and peptones such as glutamic acid, methionine and glutamine, NZ-amines, meat extract, yeast extract, malt extract, corn steep liquor, casein hydrolyzate, fish or its decomposition products, and defatted soybean cake or its decomposition products. These nitrogen sources may be used alone or as a mixture. The medium may contain, as phosphorus sources, potassium phosphate monobasic, potassium phosphate dibasic and corresponding sodium-containing salts. Examples of phosphorus sources that may be used include potassium phosphate monobasic, potassium phosphate dibasic and corresponding sodium-containing salts. Examples of inorganic compounds that may be used include sodium chloride, calcium chloride, iron chloride, magnesium sulfate, iron sulfate, manganese sulfate and calcium carbonate. Finally, in addition to the above materials, materials such as amino acids and vitamins may be used.

In addition, the culture of the transformed and adaptively evolved yeast strain may utilize xylose as a carbon source.

In addition, suitable precursors may be used in the culture medium. The above-mentioned raw materials may be added to the culture during culturing in a batch, a fed-batch, or a continuous manner by an appropriate method, although not particularly limited thereto. The pH of the culture may be adjusted by using an appropriate concentration of basic compounds, such as sodium hydroxide, potassium hydroxide, and ammonia or acidic compounds such as phosphoric acid or sulfuric acid in an appropriate amount and an appropriate manner.

Also, the culture of the transformed and adaptively evolved yeast strain may be any one selected from the group consisting of shaking culture, stationary culture, batch culture, fed-batch culture, and continuous culture. The shaking culture refers to a method of culturing a culture inoculated with a microorganism while shaking the culture. The stationary culture refers to a culture method in which a liquid culture inoculated with a microorganism is allowed to stand for culturing, without shaking. The batch culture refers to a culture method in which culture is performed with the volume of the culture fixed, without addition of a new culture from the outside. An apparatus capable of realizing this culture method is referred to as a batch reactor. The fed-batch culture is an opposite term of batch culture, in which all of the raw materials are added into a culture tank from the beginning and cultured, and it refers to a culture method in which a small amount of elements are first added, followed by repeated addition of a small amount of raw materials during culturing. An apparatus capable of realizing this culture method is referred to as a fed-batch reactor. The continuous culture refers to a culture method in which a new nutrient medium is continuously supplied and at the same time a culture containing cells and products is continuously removed. An apparatus capable of realizing this culture method is referred to as a continuous reactor. Specifically, the culture may be carried out in a batch reactor, a continuous reactor, or a fed-batch reactor. According to one embodiment of the present invention, when a yeast strain, specifically a transformed and adaptively evolved yeast strain is cultured by operating a batch reactor, a high concentration of yeast strains can be cultured and high-density lipids can be produced using the culture.

Also, the culture of the transformed and adaptively evolved yeast strain may achieve an $OD_{600}$ of 1.0 or more, 1.5 or more, or more, 2.0 or more, 2.2 or more, 2.4 or more, 2.6 or more, 2.8 or more, 3.0 or more, 3.2 or more, 3.4 or more, 3.6 or more, 3.8 or more, 4.0 or more, 4.2 or more, 4.4 or more, 4.6 or more, 4.8 or more, 5.0 or more, 5.2 or more, 5.4 or more, 5.6 or more, 5.8 or more, 6.0 or more, 6.2 or more, 6.4 or more, 6.6 or more, 6.8 or more, 7.0 or more, 7.2 or more, 7.4 or more, 7.6 or more, 7.8 or more, 8.0 or more, 8.2 or more, 8.4 or more, 8.6 or more, 8.8 or more, 9.0 or more, 9.2 or more, 9.4 or more, 9.6 or more, 9.8 or more, 10.0 or more, 10.2 or more, 10.4 or more, 10.6 or more, 10.8 or more, 11.0 or more, 11.2 or more, 11.4 or more, 11.6 or more, 11.8 or more, 12.0 or more, 12.2 or more, 12.4 or more, 12.6 or more, 12.8 or more, 13.0 or more, 13.2 or more, 13.4 or more, 13.5 or more, 13.6 or more, 13.8 or more, 14.0 or more, 20 or more, 30 or more, 40 or more, 42 or more, 44 or more and 120 or less, 115 or less, 110 or less, 105 or less, 100 or less, 95 or less, 90 or less, 85 or less, 80 or less, 70 or less, 60 or less, 50 or less, 48 or less, 46 or less, 45 or less, 44 or less, 42 or less, 40 or less, 30 or less, 20 or less, 18 or less, 16 or less, 15 or less, 14 or less, 13.8 or less, 13.6 or less, 13.5 or less, 13.4 or less, 13.2 or less, 13.0 or less, 12 or less, 10 or less, 5 or less, 2 or less or 1 or less.

In another aspect, the present invention provides a method for producing biodiesel, comprising the steps of: culturing the transformed and adaptively evolved yeast strain in a medium containing xylose as a carbon source to produce lipids; and transesterifying the produced lipids to obtain biodiesel. The descriptions of the adaptively evolved strain, the transformed and adaptively evolved yeast strain, the culture of the strain, and the production of lipids are as described above.

The "biodiesel", which is a type of biofuel, generally refers to fatty acid methyl ester (FAME) obtained by transesterification in which glycerol is separated from triglyceride, in which glycerol is bonded to three fatty acids, using methanol to form a fatty acid ester. The transesterification of the produced lipids to obtain biodiesel is not limited as long as it is a method for obtaining biodiesel from lipids.

Hereinafter, the present invention will be described in more detail through examples. However, the following examples are provided for illustrative purposes only to facilitate understanding of the present invention, and the scope of the present invention is not limited thereto.

[Example 1] Construction of a Strain Expressing the Xylose Isomerase Gene and the Xylulokinase Gene In order to develop a *Yarrowia lipolytica* strain having xylose utilizing capacity, a *Yarrowia lipolytica* strain comprising a gene encoding xylose isomerase or a gene encoding xylulokinase was constructed and the xylose utilizing capacity was compared based on the curves of growth of *Yarrowia lipolytica* strains using xylose.

Specifically, the xylA3* gene (a mutant gene obtained by modifying the xylA (xylose isomerase) gene derived from *Piromyces* sp. to obtain improved performance; hereinafter referred to as "xylA") was selected as the gene encoding xylose isomerase and the XK (xylulokinase) gene derived from *Yarrowia lipolytica* was selected as the gene encoding xylulokinase. Then, the xylA gene or the XK gene was introduced into a wild-type *Yarrowia lipolytica* strain that does not have xylose isomerase and xylulokinase according to the following method: Firstly, in order to overexpress the two genes, pMCS-UAS1B16-TEF-XylA-CYCt (SEQ ID NO: 3) as a first vector was constructed by inserting the xylA gene consisting of the sequence of SEQ ID NO: 1 into a translational elongation factor (TEF) promoter upstream of which an enhancer (UAS1B) has been added, and pMCS-UAS1B12-TEF-XK-CYCt (SEQ ID NO: 4) as a second vector was constructed by inserting the XK gene consisting of the sequence of SEQ ID NO: 2 into a translational elongation factor (TEF) promoter upstream of which an enhancer (UAS1B) has been added, according to a vector production method known in the art. Then, the following three types of strains were constructed: a transformed strain (the XYLA(O), XK(X) strain of FIG. 1) obtained by inserting only the first vector into a wild-type *Yarrowia lipolytica* strain, a transformed strain (the XYLA(X), XK(O) strain of FIG. 1) obtained by inserting only the second vector into a wild-type *Yarrowia lipolytica* strain and a transformed strain (the XYLA(O), XK(O) strain of FIG. 1) obtained by inserting both the first and second vectors into a wild-type *Yarrowia lipolytica* strain. An empty vector (pMCS-UAS1B16-TEF-CYCt and pMCS-UAS1B12-TEF-CYCt) in which neither the xylA gene nor the XK gene have been inserted was introduced into a wild-type *Yarrowia lipolytica* strain to obtain a control strain (the XYLA(X), XK(X) strain of FIG. 1).

Then, the above four strains were inoculated into a minimal medium (YSC medium (Yeast Synthetic Complete medium)) containing xylose as a carbon source and cultured at 28° C. with stirring at 200 rpm to investigate the growth of strains using xylose. Based on the results, the xylose utilizing capacity of the recombinant strains was evaluated, and the results are shown in FIG. 1. As used herein, the term "$OD_{600}$" refers to the absorbance or optical density at a wavelength of 600 nm. It can be measured using a device such as a spectrophotometer. It is possible to measure the density or concentration of microorganisms or cells in a sample by using the measured $OD_{600}$.

As shown in FIG. 1, the four strains reached a stationary phase of strain growth within 28 to 60 hours, and the strain (the XYLA (O), XK (X) strain in FIG. 1) expressing only the xylose isomerase gene exhibited an $OD_{600}$ value of 0.4961 at the stationary phase of growth at 60 hours after culture, indicating that it was a strain exhibiting the highest xylose-based growth, that is, having the highest xylose utilizing capacity. Meanwhile, the strain (the XYLA (O), XK (O) strain of FIG. 1) expressing both xylose isomerase and xylulokinase exhibited an $OD_{600}$ value of 0.4210 at 60 hours after culture, showing a slightly increased growth compared to the control (the XYLA(X), XK(X) strain of FIG. 1) ($OD_{600}$=0.3957). However, there was no significant difference between the strain and the control in the growth of cells in a xylose medium. In other words, none of the experimental groups expressing xylose isomerase or xylulokinase showed a significant improvement in cell growth as compared with the control group, and it was found that the introduction alone of the xylose isomerase and xylulokinase genes into wild-type did not lead to a significant effect on xylose utilizing capacity.

[Example 2] Construction of an Adaptively Evolved *Yarrowia lipolytica* Strain with Xylose Utilizing Capacity Through an Evolutionary Engineering Method The object of this example was to obtain a *Yarrowia lipolytica* strain adaptively evolved for xylose utilization by subculturing the wild-type strain in xylose minimal medium (YSC medium (Yeast Synthetic Complete medium)) to improve the xylose metabolism of the wild-type *Yarrowia lipolytica* strain. To this end, a wild-type *Yarrowia lipolytica* strain expressing xylose isomerase was cultured in a minimal medium (Complete Supplement Mixture (CSM)-Leu-Ura medium (6.7 g/L yeast nitrogen base, 20 g/L xylose, CSM-Leu-Ura(MP biomedicals, Solon, USA)) containing 20 g/L of xylose as the sole carbon source. As a result, an adaptively evolved strain (the YSX strain of FIG. 2) with improved xylose utilizing capacity was separated after 5 passages of subculture. It was found that the adaptively evolved strain (YSX strain) had the mutations in the genes as shown in Table 1 above.

Figure 2:
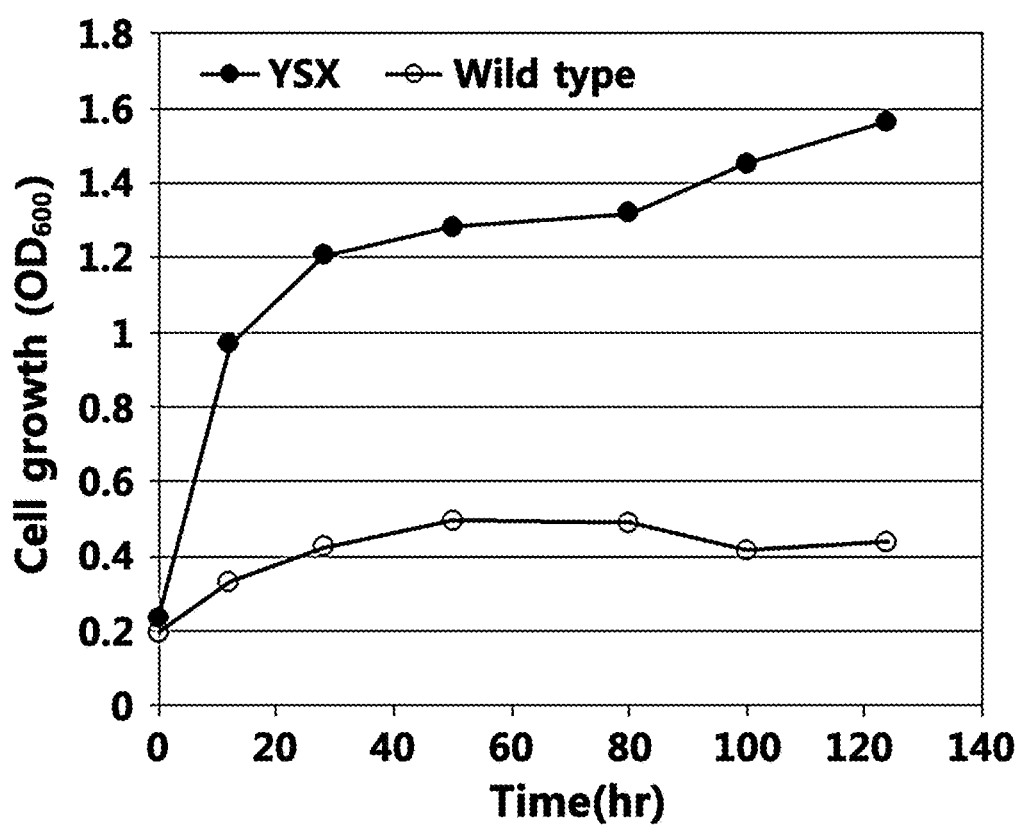
FIG. 2 shows the growth curves of a wild-type Yarrowia lipolytica strain (Wild type) and an adaptively evolved Yarrowia lipolytica strain (YSX) with xylose utilizing capacity obtained by subculturing the strain in xylose minimal medium, in a medium containing xylose as the sole carbon source.

When the xylose utilizing capacity of the adaptively evolved strain (YSX strain) was compared with that of the wild-type strain, as shown in FIG. 2, the maximum strain concentration at the stationary phase of strain growth, expressed as $OD_{600}$, was 0.50 for the wild-type strain and 1.57 for the adaptively evolved strain (YSX strain), and the adaptively evolved strain exhibited a 215% increased cell growth rate compared to the wild-type strain. In terms of growth rate (unit: μ), the adaptively evolved strain (YSK strain) exhibited a growth rate of 0.006 $h^{-1}$, indicating that it had about 3 times higher xylose utilizing capacity than the wild-type strain, which showed a growth rate of 0.002 $h^{-1}$.

From the results, it can be understood that the adaptively evolved strain has significantly improved xylose utilizing capacity as compared with the wild-type *Yarrowia lipolytica* strain which expresses xylose isomerase, and thus can grow utilizing xylose as the sole carbon source

[Example 3] Expression of the Xylose Isomerase Gene and the Xylulokinase Gene in Adaptively Evolved Strain In order to produce a *Yarrowia lipolytica* strain having increased xylose utilizing capacity, the adaptively evolved Yarrowia lipolytica strain (YSX strain) produced in Example 2 was transformed to overexpress genes related to the xylose metabolic pathway.

Specifically, a xylose isomerase gene (xylA gene) or a xylulokinase gene (XK gene) was inserted into the adaptively evolved Yarrowia lipolytica strain (YSX strain) prepared in Example 2 according to the same method as that of Example 1 to produce transformed strains. The following three types of transformed strains were produced: a strain (the YSX_xylA strain of FIG. 3) obtained by introducing only the xylose isomerase gene (xylA gene) of Example 1 into the adaptively evolved Yarrowia lipolytica strain (YSX strain) produced in Example 2, a strain (the YSX_XK strain of FIG. 3) obtained by introducing only the xylulokinase gene (XK gene) into the adaptively evolved Yarrowia lipolytica strain (YSX strain) of Example 2, and a strain (the YSX_xylA_XK strain of FIG. 3) obtained by introducing both the xylose isomerase gene (xylA gene) and xylulokinase gene (XK gene) into the adaptively evolved Yarrowia lipolytica strain (YSX strain) produced in Example 2. The adaptively evolved Yarrowia lipolytica strain (YSK strain) of Example 2 was used as the control. Then, each of the three transformed strains and the control strain was cultured in a minimal medium (Complete Supplement Mixture (CSM) medium (6.7 g/L yeast nitrogen base, 20 g/L xylose, CSM-Leu-Ura(MP biomedicals, Solon, USA)) containing 20 g/L of xylose as a carbon source, and the xylose utilizing capacity of each strain was evaluated by comparing the indexes ($OD_{600}$ and growth rate ($\mu$)) of growth of the strains using xylose, according to the same method as Example 2. The results are shown in FIG. 3.

Figure 3:
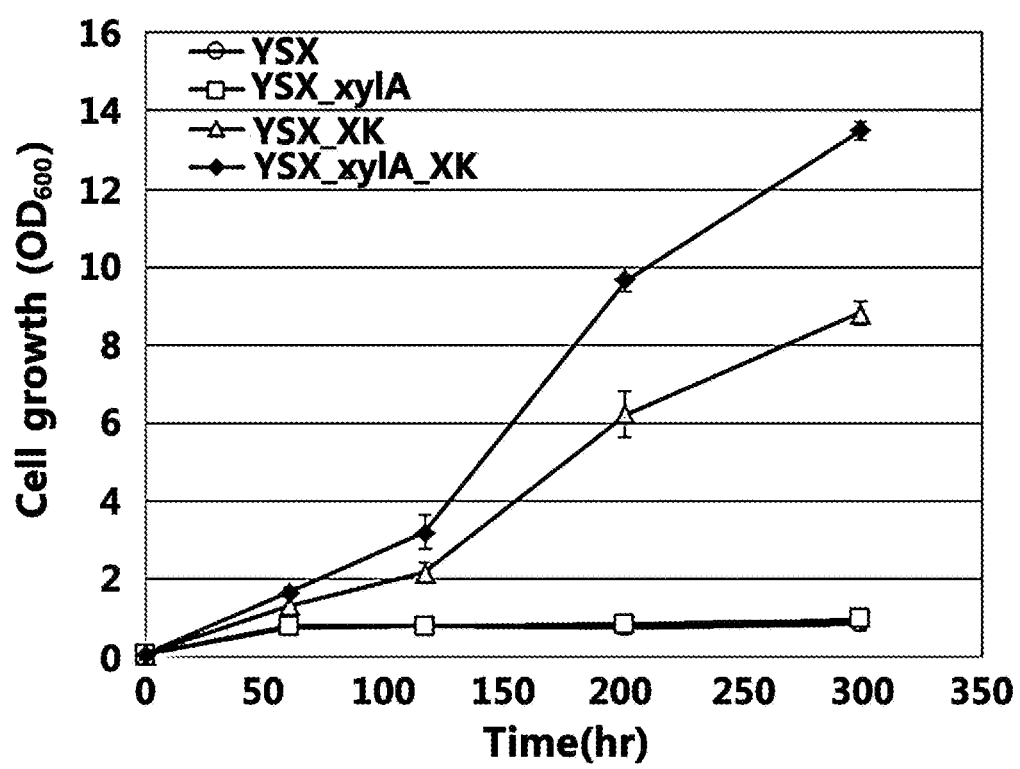
FIG. 3 shows the growth curves of an adaptively evolved Yarrowia lipolytica strain (YSX), a strain (YSX_xylA) obtained by introducing only the xylose isomerase gene into the strain, a strain (YSX_XK) obtained by introducing only the xylulokinase, and a strain (YSX_xylA_XK) obtained by introducing both the xylose isomerase gene and the xylulokinase gene, in a minimal medium containing xylose as a carbon source.

As shown in FIG. 3, the adaptively evolved control strain (YSX strain) exhibited an $OD_{600}$ of about 0.88 at the stationery phase of strain growth and a strain growth rate ($\mu$) of about 0.0158 $h^{-1}$. In contrast, the strain (YSX_xylA) in which the xylose isomerase gene (xylA) has been introduced exhibited an increased $OD_{600}$ of 0.99 and an increased strain growth rate of 0.0162 $h^{-1}$. The strain (YSX_XK) in which the xylulokinase gene (XK) has been introduced exhibited a further improved xylose utilizing capacity with an $OD_{600}$ of 8.82 and a strain growth rate of 0.0235 $h^{-1}$. The strain (YSX_xylA_XK) in which both the xylose isomerase gene (xylA) and the xylulokinase gene (XK) has been introduced exhibited an increased $OD_{600}$ of 13.51 and an increased strain growth rate of 0.0250 $h^{-1}$. Among the strain growth indexes of the YSX_xylA_XK strain, the maximum strain concentration ($OD_{600}$) was about 38 times higher than that of the wild-type control of Example 1 ($OD_{600}$=0.3596, strain growth rate 0.0027 $h^{-1}$) and the growth rate was about 9 times higher than the control.

Thus, it was confirmed that the transformed and adaptively evolved Yarrowia lipolytica strain, obtained by transforming the adaptively evolved Yarrowia lipolytica strain according to the present invention to express the xylose isomerase or xylulokinase gene, has a significantly increased xylose utilizing capacity compared to the wild-type strain.

[Example 4] Evaluation of the Xylose Utilizing Capacity and Lipid-Producing Ability of Transformed and Adaptively Evolved Yarrowia lipolytica Strain In order to evaluate the ability of the transformed and adaptively evolved Yarrowia lipolytica strains to produce lipids using xylose, the transformed and adaptively evolved Yarrowia lipolytica strain (YSX_xylA_XK) produced in Example 3 was cultured in a batch reactor while investigating the strain growth using xylose and the xylose consumption trend to evaluate the actual xylose utilizing capacity thereof. Culture of yeast strains using a batch reactor allows to culture yeast strains at a high concentration and thus enables to produce high density lipids.

Figure 4:
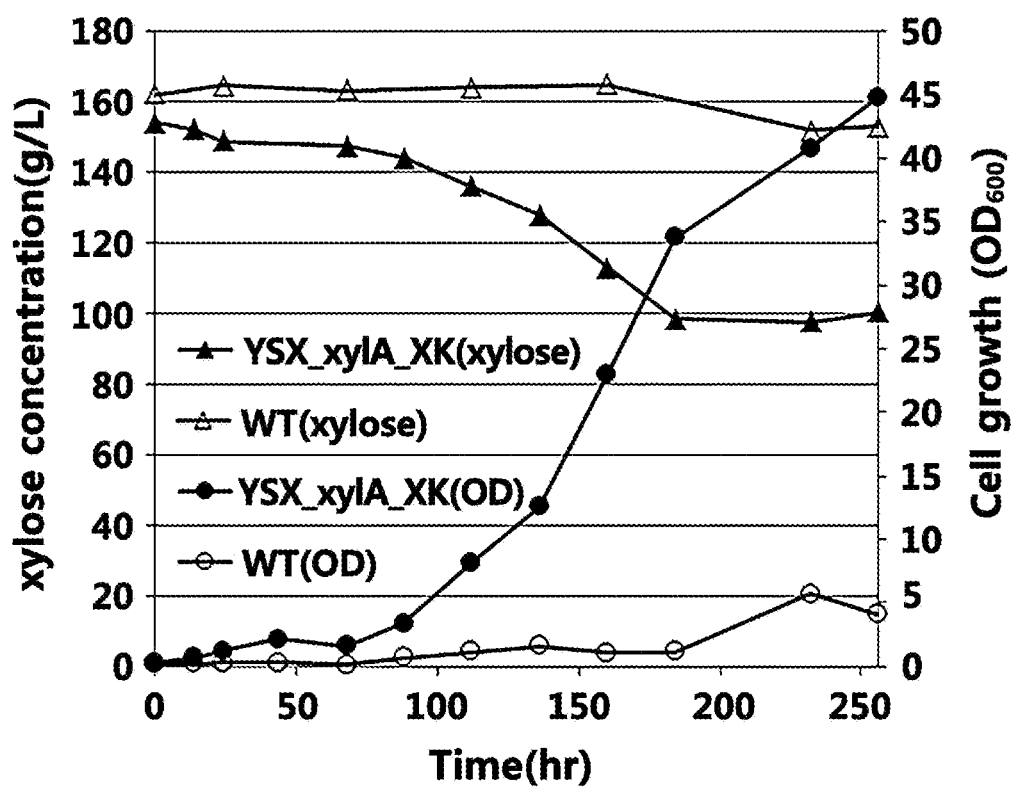
FIG. 4 is a graph showing the xylose conversion ability of a wild-type Yarrowia lipolytica strain (WT) which was not subjected to adaptive evolution and a transformed and adaptively evolved Yarrowia lipolytica strain (YSX_xylA_XK), obtained by batch reactor operation.

Specifically, the transformed and adaptively evolved Yarrowia lipolytica strain (YSX_xylA_XK) produced in Example 3 was cultured in a batch reactor. The stirring speed was adjusted to 250 to 800 rpm to maintain the dissolved oxygen concentration at 50% or more, and if necessary, a 2.5M NaOH solution was added to maintain the pH in the reactor at 3.5. At this time, 160 g/L of xylose was added to the reactor to produce high density lipids. The reactor was stopped after about 256 hours, which was the point at which xylose cannot be consumed any more. The strain growth and xylose concentration over time were measured, and the results are shown in FIG. 4. A wild-type Yarrowia lipolytica strain (control strain of Example 1), which did not have xylose isomerase and xylulokinase and did not undergo adaptive evolution as in Example 2, was used as the control.

As shown in FIG. 4, unlike the wild-type strain, which consumes almost no xylose, the transformed and adaptively evolved Yarrowia lipolytica strain (YSX_xylA_XK) produced in Example 3 showed an increase in the maximum strain concentration in a medium containing a high concentration (160 g/L) of xylose, with an $OD_{600}$ of 44.79.

Figure 5:
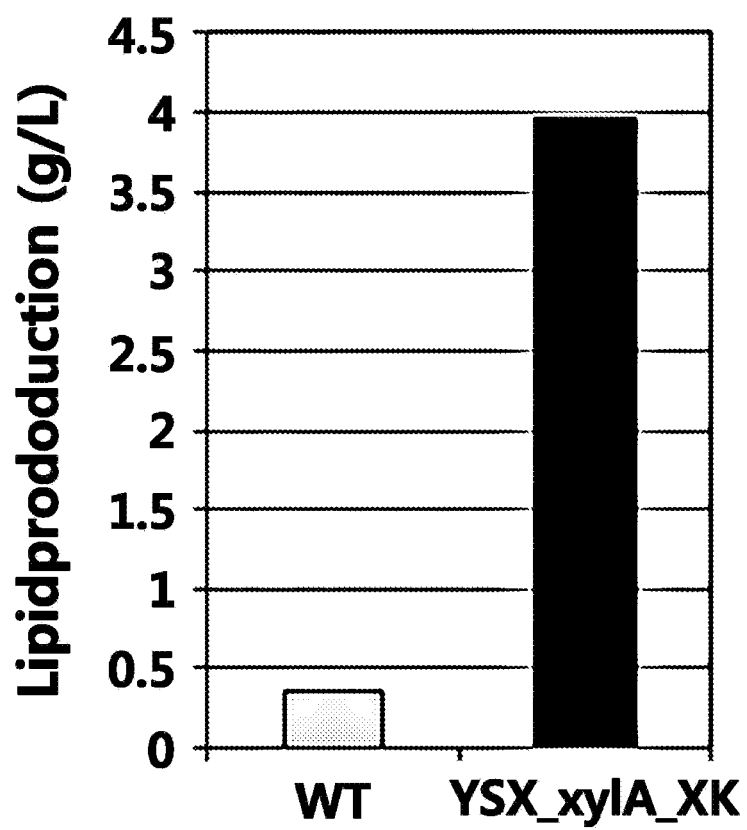
FIG. 5 is a graph comparing the concentration of the lipids produced by a transformed and adaptively evolved Yarrowia lipolytica strain (YSX_xylA_XK), obtained by batch reactor operation, compared with that of a wild-type Yarrowia lipolytica strain (WT) which was not subjected to an adaptive evolution process.

Also, as illustrated in FIG. 5, the measurement results of lipid production showed that the transformed and adaptively evolved Yarrowia lipolytica strain (YSX_xylA_XK) produced in Example 3 accumulated about 4 g/L of lipids from 60 g/L of xylose. The lipid production was about at least 11 times higher than that of the control.

Thus, it was confirmed that the transformed and adaptively evolved Yarrowia lipolytica strain, obtained by transforming the adaptively evolved Yarrowia lipolytica strain according to the present invention to express the xylose isomerase or xylulokinase gene, has a significantly superior xylose utilizing capacity and lipid-producing ability compared to the wild-type strain.

The present invention allows to impart to a wild-type yeast strain, which cannot utilize xylose as a carbon source, the ability to metabolize xylose based on xylose isomerase by adaptively evolving the wild-type yeast strain so as to activate the xylose metabolic pathway and then transforming the adaptively evolved strain. Thus, the present invention does not introduce the xylose metabolic pathway based on oxidoreductase, and thus allows to produce biodiesel and biomaterials (such as cosmetics) based on lipid and lignocellulosic biomass at a high yield without a problem of cofactor imbalance, and to greatly improve the economic feasibility and sustainability of the production processes of biodiesel and biomaterials.

While the present invention has been described with respect to the specific embodiments, it will be apparent to those skilled in the art that various changes and modifications may be made without departing from the spirit and scope of the invention as defined in the following claims.

[Accession Number]
Depository authority: Korean Collection for Type Cultures
Accession number: KCTC13615BP
Deposit date: 20180807
[Accession Number]
Depository authority: Korean Collection for Type Cultures
Accession number: KCTC13616BP
Deposit date: 20180807

What is claimed is:

1. A transformed and adaptively evolved yeast strain, comprising:
   - [1] at least one gene encoding xylose isomerase and/or xylulokinase; and
   - [2] at least one genetic mutation from the group consisting of:
     YALI0_A15642g, YALI0_A15796g, YALI0_C11165g, YALI0_C16247g, YALI0_D24849g, YALI0_D27016g, YALI0_E14388g1, YALI0_E23969g, YALI0_F04906g, and YALI0_F17468g,
     147G>A mutation in the YALI0_A15642g gene as set forth in SEQ ID NO: 11;
     567_568insACA and 576T>G mutations in the YALI0_A15796g gene as set forth in SEQ ID NO: 12;
     1523T>C mutation in the YALI0_C11165g gene as set forth in SEQ ID NO: 25;
     T1412A, G1441A, A1513G, A1534G, G1535T, T1544A, and C1847T mutations in the YALI0_C16247g gene as set forth in SEQ ID NO: 30;
     103G>A mutation in the YALI0_D24849g gene as set forth in SEQ ID NO: 39;
     446T>C mutation in the YALI0_D27016g gene as set forth in SEQ ID NO: 45;
     2525C>G, 2531T>G, 2534A>G, and 2558T>C mutations in the YALI0_E14388g1 gene as set forth in SEQ ID NO: 50;
     480_481insTCCTCTACCCCCGAG (SEQ ID NO: 64), 526_527insCCTCCACCACCGAGC (SEQ ID NO: 65), and 497A>C mutations in the YALI0_E23969g gene as set forth in SEQ ID NO: 56;
     2702T>A mutation in the YALI0_F04906g gene as set forth in SEQ ID NO: 57; and/or 482_483insGCACCA mutation in the YALI0_F17468g gene as set forth in SEQ ID NO: 61.

2. The transformed and adaptively evolved yeast strain according to claim 1, wherein the strain further comprises the following mutations in at least one gene selected from the group consisting of YALI0_A00891g, YALI0_A00935g, YALI0_A02002g, YALI0_A02497g, YALI0_A07997g, YALI0_A13849g, YALI0_A16863g, YALI0_A17578g, YALI0_A17776g, YALI0_A17853g, YALI0_A19646g, YALI0_B00748g, YALI0_B08800g, YALI0_C06424g, YALI0_C07172g, YALI0_C08437g, YALI0_C09031g, YALI0_C09614g, YALI0_C13728g, YALI0_C14476g, YALI0_C15532g, YALI0_C16148g, YALI0_D15752g, YALI0_D17820g, YALI0_D18381g, YALI0_D19822g, YALI0_D20064g, YALI0_D20526g, YALI0_D20790g, YALI0_D24563g, YALI0_D25014g, YALI0_D25058g, YALI0_D26257g, YALI0_D26510g, YALI0_D26620g, YALI0_E07832g, YALI0_E08008g, YALI0_E11363g, YALI0_E13596g, YALI0_E16731g, YALI0_E18073g, YALI0_E18216g, YALI0_E20449g, YALI0_E21109g, YALI0_F12221g, YALI0_F12793g, YALI0_F16577g, YALI0_F19030g, and YALI0_F23287g:

11_16delACGGCC mutation in the YALI0_A00891g gene as set forth in SEQ ID NO: 5;

202_203insGCTC mutation in the YALI0_A00935g gene as set forth in SEQ ID NO: 6;

1255_1256insGAGGTCAAGGTC (SEQ ID NO: 66) mutation in the YALI0_A02002g gene as set forth in SEQ ID NO: 7;

132_137dupCAACTC and 331_332insCCCACT mutations in the YALI0_A02497g gene as set forth in SEQ ID NO: 8;

2846_2847insGGAGCAGGA and 2869_2870insAGGAGGAGG mutations in the YALI0_A07997g gene as set forth in SEQ ID NO: 9;

165_166insCAAA mutation in the YALI0_A13849g gene as set forth in SEQ ID NO: 10;

888_889insGAGCTGAGATGAC (SEQ ID NO: 67) mutation in the YALI0_A16863g gene as set forth in SEQ ID NO: 13;

432_433insGCGGAGCCG mutation in the YALI0_A17578g gene as set forth in SEQ ID NO:14;

959_960insACAGCAGAT mutation in the YALI0_A17776g gene as set forth in SEQ ID NO: 15;

1940_1942delAGG, 1990_1991insAGGAGGAGGCTAAGAAGA (SEQ ID NO: 68) and 2817_2818insTCTGAG mutations in the YALI0_A17853g gene as set forth in SEQ ID NO: 16;

1462_1463insGGG mutation in the YALI0_A19646g gene as set forth in SEQ ID NO: 17;

525_526insCCCGAC mutation in the YALI0_B00748g gene as set forth in SEQ ID NO: 18;

152_153delGT mutation in the YALI0_B08800g gene as set forth in SEQ ID NO: 19;

1370_1373delACTT mutation in the YALI0_C06424g gene as set forth in SEQ ID NO: 20;

308_309insGCAGCGACA mutation in the YALI0_C07172g gene as set forth in SEQ ID NO: 21;

1592_1593insGACAGTCAGCAC (SEQ ID NO: 69) mutation in the YALI0_C08437g gene as set forth in SEQ ID NO: 22;

1789_1790insCTCCCGAGTCCTCTGCTGAGCCTACCAGCGAAGAGACTTCTTCG (SEQ ID NO: 70) mutation in the YALI0_C09031g gene as set forth in SEQ ID NO: 23;

1620_1622delACA mutation in the YALI0_C09614g gene as set forth in SEQ ID NO: 24;

99_100insAAAAAGTGGTCGAAAAAGTGGCCA (SEQ ID NO: 71) and 129_130insTGGCCGAAAAAGTGGCCAAAA (SEQ ID NO: 72) mutations in the YALI0_C13728g gene as set forth in SEQ ID NO: 26;

778_779insTGC mutation in the YALI0_C14476g gene as set forth in SEQ ID NO: 27;

1611_1616delCAGCTT mutation in the YALI0_C15532g gene as set forth in SEQ ID NO: 28;

961_969delAGCAGCAGT mutation in the YALI0_C16148g gene as set forth in SEQ ID NO: 29;

1038_1039insCAG mutation in the YALI0_D15752g gene as set forth in SEQ ID NO: 31;

619_620insCCCACCCGCAAACCC (SEQ ID NO: 73) mutation in the YALI0_D17820g gene as set forth in SEQ ID NO: 32;

114_115insCCTCTCACCAACTCA (SEQ ID NO: 74) mutation in the YALI0_D18381g gene as set forth in SEQ ID NO: 33;

310_315delAAAGAG mutation in the YALI0_D19822g gene as set forth in SEQ ID NO: 34;

67_68insGGGGGGGG mutation in the YALI0_D20064g gene as set forth in SEQ ID NO: 35;

354_355insTCCACCGGA mutation in the YALI0_D20526g gene as set forth in SEQ ID NO: 36;

37_38insCACGTGAAAGTAGCCGAA (SEQ ID NO: 75) mutation in the YALI0_D20790g gene as set forth in SEQ ID NO: 37;

84_85insGCT mutation in the YALI0_D24563g gene as set forth in SEQ ID NO: 38;

484_485insCCGCTAGCGCCAACTCTGGCTCGGAGC (SEQ ID NO: 76) mutation in the YALI0_D25014g gene as set forth in SEQ ID NO: 40;

592_594dupAAG mutation in the YALI0_D25058g gene as set forth in SEQ ID NO: 41;

1478_1480delAGA mutation in the YALI0_D26257g gene as set forth in SEQ ID NO: 42;

1287_1288insAAG mutation in the YALI0_D26510g gene as set forth in SEQ ID NO: 43;

926_927insCGATGAGGACGA (SEQ ID NO: 77) mutation in the YALI0_D26620g gene as set forth in SEQ ID NO: 44;

499_500insCCAAGCCCCCCGCTTCCAAGCCCACCGCT (SEQ ID NO: 78) mutation in the YALI0_E07832g gene as set forth in SEQ ID NO: 46;

794_795insCTCTTCCTCTTCCTCTTCCTCTTCCTCTTC (SEQ ID NO: 79) mutation in the YALI0_E08008g gene as set forth in SEQ ID NO: 47;

74_77delCACA mutation in the YALI0_E11363g gene as set forth in SEQ ID NO: 48;

1053_1054insCAACAACAACAGCAACAA (SEQ ID NO: 80) mutation in the YALI0_E13596g gene as set forth in SEQ ID NO: 49;

1622_1623insTGAGGAGGAAGAGTAGGATGAGGAGTA (SEQ ID NO: 81) mutation in the YALI0_E16731g gene as set forth in SEQ ID NO: 51;

266_267insCCCCACGCAGCAGTCTG (SEQ ID NO: 82) mutation in the YALI0_E18073g gene as set forth in SEQ ID NO: 52;

930_938delACAACAGCA mutation in the YALI0_E18216g gene as set forth in SEQ ID NO: 53;

899_900insAAACGC mutation in the YALI0_E20449g gene as set forth in SEQ ID NO: 54;

228_229insGCCCCGCCT mutation in the YALI0_E21109g gene as set forth in SEQ ID NO: 55;

1825_1827delAAG mutation in the YALI0_F12221g gene as set forth in SEQ ID NO: 58;

1855_1860delTCTTCT mutation in the YALI0_F12793g gene as set forth in SEQ ID NO: 59;

807_808insCCTCCT mutation in the YALI0_F16577g gene as set forth in SEQ ID NO: 60;

1344_1345insCCTACTACCGCCGATGTY (SEQ ID NO: 83), 2065T>A, 2098A>G, and 2099C>A mutations in the YALI0_F19030g gene as set forth in SEQ ID NO: 62; and/or 1919_1920insCTC mutation in the YALI0_F23287g gene as set forth in SEQ ID NO: 63.

3. The transformed and adaptively evolved yeast strain according to claim 1, wherein the yeast strain is a *Yarrowia lipolytica* strain.

4. The transformed and adaptively evolved yeast strain according to claim 1, wherein the gene encodes xylose isomerase.

5. The transformed and adaptively evolved yeast strain according to claim 1, wherein the gene encoding xylose isomerase is as set forth in SEQ ID NO: 1.

6. The transformed and adaptively evolved yeast strain according to claim 1, wherein the gene encodes xylulokinase.

7. The transformed and adaptively evolved yeast strain according to claim 1, wherein the gene encoding xylulokinase is as set forth in a sequence of SEQ ID NO: 2.

8. The transformed and adaptively evolved yeast strain according to claim 1, wherein the strain is transformed with at least one vector selected from the group consisting of a first vector and a second vector, wherein the first vector comprises a gene encoding xylose isomerase, and wherein the second vector comprises a gene encoding xylulokinase.

9. The transformed and adaptively evolved yeast strain according to claim 8, wherein the first vector comprises a UAS1B enhancer, a translational elongation factor (TEF) promoter, and a gene encoding xylose isomerase.

10. The transformed and adaptively evolved yeast strain according to claim 9, wherein the first vector is set forth in SEQ ID NO: 3.

11. The transformed and adaptively evolved yeast strain according to claim 8, wherein the second vector comprises a UAS1B enhancer, a translational elongation factor (TEF) promoter, and a gene encoding xylulokinase.

12. The transformed and adaptively evolved yeast strain according to claim 11, wherein the second vector is set forth in SEQ ID NO: 4.

13. The transformed and adaptively evolved yeast strain according to claim 1, wherein the strain is subcultured three times or more in a medium containing xylose as the sole carbon source.

14. The transformed and adaptively evolved yeast strain according to claim 1, wherein the yeast strain comprising mutant genes has the accession number KCTC13615BP.

15. The transformed and adaptively evolved yeast strain according to claim 1, wherein the transformed and adaptively evolved yeast strain has the accession number KCTC13616BP.

16. A method for producing the transformed and adaptively evolved yeast strain according to claim 1, comprising the steps of:

subculturing a wild-type yeast strain three times or more in a medium containing xylose as the sole carbon source; and transforming the subcultured strain to comprise at least one gene encoding xylose isomerase and/or xylulokinase.

17. A method for producing lipids, comprising the step of culturing the transformed and adaptively evolved yeast strain according to claim 1.

18. A method for producing biodiesel, comprising the steps of:

culturing the transformed and adaptively evolved yeast strain according to claim 1 in a medium containing xylose as a carbon source to produce lipids; and transesterifying the produced lipids to obtain biodiesel.

* * * * *